US012098377B2

(12) United States Patent
Torjek et al.

(10) Patent No.: US 12,098,377 B2
(45) Date of Patent: *Sep. 24, 2024

(54) GENE FOR RESISTANCE TO PLANT DISEASE

(71) Applicant: KWS SAAT SE & Co. KGaA, Einbeck (DE)

(72) Inventors: Otto Torjek, Einbeck (DE); Dietrich Borchardt, Einbeck (DE); Margaret Rekoske, Shakopee, MN (US); Wolfgang Mechelke, Einbeck (DE); Jens Christoph Lein, Gottingen (DE); Britta Schulz, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 77 days.

This patent is subject to a terminal disclaimer.

(21) Appl. No.: 17/429,674

(22) PCT Filed: Feb. 18, 2019

(86) PCT No.: PCT/EP2019/054008

§ 371 (c)(1),
(2) Date: Aug. 10, 2021

(87) PCT Pub. No.: WO2020/169178

PCT Pub. Date: Aug. 27, 2020

(65) Prior Publication Data

US 2022/0154206 A1 May 19, 2022

(51) Int. Cl.
*C12N 15/82* (2006.01)

(52) U.S. Cl.
CPC ..... *C12N 15/8282* (2013.01); *C12N 15/8213* (2013.01)

(58) Field of Classification Search
None
See application file for complete search history.

(56) References Cited

U.S. PATENT DOCUMENTS

| | | | | |
|---|---|---|---|---|
| 7,435,874 | B2 | 10/2008 | Gebhardt et al. | |
| 8,321,147 | B2 | 11/2012 | Bink et al. | |
| 9,029,635 | B2 | 5/2015 | Harms et al. | |
| 10,633,670 | B2 * | 4/2020 | Kock | C07K 14/415 |
| 10,767,191 | B1 | 9/2020 | Torjek et al. | |
| 2002/0139046 | A1 | 10/2002 | Weber et al. | |
| 2013/0227721 | A1 | 8/2013 | Becker | |
| 2016/0152999 | A1 | 6/2016 | Torjek et al. | |

FOREIGN PATENT DOCUMENTS

| | | | | |
|---|---|---|---|---|
| DE | 26 07 785 | A1 | 9/1976 | |
| DE | 3442317 | A1 | 5/1986 | |
| EP | 3696188 | A1 | 8/2020 | |
| GB | 2 323 766 | A | 10/1998 | |
| WO | WO-2018202800 | A1 * | 11/2018 | C12N 15/8213 |
| WO | 2020/064687 | A1 | 4/2020 | |

OTHER PUBLICATIONS

NCBI Reference Sequence: XP_010676066, 2016, Betula vulgaris subsp. vulgaris LRR receptor-like serine/threonine-protein kinase RCH1 (Year: 2016).*

Stevanato et al, The Sea Beet of the Adriatic Coast as Source of Resistance for Sugar Beet, 2001, Sugar Tech 3: 77-82 (Year: 2001).*

Martin et al, 2003, Understanding the functions of plant disease resistance proteins, Annual Review Plant Biology 54: 23-61 (Year: 2003).*

Guo H et al, Protein tolerance to random amino acid change, 2004, Proceedings of the National Academies of Science, 101:9205-9210. (Year: 2004) (Year: 2004).*

Panella et al, USDA-ARS Sugarbeet Releases and Breeding Over the Past 20 Years 2015, Journal of Sugar Beet Research 52: 40-85) (Year: 2015).*

Bae et al., "Cas-OFFinder: a fast and versatile algorithm that searches for potential off-target sites of Cas9 RNA-guided endonucleases"; Bioinformatics Application Notes, vol. 30, No. 10, 2014, pp. 1473-1475.

Depicker et al., "Nopaline Synthase: Transcript Mapping and DNA Sequence", Journal of Molecular and Applied Genetics, vol. 1, No. 6, 1982, pp. 561-573.

Dixon et al., "The Tomato Cf-2 Disease Resistance Locus Comprises Two Functional Genes Encoding Leucine-Rich Repeat Proteins", Cell, vol. 84, 1996, pp. 451-459.

Henikoff et al., "TILLING. Traditional Mutagenesis Meets Functional Genomics", Plant Physiology, vol. 135, Jun. 2004, pp. 630-636.

Holtschulte, "Cercospora beticola: World-wide Distribution and Incidence" 2000, pp. 1-12.

Lindsey et al., "Transformation of Sugarbeet (*Beta vulgaris*) by Agrobacterium tumefaciens", Journal of Experimental Botany, vol. 41, No. 226, May 1990, pp. 529-536.

Martin et al., "Understanding The Functions Of Plant Disease Resistance Proteins", Annu. Rev. Plant Biol. vol. 54, 2003, pp. 23-61.

Odell et al., "Identification of DNA sequences required for activity of the cauliflower mosalc virus 35S promoter" Nature, vol. 313, 1985, pp. 810-812.

Osakabe et al., "Genome Editing with Engineered Nucleases in Plants", Plant Cell Physiol, vol. 56, No. 3, 2015, pp. 389-400.

Park et al., "Cas-Designer: a web-based tool for choice of CRISPR-Cas9 target sites", Bioinformatics, vol. 31 No. 24, 2015, pp. 4014-4016.

(Continued)

*Primary Examiner* — Anne Kubelik
*Assistant Examiner* — Aleksandar Radosavljevic
(74) *Attorney, Agent, or Firm* — Troutman Pepper Hamilton Sanders LLP

(57) ABSTRACT

A more efficient breeding against plant disease, or the development of new resistant lines, is enabled via the provision of the resistance-mediating gene according to the invention; in particular, a resistance effect in the target plant is evoked by the property of the identified gene. The resistance-mediating gene, and embodiments of the present invention that are described in the preceding, offer additional applications, e.g., the use of the resistant gene allele in trans-genetic approaches, with the goal of developing new resistant cultivars.

12 Claims, 7 Drawing Sheets

Figure 2:
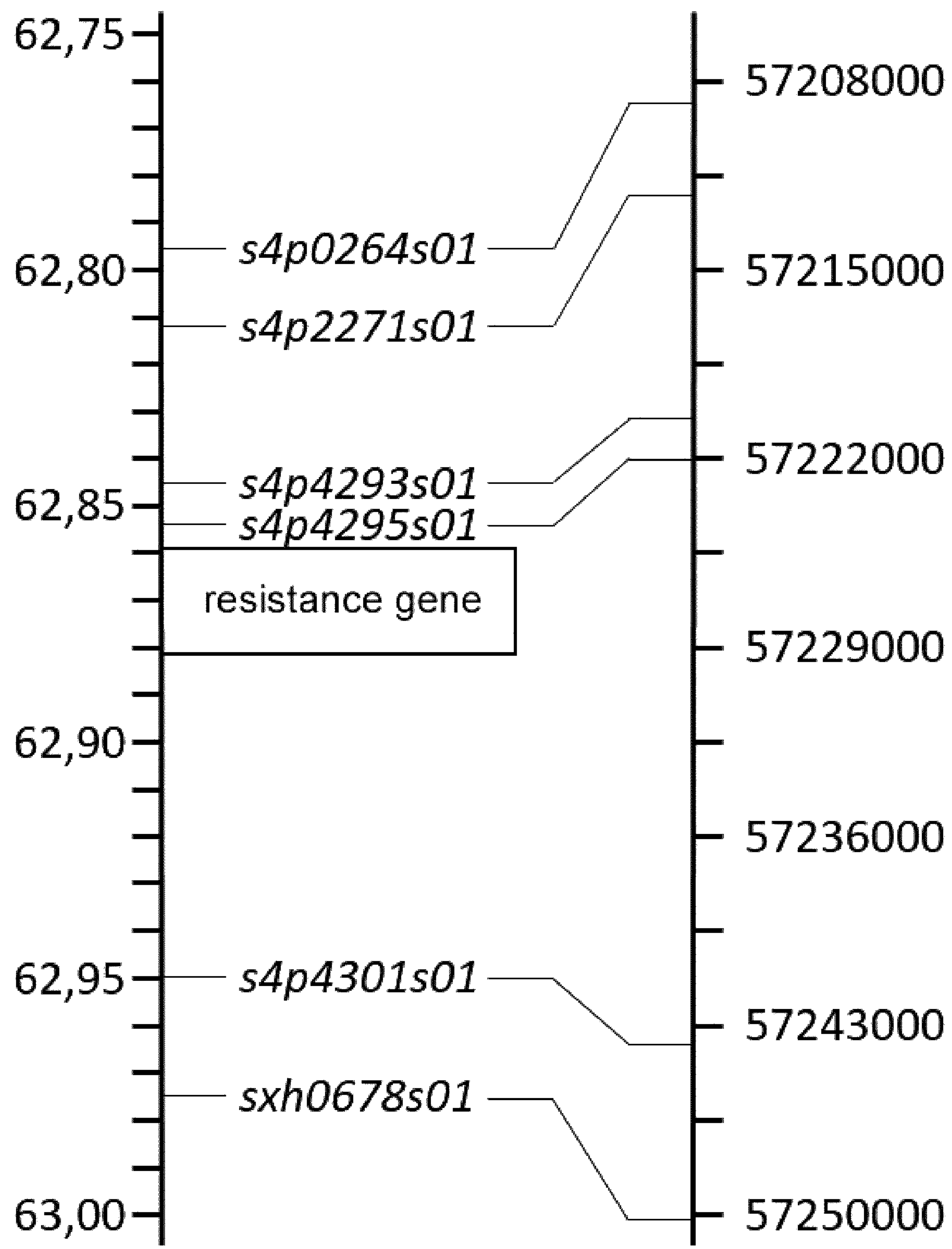

Specification includes a Sequence Listing.

(56) References Cited

OTHER PUBLICATIONS

Rushton et al., "Interaction of elicitor-induced DNA-binding proteins with elicitor response elements in the promoters of parsley PR1 genes" The EMBO Journal, vol. 15 No. 20, 1996, pp. 5690-5700.
Sambrook et al, eds. Molecular Cloning: A Laboratory Manual, vol. 2, "Analysis of Genomic DNA by Southern Hybridization", 1989, pp. 9.31-9.59.
Steinrucken, "Die Zuchtung von Cercospora-resistenten Zuckerruben" Vortr. Pflanzenzuchtg, vol. 37, pp. 76-91.
Steinrucken, "Cultivation of Cercospora-resistant sugar beet", pp. 1-7. (English translation of NPL above).
Tang et al., "A CRISPR-Cpf1 system for efficient genome editing and transcriptional repression in plants" Nature Plants, vol. 3, Article No. 17018, 2017, pp. 1-5.
UniProtKB-Q41397 "Cf-2.1—*Solanum pimpinellifolium* (Currant tomato)" https://www.uniprot/org/uniprot/Q41397, Oct. 18, 2018, pp. 1-6.
Weiland et al., "Sugarbeet leaf spot disease (*Cercospora beticola* Sacc.)", Molecular Plant Pathology, vol. 5 No. 3, 2004, pp. 157-166.
Weltmeier et al., "Transcript Profiles in Sugar Beet Genotypes Uncover Timing and Strength of Defense Reactions to Cercospora beticola Infection", Molecular Plant-Microbe Interactions (MPMI), vol. 24 No. 7, 2011, pp. 758-772.
Predicted: LRR receptor-like serine/threonine-protein kinase RCH1 [Beta vulgaris subsp. vulgaris], NCBI Reference Sequence: XP_010676066.1, 4 pages, https://www.ncbi.nlm.nih.gov/protein/XP_010676066 accessed on Mar. 15, 2019.
EM_EST:BU089571, 1 page, http://ibis.internal.epo.org/exam/dbfetch.jsp?id=EM_EST:BU089571 accessed on Mar. 15, 2019.
Stevanato et al., "The Sea Beet (*Beta vulgaris* L. ssp. maritima) of the Adriatic Coast as Source of Resistance for Sugar Beet", Sugar Tech, 2001, vol. 3, No. 3, pp. 77-82.
Larbi et al., "Effects of Cd and Pb in sugar beet plants grown in nutrient solution: Induced Fe deficiency and growth inhibition", Funct. Plant Biol., 2002, vol. 29, pp. 1453-1464.
Wyse, "Sucrose uptake by sugar beet tap root tissue", Plant Physiol, 1979, vol. 64, pp. 837-841.
Frese, "Chapter 13: Combining static and dynamic management of PGR: a case study of Beta genetic resources" Engels (eds). Managing Plant Genetic Diversity, IPGR. 2002, pp. 133-147.
Lytvyn et al., "Creation of transgenic sugar beet lines expressing insect pest resistance genes cry1C and cry2A", Cytology and Genetics, 2014, vol. 48, No. 2, pp. 3-11.
Nilsson et al., "QTL analysis of Cercospora leaf spot resistance in sugar beet", Plant Breeding, 1999, vol. 118, pp. 327-334.
Heijbroek et al., "Fungicides and insecticides applied to pelleted sugar-beet seeds—II. Control of pathogenic fungi in soil", Crop Protection, 1995, vol. 14, No. 5, pp. 363-366.
Rochalska et al., "Influence of alternating magnetic field on respiration of sugar beet seeds", International Agrophysics, 2008, vol. 22, pp. 255-259.
Trkulja et al. "Molecular and experimental evidence of multi-resistance of Cercospora beticola field populations to MBC, DMI and Qol fungicides", European Journal of Plant Pathology, 2017, vol. 149, No. 4, pp. 895-910.
International Search Report and Written Opinion issued in PCT/EP2021/071944 dated Oct. 18, 2021.
All, "Rapid detection and quantification of Cercospora beticola in soil using PCR and ELISA assays", Dissertation, 2012, 144 pages.
Bilgen et al., "Transferring Cercospora Leaf Spot Resistance From Beta Maritima to Sugarbeet by Backcrossing", Journal of the A.S.S.B.T., 1969, vol. 15, No. 5, pp. 444-449.
GenBank:JY463144.1 [on-line], 2013, [Search Date Jan. 26, 2023], Internet : <URL :https://www.ncbi.nlm.nih.gov/nuccore/jy463144 >.
GenBank:JY461792.1 [on-line], 2013, [Search Date Jan. 26, 2023], Internet : <URL : https://www.nobi.nlm.nih.gov/nuccore/jy461792 >.
Third Party Observation in EP Application No. 20191416 mailed Apr. 24, 2023, submitted Apr. 19, 2023.
Printout from the PINTO Database; printed Dec. 9, 2022.
Reformatted Table of PINTO Database of Dec. 9, 2022.
Material Transfer Agreement; https://www.geves.fr/wp-content/uploads/PROTOVATEPLANTESDESERVICES20182019; French-language original; date unknown.
Material Transfer Agreement; https://www.geves.fr/wp-content/uploads/PROTOVATEPLANTESDESERVICES20182019; English-language translation; date unknown.
Marketing Materials from KWS; Mar. 28, 2020.
Third Party Observation in EP Application No. 19704637 mailed Apr. 24, 2023, submitted Apr. 19, 2023.
Third Party Observation in EP Application No. 19157888 mailed Apr. 24, 2023, submitted Apr. 19, 2023.

* cited by examiner

```
SEQ ID NO 6  MNMKILLLFVFLHHLHYFINGRTLTEHQALLSIKSAITNDTNSYLSLWKNTTHHCSWPYITCSSSSSS--VISLDISYLELTGILSPDIGFLTNLQNLTI 98
SEQ ID NO 3  MNMKILLLFVFLHHLHYFIHGRTLTERQALLSIKSAITYDYYNSLSSWKNTTHHCSWPYITCSSSSSSSSVISLNFTMLFLEGILSPDIGFLTNLQNLSI 100
SEQ ID NO 9  MNMKILLLFVFLHHLHYFIXGRTLTEXQALLSIKSAITXDXXXXLSXWKNTTHHCSWPYITCSSSSSSSSVISLXXXXLXLXGILSPDIGFLTNLQNLXI
conservation

SEQ ID NO 6  QWNDFSGPLPTSLSLLTQLRHLDVSYNNFTGPIPSSLSLLTQLRHLDVSFNSFTGPIPSSLSLLTQLRYLDVSQNSFTGPIPSSLSLLTQLRYLDVSDNS 198
SEQ ID NO 3  RSNLFSGPLPHSLSLLTQLRYLDVSQN------------------------SFTGPIPSSLSLLTQLRYLHVSGNSFTGPIPSFLSLLTQLRYLDVSDNS 176
SEQ ID NO 9  XXNXFSGPLPXSLSLLTQLRXLDVSXNNFTGPIPSSLSLLTQLRHLDVSFNSFTGPIPSSLSLLTQLRYLXVSXNSFTGPIPSXLSLLTQLRYLDVSDNS

SEQ ID NO 6  FTGPIPSFLSLLTQLRYLDVSYNNLNGTLPLSVVE-MSELRYLNLKYNSFYGEIPPEFGKLKKLQTLDLGNNYLSGGLPFELGSLKSLKY---------- 287
SEQ ID NO 3  FTGPIPSSLSLLTQLRYLDVSYNNLNGTLPLSVVEKMSELSYLNLRYNSFYGEIPPEFGKLKKLETLNLGNNTLSGSLPSELGSLKSLKHMDFSSNMLFG 276
SEQ ID NO 9  FTGPIPSXLSLLTQLRYLDVSYNNLNGTLPLSVVEKMSELXYLNLXYNSFYGEIPPEFGKLKKLXTLXLGNNXLSGXLPXELGSLKSLKXMDFSSNMLFG

SEQ ID NO 6  --------------IDLSINNLYGSIPDYIGDFPELESLLLDSNNFTGSIPQKLGTNGKLQYLDISNNNFSGSLPASLCKGDKLQHLGVSDNLLVGPIPE 373
SEQ ID NO 3  EIPQSYSLLRNLIDIDLNRNKLYGSIPDYIGDFPELESLLLDSNNFTGSIPQKLGTNGKLQYLDISNNNFSGSLPLSLCKGDKLQDLDASYNLLVGSIPE 376
SEQ ID NO 9  EIPQSYSLLRNLIDIDLXXNXLYGSIPDYIGDFPELESLLLDSNNFTGSIPQKLGTNGKLQYLDISNNNFSGSLPXSLCKGDKLQXLXXSXNLLVGXIPE

SEQ ID NO 6  SLGSCKSLEEVNMGNNFFNGSIPKGLFGLPNIIDVSLNDNLLSGGLDEKFGDCVNLFNIDLSNNKLSGKLPATIGNCSNLQLLMLNQNNFTGSIPQEISK 473
SEQ ID NO 3  SLGSCKSLEGVYMGNNFLNGSIPKGLFGS----DVSLNDKLLSGGLDEKFGDCVNLRDIDLSNNKLSGKLPATIGNCIHLRSLTLYNNTCTGRIPQEISK 472
SEQ ID NO 9  SLGSCKSLEXVXMGNNFXNGSIPKGLFGXPNIIDVSLNDXLLSGGLDEKFGDCVNLXXIDLSNNKLSGKLPATIGNCXXLXXLXLXXNXXTGXIPQEISK

SEQ ID NO 6  CKQLRALDLSQNQFSGVIPNDIT--------------------------------------------------------------DLSDNQLEGVLPKSL 511
SEQ ID NO 3  CKQLQTLDLSQNQFSGVIPNDITGNKSICNLEKIQTLKLSNNALTGEIPHCVGNIELIALFLQSNKLNGTIPANFSKLCDSLIYLDLSDNQLEGVLPKSL 572
SEQ ID NO 9  CKQLXXLDLSQNQFSGVIPNDITGNKSICNLEKIQTLKLSNNALTGEIPHCVGNIELIALFLQSNKLNGTIPANFSKLCDSLIYLDLSDNQLEGVLPKSL

SEQ ID NO 6  SKCQNLKLLNVGNNRLRDKFPSWLDNLPHLQVFSVRFNAFYGPITSSSKVNHPFPMLQIIDLSNNEFCGKLPRRYIKNFATMRNMNESGVGDPQYLEDS- 610
SEQ ID NO 3  SKCQSLELLNVGNNRLRDKFPSWLDNLPRLQVFSVRFNAFYGPITSSPKVSHPFPMLQIIDLSNNKFCGKLPRRYIKNFATMRNMNESGVGNPQYLGDSS 672
SEQ ID NO 9  SKCQXLXLLNVGNNRLRDKFPSWLDNLPXLQVFSVRFNAFYGPITSSXKVXHPFPMLQIIDLSNNXFCGKLPRRYIKNFATMRNMNESGVGXPQYLXDSS

SEQ ID NO 6  -YS-PYSMVLTFNGLQQKYEKLIVTMSTFDISNNNFTGQIPYVIGGLHSLRNLNLSHNVLTGNIPPSIAKLSLLQDLDLSSNRLIGRIPQELVSLTFLGS 708
SEQ ID NO 3  IYSITYSMVLTFNGLQQKYEKLIVTMSTFDISSNNFTGQIPYVIGGLRSLRNLNLSHNVLTGNIPPSIAKLSLLQDLDLSSNRLTGRIPQELVSLTFLGS 772
SEQ ID NO 9  IYSIXYSMVLTFNGLQQKYEKLIVTMSTFDISXNNFTGQIPYVIGGLXSLRNLNLSHNVLTGNIPPSIAKLSLLQDLDLSSNRLXGRIPQELVSLTFLGS

SEQ ID NO 6  FNVSNNLLEGPIPIGNNFNTFSNNSYQGNVGLCGKPLPECGERRAKSTTNNQDVPKNDNERMLSMSEIVVMGFGSGVLVGLAWGYYMFSVGKPFWFIKMA 808
SEQ ID NO 3  FNVSNNLLEGSIPHGFNFDTYTANSYQGNLELCGKPLPECGERRAKGTTNNQDDPKNDNERMLSMSEIVVMGFGSGVLVGLAWGYYMFSVGKPFWFIKMA 872
SEQ ID NO 9  FNVSNNLLEGXIPXGXNFXTXXXNSYQGNXXLCGKPLPECGERRAKXTTNNQDXPKNDNERMLSMSEIVVMGFGSGVLVGLAWGYYMFSVGKPFWFIKMA

SEQ ID NO 6  SKMESILIGFF 819
SEQ ID NO 3  SKMESILIGFF 883
SEQ ID NO 9  SKMESILIGFF
```

Fig. 1

SEQUENCE LISTING

```
<160> NUMBER OF SEQ ID NOS: 99

<210> SEQ ID NO 1
<211> LENGTH: 3720
<212> TYPE: DNA
<213> ORGANISM: Beta vulgaris

<400> SEQUENCE: 1

atgaacatga aaatcctcct tttgtttgtc ttccttcatc acctccacta cttcatccat      60

ggcagaacac ttacagaacg ccaagcttta ctaagtatca aatctgccat tacttatgat     120

tattataact ctctctcctc atggaaaaac acaacacacc actgcagttg gccatacatc     180

acttgctcct cctcttcttc ttcttcttct gttatttctc tcaacttcac catgttattt     240

ctcgaaggaa ttctctcccc tgatataggc ttcctcacca acctgcaaaa cctctctatt     300

cgatctaacc ttttttctgg cccactcccc cattctctct ctctcctcac ccaactccgc     360

tatctcgacg tttcccaaaa cagtttcaca ggtccaatcc catcttctct ctctctcctc     420

acccaactcc gctatctcca cgtttccggc aacagtttca caggtccaat cccatctttt     480
```

```
ctctctctcc tcacccaact ccgctatctc gacgtttccg acaacagttt cacaggtcca    540
atcccatctt ctctctctct cctcacccaa ctccgctatc tcgacgtttc ctacaacaat    600
ctaaatggca ctcttccctt atcggtcgtt gagaagatgt cggagctcag ctaccttaac    660
cttaggtata actctttcta cggtgagatt ccaccggagt ttgggaaact taagaagctt    720
gaaacattga atcttggtaa caacactctt tctgggagtc ttccatctga gttgggttca    780
ttaaagagtt tgaaacatat ggacttttct agtaatatgc tatttggtga gatcccacaa    840
tcttattctc ttcttcgaaa cttaatcgat attgatctta atagaaacaa gttatatggg    900
agtatacctg attatattgg agattttccg gagttggaat cacttttatt agactcgaat    960
aacttcacag ggagtatccc acaaaagtta ggtacaaacg ggaagttgca atatctagat   1020
ataagtaaca acaattttag tggtagtttg ccactaagtc tttgcaaagg agacaaactc   1080
caagatctgg acgcatccta taatttgttg gttgggtcaa ttcctgagag tttgggaagt   1140
tgcaagtcac ttgaaggagt gtacatggga aataatttct taaacgggtc gattcctaag   1200
ggcttgtttg ggagtgatgt ttcacttaat gacaaacttc ttagtggagg tctcgatgag   1260
aaattcggtg attgcgttaa tcttcgggac attgatctct ctaataataa gctatcaggg   1320
aagttacctg cgaccatcgg aaactgtatt catcttcggt ccttgacgct ttataataac   1380
acctgtaccg gacgtatccc tcaagagatt agcaagtgta agcagctaca gaccctcgat   1440
ctcagccaaa atcagttctc tggtgtgata cccaatgata ttacaggtaa gaaagtatat   1500
taaacttgtt acttttgaaa atattcgctc tagtttttgt ttcagttggt ccattctcac   1560
tttgtattat tgaaatatat cccaaaaaag taaatataat tatataaaag aatcttgcta   1620
aaaataatat gaattatttt tgtatgtgca aaataatgta caaatctaac taatttgttg   1680
tggataataa tattaattgt gtgaaatagt aaatgtgtgg agatatataa ctttatttat   1740
catattcact caggttttta ggtatttatt atgagttttg cattggagat atccaacttg   1800
acaatagtat ttttgtaata taccaatata taaagattac tgtacataac caaaatgtat   1860
acttttctta tttttataaa cttatatatt cctcttcttt gtatttatca caacattttt   1920
tataccttt tgcctcatat taatagcaac acttataatt tatttattta ctttttattt   1980
cttggtctat aacctcatct acccacatat gacacaccct ataaaggacc cacatgatta   2040
accaaaatat acaaatatct tcaatgaaat taactttaac actaatatga taaaaatcat   2100
gtcccgcttt ttatcctcta actaagactc tgcataaagg tatattgcaa ttaatatgag   2160
atggaagagg tataataatt atatgatcaa attcctggat tgaaaaataa atatgagatt   2220
aaaagtggta tgtttttggt taaaagaaac tatccataaa gtatgttttt ggttaaaaga   2280
aactatgcaa cataccaatc aaatgtttat acgcttacaa tttatgtacc acttttttgt   2340
cattgttttt ctattgtttg ccatacgtac gttactaaat catgttgtct tttcacattt   2400
taactaacaa taaattacta ttgatacacc aaaaaaatct atgagcattg gagtacgttg   2460
tttgatagaa gcttcgtgct attatttctt gtcaaagaat ttcatatctc aatatcttct   2520
aatttaacaa tctaacgaaa tttttttgac ccaggaaaca aatccatttg caatctggaa   2580
aagatacaaa cacttaaatt atcaaacaat gctttgactg gtgaaatccc tcattgtgtt   2640
ggaaatatcg agctcatagc attatttctc caatcaaaca aactgaacgg taccataccc   2700
gcaaacttct caaagttatg tgattcattg atatatctag atcttagtga caatcaactc   2760
gaaggagttc tacctaagtc cttgtccaaa tgtcaaagtc tagaactcct aaatgtcggg   2820
```

```
aacaataggc taagagataa atttccttca tggttagaca acctcccacg tctccaagtt   2880

ttcagtgtgc gttttaacgc cttctacggt cctataacta gctcaccaaa agttagtcac   2940

ccatttccta tgctacaaat tatcgaccta tctaacaata agttttgtgg caagttgcca   3000

agaagatata tcaaaaactt tgcaaccatg cgcaatatga atgagtctgg tgttgggaat   3060

ccacagtacc tgggggactc atcaatatat agtattacgt actctatggt attgacattc   3120

aatgggttac aacaaaaata tgaaaagctt attgtgacga tgtcgacctt tgatatatcc   3180

agcaacaact ttactggaca gattccatat gttatagggg gattacgctc acttcgtaac   3240

cttaatctct ctcataatgt cttaaccggg aacattcctc catcaattgc aaaattgtct   3300

ttgcttcaag atttggacct ttcatcaaac agacttactg gtcgtatccc tcaagaatta   3360

gttagtttaa catttcttgg gagtttcaat gtttcgaaca atctattgga ggggtctata   3420

cctcatggtt tcaacttcga cacgtacaca gctaattcat accaggggaa tctcgaatta   3480

tgtggaaaac cattacctga gtgtggagaa agaagggcaa aaggcaccac taataatcaa   3540

gatgatccta aaaatgataa tgaacgaatg ttgtcgatgt ccgaaatcgt agttatgggg   3600

tttggcagtg gtgtactagt tgggttggct tggggatact atatgttttc agtgggaaag   3660

ccccttttggt ttatcaagat ggctagcaaa atggaatcaa tattgattgg ttttttctga   3720
```

<210> SEQ ID NO 2
<211> LENGTH: 2652
<212> TYPE: DNA
<213> ORGANISM: Artificial Sequence
<220> FEATURE:
<223> OTHER INFORMATION: cDNA sequence of the Cercospora resistance-conferring gene

<400> SEQUENCE: 2

```
atgaacatga aaatcctcct tttgtttgtc ttccttcatc acctccacta cttcatccat     60

ggcagaacac ttacagaacg ccaagcttta ctaagtatca aatctgccat tacttatgat    120

tattataact ctctctcctc atggaaaaac acaacacacc actgcagttg gccatacatc    180

acttgctcct cctcttcttc ttcttcttct gttatttctc tcaacttcac catgttattt    240

ctcgaaggaa ttctctcccc tgatataggc ttcctcacca acctgcaaaa cctctctatt    300

cgatctaacc tttttctgg cccactcccc cattctctct ctctcctcac ccaactccgc     360

tatctcgacg tttcccaaaa cagtttcaca ggtccaatcc catcttctct ctctctcctc    420

acccaactcc gctatctcca cgtttccggc aacagtttca caggtccaat cccatctttt    480

ctctctctcc tcacccaact ccgctatctc gacgtttccg acaacagttt cacaggtcca    540

atcccatctt ctctctctct cctcacccaa ctccgctatc tcgacgtttc ctacaacaat    600

ctaaatggca ctcttccctt atcggtcgtt gagaagatgt cggagctcag ctaccttaac    660

cttaggtata actctttcta cggtgagatt ccaccggagt ttgggaaact taagaagctt    720

gaaacattga atcttggtaa caacactctt tctgggagtc ttccatctga gttgggttca    780

ttaaagagtt tgaaacatat ggacttttct agtaatatgc tatttggtga gatcccacaa    840

tcttattctc ttcttcgaaa cttaatcgat attgatctta atagaaacaa gttatatggg    900

agtatacctg attatattgg agattttccg gagttggaat cacttttatt agactcgaat    960

aacttcacag ggagtatccc acaaaagtta ggtacaaacg ggaagttgca atatctagat   1020

ataagtaaca acaattttag tggtagtttg ccactaagtc tttgcaaagg agacaaactc   1080

caagatctgg acgcatccta taatttgttg gttgggtcaa ttcctgagag tttgggaagt   1140
```

```
tgcaagtcac ttgaaggagt gtacatggga aataatttct taaacgggtc gattcctaag   1200
ggcttgtttg ggagtgatgt ttcacttaat gacaaacttc ttagtggagg tctcgatgag   1260
aaattcggtg attgcgttaa tcttcgggac attgatctct ctaataataa gctatcaggg   1320
aagttacctg cgaccatcgg aaactgtatt catcttcggt ccttgacgct ttataataac   1380
acctgtaccg gacgtatccc tcaagagatt agcaagtgta agcagctaca gaccctcgat   1440
ctcagccaaa atcagttctc tggtgtgata cccaatgata ttacaggaaa caaatccatt   1500
tgcaatctgg aaaagataca aacacttaaa ttatcaaaca atgctttgac tggtgaaatc   1560
cctcattgtg ttggaaatat cgagctcata gcattatttc tccaatcaaa caaactgaac   1620
ggtaccatac ccgcaaactt ctcaaagtta tgtgattcat tgatatatct agatcttagt   1680
gacaatcaac tcgaaggagt tctacctaag tccttgtcca aatgtcaaag tctagaactc   1740
ctaaatgtcg ggaacaatag gctaagagat aaatttcctt catggttaga caacctccca   1800
cgtctccaag ttttcagtgt gcgttttaac gccttctacg gtcctataac tagctcacca   1860
aaagttagtc acccatttcc tatgctacaa attatcgacc tatctaacaa taagttttgt   1920
ggcaagttgc caagaagata tatcaaaaac tttgcaacca tgcgcaatat gaatgagtct   1980
ggtgttggga atccacagta cctgggggac tcatcaatat atagtattac gtactctatg   2040
gtattgacat tcaatgggtt acaacaaaaa tatgaaaagc ttattgtgac gatgtcgacc   2100
tttgatatat ccagcaacaa ctttactgga cagattccat atgttatagg gggattacgc   2160
tcacttcgta accttaatct ctctcataat gtcttaaccg ggaacattcc tccatcaatt   2220
gcaaaattgt ctttgcttca agatttggac ctttcatcaa acagacttac tggtcgtatc   2280
cctcaagaat tagttagttt aacatttctt gggagtttca atgtttcgaa caatctattg   2340
gaggggtcta tacctcatgg tttcaacttc gacacgtaca cagctaattc ataccagggg   2400
aatctcgaat tatgtggaaa accattacct gagtgtggag aaagaagggc aaaaggcacc   2460
actaataatc aagatgatcc taaaaatgat aatgaacgaa tgttgtcgat gtccgaaatc   2520
gtagttatgg ggtttggcag tggtgtacta gttgggttgg cttggggata ctatatgttt   2580
tcagtgggaa agcccttttg gtttatcaag atggctagca aaatggaatc aatattgatt   2640
ggtttttct ga                                                       2652
```

<210> SEQ ID NO 3
<211> LENGTH: 883
<212> TYPE: PRT
<213> ORGANISM: Beta vulgaris

<400> SEQUENCE: 3

```
Met Asn Met Lys Ile Leu Leu Leu Phe Val Phe Leu His His Leu His
1               5                   10                  15

Tyr Phe Ile His Gly Arg Thr Leu Thr Glu Arg Gln Ala Leu Leu Ser
            20                  25                  30

Ile Lys Ser Ala Ile Thr Tyr Asp Tyr Tyr Asn Ser Leu Ser Ser Trp
        35                  40                  45

Lys Asn Thr Thr His His Cys Ser Trp Pro Tyr Ile Thr Cys Ser Ser
    50                  55                  60

Ser Ser Ser Ser Ser Ser Val Ile Ser Leu Asn Phe Thr Met Leu Phe
65                  70                  75                  80

Leu Glu Gly Ile Leu Ser Pro Asp Ile Gly Phe Leu Thr Asn Leu Gln
                85                  90                  95

Asn Leu Ser Ile Arg Ser Asn Leu Phe Ser Gly Pro Leu Pro His Ser
```

```
            100                 105                 110

Leu Ser Leu Leu Thr Gln Leu Arg Tyr Leu Asp Val Ser Gln Asn Ser
        115                 120                 125

Phe Thr Gly Pro Ile Pro Ser Ser Leu Ser Leu Leu Thr Gln Leu Arg
    130                 135                 140

Tyr Leu His Val Ser Gly Asn Ser Phe Thr Gly Pro Ile Pro Ser Phe
145                 150                 155                 160

Leu Ser Leu Leu Thr Gln Leu Arg Tyr Leu Asp Val Ser Asp Asn Ser
                165                 170                 175

Phe Thr Gly Pro Ile Pro Ser Ser Leu Ser Leu Leu Thr Gln Leu Arg
            180                 185                 190

Tyr Leu Asp Val Ser Tyr Asn Asn Leu Asn Gly Thr Leu Pro Leu Ser
        195                 200                 205

Val Val Glu Lys Met Ser Glu Leu Ser Tyr Leu Asn Leu Arg Tyr Asn
    210                 215                 220

Ser Phe Tyr Gly Glu Ile Pro Pro Glu Phe Gly Lys Leu Lys Lys Leu
225                 230                 235                 240

Glu Thr Leu Asn Leu Gly Asn Asn Thr Leu Ser Gly Ser Leu Pro Ser
                245                 250                 255

Glu Leu Gly Ser Leu Lys Ser Leu Lys His Met Asp Phe Ser Ser Asn
            260                 265                 270

Met Leu Phe Gly Glu Ile Pro Gln Ser Tyr Ser Leu Leu Arg Asn Leu
        275                 280                 285

Ile Asp Ile Asp Leu Asn Arg Asn Lys Leu Tyr Gly Ser Ile Pro Asp
    290                 295                 300

Tyr Ile Gly Asp Phe Pro Glu Leu Glu Ser Leu Leu Leu Asp Ser Asn
305                 310                 315                 320

Asn Phe Thr Gly Ser Ile Pro Gln Lys Leu Gly Thr Asn Gly Lys Leu
                325                 330                 335

Gln Tyr Leu Asp Ile Ser Asn Asn Asn Phe Ser Gly Ser Leu Pro Leu
            340                 345                 350

Ser Leu Cys Lys Gly Asp Lys Leu Gln Asp Leu Asp Ala Ser Tyr Asn
        355                 360                 365

Leu Leu Val Gly Ser Ile Pro Glu Ser Leu Gly Ser Cys Lys Ser Leu
    370                 375                 380

Glu Gly Val Tyr Met Gly Asn Asn Phe Leu Asn Gly Ser Ile Pro Lys
385                 390                 395                 400

Gly Leu Phe Gly Ser Asp Val Ser Leu Asn Asp Lys Leu Leu Ser Gly
                405                 410                 415

Gly Leu Asp Glu Lys Phe Gly Asp Cys Val Asn Leu Arg Asp Ile Asp
            420                 425                 430

Leu Ser Asn Asn Lys Leu Ser Gly Lys Leu Pro Ala Thr Ile Gly Asn
        435                 440                 445

Cys Ile His Leu Arg Ser Leu Thr Leu Tyr Asn Asn Thr Cys Thr Gly
    450                 455                 460

Arg Ile Pro Gln Glu Ile Ser Lys Cys Lys Gln Leu Gln Thr Leu Asp
465                 470                 475                 480

Leu Ser Gln Asn Gln Phe Ser Gly Val Ile Pro Asn Asp Ile Thr Gly
                485                 490                 495

Asn Lys Ser Ile Cys Asn Leu Glu Lys Ile Gln Thr Leu Lys Leu Ser
            500                 505                 510

Asn Asn Ala Leu Thr Gly Glu Ile Pro His Cys Val Gly Asn Ile Glu
        515                 520                 525
```

```
Leu Ile Ala Leu Phe Leu Gln Ser Asn Lys Leu Asn Gly Thr Ile Pro
    530                 535                 540

Ala Asn Phe Ser Lys Leu Cys Asp Ser Leu Ile Tyr Leu Asp Leu Ser
545                 550                 555                 560

Asp Asn Gln Leu Glu Gly Val Leu Pro Lys Ser Leu Ser Lys Cys Gln
                565                 570                 575

Ser Leu Glu Leu Leu Asn Val Gly Asn Asn Arg Leu Arg Asp Lys Phe
            580                 585                 590

Pro Ser Trp Leu Asp Asn Leu Pro Arg Leu Gln Val Phe Ser Val Arg
        595                 600                 605

Phe Asn Ala Phe Tyr Gly Pro Ile Thr Ser Ser Pro Lys Val Ser His
    610                 615                 620

Pro Phe Pro Met Leu Gln Ile Ile Asp Leu Ser Asn Asn Lys Phe Cys
625                 630                 635                 640

Gly Lys Leu Pro Arg Arg Tyr Ile Lys Asn Phe Ala Thr Met Arg Asn
                645                 650                 655

Met Asn Glu Ser Gly Val Gly Asn Pro Gln Tyr Leu Gly Asp Ser Ser
            660                 665                 670

Ile Tyr Ser Ile Thr Tyr Ser Met Val Leu Thr Phe Asn Gly Leu Gln
        675                 680                 685

Gln Lys Tyr Glu Lys Leu Ile Val Thr Met Ser Thr Phe Asp Ile Ser
    690                 695                 700

Ser Asn Asn Phe Thr Gly Gln Ile Pro Tyr Val Ile Gly Gly Leu Arg
705                 710                 715                 720

Ser Leu Arg Asn Leu Asn Leu Ser His Asn Val Leu Thr Gly Asn Ile
                725                 730                 735

Pro Pro Ser Ile Ala Lys Leu Ser Leu Leu Gln Asp Leu Asp Leu Ser
            740                 745                 750

Ser Asn Arg Leu Thr Gly Arg Ile Pro Gln Glu Leu Val Ser Leu Thr
        755                 760                 765

Phe Leu Gly Ser Phe Asn Val Ser Asn Asn Leu Leu Glu Gly Ser Ile
    770                 775                 780

Pro His Gly Phe Asn Phe Asp Thr Tyr Thr Ala Asn Ser Tyr Gln Gly
785                 790                 795                 800

Asn Leu Glu Leu Cys Gly Lys Pro Leu Pro Glu Cys Gly Glu Arg Arg
                805                 810                 815

Ala Lys Gly Thr Thr Asn Asn Gln Asp Asp Pro Lys Asn Asp Asn Glu
            820                 825                 830

Arg Met Leu Ser Met Ser Glu Ile Val Val Met Gly Phe Gly Ser Gly
        835                 840                 845

Val Leu Val Gly Leu Ala Trp Gly Tyr Tyr Met Phe Ser Val Gly Lys
    850                 855                 860

Pro Phe Trp Phe Ile Lys Met Ala Ser Lys Met Glu Ser Ile Leu Ile
865                 870                 875                 880

Gly Phe Phe


<210> SEQ ID NO 4
<211> LENGTH: 4748
<212> TYPE: DNA
<213> ORGANISM: Beta vulgaris

<400> SEQUENCE: 4

ttactatgaa caataccta atatcattag gttttcccct tctctctcct aagtgccaaa      60
```

-continued

```
ctgccaaccc cctcccatct ttatttcaat aagagcacca ttaaattatt gtgtaacaaa    120

gaccattatt ttaagatcac taataaggtt gctctaatta ttcctagaat tctagtgaaa    180

aaagaaagat aaaagatgaa catggggtga tgactgatga ctgagagaca acagacaaca    240

cttggttgag ttgatatttg acgcaaagac ttggcgtgtt ggaaggttca ttacacattt    300

tatccaagtc aactttgaag tcttcttagc tagagactaa tagagtgaac gtgttggaag    360

gttcatgttc atgacattat aaaagtaata atagtgaaat ttcacaaagt atttataaac    420

ccaggacaga ctcaagagct ctacttatta tattagtgaa aaacaaacat acacacgaca    480

ataacacaac ataaacaata atgaacatga aaatcctcct tttgtttgtc ttccttcatc    540

acctccacta cttcatcaat ggcagaacac taacagaaca tcaagcttta ctaagtatca    600

aatctgccat tactaatgat acgaatagct atctctcctt atggaaaaac acaacacacc    660

actgcagttg gccatacatc acttgctcct cctcttcttc ttctgtcatt tctctcgata    720

tctcctactt agagctcacc ggaattctct cccctgatat aggcttcctc accaacctcc    780

aaaacctcac tattcaatgg aacgattttt ctggcccccct ccccacttct ctctctctcc    840

tcacccaact ccgccatctc gacgtttcct acaacaattt cacaggtcca atcccatctt    900

ctctctctct cctcacccaa ctccgccatc tcgacgtttc cttcaacagt ttcacaggtc    960

caatcccatc ttctctctct ctcctcaccc aactccgcta tctcgacgtt tcccaaaaca   1020

gtttcacagg tccaatccca tcttctctct ctctcctcac ccaactccgc tatctcgacg   1080

tttccgacaa cagtttcaca ggtccaatcc catcttttct ctctctcctc acccaactcc   1140

gctatctaga cgtttcctac aacaatctaa atggcactct tcccttatcg gtcgttgaga   1200

tgtcggaact caggtacctt aaccttaagt ataactcttt ctacggtgag attccaccgg   1260

agtttgggaa acttaagaag cttcaaacat tggatcttgg taacaactat ctttctgggg   1320

gtcttccatt tgagttgggt tcattaaaga gtttgaaata tattgatctt agtataaaca   1380

atttatatgg gagtatacct gattatattg gagattttcc ggagttggaa tcacttttat   1440

tagactcgaa taacttcaca gggagtatcc cacaaaagtt aggtacaaac gggaagttgc   1500

aatatctaga tataagtaac aacaatttta gtgggagttt gccagcaagt ctttgcaaag   1560

gagacaaact ccaacatttg ggagtatccg ataatttgtt ggttgggcca attcctgaga   1620

gtttgggaag ttgcaagtca cttgaagaag tgaacatggg aaataatttc tttaacgggt   1680

cgattcctaa gggcttgttt ggcctcccaa acattattga tgtttcactc aatgacaatc   1740

ttcttagcgg aggtctcgat gagaaatttg gtgattgtgt taatcttttc aacattgatc   1800

tctctaataa taagctatca gggaagttac ctgcgactat tggaaactgt tctaatcttc   1860

agttgttgat gcttaatcag aataacttca ccggaagtat ccctcaagag attagcaagt   1920

gtaagcagct acgggccctc gatctcagcc aaaatcagtt ctctggtgtg atacccaatg   1980

atattacagg taagaaagta tattaaactt gttacttttg aaaatattcg ctctagtttt   2040

ctttcagttg gtccattctc acttttgcat tattgaaata tatccctaaa aaagtaaatg   2100

taattatata aaagaatctt gctcaaaata atatgaatta tttttgtatg tgcaaaataa   2160

tgtacaatct aactaatttg ttgtgaaaaa taatataatt gtgtgaaata gtaaatgtgt   2220

ggagatatat aactttattt atcatattca ctaagggttt taggtatttt actatgactt   2280

ttgcattatg gagatatcca acttgacaat agtatttttg taatatactt cctccgtttc   2340

taaataagtg caacatttac atagtgttta ctattcacag tttaaacttt aattagcttt   2400

ggtgatttac attttaggaa aaacatagtc atgtgggatc ttattagatt cgtctgaatg   2460
```

```
tgaatttttt taatatcaac tttttataat ttttacttat tgacaattga agatattaat   2520
ggttaaaata atgcattggc aaacgtgcaa acaagaaatg ttgcacttat ttagaaacgg   2580
aggaagtatc atatatgaag attattgtac ataacacttt tcttattttt ataaactata   2640
tattcttctt ctttgtattt atcacaacac tttttatatc tttgcctcat attaatggca   2700
acacttttaa tttatctatt tactttttat ttcttggtct atagcccatt tacatactta   2760
tgacacacct cataaaggac ccacacgatt aaccaaaata tacaaatatc ttcaatgaaa   2820
ttaacttcaa tactaatatg ataaaaatca tgccccgctg tttatcctca tcctaagact   2880
ctgcataaaa ttattatttc ttgtccatac ttaatcatgt tgtgttttca cattttaact   2940
aataataaat tacaattgat acaccaaaaa actctatgag cattgggtat gttgtttgat   3000
agaagcttca tgctattatt tcttgtcaaa gaatttcata tctcgatatc ttctatacca   3060
tctaacgaac aattattttc tgcaggaaac aaaaccattt gcaattttga agaaattaaa   3120
ttacttgatt tatcaaacaa tattttgacc ggtgaaatcc ctcgttgtct tggaaatact   3180
agtactcaac tcgaaacatt atttcttcaa tcaaacaaac tgaacggtac catacccgca   3240
aacttctcaa agttatgtga ttcattgatg tatctagatc ttagtgacaa tcaactcgaa   3300
ggagttctac ctaagtcatt gtccaaatgt caaaatttga aactcctaaa tgtcgggaac   3360
aacaggctaa gagataaatt tccctcatgg ctagacaacc tcccacatct ccaagttttc   3420
agtgtgcgtt tcaatgcctt ctacggtcct ataactagct catcaaaggt taatcaccca   3480
tttcctatgc tacaaattat cgacctatct aacaatgagt tttgtggcaa gttgccaaga   3540
agatatatca aaaattttgc aaccatgcgc aatatgaatg agtctggtgt tggggatcca   3600
cagtacctgg aggactcata tagtccgtac tctatggtat tgacattcaa tgggttacaa   3660
caaaaatatg aaaagcttat tgtgacgatg tcgacctttg atatatccaa caacaacttt   3720
actggacaga ttccatatgt tataggggga ttacactcac ttcgtaacct taatctctcg   3780
cataatgtct taaccgggaa cattcctcca tcaattgcaa aattgtcttt gcttcaggat   3840
ttggaccttt catcaaacag acttattggt cgtatccctc aagaattagt tagtttaaca   3900
tttcttggga gcttcaatgt ttcgaacaat ctattggagg ggcctatacc tattggtaac   3960
aacttcaata cattctcgaa taattcatac caggggaatg tcggattgtg tggaaaacca   4020
ttacctgagt gtggagaaag aagggcaaaa agcaccacta ataatcaaga tgttcctaaa   4080
aatgataatg aacgaatgtt gtcgatgtcc gaaatcgtag ttatggggtt tggcagtggt   4140
gtactagttg ggttggcttg gggatactat atgttttcag tgggaaagcc cttttggttt   4200
atcaagatgg ctagcaaaat ggaatcaata ttgattggtt ttttctgacc aacaatttgt   4260
tagccgatga agagcatcaa aaccaaaaaa acaaaaaaat tgagtaatat gcatgagtgt   4320
gaccttgttt tccaaagttt agcattacta ttagtgtctc aattcataat aataaaaaaa   4380
ttagcttgtt caagatttgt attttattca aagatttttt atgtctcttg tgcttctttt   4440
atcttatata tattttttgt atggtttgtt tttgtttaat attagtccct ccgctcaaaa   4500
tgatctttca cgcttgagat tggcattaag gtcaagagat gttgctaagc tttagaataa   4560
aaaaattcca aatgcataga gggaaagaaa gcgagacaaa atgttggaga aggcagagta   4620
aatgatgtga tggaggataa atagtagaag tgtgataccg aaagtttgaa aataataagg   4680
aattttattt cttgctggca cttcgttcta gtacaggttt ttggcccttc aaaatgctta   4740
taatgtag                                                            4748
```

<210> SEQ ID NO 5
<211> LENGTH: 2460
<212> TYPE: DNA
<213> ORGANISM: Artificial Sequence
<220> FEATURE:
<223> OTHER INFORMATION: cDNA sequence of the sensitive variant of the Cercospora resistance-mediating gene

<400> SEQUENCE: 5

```
atgaacatga aaatcctcct tttgtttgtc ttccttcatc acctccacta cttcatcaat     60
ggcagaacac taacagaaca tcaagcttta ctaagtatca aatctgccat tactaatgat    120
acgaatagct atctctcctt atggaaaaac acaacacacc actgcagttg gccatacatc    180
acttgctcct cctcttcttc ttctgtcatt tctctcgata tctcctactt agagctcacc    240
ggaattctct cccctgatat aggcttcctc accaacctcc aaaacctcac tattcaatgg    300
aacgattttt ctggccccct ccccacttct ctctctctcc tcacccaact ccgccatctc    360
gacgtttcct acaacaattt cacaggtcca atcccatctt ctctctctct cctcacccaa    420
ctccgccatc tcgacgtttc cttcaacagt ttcacaggtc caatcccatc ttctctctct    480
ctcctcaccc aactccgcta tctcgacgtt tcccaaaaca gtttcacagg tccaatccca    540
tcttctctct ctctcctcac ccaactccgc tatctcgacg tttccgacaa cagtttcaca    600
ggtccaatcc catcttttct ctctctcctc acccaactcc gctatctaga cgtttcctac    660
aacaatctaa atggcactct tcccttatcg gtcgttgaga tgtcggaact caggtacctt    720
aaccttaagt ataactcttt ctacggtgag attccaccgg agtttgggaa acttaagaag    780
cttcaaacat tggatcttgg taacaactat ctttctgggg gtcttccatt tgagttgggt    840
tcattaaaga gtttgaaata tattgatctt agtataaaca atttatatgg gagtatacct    900
gattatattg gagattttcc ggagttggaa tcacttttat tagactcgaa taacttcaca    960
gggagtatcc cacaaaagtt aggtacaaac gggaagttgc aatatctaga tataagtaac   1020
aacaatttta gtgggagttt gccagcaagt ctttgcaaag gagacaaact ccaacatttg   1080
ggagtatccg ataatttgtt ggttgggcca attcctgaga gtttgggaag ttgcaagtca   1140
cttgaagaag tgaacatggg aaataatttc tttaacgggt cgattcctaa gggcttgttt   1200
ggcctcccaa acattattga tgtttcactc aatgacaatc ttcttagcgg aggtctcgat   1260
gagaaatttg gtgattgtgt taatcttttc aacattgatc tctctaataa taagctatca   1320
gggaagttac ctgcgactat tggaaactgt tctaatcttc agttgttgat gcttaatcag   1380
aataacttca ccggaagtat ccctcaagag attagcaagt gtaagcagct acgggccctc   1440
gatctcagcc aaaatcagtt ctctggtgtg atacccaatg atattacaga tcttagtgac   1500
aatcaactcg aaggagttct acctaagtca ttgtccaaat gtcaaaattt gaaactccta   1560
aatgtcggga acaacaggct aagagataaa tttccctcat ggctagacaa cctcccacat   1620
ctccaagttt tcagtgtgcg tttcaatgcc ttctacggtc ctataactag ctcatcaaag   1680
gttaatcacc catttcctat gctacaaatt atcgacctat ctaacaatga gttttgtggc   1740
aagttgccaa gaagatatat caaaaatttt gcaaccatgc gcaatatgaa tgagtctggt   1800
gttggggatc cacagtacct ggaggactca tatagtccgt actctatggt attgacattc   1860
aatgggttac aacaaaaata tgaaaagctt attgtgacga tgtcgacctt tgatatatcc   1920
aacaacaact ttactggaca gattccatat gttatagggg gattacactc acttcgtaac   1980
cttaatctct cgcataatgt cttaaccggg aacattcctc catcaattgc aaaattgtct   2040
```

```
ttgcttcagg atttggacct ttcatcaaac agacttattg gtcgtatccc tcaagaatta   2100

gttagtttaa catttcttgg gagcttcaat gtttcgaaca atctattgga ggggcctata   2160

cctattggta acaacttcaa tacattctcg aataattcat accaggggaa tgtcggattg   2220

tgtggaaaac cattacctga gtgtggagaa agaagggcaa aaagcaccac taataatcaa   2280

gatgttccta aaaatgataa tgaacgaatg ttgtcgatgt ccgaaatcgt agttatgggg   2340

tttggcagtg gtgtactagt tgggttggct tggggatact atatgttttc agtgggaaag   2400

cccttttggt ttatcaagat ggctagcaaa atggaatcaa tattgattgg ttttttctga   2460


<210> SEQ ID NO 6
<211> LENGTH: 819
<212> TYPE: PRT
<213> ORGANISM: Beta vulgaris

<400> SEQUENCE: 6

Met Asn Met Lys Ile Leu Leu Leu Phe Val Phe Leu His His Leu His
1               5                   10                  15

Tyr Phe Ile Asn Gly Arg Thr Leu Thr Glu His Gln Ala Leu Leu Ser
            20                  25                  30

Ile Lys Ser Ala Ile Thr Asn Asp Thr Asn Ser Tyr Leu Ser Leu Trp
        35                  40                  45

Lys Asn Thr Thr His His Cys Ser Trp Pro Tyr Ile Thr Cys Ser Ser
    50                  55                  60

Ser Ser Ser Ser Val Ile Ser Leu Asp Ile Ser Tyr Leu Glu Leu Thr
65                  70                  75                  80

Gly Ile Leu Ser Pro Asp Ile Gly Phe Leu Thr Asn Leu Gln Asn Leu
                85                  90                  95

Thr Ile Gln Trp Asn Asp Phe Ser Gly Pro Leu Pro Thr Ser Leu Ser
            100                 105                 110

Leu Leu Thr Gln Leu Arg His Leu Asp Val Ser Tyr Asn Asn Phe Thr
        115                 120                 125

Gly Pro Ile Pro Ser Ser Leu Ser Leu Leu Thr Gln Leu Arg His Leu
    130                 135                 140

Asp Val Ser Phe Asn Ser Phe Thr Gly Pro Ile Pro Ser Ser Leu Ser
145                 150                 155                 160

Leu Leu Thr Gln Leu Arg Tyr Leu Asp Val Ser Gln Asn Ser Phe Thr
                165                 170                 175

Gly Pro Ile Pro Ser Ser Leu Ser Leu Leu Thr Gln Leu Arg Tyr Leu
            180                 185                 190

Asp Val Ser Asp Asn Ser Phe Thr Gly Pro Ile Pro Ser Phe Leu Ser
        195                 200                 205

Leu Leu Thr Gln Leu Arg Tyr Leu Asp Val Ser Tyr Asn Asn Leu Asn
    210                 215                 220

Gly Thr Leu Pro Leu Ser Val Val Glu Met Ser Glu Leu Arg Tyr Leu
225                 230                 235                 240

Asn Leu Lys Tyr Asn Ser Phe Tyr Gly Glu Ile Pro Pro Glu Phe Gly
                245                 250                 255

Lys Leu Lys Lys Leu Gln Thr Leu Asp Leu Gly Asn Asn Tyr Leu Ser
            260                 265                 270

Gly Gly Leu Pro Phe Glu Leu Gly Ser Leu Lys Ser Leu Lys Tyr Ile
        275                 280                 285

Asp Leu Ser Ile Asn Asn Leu Tyr Gly Ser Ile Pro Asp Tyr Ile Gly
    290                 295                 300
```

```
Asp Phe Pro Glu Leu Glu Ser Leu Leu Leu Asp Ser Asn Asn Phe Thr
305                 310                 315                 320

Gly Ser Ile Pro Gln Lys Leu Gly Thr Asn Gly Lys Leu Gln Tyr Leu
                325                 330                 335

Asp Ile Ser Asn Asn Asn Phe Ser Gly Ser Leu Pro Ala Ser Leu Cys
            340                 345                 350

Lys Gly Asp Lys Leu Gln His Leu Gly Val Ser Asp Asn Leu Leu Val
        355                 360                 365

Gly Pro Ile Pro Glu Ser Leu Gly Ser Cys Lys Ser Leu Glu Glu Val
    370                 375                 380

Asn Met Gly Asn Asn Phe Phe Asn Gly Ser Ile Pro Lys Gly Leu Phe
385                 390                 395                 400

Gly Leu Pro Asn Ile Ile Asp Val Ser Leu Asn Asp Asn Leu Leu Ser
                405                 410                 415

Gly Gly Leu Asp Glu Lys Phe Gly Asp Cys Val Asn Leu Phe Asn Ile
            420                 425                 430

Asp Leu Ser Asn Asn Lys Leu Ser Gly Lys Leu Pro Ala Thr Ile Gly
        435                 440                 445

Asn Cys Ser Asn Leu Gln Leu Leu Met Leu Asn Gln Asn Asn Phe Thr
    450                 455                 460

Gly Ser Ile Pro Gln Glu Ile Ser Lys Cys Lys Gln Leu Arg Ala Leu
465                 470                 475                 480

Asp Leu Ser Gln Asn Gln Phe Ser Gly Val Ile Pro Asn Asp Ile Thr
                485                 490                 495

Asp Leu Ser Asp Asn Gln Leu Glu Gly Val Leu Pro Lys Ser Leu Ser
            500                 505                 510

Lys Cys Gln Asn Leu Lys Leu Leu Asn Val Gly Asn Asn Arg Leu Arg
        515                 520                 525

Asp Lys Phe Pro Ser Trp Leu Asp Asn Leu Pro His Leu Gln Val Phe
    530                 535                 540

Ser Val Arg Phe Asn Ala Phe Tyr Gly Pro Ile Thr Ser Ser Ser Lys
545                 550                 555                 560

Val Asn His Pro Phe Pro Met Leu Gln Ile Ile Asp Leu Ser Asn Asn
                565                 570                 575

Glu Phe Cys Gly Lys Leu Pro Arg Arg Tyr Ile Lys Asn Phe Ala Thr
            580                 585                 590

Met Arg Asn Met Asn Glu Ser Gly Val Gly Asp Pro Gln Tyr Leu Glu
        595                 600                 605

Asp Ser Tyr Ser Pro Tyr Ser Met Val Leu Thr Phe Asn Gly Leu Gln
    610                 615                 620

Gln Lys Tyr Glu Lys Leu Ile Val Thr Met Ser Thr Phe Asp Ile Ser
625                 630                 635                 640

Asn Asn Asn Phe Thr Gly Gln Ile Pro Tyr Val Ile Gly Gly Leu His
                645                 650                 655

Ser Leu Arg Asn Leu Asn Leu Ser His Asn Val Leu Thr Gly Asn Ile
            660                 665                 670

Pro Pro Ser Ile Ala Lys Leu Ser Leu Leu Gln Asp Leu Asp Leu Ser
        675                 680                 685

Ser Asn Arg Leu Ile Gly Arg Ile Pro Gln Glu Leu Val Ser Leu Thr
    690                 695                 700

Phe Leu Gly Ser Phe Asn Val Ser Asn Asn Leu Leu Glu Gly Pro Ile
705                 710                 715                 720

Pro Ile Gly Asn Asn Phe Asn Thr Phe Ser Asn Asn Ser Tyr Gln Gly
```

```
                725                 730                 735

Asn Val Gly Leu Cys Gly Lys Pro Leu Pro Glu Cys Gly Glu Arg Arg
            740                 745                 750

Ala Lys Ser Thr Thr Asn Asn Gln Asp Val Pro Lys Asn Asp Asn Glu
        755                 760                 765

Arg Met Leu Ser Met Ser Glu Ile Val Val Met Gly Phe Gly Ser Gly
    770                 775                 780

Val Leu Val Gly Leu Ala Trp Gly Tyr Tyr Met Phe Ser Val Gly Lys
785                 790                 795                 800

Pro Phe Trp Phe Ile Lys Met Ala Ser Lys Met Glu Ser Ile Leu Ile
                805                 810                 815

Gly Phe Phe
```

<210> SEQ ID NO 7
<211> LENGTH: 1998
<212> TYPE: DNA
<213> ORGANISM: Beta vulgaris
<220> FEATURE:
<221> NAME/KEY: promoter
<222> LOCATION: (1)..(1998)
<223> OTHER INFORMATION: native promoter of the Cercospora resistance-
      conferring gene Beta vulgaris subsp. maritima

<400> SEQUENCE: 7

```
gagcatagtg agtgcaaaag ccatggaagc tagattaaaa aggccatcat tctaagttag     60

acaattggaa acaacatcga gatacacgta cacataaggg ctgctcttct ctattactcc    120

ctctgttcct aatcatttgc ttttttagcg ggttccaaag gcctatgttt gaccactaat    180

atatttaaat taaaactggt gatatatatt aaaagaaaat tatgatgaat ttaacaaaaa    240

ccatatatgt tatgtccttt tttttcctat attaatgaat ttttacagtc aaagttggtg    300

aactttgacc caaaaaaaga aatggagcaa aaaaaaaaaa aaaaaaaaaa aactagggac    360

aatgagtaac atttttatct atgtcttttt aatatgaata tacgtaacaa attctgcaaa    420

aatagagata gcaactaata acacgcatga aaatgacaag ttatattata cctttttttc    480

tcaatatatg aatatacgta acaaattaac tccagtagtt tttagtaaaa ctattagatt    540

attgtgtaac atatactctg gaaatagtac taagatccat tacaatcttt attgagaaat    600

ttcctcatgt accccctgag gtttggcgta atttccaaat acccctcata tttgaggaat    660

ttctcaaata ccctgatgtt tttgtttaga ctcaaaatac ctttactatg gacagtaccc    720

taatgtcatt aagttttccc cttctctctc cccaattttc tctctcctcc cattccccca    780

cccactaccc actgcccact gccaagtagg ggtgtaagtg gattggactg gattggactt    840

tgccaaattc aaatccagtc caaagttttt tggactcgag aaattgagtc caagtccgat    900

ccaaatattt tttgagtcca gtccaatcta gtccgataat tttttcttga gtccgaatcc    960

agtccagtcc agtccgatta ttatatcttt tttcccgatt taggttcaat gattcacaac   1020

attttttgag atgcttgagc atttgacatc tgattcaatt atcaatatcc acaaataaga   1080

ttgaaagctt aaattaaagt aaaatactat gaataaaaag ttgaattaga tgcttacctt   1140

gatctaagtt gagaggaagc atagagactg agaattaatc tgagggacaa atagagaatg   1200

cgagagtcga gacagtgagg tagaaagaaa atgaagagta agaggaagtg agtattaagg   1260

actgaggagt aaagtaagat agaattagtt ggctactagc ctactaatgc agtattgcta   1320

gtataattta cttatttaac aaatggagct aagtgcaata gtttagcgcc aattgacata   1380

tttagagaga gaaggctgaa aaatccaata tttttaaaat agtatcatta tttttaatat   1440
```

```
atacattata tataaaaata tttttggact ggactggaca tattggactc caaagggatg   1500

agtccaaatc cagacaaaaa atatttggac ttgaaaattt aagtccgagt ccagtccgaa   1560

aaattttcag tccaatccag tccgacaaat ttggactgga ctggattgga ctctgaactt   1620

ttcgtagtcc gcttacaccc ctactgccaa gtgccaaact gccaaccccc ttttggttga   1680

gttgatattt gacgcaaaga cttggcgtgt tggaaggttc attacacatt ttatccaagt   1740

caactttgaa gtcttcttag ctagagacta gagtgaacgt gttggaaggt tcattacaca   1800

ttttatccaa tcaaactttg aagtcttctt agctagagac tagagtgaac gtgttggaag   1860

gttcatgttc atgacattat aaaagtaata atagtgaaat ttcacaaagt atttataaac   1920

ccaggacaga ctcaagagct ctacttatta ttagtgaaaa acaaacatac acacgacaat   1980

aacacaacat aaacaata                                                 1998
```

```
<210> SEQ ID NO 8
<211> LENGTH: 2000
<212> TYPE: DNA
<213> ORGANISM: Beta vulgaris
<220> FEATURE:
<221> NAME/KEY: terminator
<222> LOCATION: (1)..(2000)
<223> OTHER INFORMATION: native terminator of the Cercospora resistance-
      conferring gene from Beta vulgaris subsp. maritima

<400> SEQUENCE: 8

ccaacaattt gttagccgat gaagagcatc aaaaccaaaa aaaacaaaaa aaattgatta     60

atatgcatga gtgtgacctt gttttccaaa gtttagcatt actattagtg tctcaattca    120

taataataaa aaaattagct tgttcaagat ttgtattttt attcaaagat ttttttgtc    180

tcttgtgctt cttttatctt atatatattt tttgtatggt ttgtttttgt ttaatattag    240

tccctccgct caaaatgatc tttcacgctt gagattggca ttaaggtcaa gagatgttgc    300

taagctttag aataaaaaaa ttccaaatgc atagagggaa agaaagcgag acaaaatgtt    360

ggagaaggca gagtaaatga tgtgatggag gataaatagt agaagtgtga taccgaaagt    420

ttgaaaataa taaggaattt tatttcttgc tggcactttg ttctagtaca ggtttttagc    480

ccttcaaaat gtttataatg tagagtcaaa attaatatcc ttaactagtt tttaagtccg    540

ggttatatcc tagatattaa taatattcat ttattagtaa cattttattt tataaatata    600

atactaagca ttatttggtt tgctggttaa gactttagtg tatatctatt tcttttttt    660

tttattgtat gcgtgtttac ataaactaaa gactataagg gatagtacca cgtggcgcag    720

ttccttgctt aggaacgtct tttaatatat taactagtat ttgggcccgg gcgttgctcc    780

gggttggtat tgtgtttccg aacatgatgt gcagtttttc ccattcccac taaaatatat    840

aaaggaaaac tcaacattta aaagatacaa atataataat atggacactt aaaacatgat    900

taaaagttga ttgagatggt aattgtgtca tgttataata gtaagaggtt gcctaattga    960

ggttgaggtg gtggagtagt ggtatcgctt cccatctgtt atccctgagg tataaggatc   1020

aaacctcata ggactcattt gagtaatttc ccatatcctc ctctcaaatg agtccttttc   1080

atctgacaaa aaaaaagagt ctaattttaa attaaaatta gacgatcttt tataaaatcg   1140

gcactttctg cacataggtc acaatttttt tgtttctatc tctctgcttt ctttaatttc   1200

acagtctcca actctccatc aacatcttac ttattttaga atagatgatg tatggtagta   1260

ttaaatggta aagtactaaa gctcctataa tacacagaag cttacatagt atagattcgt   1320

acatgagaca aggttacaat atactttctc cgttcttttt atattacaat aattactatt   1380
```

```
ttaagtagtt tcacatctat tgtaacaatt ccaattttgt tatagaaagc aactttaata   1440

attgacaata ttgcccttac tttatcttat taaaaccatc attaattact cactttctct   1500

tataaaattg cttttatttt ctaaggatga tttctctcct attctagtta attaaagagt   1560

tacttttgtg ctaaactgct catttattcc aaatccttaa aaattgtgtc caaacgtatt   1620

gttgtaatat aaaaagaaca gaggtactat tagtttgaat aaattttgat cagattaggt   1680

cacctttagg gggcgtttgg ttaggggtat tctggaaagg gtaagggaat caacttactt   1740

aattccctta cttgttgttt gtttgctcaa tttaatgatt ccctttaccc accccttact   1800

cccaaagtcc tttactctca ttctccccac cccccaaggt ttcacttacc ctttcttgat   1860

tcatcattga ccatatcttt gaccacccaa ctaccaccac cacttgacca cctaatcacc   1920

taaccaccta attacccaac cactattacc acccaacccc tccacctgcc caccaatcgg   1980

caccataact gcccaaccgt                                                2000
```

<210> SEQ ID NO 9
<211> LENGTH: 911
<212> TYPE: PRT
<213> ORGANISM: Beta vulgaris
<220> FEATURE:
<221> NAME/KEY: PEPTIDE
<222> LOCATION: (1)..(911)
<223> OTHER INFORMATION: Konsensus Sequenz aus Abbildung 1
<220> FEATURE:
<221> NAME/KEY: VARIANT
<222> LOCATION: (20)..(20)
<223> OTHER INFORMATION: N or H
<220> FEATURE:
<221> NAME/KEY: VARIANT
<222> LOCATION: (27)..(27)
<223> OTHER INFORMATION: H or R
<220> FEATURE:
<221> NAME/KEY: VARIANT
<222> LOCATION: (39)..(39)
<223> OTHER INFORMATION: N or Y
<220> FEATURE:
<221> NAME/KEY: VARIANT
<222> LOCATION: (41)..(41)
<223> OTHER INFORMATION: T or Y
<220> FEATURE:
<221> NAME/KEY: VARIANT
<222> LOCATION: (42)..(42)
<223> OTHER INFORMATION: N or Y
<220> FEATURE:
<221> NAME/KEY: VARIANT
<222> LOCATION: (42)..(42)
<223> OTHER INFORMATION: S or N
<220> FEATURE:
<221> NAME/KEY: VARIANT
<222> LOCATION: (43)..(43)
<223> OTHER INFORMATION: Y or S
<220> FEATURE:
<221> NAME/KEY: VARIANT
<222> LOCATION: (47)..(47)
<223> OTHER INFORMATION: L or S
<220> FEATURE:
<221> NAME/KEY: VARIANT
<222> LOCATION: (75)..(75)
<223> OTHER INFORMATION: D or N
<220> FEATURE:
<221> NAME/KEY: VARIANT
<222> LOCATION: (76)..(76)
<223> OTHER INFORMATION: I or F
<220> FEATURE:
<221> NAME/KEY: VARIANT
<222> LOCATION: (77)..(77)
<223> OTHER INFORMATION: S or T
<220> FEATURE:
<221> NAME/KEY: VARIANT
<222> LOCATION: (78)..(78)

<223> OTHER INFORMATION: Y or M
<220> FEATURE:
<221> NAME/KEY: VARIANT
<222> LOCATION: (80)..(80)
<223> OTHER INFORMATION: E or F
<220> FEATURE:
<221> NAME/KEY: VARIANT
<222> LOCATION: (82)..(82)
<223> OTHER INFORMATION: T or E
<220> FEATURE:
<221> NAME/KEY: VARIANT
<222> LOCATION: (99)..(99)
<223> OTHER INFORMATION: T or S
<220> FEATURE:
<221> NAME/KEY: VARIANT
<222> LOCATION: (101)..(101)
<223> OTHER INFORMATION: Q or R
<220> FEATURE:
<221> NAME/KEY: VARIANT
<222> LOCATION: (102)..(102)
<223> OTHER INFORMATION: W or S
<220> FEATURE:
<221> NAME/KEY: VARIANT
<222> LOCATION: (104)..(104)
<223> OTHER INFORMATION: D or L
<220> FEATURE:
<221> NAME/KEY: VARIANT
<222> LOCATION: (111)..(111)
<223> OTHER INFORMATION: T or H
<220> FEATURE:
<221> NAME/KEY: VARIANT
<222> LOCATION: (121)..(121)
<223> OTHER INFORMATION: H or Y
<220> FEATURE:
<221> NAME/KEY: VARIANT
<222> LOCATION: (126)..(126)
<223> OTHER INFORMATION: Y or Q
<220> FEATURE:
<221> NAME/KEY: VARIANT
<222> LOCATION: (171)..(171)
<223> OTHER INFORMATION: D or H
<220> FEATURE:
<221> NAME/KEY: VARIANT
<222> LOCATION: (174)..(174)
<223> OTHER INFORMATION: Q or G
<220> FEATURE:
<221> NAME/KEY: VARIANT
<222> LOCATION: (184)..(184)
<223> OTHER INFORMATION: S or F
<220> FEATURE:
<221> NAME/KEY: VARIANT
<222> LOCATION: (208)..(208)
<223> OTHER INFORMATION: F or S
<220> FEATURE:
<221> NAME/KEY: VARIANT
<222> LOCATION: (246)..(246)
<223> OTHER INFORMATION: K or R
<220> FEATURE:
<221> NAME/KEY: VARIANT
<222> LOCATION: (265)..(265)
<223> OTHER INFORMATION: Q or E
<220> FEATURE:
<221> NAME/KEY: VARIANT
<222> LOCATION: (268)..(268)
<223> OTHER INFORMATION: D or N
<220> FEATURE:
<221> NAME/KEY: VARIANT
<222> LOCATION: (277)..(277)
<223> OTHER INFORMATION: G or S
<220> FEATURE:
<221> NAME/KEY: VARIANT
<222> LOCATION: (280)..(280)
<223> OTHER INFORMATION: F or S
<220> FEATURE:
<221> NAME/KEY: VARIANT
<222> LOCATION: (290)..(290)
<223> OTHER INFORMATION: Y or H
<220> FEATURE:
<221> NAME/KEY: VARIANT

<222> LOCATION: (318)..(318)
<223> OTHER INFORMATION: S or N
<220> FEATURE:
<221> NAME/KEY: VARIANT
<222> LOCATION: (319)..(319)
<223> OTHER INFORMATION: I or R
<220> FEATURE:
<221> NAME/KEY: VARIANT
<222> LOCATION: (321)..(321)
<223> OTHER INFORMATION: N or K
<220> FEATURE:
<221> NAME/KEY: VARIANT
<222> LOCATION: (376)..(376)
<223> OTHER INFORMATION: A or L
<220> FEATURE:
<221> NAME/KEY: VARIANT
<222> LOCATION: (386)..(386)
<223> OTHER INFORMATION: H or D
<220> FEATURE:
<221> NAME/KEY: VARIANT
<222> LOCATION: (388)..(388)
<223> OTHER INFORMATION: G or D
<220> FEATURE:
<221> NAME/KEY: VARIANT
<222> LOCATION: (389)..(389)
<223> OTHER INFORMATION: V or A
<220> FEATURE:
<221> NAME/KEY: VARIANT
<222> LOCATION: (391)..(391)
<223> OTHER INFORMATION: D or Y
<220> FEATURE:
<221> NAME/KEY: VARIANT
<222> LOCATION: (397)..(397)
<223> OTHER INFORMATION: P or S
<220> FEATURE:
<221> NAME/KEY: VARIANT
<222> LOCATION: (410)..(410)
<223> OTHER INFORMATION: E or G
<220> FEATURE:
<221> NAME/KEY: VARIANT
<222> LOCATION: (412)..(412)
<223> OTHER INFORMATION: N or Y
<220> FEATURE:
<221> NAME/KEY: VARIANT
<222> LOCATION: (418)..(418)
<223> OTHER INFORMATION: F or L
<220> FEATURE:
<221> NAME/KEY: VARIANT
<222> LOCATION: (429)..(429)
<223> OTHER INFORMATION: L or S
<220> FEATURE:
<221> NAME/KEY: VARIANT
<222> LOCATION: (440)..(440)
<223> OTHER INFORMATION: N or K
<220> FEATURE:
<221> NAME/KEY: VARIANT
<222> LOCATION: (457)..(457)
<223> OTHER INFORMATION: F or R
<220> FEATURE:
<221> NAME/KEY: VARIANT
<222> LOCATION: (458)..(458)
<223> OTHER INFORMATION: N or D
<220> FEATURE:
<221> NAME/KEY: VARIANT
<222> LOCATION: (478)..(478)
<223> OTHER INFORMATION: S or I
<220> FEATURE:
<221> NAME/KEY: VARIANT
<222> LOCATION: (479)..(479)
<223> OTHER INFORMATION: N or H
<220> FEATURE:
<221> NAME/KEY: VARIANT
<222> LOCATION: (481)..(481)
<223> OTHER INFORMATION: Q or R
<220> FEATURE:
<221> NAME/KEY: VARIANT
<222> LOCATION: (482)..(482)
<223> OTHER INFORMATION: L or S
<220> FEATURE:

<221> NAME/KEY: VARIANT
<222> LOCATION: (484)..(484)
<223> OTHER INFORMATION: M or T
<220> FEATURE:
<221> NAME/KEY: VARIANT
<222> LOCATION: (486)..(486)
<223> OTHER INFORMATION: N or Y
<220> FEATURE:
<221> NAME/KEY: VARIANT
<222> LOCATION: (487)..(487)
<223> OTHER INFORMATION: Q or N
<220> FEATURE:
<221> NAME/KEY: VARIANT
<222> LOCATION: (489)..(489)
<223> OTHER INFORMATION: N or T
<220> FEATURE:
<221> NAME/KEY: VARIANT
<222> LOCATION: (490)..(490)
<223> OTHER INFORMATION: F or C
<220> FEATURE:
<221> NAME/KEY: VARIANT
<222> LOCATION: (493)..(493)
<223> OTHER INFORMATION: S or R
<220> FEATURE:
<221> NAME/KEY: VARIANT
<222> LOCATION: (505)..(505)
<223> OTHER INFORMATION: R or Q
<220> FEATURE:
<221> NAME/KEY: VARIANT
<222> LOCATION: (506)..(506)
<223> OTHER INFORMATION: A or T
<220> FEATURE:
<221> NAME/KEY: VARIANT
<222> LOCATION: (605)..(605)
<223> OTHER INFORMATION: R or Q
<220> FEATURE:
<221> NAME/KEY: VARIANT
<222> LOCATION: (607)..(607)
<223> OTHER INFORMATION: K or E
<220> FEATURE:
<221> NAME/KEY: VARIANT
<222> LOCATION: (629)..(629)
<223> OTHER INFORMATION: H or R
<220> FEATURE:
<221> NAME/KEY: VARIANT
<222> LOCATION: (648)..(648)
<223> OTHER INFORMATION: S or P
<220> FEATURE:
<221> NAME/KEY: VARIANT
<222> LOCATION: (651)..(651)
<223> OTHER INFORMATION: N or S
<220> FEATURE:
<221> NAME/KEY: VARIANT
<222> LOCATION: (666)..(666)
<223> OTHER INFORMATION: E or K
<220> FEATURE:
<221> NAME/KEY: VARIANT
<222> LOCATION: (692)..(692)
<223> OTHER INFORMATION: D or N
<220> FEATURE:
<221> NAME/KEY: VARIANT
<222> LOCATION: (697)..(697)
<223> OTHER INFORMATION: E or G
<220> FEATURE:
<221> NAME/KEY: VARIANT
<222> LOCATION: (705)..(705)
<223> OTHER INFORMATION: P or T
<220> FEATURE:
<221> NAME/KEY: VARIANT
<222> LOCATION: (733)..(733)
<223> OTHER INFORMATION: H or R
<220> FEATURE:
<221> NAME/KEY: VARIANT
<222> LOCATION: (733)..(733)
<223> OTHER INFORMATION: N or S
<220> FEATURE:
<221> NAME/KEY: VARIANT
<222> LOCATION: (748)..(748)
<223> OTHER INFORMATION: H or R

```
<220> FEATURE:
<221> NAME/KEY: VARIANT
<222> LOCATION: (785)..(785)
<223> OTHER INFORMATION: I or T
<220> FEATURE:
<221> NAME/KEY: VARIANT
<222> LOCATION: (811)..(811)
<223> OTHER INFORMATION: P or S
<220> FEATURE:
<221> NAME/KEY: VARIANT
<222> LOCATION: (814)..(814)
<223> OTHER INFORMATION: I or H
<220> FEATURE:
<221> NAME/KEY: VARIANT
<222> LOCATION: (816)..(816)
<223> OTHER INFORMATION: N or F
<220> FEATURE:
<221> NAME/KEY: VARIANT
<222> LOCATION: (819)..(819)
<223> OTHER INFORMATION: N or D
<220> FEATURE:
<221> NAME/KEY: VARIANT
<222> LOCATION: (821)..(821)
<223> OTHER INFORMATION: F or Y
<220> FEATURE:
<221> NAME/KEY: VARIANT
<222> LOCATION: (822)..(822)
<223> OTHER INFORMATION: S or T
<220> FEATURE:
<221> NAME/KEY: VARIANT
<222> LOCATION: (823)..(823)
<223> OTHER INFORMATION: N or A
<220> FEATURE:
<221> NAME/KEY: VARIANT
<222> LOCATION: (823)..(823)
<223> OTHER INFORMATION: N or A
<220> FEATURE:
<221> NAME/KEY: VARIANT
<222> LOCATION: (830)..(830)
<223> OTHER INFORMATION: V or L
<220> FEATURE:
<221> NAME/KEY: VARIANT
<222> LOCATION: (831)..(831)
<223> OTHER INFORMATION: G or E
<220> FEATURE:
<221> NAME/KEY: VARIANT
<222> LOCATION: (847)..(847)
<223> OTHER INFORMATION: S or G
<220> FEATURE:
<221> NAME/KEY: VARIANT
<222> LOCATION: (854)..(854)
<223> OTHER INFORMATION: V or D

<400> SEQUENCE: 9

Met Asn Met Lys Ile Leu Leu Leu Phe Val Phe Leu His His Leu His
1               5                   10                  15

Tyr Phe Ile Xaa Gly Arg Thr Leu Thr Glu Xaa Gln Ala Leu Leu Ser
            20                  25                  30

Ile Lys Ser Ala Ile Thr Xaa Asp Xaa Xaa Xaa Xaa Leu Ser Xaa Trp
        35                  40                  45

Lys Asn Thr Thr His His Cys Ser Trp Pro Tyr Ile Thr Cys Ser Ser
    50                  55                  60

Ser Ser Ser Ser Ser Ser Val Ile Ser Leu Xaa Xaa Xaa Xaa Leu Xaa
65                  70                  75                  80

Leu Xaa Gly Ile Leu Ser Pro Asp Ile Gly Phe Leu Thr Asn Leu Gln
                85                  90                  95

Asn Leu Xaa Ile Xaa Xaa Asn Xaa Phe Ser Gly Pro Leu Pro Xaa Ser
            100                 105                 110

Leu Ser Leu Leu Thr Gln Leu Arg Xaa Leu Asp Val Ser Xaa Asn Asn
        115                 120                 125
```

-continued

```
Phe Thr Gly Pro Ile Pro Ser Ser Leu Ser Leu Leu Thr Gln Leu Arg
    130                 135                 140

His Leu Asp Val Ser Phe Asn Ser Phe Thr Gly Pro Ile Pro Ser Ser
145                 150                 155                 160

Leu Ser Leu Leu Thr Gln Leu Arg Tyr Leu Xaa Val Ser Xaa Asn Ser
                165                 170                 175

Phe Thr Gly Pro Ile Pro Ser Xaa Leu Ser Leu Leu Thr Gln Leu Arg
            180                 185                 190

Tyr Leu Asp Val Ser Asp Asn Ser Phe Thr Gly Pro Ile Pro Ser Xaa
        195                 200                 205

Leu Ser Leu Leu Thr Gln Leu Arg Tyr Leu Asp Val Ser Tyr Asn Asn
    210                 215                 220

Leu Asn Gly Thr Leu Pro Leu Ser Val Val Glu Lys Met Ser Glu Leu
225                 230                 235                 240

Xaa Tyr Leu Asn Leu Xaa Tyr Asn Ser Phe Tyr Gly Glu Ile Pro Pro
                245                 250                 255

Glu Phe Gly Lys Leu Lys Lys Leu Xaa Thr Leu Xaa Leu Gly Asn Asn
            260                 265                 270

Xaa Leu Ser Gly Xaa Leu Pro Xaa Glu Leu Gly Ser Leu Lys Ser Leu
        275                 280                 285

Lys Xaa Met Asp Phe Ser Ser Asn Met Leu Phe Gly Glu Ile Pro Gln
    290                 295                 300

Ser Tyr Ser Leu Leu Arg Asn Leu Ile Asp Ile Asp Leu Xaa Xaa Asn
305                 310                 315                 320

Xaa Leu Tyr Gly Ser Ile Pro Asp Tyr Ile Gly Asp Phe Pro Glu Leu
                325                 330                 335

Glu Ser Leu Leu Leu Asp Ser Asn Asn Phe Thr Gly Ser Ile Pro Gln
            340                 345                 350

Lys Leu Gly Thr Asn Gly Lys Leu Gln Tyr Leu Asp Ile Ser Asn Asn
        355                 360                 365

Asn Phe Ser Gly Ser Leu Pro Xaa Ser Leu Cys Lys Gly Asp Lys Leu
    370                 375                 380

Gln Xaa Leu Xaa Xaa Ser Xaa Asn Leu Leu Val Gly Xaa Ile Pro Glu
385                 390                 395                 400

Ser Leu Gly Ser Cys Lys Ser Leu Glu Xaa Val Xaa Met Gly Asn Asn
                405                 410                 415

Phe Xaa Asn Gly Ser Ile Pro Lys Gly Leu Phe Gly Xaa Pro Asn Ile
            420                 425                 430

Ile Asp Val Ser Leu Asn Asp Xaa Leu Leu Ser Gly Gly Leu Asp Glu
        435                 440                 445

Lys Phe Gly Asp Cys Val Asn Leu Xaa Xaa Ile Asp Leu Ser Asn Asn
    450                 455                 460

Lys Leu Ser Gly Lys Leu Pro Ala Thr Ile Gly Asn Cys Xaa Xaa Leu
465                 470                 475                 480

Xaa Xaa Leu Xaa Leu Xaa Xaa Asn Xaa Xaa Thr Gly Xaa Ile Pro Gln
                485                 490                 495

Glu Ile Ser Lys Cys Lys Gln Leu Xaa Xaa Leu Asp Leu Ser Gln Asn
            500                 505                 510

Gln Phe Ser Gly Val Ile Pro Asn Asp Ile Thr Gly Asn Lys Ser Ile
        515                 520                 525

Cys Asn Leu Glu Lys Ile Gln Thr Leu Lys Leu Ser Asn Asn Ala Leu
    530                 535                 540

Thr Gly Glu Ile Pro His Cys Val Gly Asn Ile Glu Leu Ile Ala Leu
```

```
545                 550                 555                 560

Phe Leu Gln Ser Asn Lys Leu Asn Gly Thr Ile Pro Ala Asn Phe Ser
                565                 570                 575

Lys Leu Cys Asp Ser Leu Ile Tyr Leu Asp Leu Ser Asp Asn Gln Leu
            580                 585                 590

Glu Gly Val Leu Pro Lys Ser Leu Ser Lys Cys Gln Xaa Leu Xaa Leu
        595                 600                 605

Leu Asn Val Gly Asn Asn Arg Leu Arg Asp Lys Phe Pro Ser Trp Leu
    610                 615                 620

Asp Asn Leu Pro Xaa Leu Gln Val Phe Ser Val Arg Phe Asn Ala Phe
625                 630                 635                 640

Tyr Gly Pro Ile Thr Ser Ser Xaa Lys Val Xaa His Pro Phe Pro Met
                645                 650                 655

Leu Gln Ile Ile Asp Leu Ser Asn Asn Xaa Phe Cys Gly Lys Leu Pro
            660                 665                 670

Arg Arg Tyr Ile Lys Asn Phe Ala Thr Met Arg Asn Met Asn Glu Ser
        675                 680                 685

Gly Val Gly Xaa Pro Gln Tyr Leu Xaa Asp Ser Ser Ile Tyr Ser Ile
    690                 695                 700

Xaa Tyr Ser Met Val Leu Thr Phe Asn Gly Leu Gln Gln Lys Tyr Glu
705                 710                 715                 720

Lys Leu Ile Val Thr Met Ser Thr Phe Asp Ile Ser Xaa Asn Asn Phe
                725                 730                 735

Thr Gly Gln Ile Pro Tyr Val Ile Gly Gly Leu Xaa Ser Leu Arg Asn
            740                 745                 750

Leu Asn Leu Ser His Asn Val Leu Thr Gly Asn Ile Pro Pro Ser Ile
        755                 760                 765

Ala Lys Leu Ser Leu Leu Gln Asp Leu Asp Leu Ser Ser Asn Arg Leu
    770                 775                 780

Xaa Gly Arg Ile Pro Gln Glu Leu Val Ser Leu Thr Phe Leu Gly Ser
785                 790                 795                 800

Phe Asn Val Ser Asn Asn Leu Leu Glu Gly Xaa Ile Pro Xaa Gly Xaa
                805                 810                 815

Asn Phe Xaa Thr Xaa Xaa Xaa Asn Ser Tyr Gln Gly Asn Xaa Xaa Leu
            820                 825                 830

Cys Gly Lys Pro Leu Pro Glu Cys Gly Glu Arg Arg Ala Lys Xaa Thr
        835                 840                 845

Thr Asn Asn Gln Asp Xaa Pro Lys Asn Asp Asn Glu Arg Met Leu Ser
    850                 855                 860

Met Ser Glu Ile Val Val Met Gly Phe Gly Ser Gly Val Leu Val Gly
865                 870                 875                 880

Leu Ala Trp Gly Tyr Tyr Met Phe Ser Val Gly Lys Pro Phe Trp Phe
                885                 890                 895

Ile Lys Met Ala Ser Lys Met Glu Ser Ile Leu Ile Gly Phe Phe
            900                 905                 910


<210> SEQ ID NO 10
<211> LENGTH: 201
<212> TYPE: DNA
<213> ORGANISM: Beta vulgaris

<400> SEQUENCE: 10

agagcagatt ggcatacttr tgaatattct cactggctat taaattctca gaagaaaaat      60

caacaccaag attatgacat gcttgtgcaa agacacaccc rgtcatgaat gcatcatagc     120
```

cagcttcatg cttagcccca gagttccaat ttgaggayct gcaagaaaac atgggagtaa 180
gatggtttca cataaaacat g 201

<210> SEQ ID NO 11
<211> LENGTH: 201
<212> TYPE: DNA
<213> ORGANISM: Beta vulgaris

<400> SEQUENCE: 11
gggtttcttc gaagtttgat tttgttacat ttttcaaaga gaaattagtt gttgatgttg 60
aataatgatg ataagtagtt agggttcgta gtaaggtgga sgaragagaa aatggcgtca 120
ctctgayrag cttcttcatt ttgttcttct tccttagctc tgttttcagt cactgcgcca 180 ttttttttt aaaaggaaga t 201

<210> SEQ ID NO 12
<211> LENGTH: 134
<212> TYPE: DNA
<213> ORGANISM: Beta vulgaris

<400> SEQUENCE: 12
caagcacaaa atcaaataat gagaatcaca ctatccaaag aaaatttcca tccacattta 60
tccaacacar ttatctctct tttacaccca aattatgtca accaaaaaca staaaacaag 120
tgagtgcagt agct 134

<210> SEQ ID NO 13
<211> LENGTH: 134
<212> TYPE: DNA
<213> ORGANISM: Beta vulgaris

<400> SEQUENCE: 13
taagtaaaaa gtggtaaaag aattaccaaa arcgcacara ataaattaat tagytggatw 60
taactawtta acctattcct tttttctgtc gctataacta cttttgctta acttattgat 120
ggtttgatcg ttga 134

<210> SEQ ID NO 14
<211> LENGTH: 150
<212> TYPE: DNA
<213> ORGANISM: Beta vulgaris

<400> SEQUENCE: 14
ttataatgta gagtcaaaat taatatcctt aactagtttt taagtccggg ttatatccta 60
gatattwata atattcattt attagtaaca ttttatttta taaatataat actaagcatt 120
atttggtttg ctggttaaga ctttagtgta 150

<210> SEQ ID NO 15
<211> LENGTH: 201
<212> TYPE: DNA
<213> ORGANISM: Beta vulgaris

<400> SEQUENCE: 15
acatctacac tgggagactg ataaggacgt ttgcagatgt caagtatggg aatcatcatc 60
taacatgggt ggagattgtg tacaatgtta tttcattcat mgtggcaata attaccattg 120
ttgcgtttac tgtatatgcc aagagagcct tcgaagaact taagagggca gaagctaagg 180
aggatcgaga agaagaaacc t 201

<210> SEQ ID NO 16
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 5'crRNA # 1

<400> SEQUENCE: 16
tttatttcga tttcgattct tggattat 28

<210> SEQ ID NO 17
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 5'crRNA # 2

<400> SEQUENCE: 17
tttcaaccca gtatccttat ccgtcact 28

<210> SEQ ID NO 18
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 5'crRNA # 3

<400> SEQUENCE: 18
tttatttaaa catgatacgt atcatatt 28

<210> SEQ ID NO 19
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 5'crRNA # 4

<400> SEQUENCE: 19
tttaaacatg atacgtatca tattgagt 28

<210> SEQ ID NO 20
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 3'crRNA # 1

<400> SEQUENCE: 20
tttgtgggtg ggtggttttc acgtgtgt 28

<210> SEQ ID NO 21
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 3'crRNA # 2

<400> SEQUENCE: 21
tttcccctcc ctttgccgct gcgaagtt 28

<210> SEQ ID NO 22
<211> LENGTH: 28
<212> TYPE: DNA
<213> ORGANISM: Artificial Sequence
<220> FEATURE:
<223> OTHER INFORMATION: genomic target sequence with 5'-flanking PAM (4 bp) 3'crRNA # 3

<400> SEQUENCE: 22
tttcttcttc ttgcttccac cataacac 28

<210> SEQ ID NO 23
<211> LENGTH: 28
<212> TYPE: DNA
<213> ORGANISM: Artificial Sequence
<220> FEATURE:
<223> OTHER INFORMATION: Mutagenesis primer 1

<400> SEQUENCE: 23
tcagtgcagc cgtcgtctga aaacgaca 28

<210> SEQ ID NO 24
<211> LENGTH: 28
<212> TYPE: DNA
<213> ORGANISM: Artificial Sequence
<220> FEATURE:
<223> OTHER INFORMATION: Mutagenesis primer 2

<400> SEQUENCE: 24
tgtcgttttc agacgacggc tgcactga 28

<210> SEQ ID NO 25
<211> LENGTH: 20
<212> TYPE: DNA
<213> ORGANISM: Artificial Sequence
<220> FEATURE:
<223> OTHER INFORMATION: pSeq_CRBM4_F1

<400> SEQUENCE: 25
agcgcaacgc aattaatgtg 20

<210> SEQ ID NO 26
<211> LENGTH: 20
<212> TYPE: DNA
<213> ORGANISM: Artificial Sequence
<220> FEATURE:
<223> OTHER INFORMATION: pSeq_CRBM4_R1

<400> SEQUENCE: 26
gatgaagctg aggtagtacc 20

<210> SEQ ID NO 27
<211> LENGTH: 21
<212> TYPE: DNA
<213> ORGANISM: Artificial Sequence
<220> FEATURE:
<223> OTHER INFORMATION: pSeq_CRBM4_F2

<400> SEQUENCE: 27
aggaaggtta gcaagctcga g 21

<210> SEQ ID NO 28
<211> LENGTH: 20
<212> TYPE: DNA
<213> ORGANISM: Artificial Sequence
<220> FEATURE:
<223> OTHER INFORMATION: pSeq_CRBM4_R2

<400> SEQUENCE: 28
tctcgtcgac cttctggatg 20

<210> SEQ ID NO 29
<211> LENGTH: 21
<212> TYPE: DNA
<213> ORGANISM: Artificial Sequence
<220> FEATURE:
<223> OTHER INFORMATION: pSeq_CRBM4_F3

<400> SEQUENCE: 29
atgctgagta cgatgacatc c 21

<210> SEQ ID NO 30
<211> LENGTH: 22
<212> TYPE: DNA
<213> ORGANISM: Artificial Sequence
<220> FEATURE:
<223> OTHER INFORMATION: pSeq_CRBM4_R3

<400> SEQUENCE: 30
tagacctgct tctcaacctt ca 22

<210> SEQ ID NO 31
<211> LENGTH: 20
<212> TYPE: DNA
<213> ORGANISM: Artificial Sequence
<220> FEATURE:
<223> OTHER INFORMATION: pSeq_CRBM4_F4

<400> SEQUENCE: 31
accactcact cctcgataag 20

<210> SEQ ID NO 32
<211> LENGTH: 21
<212> TYPE: DNA
<213> ORGANISM: Artificial Sequence
<220> FEATURE:
<223> OTHER INFORMATION: pSeq_CRBM4_R4

<400> SEQUENCE: 32
aacgacaatc tgatcgggta c 21

<210> SEQ ID NO 33
<211> LENGTH: 28
<212> TYPE: DNA
<213> ORGANISM: Artificial Sequence
<220> FEATURE:
<223> OTHER INFORMATION: Oligonucleotide fw for the generation of short 24-bp protospacers (5'crRNA # 1)

<400> SEQUENCE: 33
agattttcga tttcgattct tggattat 28

<210> SEQ ID NO 34
<211> LENGTH: 28
<212> TYPE: DNA
<213> ORGANISM: Artificial Sequence
<220> FEATURE:
<223> OTHER INFORMATION: Oligonucleotide rev for the generation of short 24-bp protospacers (5'crRNA # 1)

<400> SEQUENCE: 34
ggccataatc caagaatcga aatcgaaa 28

<210> SEQ ID NO 35
<211> LENGTH: 28
<212> TYPE: DNA
<213> ORGANISM: Artificial Sequence
<220> FEATURE:
<223> OTHER INFORMATION: Oligonucleotide fw for the generation of short 24-bp protospacers (5'crRNA # 2)

<400> SEQUENCE: 35
agataaccca gtatccttat ccgtcact 28

<210> SEQ ID NO 36
<211> LENGTH: 28
<212> TYPE: DNA
<213> ORGANISM: Artificial Sequence
<220> FEATURE:
<223> OTHER INFORMATION: Oligonucleotide rev for the generation of short 24-bp protospacers (5'crRNA # 2)

<400> SEQUENCE: 36
ggccagtgac ggataaggat actgggtt 28

<210> SEQ ID NO 37
<211> LENGTH: 28
<212> TYPE: DNA
<213> ORGANISM: Artificial Sequence
<220> FEATURE:
<223> OTHER INFORMATION: Oligonucleotide fw for the generation of short 24-bp protospacers (5'crRNA # 3)

<400> SEQUENCE: 37
agattttaaa catgatacgt atcatatt 28

<210> SEQ ID NO 38
<211> LENGTH: 28
<212> TYPE: DNA
<213> ORGANISM: Artificial Sequence
<220> FEATURE:
<223> OTHER INFORMATION: Oligonucleotide rev for the generation of short 24-bp protospacers (5'crRNA # 3)

<400> SEQUENCE: 38
ggccaatatg atacgtatca tgtttaaa 28

<210> SEQ ID NO 39
<211> LENGTH: 28
<212> TYPE: DNA
<213> ORGANISM: Artificial Sequence
<220> FEATURE:
<223> OTHER INFORMATION: Oligonucleotide fw for the generation of short 24-bp protospacers (5'crRNA # 4)

<400> SEQUENCE: 39
agataacatg atacgtatca tattgagt 28

<210> SEQ ID NO 40
<211> LENGTH: 28
<212> TYPE: DNA
<213> ORGANISM: Artificial Sequence
<220> FEATURE:
<223> OTHER INFORMATION: Oligonucleotide rev for the generation of short 24-bp protospacers (5'crRNA # 4)

<400> SEQUENCE: 40
ggccactcaa tatgatacgt atcatgtt 28

```
<210> SEQ ID NO 41
<211> LENGTH: 28
<212> TYPE: DNA
<213> ORGANISM: Artificial Sequence
<220> FEATURE:
<223> OTHER INFORMATION: Oligonucleotide fw for the generation of short
      24-bp protospacers (3'crRNA # 1)

<400> SEQUENCE: 41

agattgggtg ggtggttttc acgtgtgt                                        28


<210> SEQ ID NO 42
<211> LENGTH: 28
<212> TYPE: DNA
<213> ORGANISM: Artificial Sequence
<220> FEATURE:
<223> OTHER INFORMATION: Oligonucleotide rev for the generation of short
      24-bp protospacers (3'crRNA # 1)

<400> SEQUENCE: 42

ggccacacac gtgaaaacca cccaccca                                        28


<210> SEQ ID NO 43
<211> LENGTH: 28
<212> TYPE: DNA
<213> ORGANISM: Artificial Sequence
<220> FEATURE:
<223> OTHER INFORMATION: Oligonucleotide fw for the generation of short
      24-bp protospacers (3'crRNA # 2)

<400> SEQUENCE: 43

agatccctcc ctttgccgct gcgaagtt                                        28


<210> SEQ ID NO 44
<211> LENGTH: 28
<212> TYPE: DNA
<213> ORGANISM: Artificial Sequence
<220> FEATURE:
<223> OTHER INFORMATION: Oligonukleotid rev fuer die Generierung kurzer
      24-bp Protospacer (3'crRNA#2)

<400> SEQUENCE: 44

ggccaacttc gcagcggcaa agggaggg                                        28


<210> SEQ ID NO 45
<211> LENGTH: 28
<212> TYPE: DNA
<213> ORGANISM: Artificial Sequence
<220> FEATURE:
<223> OTHER INFORMATION: Oligonucleotide fw for the generation of short
      24-bp protospacers (3'crRNA # 3)

<400> SEQUENCE: 45

agatttcttc ttgcttccac cataacac                                        28


<210> SEQ ID NO 46
<211> LENGTH: 28
<212> TYPE: DNA
<213> ORGANISM: Artificial Sequence
<220> FEATURE:
<223> OTHER INFORMATION: Oligonucleotide rev for the generation of short
      24-bp protospacers (3'crRNA # 3)

<400> SEQUENCE: 46

ggccgtgtta tggtggaagc aagaagaa                                        28


<210> SEQ ID NO 47
```

<211> LENGTH: 24
<212> TYPE: DNA
<213> ORGANISM: Artificial Sequence
<220> FEATURE:
<223> OTHER INFORMATION: Primer pCRBM4_F1

<400> SEQUENCE: 47
cacattttat ccaatcaaac tttg 24

<210> SEQ ID NO 48
<211> LENGTH: 23
<212> TYPE: DNA
<213> ORGANISM: Artificial Sequence
<220> FEATURE:
<223> OTHER INFORMATION: Primer pCRBM4_R1

<400> SEQUENCE: 48
ccttcgagaa ataacatggt gaa 23

<210> SEQ ID NO 49
<211> LENGTH: 25
<212> TYPE: DNA
<213> ORGANISM: Artificial Sequence
<220> FEATURE:
<223> OTHER INFORMATION: Primer pCRBM4_F2

<400> SEQUENCE: 49
gtacagtgac ggataaggat actgg 25

<210> SEQ ID NO 50
<211> LENGTH: 25
<212> TYPE: DNA
<213> ORGANISM: Artificial Sequence
<220> FEATURE:
<223> OTHER INFORMATION: Primer pCRBM4_R2

<400> SEQUENCE: 50
ttagtggtca aacataggcc tttgg 25

<210> SEQ ID NO 51
<211> LENGTH: 23
<212> TYPE: DNA
<213> ORGANISM: Artificial Sequence
<220> FEATURE:
<223> OTHER INFORMATION: Primer pCRBM4_F3

<400> SEQUENCE: 51
agtaagaggt tgcctaattg agg 23

<210> SEQ ID NO 52
<211> LENGTH: 23
<212> TYPE: DNA
<213> ORGANISM: Artificial Sequence
<220> FEATURE:
<223> OTHER INFORMATION: Primer pCRBM4_R3

<400> SEQUENCE: 52
ttgccgctgc gaagttccct ctc 23

<210> SEQ ID NO 53
<211> LENGTH: 42480
<212> TYPE: DNA
<213> ORGANISM: Beta vulgaris

<400> SEQUENCE: 53
aaatgataca ggggtatatt tgactctatg aatttcagaa atctaatcaa atttgctaag 60

```
cttccaatga ttctactaag ccctacaaat tacaagaatt agttactttc atctctctgt    120

cggcttcaga accagaagtg tacaatatct tgtcaaacaa actctgctta gaggagctct    180

ttcgatcatc tttttcgat ttggaagttc ccggtgatag gattgacatt gctgttttct    240

cggtcaattc ttctggatct tggttctgtc catctatctc tggctccatt aatctggtct    300

tccaattaat tccgatagcc tcagcttgct ctgcaaacaa gacctttgag atcggggagc    360

tgcagatatc cttataaact tcataaccag cagcacaggt tttcccacct tccaacaact    420

ttgataaagg atgtaggaga gagatagaat catcactcgt ttctaaccta tccttcaagg    480

caaggaagtt aacagccaag tctgccttac taaactgaac aaatactgca gtttcatcca    540

agttatagat gcaagcaact gagtatatac caaacacttt acagatgcat tgttttatgt    600

cacttgcctt gagttttggg gagaatcccc aaatcaaaac tatgttagga tgcaaaatgt    660

taagaaacct ccttttagct gaactgataa cgggaatttc attcatatca ccagtgctta    720

gattgatcac atctccactg ttccaactaa gatagagcag attggcatac ttgtgaatat    780

tctcactggc tattaaattc tcagaagaaa aatcaacacc aagattatga catgcttgtg    840

caaagacaca cccggtcatg aatgcatcat agccagcttc atgcttagcc ccagagttcc    900

aatttgagga cctgcaagaa aacatgggag taagatggtt tcacataaaa catgtgtaga    960

agtgcagtga acactggcga aaacaatcta attttacgaa ttcattcact cactcagctt   1020

caaattaagt ttccccttta tttagggtgc cccaaaaaga tacactcttc tgtttacctt   1080

ctctctccaa gcgaccaatc ttttctctct tctccaacat cgttttcttt ttctctctct   1140

acccactatc cattttgtcc tcctacattt gataactatt cttaatctcc aagaaaatcc   1200

aatgtgtgaa ataattacgg gacagggagt atacagaagc agcccccttg ccaatatagt   1260

ttacaaatta ccctcagaat taggcttacc tttcccaaag gagcaataaa ttcaaacaaa   1320

tctaaaaggt acaaggcatt aagtgccgaa cctcatgtca tcaacctgga cctccacctt   1380

cacacatgga tgtacaccac cattagagga ttgtccagag gctatctcag ggcacaacag   1440

agaaaatgct gaggccaatg acgtgctggc tttattcaag aatttttgaa ggctcgtgtc   1500

tgcattcaaa agtattttcg tgtcgacaac atgaggaaaa tacttgtgga tctcgagaac   1560

aaactcttca acagttgatg gaagaggacc aaagaattta tggtaaatat gtgccatatc   1620

tgcaaaaaat tataatggat aagatgacaa gaaaagatac taggaaggcc ttcaagtaca   1680

aatattatat catgatgctg gacgaccgat gctcccacaa ttatgtttgt taccaaatgc   1740

ttcgaaggat aattactaaa ttatgtgaat ggtggttacc aagtgtcccg gaccatgcaa   1800

taacttctcc tttcagtgac caacaagaag aagacgtacc taaaaagcaa ttgtgaccta   1860

caattagctt cttttcagca gcgagaaggt caaggacatg ccggaaacct gcagctgctt   1920

ttattttgcg agttgcttgc tggtgagacc catacttcac ctcctcctac aagaacaaac   1980

agaacaatca cacatgcaga aagttcccca cataccaagt tgctgtctgc taaacactga   2040

aactaactta tctctacaaa caatgaagga agttcctcac cagaaggttg atcttatcat   2100

tgtcagattc tacaaaaaca ataagcttct gcaagatggc actgccgtca tgagcacaca   2160

caaaaacaag atccttgaag tgcttccttg taacctgtaa ttgcagatca ttagtatata   2220

ttcaagatgt tataaattta ttgaaaagca gcgtctaaaa caataaaagt catgcttaag   2280

gcatagagcg atagagcata gacacttcag agtttaataa gagcaaatac tccaggagaa   2340

cataaatata tttcatatca caaatcctag taccaactgg caacggctaa ctgccaattt   2400
```

```
atgtactgct caaaaaggcc aagcatctaa aagatggctt aaaagtcgga ttttataaga   2460
aagtcgtcac atgattgcta ttacattgac atatcaaagg tcaaatgctg aaatttggtt   2520
cagcttgata tatattaagc atacaaacga tacgttgaca agaaagccta acaagacatg   2580
aagcatcagg cacataacat tcaaaagatt accaattcaa tcaacttcag ctgatgagaa   2640
gtaaatccat tcaatcgaag agcaggacgc atactaaaaa atatggtttc aaattgttgt   2700
ttagattcaa cagcacttgg aagctcggca tttctgttct gtagcaacat atcatgccaa   2760
tcactgagcc gaattttcat ccgttcggag aataaaatat cagctacatt gcccaaaggt   2820
aaatctctaa cttcattaga atatgcccat ttcccgttat atactgaatt caagcgactc   2880
aaagcctcgt cttcctgtcg tctagataaa taagacacgc ctgagattat acaatgtgta   2940
aatttaccac aataatgaca tcatactgac aaaatctcaa acaaatagtt ctaataaagt   3000
catgttatct gaaatttcta tgaataggaa attgaacaaa accttcatgc tttttttccaa   3060
ctaaaattga catcttctac attaccttca tgtatgcatg cattgaagtc aaactggtat   3120
tttgccaaga agtcaatcga agttgtttgg cacaggaatt catatgatgg gccatcagtg   3180
ggaagctctt gacgtggaaa tatataaaaa ttatgcctga caatgaacca ttgtaaaatt   3240
attagatgga gtatctctat ttattgttta cagccaattg agcttttaac aattactata   3300
ggtagtgttt ggaaacttgt atttcatttc aaataatgga attgaaatct ggaatttaaa   3360
gtttgtattt caattcctaa tcactgtttt gtaaaggggg tttgatagaa gagagagaaa   3420
tagaggttta atggaggaga gagaaaaagt gtgggtttac taaaaaaaag agaaataaat   3480
attagaaagt gtgggtttac tcatagagtt gggatatgta tgaggagaga attttcaaat   3540
gccaaggtaa tagcttgaat gacaaattta ataatttcaa attccatgtc atccaaacaa   3600
tagatttcat ccaaatccaa gatttgaaat gaaatcttgc tatccaaaca tatcataaat   3660
taattagtaa tttagacttg ctttctgctg cacttactta tggaaataat tttacttcag   3720
tccttaaata acccgcaatt tacatcaaag gcactaatat aaacacctag ttacgaaatg   3780
gaaatatcag atatacctgt aaaagtaaag aaacaaaaat acaaccctga gcatgaaggt   3840
atccttcaaa agtgcaatat ctgcatactt agaaccggaa ttagaagtgc gaatgcagac   3900
aataaccatc ccaggatcag aaacgtccaa gaaagttgag attcatcatc cattctcttt   3960
agcaaattta tgaactctaa tatataaatc atacccccccc ccccatccaa aagcaattgt   4020
caagctgcct gaacccctca taatttagga tacaacaaag taatcctaaa agacccttta   4080
caatactagt actcgggtat ttccacaatc ttctcatcat tgaatccaaa gcattgcatt   4140
tgaagaaatc aaatcataat ccattactat attagagcaa aatctatgtc attatagtat   4200
tggagagcaa gtatgactat taccccttta cactaggcaa aacacattgt cacaatgcta   4260
acttagtcat taaccaatat caatatggga ctgtggatat tcataaaatc gaagtttttc   4320
gcttgctcat aaactatctt tcattccagc acagtacaag agagaaaaga cagcattttc   4380
atacacttct ttctttagtt caaattcaca cagcagcaaa aaattcactt cttcatagct   4440
ttagctcagc aaacaaagca caaagcatgc aattactctc acacatagca caccaaaaaa   4500
acaaaaacca ctaaaaattc acacaaaaaa aaccaacaaa aattccatcg caatttcaac   4560
aatcaaaaca atcttctaag ttaaaaagag agataaagat gagaagaaaa actaacggat   4620
gagcaacgaa ggaattcttc gaagaatccc atcgaaatgg acaaacacca aattgaacaa   4680
cggcgaattt ctcagcagaa tctttcattt taaggtatcg aacatcgtgc cgatcaaact   4740
cgaacgattc gcgccaaggt gagcttgtaa ttccagtcat ttcgagatca atggcgacaa   4800
```

```
aatcggcaga ttttacatgc gtagtgaggt caattagggt ttcttcgaag tttgattttg   4860
ttacattttt caaagagaaa ttagttgttg atgttgaata atgatgataa gtagttaggg   4920
ttcgtagtaa ggtggaggaa agagaaaatg gcgtcactct gacaagcttc ttcattttgt   4980
tcttcttcct tagctctgtt ttcagtcact gcgccatttt tttaaaaaaa aggaagatga   5040
acaaagcaaa tattgaaccc aaattttgta attttggccc actttatatg taccccctccg   5100
tttcaaaata tggagcacgc cgcacacacg acatttaggg tcgaattttg aacattcttc   5160
aagatgatct aatggtataa tctctataat ttatatgtgg catattataa taagagtttt   5220
atgaagtcaa aaagtggatg tcatatattt aatgcatggt aagtttttcc taaatctgta   5280
tactagggta acatacatat gttgacttga agtatatata attcttgtag tataaatatg   5340
gctttggcca taagtagtaa tacacaacaa ctagaaaaat tgaaatcagt ccactgttat   5400
cttgtactct ataattttct gtttcctttt gtttcgcaac aaagacatat ttgtggtgaa   5460
agataatttt cgtaaattga atgacttata ttttgaaata aagagagtat taggtaaggt   5520
tacgtgcttt tcgcttgaat ttgttagacc tcaaatgtat atgtgattag aacggattgg   5580
ctctagtttt tattttatag aagtatatat gcatttttct tagagcacac tcgaaattac   5640
tttcggatag atatattcgg gaaaaaaaga ggttgaaggg aagttcatca ataattatgg   5700
taaaggaaaa aggacatcgt tacaattcta aattctagat aggatgtgat gataatccaa   5760
aagtcatctg aaaaactaaa caagtccaag atgctaatga ttcgagtaga gattgaatga   5820
gtgaccctaa ggattgtcaa ccctcttatt ctaacgtgtg taaaagaatt gacaactcta   5880
agagttactc aaacattttt cgattcgagt ggttaatata ccaatttgaa actattgaca   5940
ggagttattt taatgagtat aatggtcaat ggagcactga attccatctc acatagtcac   6000
atatttcatc tcaagttctg atgatttcaa acattgaaaa aagatgatac aagcaattaa   6060
ttcctaggga aacatattgt ggttttcatg gatacaagag tgagaataaa tcaaaactta   6120
ggctctaaca tttcttttct ctactagtaa ttgctaatta tatcaattca attgtcagtg   6180
taatcagtta atcaccaaat ctcttgtata gtcagtaaac tatacactgt ttagtcctct   6240
ggattttgcc cggtcgaatt atgcagcata accaaacttt gaagtttagt acttcctttg   6300
cacccaagtt agcttcacgg cccctgcctt ctggtggatg gtcaccctat gctttgagca   6360
ttctctgcaa tgcgcacgat attcaatgag aacgtcgcct tgaaaatcta aattgcaact   6420
aaaaattaga ttgaaatgaa acccacaaga gttgtttttc tgagtagttg gtgtagaatt   6480
cacaagtctt gctccattgt ttgaagatat gaagacaata atgtgctatg taaagtgcag   6540
ccgctagcta acagtggaag tggaaacttg atcattttac actcgcacaa gcgaaagctc   6600
ggctgacgtt gcaaactgaa gaaaaacctc tcaaaccaat tcgacttttg ctcaaagttg   6660
caaactaaag aaaaaggctg aatgcaaagc aagttcacca atgaacaata gatcggtgtt   6720
ggcctgaggc cacatcaagt gaagttgcct aattgcggcc ctctcatctg ttcacaggaa   6780
tcattttcca tatagaatca ctccaaaata aaagagcaaa gctgcaccag atgcagaagc   6840
ataactttca agacaactga tgacagataa atagcaaaag aatgcttaag aaatgatcaa   6900
aattgaatgg ctctggaatt acctcatcag ctgattttcc tttctctcta tctctctatc   6960
tctttactcg tctatggagc taccacatca catggcgttt catatgcttt ctgccgtcga   7020
actagacgtg cagcaaaagc tccatccatt gaatgcttca ctgggcatga gcgataaaac   7080
ccatcttcag ttaaaaagtc agatggaaca tatctgctta cagaatctct ttggaagtcc   7140
```

```
tatcacccaa caaagaatat attaaaatag agaaggagaa aagaacgtat ctatctgtca   7200
gcatccatat gaggtggaaa ctaggagtac tatataaagc cagtgcagta gctcctaccg   7260
gatgtctaag aaggaaggca gaaaccctat cttcgttttc ttcaagatca atggagcagg   7320
tactgtacac aagcacgcca tctggtttga ccagcctgta gatgttaaac aatcccacag   7380
acaaaaggga ataatatgag tgaaacaagt caacaggggg aaataaccaa taattctagg   7440
actgtcaaac tcaagctctt caaaaacaaa gatagctctt aatctcactt gcaagcagca   7500
tcgaacagct cgtcctgcaa cttctttagc tcttccatat cctctgactt tctattccaa   7560
cgcaaatccg gcctcttcag caaaaatata aagttggaac aaggctctta gatacaagaa   7620
ctgaaaaacc ttcgacatat aatggactct atcaagggca caatgacaaa ttctaaacat   7680
gagcatgtat atcaataaaa tactaagaac cctttcaatg gtactgctag aaggtttatt   7740
gctacacttt ttagtacacc atctataggt tttatagtac catcaaaatg gttcatggtg   7800
ccataagaaa attttatgta tttatggtac tatctaccat atctaatttt ctctgtaaaa   7860
atgtatttgt agatagagac cacgagttcc tcttttagat actgactttt ttttttctac   7920
atgatggcca acagacttct caaacaaaaa gaaaaagaaa atatttagat aatatgagca   7980
acaaaatagc aaccacctac ttttgatagt acacccaggc ccgaacaagg aacatctaaa   8040
agaactttat caaacttcga agtgttgctg tcctgaaaag aatagaaagt aactgcttca   8100
acaaagaaga agaggcagaa agcaaagcta gtacgcattt tgcaatgact tactgaaaag   8160
gagcgaagat cagcatggat gcaagtgatc acattatcaa cacgctgcag cttggctgtt   8220
tcttcaagta tccgtaaccg acctttattt atgtccattg ctgatatcat acctgaaaag   8280
ctacacattt agaatgcaga accagcatca ttggtagtta agttatcact ataccttggc   8340
cattcaagcg agatgccatg aagagtgtct tccctccagg agcagcacag caatcaatga   8400
tgtgatcacc aggctgtgga tccagaacag aaacagctag acctgcagcg aagtatagat   8460
gtaaacttgg gttgggctgt cacatttttt cacatcttat cttcctttct attctttcaa   8520
aactgaggag aaatggttgg gatttctata aacgtgagaa aaatggcatc agattagatg   8580
gttttactgc atgaaaaaaa ttgaatgtgt ttcggcatca cattactaca aggtcaaaag   8640
cactatcttt gaaaatgtag gacataatgg gacagagatg tgctgacctg cactctcatc   8700
ctggactgag cataaacctt cttttagaag tccagtttgt atcacaatct aggatatgag   8760
aaaacaactc aagatgtaat tgctcctaag atatcaatca tttcataata aacataaaag   8820
ttattattac aagacagcac ctgcatccca cttctgatgc agacaaagtc atccaaatgc   8880
aaggaaggct catgcgggac ctgcggacaa agtgttgtga tgcgcataga tatcgaaaga   8940
aggccctgta tagcactaat gagataagat tcagtaacct tcagcatgtt gagcttcaca   9000
acaaggtcat ctcgagttaa tccttttgca atattggccc tagtaccaag aaaaccatat   9060
gtattaacaa gagaaaagtg gcatagggat ctttatgact taggtaagca gttggcaatt   9120
agagagaata aaacccccaa acctcaagct gaaactcgga acactattgt tccacatcat   9180
caatttgata gctccttctt gcccaagata cttggtccac cgtcttacca tccactgaaa   9240
ggaaggtatt aaaagggaga aaagactcgt cagcatagaa aattgtacat cttaaatttt   9300
agaagtatag caccatcttc aggcatcagt caacgtaaat aaataccaca tctacaaata   9360
gaaccatact ttctggacag tcgggatcat gagcacagac aatactgcat gattattgcc   9420
tcgtattctc atgtatacaa gtatatgtaa cattaaatag cagtatttct tgagaaactc   9480
accacgggat gggaataagt tgtagcaagg gcacgtgctt gtgaacgatc atcaccctcc   9540
```

```
aatttgggta caggaaggga gtcattatcc tataaagaga aacagctttt gttttcaacc   9600
atatcaagac aaacagttta ttaaactata aacaacaaca atacacatgc acacacctac   9660
tgggaacaag atatatacta ctgataagta ttttctgatt gaagaaaaaa aatctcattt   9720
atttgcaaat atagatttaa tgacaagaaa gctttgaacc ttaaggaaaa ctagctttcg   9780
gaggatccca ttcaccatgt ttcctgcgcc tggtctaaga gcatacttgg caagattcac   9840
attctgcaat ataatccaac agtaagaaca cgacatggat ttagactcaa gtctctgaac   9900
ctatagaaca agtaaaatta gatcttatct catttgacaa tttaaaatta gatagtgcaa   9960
tattctgcag ttataagact tcatgtgtgc atactgcaca agtcatctta aaggtgttat  10020
taaagcttta attgccattt gacatcccct tgctcaactt tagcatgttt ttaggctaca  10080
acaatacgca ctgtctacat ggacatacaa attacaagcg tatggaaaag caataagcgc  10140
aaggaagtct tcagccagaa actctctatg agtccaacaa tatgcaacta aatatccaag  10200
taccgtgaat gagtaagaac taacctcgtc aacaacagca tatggtggca tttccagttt  10260
cacaatctca tagcatccaa tcctgaggat ctaaaattaa agataaatca atacacaaca  10320
tatgatatgg gtcggagcgt atataacaag tatagcaact acatttgaac agataacagc  10380
ctttgagaca ataaggaact ccgacattcc agtatatgcc agatttcata tctttagctc  10440
taaattgcca cgcaaaatgt tattgggcaa tatacctgta gcaggagagg ttccatgttc  10500
ctaaaggagc tttcatcatg gcatgaagaa acaataagat aatccagata ttttctccaa  10560
cgaattgaac caccaacaat gtcagtgacc tacaaagaca agttgtcaac ttaaaacttt  10620
tgaagcgtca tttcacttct gtagaccaat acaaaagcta ctactgcttt acatcataaa  10680
acctttagtc cttaggttca tctgattggc aaaaaaggtc cagatgcaag aaaagcaagt  10740
agctgtaatg ctgtattata tcagcattat tcagaacaga ataataaata tctacagatt  10800
ttgggtggaa gcttgatgat agagtatctc cacaaagaga actcgcttga gtcccaactc  10860
ccaaatctac ttttttggag tcacattatc agtcattttt tctggactct tataggaata  10920
gtgtgctatg taatgattta tggagcaggg gcatttcatg aatagcttta taagttagta  10980
tgggtgtctt ggggaataag ttaaagggtt agttagaggg aagaagtaca acatatatat  11040
agagcttttg taagaagggt ggttatgttg aaaatagatg agaaattggg tgagctcata  11100
gtagttcaat ttggactttg ggagagaatt aagcctcttg aaagcttgaa tatcatttac  11160
atttgttgtt tttactctta ttaatcaacc aaagttcatt ttcttccttt aatttctcca  11220
ttttagcact atgatttgtc caagctaagt gatttcttag catagtgcac agtgtagtat  11280
atcggagaac tcatttgagt cctgaaaggt cccacaagtt acatttttcc tactactact  11340
tgcaccaaaa caataagcat cattaagaca ttgtcactgg tccttcttag gttcttttgg  11400
aggggattcc tcagatgggg gaggcaccca tgaaggaaca tgttaccaag caatgggaca  11460
atgcaaaatg caccaataca gtagcttcac ttcattgatt gcatctatgt cacggaaaac  11520
tgaagaaaga agcaacacct caactttatc caggacagat atccactaac ctaggatgca  11580
agcttgagac tatttagcaa ttgcctctgg gatattaaat cagattacga ctatatttct  11640
acagttattg cttaagaaaa aggtacgatt tgaagcttgg gaagaaagag aacaagagta  11700
aaagaccaat ctgagatctc tttcatccag gtctctggtg cgaaatccaa gagtcctctc  11760
aacatattcc atctcattgt tccctgaacc ctttcctctc tcatttagaa gatcagcgaa  11820
ggcaccacca aactctatcc gcatcaatct cacagcagcc actggattta cacatgaaag  11880
```

-continued

```
caaaccagga gaaccataaa aatcacaaca aacttcctga tagcctactc actagcatca  11940
accattgtgt tcagcctaaa atgagcggct gttttcaatt gaacagcaac ttacatggac  12000
cactgcataa aagtgatttc ttaatccaga caaacaaaaa tgtttacttc aaccaactga  12060
atttgcatca gctcattagt gatttgacaa gttctaattt atgtatcaac aaacaagacc  12120
atatagctag gaaacaagag gcttaggcta agcttaatgc gtgaacaatg ttagatttca  12180
acctatcagc actgtggata actgcaaact gcgacttaaa taaggaagat aaaggaactg  12240
aatatgcaat ttcaaggtgc tcagcatttg aatcaacagt tacttcagat aattcagaac  12300
ataaaagatt tgaacattct aaggctacct catgattgca agcaatgtta cctgattcgc  12360
taaccctcac aagccacaag ccaaagaagc aatttggtaa atggttcatg gtacaactgt  12420
tcgcttttgg actaatctaa caatactagg tggtaaatta tgttcccata tctattacca  12480
taatgtacag caaattaggc agcactaatt ccaaatgacc caacaaaaaa agaggaagaa  12540
aatccaaaaa ttcaagccaa catatgcact aaaattacaa gcacaaaatc aaataatgag  12600
aatcacacta tccaaagaaa atttccatcc acatttatcc aacacaatta tctctctttt  12660
acacccaaat tatgtcaacc aaaaacacta aaacaagtga gtgcagtagc ttcacatcaa  12720
agaatatcaa tcacaaacac cacataataa aatttcaact cctgcccaaa caaaaaaaat  12780
ataaagaaaa aaaaacagca aaatttcaaa gataaaatag aaaaaaaaaa atcaaaatac  12840
agggggaaaa aaagtaaatt taccagctct atgaggcgaa acctgcaaat tcagcttctg  12900
ggttttctct gaaatatcaa gcacaataac cagcaattaa aaaaaattat aaataaaatt  12960
aaaaagaaaa gattgataat taaaatcaaa agagagcaat ttaaagcaca atccttttt  13020
taccattttt tctgggagga agagcatcct tcgttttggg tttagacgaa aaaaatgaga  13080
gttgttgtat ttgtgcgcat gagtgatcat tgctggaaat gaaagtggga aagtggtaaa  13140
tgagtgcttt gtgaaattgg gttttgagga aaagtagaaa gaagaagaag ggtcgatgtc  13200
agagaagaga gagagtggat ggaaagtagt gatgattgcc tccattgttg ccggtgaagt  13260
gagctttctg caaatatttc actggactag tttttttag cagataacgc taaaacagag  13320
aaagatgttc ggttaatttt aatttttgga catttaaatg actattcaat atgtttcaac  13380
cttttttttt taaaacaaag gaacaatact agtattagat tacgttaatg tttagtacat  13440
ccaatactta tgtgtgtttg acctaactta aaatcgtaag ttgtttaaaa tgtcggtgtc  13500
ttgtttttaa gagatatcat acttactatc tttggttttt actcttccat tgttaacaga  13560
aactgtattt atttgggtaa ggggtttgag tgaattcctg taagtatgag aaagttttga  13620
gtgaagcaag agaaagagag aagaaaggaa cttcgagtga agattgagag aaacaacagt  13680
tagtgggaac tgttgttggg aacttgagtt taggagctca ggttgtaccc cgagagaatt  13740
aataggtttg taacagagtc ggtggcctat tatagtggaa agtttgagtc aaaatccatt  13800
gtggccgatg tcgtttcttc ttattgggcc taggaagttt ttcctcgcta aaatttcctg  13860
tgttcccatt gtgtgttcct tagctagctt tcaattccgc aaaaagttac gtttattctc  13920
tcactataat tcaccccccct cttatagtgc tcatattata caacaattga tatcaaagca  13980
ggaactctaa aaatacagaa atcatgttga gttcaagatc ttggaaaata tgaatactac  14040
agaaaaactg gaagaaaggt actctactca gagaccaccg atgttcaatg gcaaattcta  14100
cacaaactgg aagaactgaa tgaagatctt catcaaagcc gacaaatatc aggtttgtag  14160
aatcatagag gcaggcgatt ttgaagtcac taccactaat gacacatatg aggtaattcc  14220
taaattcata actcatttcg ataaagtata tttcgaaaag ttggaaatta acgttcttgc  14280
```

```
tattaaactg cttcattgtg gtcttagacc tcatgaacac aatcatgtca tgggatgcaa  14340
aatcgcaaaa caaatttggg atcttcttga agtcactcat gaaggtacgg gtaaagttaa  14400
gagatcaaaa atcgatcttt taatgaatca atatgaactt tttcaaatga aatataagga  14460
gtccactcaa gagatgttta cacgctttac taatactatt aatgagctaa cctctcttgg  14520
aaaagaaatt acatatgatg aacaggtaag aaaggtccca aggatcgttg gatggctaag  14580
gttacgcctt acaaaaaact aaggacttta cgaagttcaa tccggaacaa cttactggct  14640
cccttatgac tcacgagcta cacttggaca ctgagaatgg tgacttgtcc aaacagaagt  14700
cgattgcctt gaaagccatt tttgtcatac cgtcaattaa ttaagtaaaa agtggtaaaa  14760
gaattaccaa aaacgcacaa aataaattaa ttagttggat ataactaatt aacctattcc  14820
ttttttctgt cgctataact acttttgctt aacttattga tggtttgatc gttgaatcca  14880
agttttctcc acccacaaag atattataga ctttacttta aaaggtacga taaataatgt  14940
ttaatcaggt atgcatcaac cttgaaatta ttaatttatt aagatcaaat tatgcatatt  15000
tatattaaac gtacaggact tgtgcacaat ccatggatga tattgtagat tttgttgtaa  15060
aggagttagg gacaaatgat gttgaattaa gaatgatgag gaacaacatt gaggtaccta  15120
atggcataca agattatgtg gtaacaaagg tgaagaagtt ggttgtacca ggcaatacag  15180
cagcggcaag ccatatatag gatgagctac catacccta tgttgtgaac tattgtcacc  15240
accaacaaga cattggtcat tacgacatca ctttagttga ggaatgataa acctcttttt  15300
gctagatatt tgcaaacatc tagcagataa agaggaataa aacactattt atatttcatg  15360
aacactattt gttagttgca tgaacactat ttttagttac acgaacacta gttttagtag  15420
catcatgaac actatttttt agcatcggaa ttttcacgac tactttttgg tttgactgac  15480
actctgcaat tttcgagata actttttggt gatatgggtc ccatgaaata gaagatttat  15540
atttcatgaa cactatttgt tagttgcatg aacaatattt ttagttacac gaacactagt  15600
tttagtagca tgaacactat tttttagcat cggaatcttt gcgactactt tttggtttga  15660
ctgacacttt gcaattttcg agataacttt tttgtttgac tgacaactat ttcctatata  15720
tattgacagt tttacccctg ttagatgttt gcaaacatct agcaaaaaga ggtttatcat  15780
tcctccactt tagttagccc aacctccagt aacgccatcc agaccactgt cgtttgtcac  15840
tacgacactt acgcttggca accctatgtc ctagcccttc gatacctcga tatccgtccg  15900
ggcaatgtcc ccagtttgtc acttctctgc cattaatgac atattttgga gtatcaaacc  15960
caactccaag tatatatcgc aacatggctc agtaaagaga gtcatataat catgacgtag  16020
tttctatatg ccatcctacg tagtatcttg taacatgaat aacagcctgg tttgcaggtt  16080
gatggtacat ggtataaatt ggtattactc cctccggtct ttattagttt aatcctttct  16140
tttgtacaga gttataggag aaataatatt gtgggtcata gaaggaaaga gaaattatta  16200
ttttatgtta aagttgaatg tatgtgtgat gaaaagttag tagtcccatt tcaaaataga  16260
aaaaaaaaag gtaaactaat aagggacatc ccaaaaagga atacgggtaa actaataaat  16320
atccatgcag gttgttggta catggtacat gaagccgtcc aaaaccttca aaagcagtaa  16380
gtcctgctgc tatgccatat tcaaatattc aactccaaaa aaaaaaaaaa aaaaaatcaa  16440
aaatccgctt ttcagcgaaa atataggaaa taatccaaga atcgaaatcg aaataaagtc  16500
atgatgcaag tttggagagc tgaagttaca ctatatcgga gtacttactc aaatgttgat  16560
tagtactccg tgcgtttgaa gtaaagtcac atatggagta gttccaagct aggttgtaca  16620
```

```
gtgacggata aggatactgg gttgaaaagg tgaacgtcga gatttatacg tgtatttatt  16680
taaacaggat acgtatcata ttgggttctc atacgcgtac cagctgtgac ttagaaaaat  16740
taaccacgct atataggttc caagccctca tgattacctt ttcatagtgt aaatttcatg  16800
tagttgaatg gtgggaatcc aatcacaaaa acactgcagg taatggaaat gttccaactt  16860
tttccaagca ttttaaaata agacatgtga ttactaatta gggcgtgttc ggcaacagta  16920
attgtggtga tagtttttag ctgtgagagt agttgttagc tgtgctatta gcttttagtg  16980
gttggtgtgt agctgttagc tgttagatgt ccaagtagcg gtgtaaaata ttgatgttcg  17040
gtaaaagaag ctgtcaaagt agctgtctaa gaataactag ttaaaaattc aaataaaact  17100
ttaacatata atttatacac cactaaaagc tacccaaaag ctacaaattg tagcttttga  17160
caaacactac taaaacacta cttgtaccac taaaagctac ttacaccact atcttgccaa  17220
acactcttat tttttctaat tagtgttttg acctagtcaa gacactaaaa gctacttaaa  17280
aagcttgtgc cgaacatgcc aattctgaac caaggaacaa actataacaa aaaagtgcta  17340
tgtgaaactt ttgtaggcaa cagaagtaag gcatttttgg aatgtactaa caaatccgta  17400
ttaagacttg tacatgaaaa ttaccgtggt aacatttacc cacacttcct cattcacgta  17460
ctccgattca ttcttataag ggcataaccg cataaggcac atcaagatcc atgtatctaa  17520
tagtttaatt tgcctctgtg tttctgtatt aacaatgagc atagtgagtg caaaagccat  17580
ggaagctaga ttaaaaaggc catcattcta agttagacaa ttggaaacaa catcgagata  17640
cacgtacaca taagggctgc tcttctctat tactccctct gttcctaatc atttgctttt  17700
ttagcgggtt ccaaaggcct atgtttgacc actaatatat ttaaattaaa actggtgata  17760
tatattaaaa gaaaattatg atgaatttaa caaaaaccat atatgttatg tccttttttt  17820
tcctatatta atgaattttt acagtcaaag ttggtgaact ttgacccaaa aaaagaaatg  17880
gagcaaaaaa aaaaaaaaaa aaaaaaaact agggacaatg agtaacattt ttatctatgt  17940
ctttttaata tgaatatacg taacaaattc tgcaaaaata gagatagcaa ctaataacac  18000
gcatgaaaat gacaagttat attataccttttttctcaa tatatgaata tacgtaacaa  18060
attaactcca gtagttttta gtaaaactat tagattattg tgtaacatat actctggaaa  18120
tagtactaag atccattaca atctttattg agaaatttcc tcatgtaccc cctgaggttt  18180
ggcgtaattt ccaaataccc ctcatatttg aggaatttct caaataccct gatgtttttg  18240
tttagactca aaatacctttt actatggaca gtaccctaat gtcattaagt tttccccttc  18300
tctctcccca attttctctc tcctcccatt cccccaccca ctacccactg cccactgcca  18360
agtaggggtg taagtggatt ggactggatt ggactttgcc aaattcaaat ccagtccaaa  18420
gtttttttgga ctcgagaaat tgagtccaag tccgatccaa atattttttg agtccagtcc  18480
aatctagtcc gataattttt tcttgagtcc gaatccagtc cagtccagtc cgattattat  18540
atctttttttc ccgatttagg ttcaatgatt cacaacattt tttgagatgc ttgagcattt  18600
gacatctgat tcaattatca atatccacaa ataagattga aagcttaaat taaagtaaaa  18660
tactatgaat aaaaagttga attagatgct taccttgatc taagttgaga ggaagcatag  18720
agactgagaa ttaatctgag ggacaaatag agaatgcgag agtcgagaca gtgaggtaga  18780
aagaaaatga agagtaagag gaagtgagta ttaaggactg aggagtaaag taagatagaa  18840
ttagttggct actagcctac taatgcagta ttgctagtat aatttactta tttaacaaat  18900
ggagctaagt gcaatagttt agcgccaatt gacatattta gagagagaag gctgaaaaat  18960
ccaatatttt taaaatagta tcattatttt taatatatac attatatata aaaatatttt  19020
```

```
tggactggac tggacatatt ggactccaaa gggatgagtc caaatccaga caaaaaatat  19080
ttggacttga aaatttaagt ccgagtccag tccgaaaaat tttcagtcca atccagtccg  19140
acaaatttgg actggactgg attggactct gaacttttcg tagtccgctt acacccctac  19200
tgccaagtgc caaactgcca accccctttt ggttgagttg atatttgacg caaagacttg  19260
gcgtgttgga aggttcatta cacattttat ccaagtcaac tttgaagtct tcttagctag  19320
agactagagt gaacgtgttg gaaggttcat tacacatttt atccaatcaa actttgaagt  19380
cttcttagct agagactaga gtgaacgtgt tggaaggttc atgttcatga cattataaaa  19440
gtaataatag tgaaatttca caaagtattt ataaacccag gacagactca agagctctac  19500
ttattattag tgaaaaacaa acatacacac gacaataaca caacataaac aataatgaac  19560
atgaaaatcc tccttttgtt tgtcttcctt catcacctcc actacttcat ccatggcaga  19620
acacttacag aacgccaagc tttactaagt atcaaatctg ccattactta tgattattat  19680
aactctctct cctcatggaa aaacacaaca caccactgca gttggccata catcacttgc  19740
tcctcctctt cttcttcttc ttctgttatt tctctcaact tcaccatgtt atttctcgaa  19800
ggaattctct cccctgatat aggcttcctc accaacctgc aaaacctctc tattcgatct  19860
aacctttttt ctggcccact cccccattct ctctctctcc tcacccaact ccgctatctc  19920
gacgtttccc aaaacagttt cacaggtcca atcccatctt ctctctctct cctcacccaa  19980
ctccgctatc tccacgtttc cggcaacagt ttcacaggtc caatcccatc ttttctctct  20040
ctcctcaccc aactccgcta tctcgacgtt tccgacaaca gtttcacagg tccaatccca  20100
tcttctctct ctctcctcac ccaactccgc tatctcgacg tttcctacaa caatctaaat  20160
ggcactcttc ccttatcggt cgttgagaag atgtcggagc tcagctacct taaccttagg  20220
tataactctt tctacggtga gattccaccg gagtttggga aacttaagaa gcttgaaaca  20280
ttgaatcttg gtaacaacac tctttctggg agtcttccat ctgagttggg ttcattaaag  20340
agtttgaaac atatggactt ttctagtaat atgctatttg gtgagatccc acaatcttat  20400
tctcttcttc gaaacttaat cgatattgat cttaatagaa acaagttata tgggagtata  20460
cctgattata ttggagattt tccggagttg gaatcacttt tattagactc gaataacttc  20520
acagggagta tcccacaaaa gttaggtaca aacgggaagt tgcaatatct agatataagt  20580
aacaacaatt ttagtggtag tttgccacta agtctttgca aaggagacaa actccaagat  20640
ctggacgcat cctataattt gttggttggg tcaattcctg agagtttggg aagttgcaag  20700
tcacttgaag gagtgtacat gggaaataat ttcttaaacg ggtcgattcc taagggcttg  20760
tttgggagtg atgtttcact taatgacaaa cttcttagtg gaggtctcga tgagaaattc  20820
ggtgattgcg ttaatcttcg ggacattgat ctctctaata ataagctatc agggaagtta  20880
cctgcgacca tcggaaactg tattcatctt cggtccttga cgctttataa taacacctgt  20940
accggacgta tccctcaaga gattagcaag tgtaagcagc tacagaccct cgatctcagc  21000
caaaatcagt tctctggtgt gatacccaat gatattacag gtaagaaagt atattaaact  21060
tgttactttt gaaaatattc gctctagttt ttgtttcagt tggtccattc tcactttgta  21120
ttattgaaat atatcccaaa aaagtaaata taattatata aaagaatctt gctaaaaata  21180
atatgaatta tttttgtatg tgcaaaataa tgtacaaatc taactaattt gttgtggata  21240
ataatattaa ttgtgtgaaa tagtaaatgt gtggagatat ataactttat ttatcatatt  21300
cactcaggtt tttaggtatt tattatgagt tttgcattgg agatatccaa cttgacaata  21360
```

```
gtatttttgt aatataccaa tatataaaga ttactgtaca taaccaaaat gtatactttt  21420
cttattttta taaacttata tattcctctt ctttgtattt atcacaacat tttttatacc  21480
cttttgcctc atattaatag caacacttat aatttattta tttacttttt atttcttggt  21540
ctataacctc atctacccac atatgacaca ccctataaag gacccacatg attaaccaaa  21600
atatacaaat atcttcaatg aaattaactt taacactaat atgataaaaa tcatgtcccg  21660
ctttttatcc tctaactaag actctgcata aaggtatatt gcaattaata tgagatggaa  21720
gaggtataat aattatatga tcaaattcct ggattgaaaa ataaatatga gattaaaagt  21780
ggtatgtttt tggttaaaag aaactatcca taaagtatgt ttttggttaa aagaaactat  21840
gcaacatacc aatcaaatgt ttatacgctt acaatttatg taccactttt ttgtcattgt  21900
ttttctattg tttgccatac gtacgttact aaatcatgtt gtcttttcac attttaacta  21960
acaataaatt actattgata caccaaaaaa atctatgagc attggagtac gttgtttgat  22020
agaagcttcg tgctattatt tcttgtcaaa gaatttcata tctcaatatc ttctaattta  22080
acaatctaac gaaatttttt tgacccagga aacaaatcca tttgcaatct ggaaaagata  22140
caaacactta aattatcaaa caatgctttg actggtgaaa tccctcattg tgttggaaat  22200
atcgagctca tagcattatt tctccaatca aacaaactga acggtaccat acccgcaaac  22260
ttctcaaagt tatgtgattc attgatatat ctagatctta gtgacaatca actcgaagga  22320
gttctaccta agtccttgtc caaatgtcaa agtctagaac tcctaaatgt cgggaacaat  22380
aggctaagag ataaatttcc ttcatggtta gacaacctcc cacgtctcca agttttcagt  22440
gtgcgtttta acgccttcta cggtcctata actagctcac caaaagttag tcacccattt  22500
cctatgctac aaattatcga cctatctaac aataagtttt gtggcaagtt gccaagaaga  22560
tatatcaaaa actttgcaac catgcgcaat atgaatgagt ctggtgttgg gaatccacag  22620
tacctggggg actcatcaat atatagtatt acgtactcta tggtattgac attcaatggg  22680
ttacaacaaa aatatgaaaa gcttattgtg acgatgtcga cctttgatat atccagcaac  22740
aactttactg gacagattcc atatgttata gggggattac gctcacttcg taaccttaat  22800
ctctctcata atgtcttaac cgggaacatt cctccatcaa ttgcaaaatt gtctttgctt  22860
caagatttgg acctttcatc aaacagactt actggtcgta tccctcaaga attagttagt  22920
ttaacatttc ttgggagttt caatgtttcg aacaatctat tggaggggtc tatacctcat  22980
ggtttcaact tcgacacgta cacagctaat tcataccagg ggaatctcga attatgtgga  23040
aaaccattac ctgagtgtgg agaaagaagg gcaaaaggca ccactaataa tcaagatgat  23100
cctaaaaatg ataatgaacg aatgttgtcg atgtccgaaa tcgtagttat ggggtttggc  23160
agtggtgtac tagttgggtt ggcttgggga tactatatgt tttcagtggg aaagcccttt  23220
tggtttatca agatggctag caaaatggaa tcaatattga ttggtttttt ctgaccaaca  23280
atttgttagc cgatgaagag catcaaaacc aaaaaaaaca aaaaaaattg attaatatgc  23340
atgagtgtga ccttgttttc caaagtttag cattactatt agtgtctcaa ttcataataa  23400
taaaaaaatt agcttgttca agatttgtat ttttattcaa agattttttt tgtctcttgt  23460
gcttctttta tcttatatat attttttgta tggtttgttt ttgtttaata ttagtccctc  23520
cgctcaaaat gatctttcac gcttgagatt ggcattaagg tcaagagatg ttgctaagct  23580
ttagaataaa aaaattccaa atgcatagag ggaaagaaag cgagacaaaa tgttggagaa  23640
ggcagagtaa atgatgtgat ggaggataaa tagtagaagt gtgataccga aagtttgaaa  23700
ataataagga attttatttc ttgctggcac tttgttctag tacaggtttt tagcccttca  23760
```

```
aaatgtttat aatgtagagt caaaattaat atccttaact agtttttaag tccgggttat  23820
atcctagata ttaataatat tcatttatta gtaacatttt attttataaa tataatacta  23880
agcattattt ggtttgctgg ttaagacttt agtgtatatc tatttctttt tttttttatt  23940
gtatgcgtgt ttacataaac taaagactat aagggatagt accacgtggc gcagttcctt  24000
gcttaggaac gtcttttaat atattaacta gtatttgggc ccgggcgttg ctccgggttg  24060
gtattgtgtt tccgaacatg atgtgcagtt tttcccattc ccactaaaat atataaagga  24120
aaactcaaca tttaaaagat acaaatataa taatatggac acttaaaaca tgattaaaag  24180
ttgattgaga tggtaattgt gtcatgttat aatagtaaga ggttgcctaa ttgaggttga  24240
ggtggtggag tagtggtatc gcttcccatc tgttatccct gaggtataag gatcaaacct  24300
cataggactc atttgagtaa tttcccatat cctcctctca aatgagtcct tttcatctga  24360
caaaaaaaaa gagtctaatt ttaaattaaa attagacgat cttttataaa atcggcactt  24420
tctgcacata ggtcacaatt tttttgtttc tatctctctg ctttctttaa tttcacagtc  24480
tccaactctc catcaacatc ttacttattt tagaatagat gatgtatggt agtattaaat  24540
ggtaaagtac taaagctcct ataatacaca gaagcttaca tagtatagat tcgtacatga  24600
gacaaggtta caatatactt tctccgttct ttttatatta caataattac tattttaagt  24660
agtttcacat ctattgtaac aattccaatt ttgttataga aagcaacttt aataattgac  24720
aatattgccc ttactttatc ttattaaaac catcattaat tactcacttt ctcttataaa  24780
attgctttta ttttctaagg atgatttctc tcctattcta gttaattaaa gagttacttt  24840
tgtgctaaac tgctcattta ttccaaatcc ttaaaaattg tgtccaaacg tattgttgta  24900
atataaaaag aacagaggta ctattagttt gaataaattt tgatcagatt aggtcacctt  24960
tagggggcgt ttggttaggg gtattctgga aagggtaagg gaatcaactt acttaattcc  25020
cttacttgtt gtttgtttgc tcaatttaat gattcccttt acccacccct tactcccaaa  25080
gtcctttact ctcattctcc ccacccccca aggtttcact taccctttct tgattcatca  25140
ttgaccatat ctttgaccac ccaactacca ccaccacttg accacctaat cacctaacca  25200
cctaattacc caaccactat taccacccaa cccctccacc tgcccaccaa tcggcaccat  25260
aactgcccaa ccgtcgccca atcaagccac ccaaccggca ccataaccgc ccaaccaagc  25320
cacccaaccg gcaccagaaa ttgtaccaag ctacccacac acgtgaaaac cacccaccca  25380
caagccctag aaaaaatgga agaatcgaga gaaagggagg ggagagaaaa gatgcagcga  25440
ctagaagggg agggggagga tgtgacggca aggggagagg gaacttcgca gcggcaaagg  25500
gaggggaaac gtcgcgtcgg caaagggcta aggtggaatt gacggggttg cagcaacaag  25560
gggagggcat ggagacgtcg taaccgcaag gggaggggca gcggcagtgg aactggggtg  25620
gagaggggta gtggcggcac tagggtgtgg gagaggtggc gggggatatc aagagagggg  25680
ggatatggtg gtgttatggt ggaagcaaga agaagaaaga ggaaagacaa tgtactaacc  25740
aaacaacaca ttaaatctaa gggttttggt ttcctttccc catctacccc tttcttgatt  25800
ccattccctt taccccttta caaccaaact ccccccttagt ttttactact tataaccttc  25860
aattttggct gttttttgtg acattttttta cttctccgag cctggtcata ttttctcccg  25920
aaacatttcg aggaaagtcg aagtgacttg tgaagttgtg cgggtgcttg gcaccatttg  25980
tgttgcctcg aaaagcatct gaataccccca tttattcctt tctcctgaaa cccaaaatta  26040
cctcgcaata aacgaaaaga tatccatata tttgttccaa gccacatgac tcctttccaa  26100
```

```
cgacctccca tgtgaccatg tccttagaag gcatcccgtg gcgttcgaag ctcggacccc  26160
cggaaagtcc gaaagtgtgt attataactt tcaattttgg ctgtttttgg gatatttttt  26220
acttcttcgg gccttgtcat attttctctc gaaacattca taggattgtc aatgtgactt  26280
gtaagttgta acgttgcacg ggtgcttggc acaatttgca ttgcctcgaa aagcctctga  26340
acaccccatt tgttcatttc tcgtgaaatc caaaattgcc tcgaaaaaaa cgtaaaggca  26400
tccacatatt cgttccaagc cacataactc atttccaatg acctcccata gagtccgtag  26460
ctcggacccc aggaaagtcc aaaaacgtgt actataacct tcaattttgg ctgtttttgg  26520
gacatgtttg gacttcaccg gcctggtcat attatcttcc gaagcattcc tacaaaatcc  26580
gacgagacta gtaacgttgt tacgcgggtg cttgacacca tatgtgttgc cttagaaagc  26640
ctttaaacac cccatttgtt catttttcgt gaaacccaaa attgtcccga aatgaacata  26700
aatgcatcca tgtattcgtt gcaagccaca tgatttcttt ccaatgacct cccatatcct  26760
taggaggcat gcatcatgtg gcgttcggcg agcgggtctc gggaaagtcc gaaagcctgt  26820
gttataacct tcaattttgg ctatttttgg gacattttttg gcctttttca agcgtgttca  26880
tattttctcc cgaagcattc ctaggttagg cgatgtgact tgtaaagcgt gggtacttgg  26940
caccattttc tttgcctcga aaagtctttg agcaccacat ttgttcattt ctcgtgaaat  27000
tcaaaattgc ctcgaaatga acgtaaagac attcacatat tcattccaag ccacacatga  27060
ctcctttcca atgacctccc aagcccctag gagtcgtccc gtggcgttcg gatccggagc  27120
tcgggccccc gagaatgtcc gaaaccgtgt attatgacct tcaatttttg ctgtttttgg  27180
aacatttttt gacttctctg ggctggtcat attttctccc gaaacatttg taggactacc  27240
gacgtgactt gtaatgttgc gtgggtgctt ggcacaattt gcattgcctc gaaaaacctt  27300
taaacaccgc atttgttcat ttctcgtgac acccaaaact gcctcgaaat gaacgtaaag  27360
gcatccatat attcgtttca tgccacatga ctcctttcca ctgacctccc atgtccctag  27420
aaagcacccc atatccgaaa gcttgtatta taaccttcaa ttttggctgt ttttgggaca  27480
cttggacttt ttcggttcgt tcatattttc tctcgaaatg ttcctagaaa aggtgacgtg  27540
agttgtaacg ttgcgcgggt acatggaacc atttgccttg cctcgaaaaa cctctgaaca  27600
ccgcatttgt tcatttctcg tgaaactcat aattacctca aaatgaacgt aaatgcatcc  27660
atatattttt tccaagccac ttgactctta tccaatgaca ttctatgtcc ttagaaggca  27720
ctgcttgtcg tccataattc gggccaggga aatgtatgaa agtgtgtatt ataaccttca  27780
attttggctg tttttgagac aattttttac ttctccggga ctggtcatat tttctcccga  27840
aaaaatactt cgagtgccga cgtgacttgt aacgtcgcgc ggatgcttga caccatttgt  27900
gttacctcga aaagcctttg aacaccacat ttgttcattt ctcgtgaaac ccaaaattgc  27960
ctcgaaatga acgtaaaggc atccacatat ttgttccaag ccacatgact catttccaat  28020
tctctcccat gtccctagga ggcatcccgt ggcgttcgga gctcggaccc tgggaaagtc  28080
cgaaagcgtg tattataacc ttcaattttg gctgtttttg ggtcattttt tgacgtctct  28140
tggcttggtc atattttgtg ccgaaacatt cccaggattg ccgacttgac ttgtaacatt  28200
gctcgagtgc ttggcacaat ttgcattgcc tcaaaaagac tctaaacacc ccatttgttc  28260
atttctcggg aaacccaaaa ttacctcgaa atgaacgtaa aggcatccac atattcgttc  28320
catgccacat gactcttttc caatgacctc ccatgtccct aggaggcatc ccatggcatt  28380
cggagctcga acactgggaa agtccgaaag cgtgtattgt aaccttcaat tttggttgtt  28440
tgtgggacat ttttgggctt ctccgggcct ggccatattt tctcccgaaa cgttccttgg  28500
```

```
aaagccgaag tgagttgtaa cattgcacgg gtgtttggca ccattagtgt tgcctcgaaa  28560
agcctttaac caacccattt gttcatttct cgtgaaacct aaaactgcct cgaaatgaac  28620
gtaaatgcat ccacatattc gttccaagcc acatgactcc tttccaatga ccttccaggc  28680
ccctaggagt catcttgtgg cgtttggagc tcagtccccg gtaaagtctg aaagcgtgta  28740
ttataacctt caattttggt tgtttttaag acattatttg acttctccgg gactgggcat  28800
attatctccc gaaacattac taggagtgcc gacgtgactt gtaacgccgc gtgggtgctt  28860
ggcgcaattg tgttgcctcg aaaagccatt gaacaccccc atttgttcat ttctcgagaa  28920
acccaaaatt gcctcgaaat gaatgtaaag gcatcgacat attcattcca agccacatgg  28980
ctcatttcca atgacctccc atatccctag gtgtacaccc catttgtctg atgttataat  29040
agcaagaggt cacgggttca aatcttgtta caagctaatt ttacttttgt taattgacat  29100
gacttatgta cacattggac aattatagtg gagtaacaaa ggtgacatgt gacgcgtata  29160
cattatcaca cacgtctttt aatatatttg tatagatcta gatttaagag taattttttt  29220
aatgcgcaat acttggccaa tttcttctgt atcaaatcat aggtctttgg ttggttcata  29280
agagtaaaga ccaaaataat aatctgaact gcaaaaattt tctccaagag ttaaaagttt  29340
gtataagtta gattaaaaaa attaatgaca tatgatgtag ttggacatta aatatgtaag  29400
tttagaagta attgtgttaa cataaaaaaa gattcgatta taacataaaa actaaagaaa  29460
cacaaaggcg ccgtacaaca atcaatatta cccaagtccc ctcattaata ttaagggatg  29520
acctagctcg tacatattta attatctttg aaaattcgtt gttcagactt gctagttgct  29580
attctatatt tgtatattca ttaatcaatt tttcaatatg tgagcattta cattttaaac  29640
tagagcaaat attgtctctt ttactatttt gttgttgtca aattttcaaa aataaattgc  29700
tcaaatactt ttcctagtga cataaaaaat agagcaaata atcaaacagt agcagaccca  29760
ggaactttta cataatgtag acggcataat gtgttaattt ttgcttcttt tttctaatat  29820
catccaataa cacaattctg cttctattag tttgtagttt cagatgatga tacccaaaca  29880
ataagaccaa gcaacaaatt gataagattt tgcttctctt tcttccactt ggtgtaactg  29940
taacagcttt gaagtttaac ttcagtaatc agttgcatat ttggcatatg atcaaaacaa  30000
tcaaattatt atgtatggaa aagcaaaaaa cttccaggtt tccatctgaa caaggaggcc  30060
aagagggtgg aagcaagcaa ggatatatga tcataaaatc ctatgaatat gatgtacaaa  30120
ccttttctac tgcaattagg taacctaaat gataccacct aggaacagca acaacttatt  30180
tacagcacta aacctaaatc aggttaaagt taatcagacc accatgtatc tgggtggtct  30240
ctcgagggaa agcgtctcca tctgtatccg ggtaacagag gtttcttctt ctcgatcctc  30300
cttggcttct gccctcttaa gttcttcgaa ggctctcttg gcatatacag taaacgcaac  30360
aatggtaatt attgccacta tgaatgaaat aacattgtac acaatctcca cccatgttag  30420
atgatgattc ccatacttga catctgcgaa cgtccttatc agtctcccac tgcaaatgaa  30480
tgctatcagc gtcaatattc gagataccaa ctcatttaac tattgaattg ccaaaaacag  30540
atatctttga ccatatattt gttactaaaa ataacgattg ataatgtgaa actatcactg  30600
atagatttaa aagaactttt ataaaagtat agtttctcta atgtataact gcagaaaata  30660
gaatggggta gacaaatgaa gtaattgttt tgaagaatgc aaaaggtcaa ttcagtaata  30720
cttttatacg tgattggggg aagcattaaa aatcccttct aagataaaga tgacctcatt  30780
ggcaatggaa tcgacatcca cagacccttg cattagaaca gagtggaagt ttctgtgaac  30840
```

```
ttacgtgtag atgtaaagaa aagcttctgg caccatccct gcaattgatc cccatagata  30900
aggccaaaac gtcatacttg tcaccacaac tgcgtagttg aagatagtat agggaaatgg  30960
tgaaacccta aagagtgcca ccacgcggaa ctgatgaaac cagctacctt cggcagcaag  31020
cctaagcata gcagccttat ccggccatct ttgcaaccat tgctaacaag gtacaaaaac  31080
ataaacattg tggacttaat tagacaagaa agttaaatta aaatcaacat tagataatca  31140
ataaatcaaa tgtaagcagg gaacatattt cttacatgga ttctatcccg gaagagcaat  31200
ccaagtaaat agggaagaat cattccaata gtagttccaa ccatgattat cacaaaacca  31260
agaccataac caaagatcat gcctgcaagc cacatggatg ggccagaagg aatcagaaat  31320
acagggaaga ttgctaggga agtaacaagg accacagcaa gaaccggacg gccaaaggca  31380
gtggcttccc attgcatcat tggaacaaga acctgcagag aaagtaccaa aaactttgag  31440
gcaaaaattt cctgcttgta tattgcaaaa agtagtacag cgaaggcatt ccgtgcagaa  31500
tggcttatag attggaaata cggagaacaa tgcaactata agcacaggcc catctcttga  31560
cttttgggac aataacatgg acccccagat tgatttataa gttctcacac catagctaga  31620
ttttgttgga actttcataa atcatagtga cataagtata gcataatatt catgccttcg  31680
acagaagttt tcgcatatgg taaggctact attgaaaaaa ttcccttgtg tttgaagtac  31740
gcataaaaat atctagtggc agtcaaccaa ataaaacatt ctaggagtcc ctcaaaaaat  31800
taaagagtca tcagttcaga agactttaat atcaatactt tctattatcc gggtttggca  31860
tgcagtaaat ttcatgagaa aaggaaaaat cagctatttg attatataag gaactaattc  31920
ggatgtatca ctaagctttc catcgactgg aacatcggga gctagtctcc aatactcgtc  31980
aaggatctaa cataaacatc ttctccgcaa tcaaaaagcc aaggtcacat acatctaggc  32040
ctctgtctca ttctgatggc atggtatgat gcaagttaga caacactatt atttggcaga  32100
tgacacttag gggtctaata tttaagctca ttcaagataa tcaagtaatc aagttcaatc  32160
tcaaggtttc agttgcgcta aaaaatgtaa tacttggctc attcagaatt agtttgttga  32220
agctggttgg tatttgcttc atttgttaat ggaaccaggc tcataaacaa gctttcatta  32280
ggctaaactt atttaacaaa atcaaaagct taatactata atttttgata ggatttcttt  32340
tgggcagtta tacatgagta atgaacaagc tctacacaat ctttttttaat gaacaagctt  32400
taatcgagct agggtacgtt ctattcaact tattggacct gaacttattg gaacttatct  32460
gaactgaact tattgaacct gaactgaact tattggaact tattaaacct gattggacct  32520
gattcaactt attggacctg attgaacctg attggaactt attggacctg attgaacctg  32580
attgacctta ttggacctta ttggaactta ttgaccctga ttgaaactta ttagacctta  32640
ttggacctga ttgaaactta ttagacctta ttgaacctga ttgaaactta tttgacctta  32700
ttagacaaaa acattattat tattattgtt attattatta ttattattat tattattatt  32760
attattatta ttattattat tattattatt gttaacctga ttgataacat ttatatcttt  32820
catagttatt agtaacgaaa acatgttatc tctagttatt caaagacgaa ttgcaaaata  32880
ttgtaataat aataataata atatattatt attattatta ttgttaacct taattatttg  32940
accatgatta taatattatt caatagcaat atgaataatc aaataataga caataataca  33000
agtataatac tatacattgt ggtactttaa taaaaaaatt ctaataataa cataatcagc  33060
taatagtaat atgaataata aaataataga cataatacaa ataaataata aaataataga  33120
cataatacag ataaataata aaataattta cactaataca agtataatac tatataatca  33180
ttgtggtact ttaattaaaa ttctaataat aacataatcc gctaatagtg atatgaaatt  33240
```

```
atgaataaca aaatagtgga caataataca aatgtttatt aaacattgac tatttggacc  33300
ttattggacc ttattagacc tgattggaac ttattggacc ttattagacc tgattggaac  33360
ttattgcacc tgattggaac ttattacacc tgattggaac ttattgcacc tgattggaac  33420
ttattgcacc tgattggaac ttattgcact tattagacct tattgcaact tatctgaact  33480
tatctgaact tattggacct gaaacttaat tttttaagtt gaacagaacg cacccctagt  33540
atccacgaac atagttagtt gttcatcgac aagggtgtta attccttgac tataaaaaaa  33600
atatctgcta atatgtcctc cataccatgt cttgatctga ttcccaaaat cacgtgtttt  33660
cgtgtctggt gaccacgttg ctagacatgg aagacaggtc taattgttca gtttcaagtc  33720
aggttgatta aacatatgtt agcaatatac aatcattatt agtcaaacta attcaactcg  33780
ggtttggttt gattcaggtt atgtcgagga tcaggtccaa atcgggttaa tccttccagg  33840
tcaaatatat ctaagtctgt tttgccaaag tctacttttt gtatccgtgt ccatgctaaa  33900
tgacaaacaa aaagcagctt ttaccaagct cgaatcagat ttgttcgctt aaagagtcac  33960
ttcgctcatt tacagcaaca attaaaggac aaaacattgt ccattcaact acttacggat  34020
attaacttat tggcaactgc tagcgtaata aggcaatcaa cagcactcgg cctcaataat  34080
gaacctacaa ggagtccaat gaccaataca aattatcact ggcatcatct agcacgacaa  34140
tctcttaact ctaagagtct aagtgccttg acatacaaaa gtattccttt taaaagtacc  34200
cccgtgtgga tattctgcca agcaaatgca atcgatacac ccaattaggg cttttccatt  34260
atgagtcctc agagcctcag attgtaaaac aggtcagtaa aagaggaaaa tagtatttga  34320
ttcttttgct aaacccttgg atataagaat ggtgacttgt attgtcacgc caagcttctt  34380
tcataaaagc tgatcatatt attatatgag agttctgagt ttcaaggtcc gcattcgatc  34440
taactagaca tcacttccaa ttaaagttga gaaacgaaac taggtgtcct ctttgtttcc  34500
caaaggtgaa ctttagatac ttattataag catattttgt tatgaatcgg gctaaggaga  34560
gggctactct tggtattgca taattagtta attacttagt agtagcttga ggaataagga  34620
agcaagtaag ttagaggaaa gagtatgaaa atctgctata aagtgaggag aggagggata  34680
gaaggataat cacaaaatta ttgagttaac tttggtttta gttgcttagg ttgggagtgt  34740
ccagccactc gaatgtcttg ggactgtaaa caccattgtt catgatctaa ttgcatcaat  34800
attacaatta actcatttct cttcttatcc atattcatct tcttacaatc acaactattt  34860
ccagatcatc catccaaatc ttcatccact tgccttagtt tctactccag atttcagtct  34920
attacaaatt gatttctaca atatgtcaat tcatcacaaa ttatcatgtt ttctgaacaa  34980
aagttcactg tttcaggaca aatacagaaa gaactacttt gatgcttaga acagatatat  35040
tgtaaaattg tattcggaat ttgggataca actggagaag atatgaataa ataggcattc  35100
agggagctca gaaaaacaga ccgtgccata tggtgctctg ctgcataaca ggaaataatg  35160
gataaagtat gaataacgtt ataacttctt aaaaacctag atgacaagta ttttggttgc  35220
tttttattat tggtaggcaa ggagaatact caacaacagt ttagccttaa actgcttctt  35280
atttctcctc ttccccttttt tcctgatgat ttggggttgt cactcagttc ttttacctct  35340
catttccagg tactttagag ttatattaca caaaggattg caagagaaga acaggtcgcc  35400
ctggcatgca ctcagaaagt atacgaccct tcacaggaaa tgtggtgctc caagacttat  35460
atctcaggct ctcatgagtc atgtcaagga ccatctttaa tcatttgtat tctaggtttc  35520
tcaggcgatg cggtgtgctg gtgtgtctct ccctcccact tgagtgtgtg tattgtttgt  35580
```

```
gcccctaagt ttttatctta acaatcacta ctagtcaatt agtcattacc aaccctaccc  35640
acctctcttg ttactgttgt tcttggagat atttcatata tgtcagctta gaacttatat  35700
tacgtttctt attacatatt ctcttaagct cgcgcacata ctctgtgatc gaagggatcc  35760
atattagtta tcttttagtg gagttgttgt gaaaaaagac tgcatagaaa aattaagata  35820
gctcatagtt gtaaatgtaa ttgaactttt agattgatag ccttgaggct gcttgcattg  35880
aaccaaccaa attcagccag gctagtctat gcctctttgg tgtcacctgg taggttgaat  35940
ttgtgtagct gtagttctac aagagactga tttaaaaatg ttttcgcact gaaacagctt  36000
aaaccacaaa acaggaaagt gcagaacaaa ctccagaaaa tggtgcagaa cataccttct  36060
caaaaaggaa aggaactccc cattttaaca gtacgaggac aactgctaca gcactaatgg  36120
aggagatcaa gattttgatc caccagatga aggattctga tcttgtttca gcctgagaat  36180
gtaaggttga agcttcaggc ctctttgtaa tagcagatgt caccagacta acaaattcac  36240
tgtcgtcttg catagcaggc ccaacatcta tgtcatgctt agttagctcc attgaatttg  36300
gcatctccaa gagatctcaa gagctgccca aaaagacggt acaatattat gagcatacat  36360
gacatgatga caacccataa agaatatcat aacctgtcac attttttatt caaagttcaa  36420
cagccctctt acaacatgat tgagaatgga ggggaagaga gagagagttg gtctcagaca  36480
ttgatcacat aatcatttca attagtttta aaggtgctca tgaaatagaa ctagtgtctt  36540
aagctggaga cttctgtatt tttcatggtt ttagattatc aatcatattc ttagaatctt  36600
tgatctctag aactctttcc tttcctccca atattttttc cactttgtct tttgttaatt  36660
acggcttcgc tgcaggcctg caataaatct tttaaatttt tacagatact atgtagagtt  36720
gtatacataa gctctaatct gaagacgatt ggtttcgatg ctagttaata caaataaata  36780
tattatggat ataatatgca gtaaattggg ccatgggcac cagggacaac ttagacaagt  36840
atagtgcaac taccaggaaa tttaagctgg gtacctctga ttcatcatgc tggttgataa  36900
tattattgct tccacaagtg ttcgctacgg ctcaaccaaa ctaagtcaca actcacaagc  36960
tgcacaaccc aactgacaat tatcgcctat tgtctaagct atacattaca ttaccccaat  37020
gccacaacgt ggctcacgcc taggcatggt aaggaagttc agatgtacgc agccttaccc  37080
ttttaataac aaagaggctg tttccaggtg acccttaaat cttaattgca aacaccatct  37140
gctgcttcac ataaataagc gacttcaaaa ttgtaaatta aagaatttga atgcaaattg  37200
tgtgaaaaac aactccatca agaatccatt aagcacgctt tactattagt atcaataata  37260
ggaaaccctt atatcccttt tgacgaaggc acacatgcaa cactaatgtg tccttataaa  37320
cttcatgaaa gtatatctct acgaaaccct tttagtctta tgtgattctt taagtgtcca  37380
actgatgatt ggttacaagg tatttagccc aaagtagcat ttcagagaga tggtgtagaa  37440
tgagtagctt ataaaccgag gttgaggtgt aatcctaata aattaggaac taataccaca  37500
agagagatgg acatgtagag atacaatata gtacagaata agattatttg aaatcttttt  37560
accagggaaa ctccagaggt gttccataaa acacaatacc atataactgg gagatcaata  37620
ttttagatta aaaaatataa aaatctattt gggttgagta tatagttggt tagtccaata  37680
atatataaat ttataaggtg gaggtcttcg gtatatgaca ttccaaattt gagtatcaaa  37740
tgatatatat ggttttccat acttgaatcc cttttcatgt actacctctg tttcaaatta  37800
atagttacac ttacactttt cacgcatgcc aatgcagaac tttgaggaca tatatcttta  37860
gttttgtatt tgtaaaaatt ataaaaagta catattaata aaatacatat taatacgaat  37920
ctaacaagat cccacatgac tatgatttta ttcacgtata aatcacaaac gagggtcaaa  37980
```

```
atgcaattgt gaatagtgta aaatgtcaaa gtgtaactat taatttgaaa cggaggtagt  38040
atgtgtttat gcaacacttt tcctttttcc ctttttgcta tttagtaatt tatgtaaaat  38100
acttccattg acccaaaagt tgggtgatta tagtttacat ctatcattat tatttatcat  38160
tactatagat tattcaccat tgtaatcaac tttataaaag tatacacagg taactcagga  38220
gtcaggggtg ctgggccaaa cacttttata gtttaaggtg aaaaatctcg agaatcttct  38280
cctgccacgc aaaatgagtg ttcttccact ttaaagatgt tataacactt atcttaacct  38340
actattcgta aataacactt atcttaacct actattcgtc aagacatact tgcttcatct  38400
cactaagaac gtcttagttt tcatttgaaa ttcgtaccag aaagattcac ttcaaatcta  38460
tttattttta gataaattgt tattaaaaac gacgaagaaa cgtcagagga caacaaatcc  38520
tctaaactcc aaattataag tgagtccaac tatgttgacg taaggtaatt agagtatcca  38580
taaaagccct ggccgctttg gcccacaaag cagcttagaa tactacccaa ccccaaatat  38640
aatcaatcag gtgaggaagc tcgcaacaga tgcgagagtt ccactccaat caaaggcacc  38700
agaacatagc catcgacatc ttctcttctt taccccoctt gaaaccaaca gatcttaagg  38760
aagtccacta gtgaacaagg acataaccac tactcatgtg gaatgccaat cagcctctgt  38820
caaagggaag tccattagtg aacaaggaca tacccactgc tcaaggtagt catgtggaaa  38880
ttggaatccc aatcagcctt tgtcaaaagg aataagccac atcgcaatga agaaaaaggt  38940
gcaaaccaga tttattgcat ctccaacacg acataaatat cgagaatgag gcctttactg  39000
acaaaggaac tctggatttc caatttccac tgagcattgg actcagttga gaagtaattg  39060
gtcttgctag attctgttta cgcacatact cttaatgata aataaatgta acaggccaat  39120
tggtctggaa aaaaacagtt gataaaaggc tagtttgggc cttggggata aatataatct  39180
ggtatgagtt aataaatttc tgtttaaggt aaagagaatg tgttatgtgg gataatttaa  39240
tcaagaaaat cttagtaaga tggaggtagt ctaacttcca ttcctcaaaa tgtgtaattc  39300
cttataaaat cagtcagcct ctagatacat agttagcaaa aatggaaggt atagaagtgg  39360
gggtgaggga agaggaagga aagagaaccg cgatcaatca tattgttcgt gctcaagttt  39420
gagttgtgcc tatagctagt tagagtttgt ctatttcatt gtttttggtc agtgttcata  39480
ttctgagtgt catcgtgttt gggttctaga atgctccttt tcctaatgtc gacatttctc  39540
cactttactc tagaaaaatg atctcattgt agccattcca gcttcaattt taatggatac  39600
taagatccct ttcaggaaca atgttaaggt agatgttagt gttttaacag ccatgtggat  39660
gttagtgtct agaacgagtg gtcaaaacac tactagcctc aaaatattgt gatcagtctg  39720
aaaactctat gttagatggt tgcttttttt ggtaggttcg cttgttttgg ggggttagct  39780
ttgtttattt tcttcacaat ttgcccttaa acttttcaca aaatctacaa ttgaagattc  39840
ttaaatagat aacagacgtg tcagctactt caacagctaa ttgtacgaaa aagttcagct  39900
accttgaaac caaaccacta acagctagta cagtttgttt ctactattac atttatctaa  39960
tataacagct agtatttagt ccaacgatgt ataatatcaa tgaaatggaa ctaatctgta  40020
aattggacct taggcataag agtcgagttg agcaggtaca ctccaatcac caagttattt  40080
aagcttaaaa tgtctaactt ccaatgctgt ttgacgatac tcattgccaa gtgtttgtta  40140
cagatcaacc aagcaaataa agcaacaagt gaacagctgc actagtaccc aactgcgaat  40200
tttcgtcgat tgccaagtgc atgtctggga cacaatacca tcatgtccat acccattacc  40260
ttgcttagcc agctatcgta atccataaca cataaaaacc aacaaagtct tgatagtttc  40320
```

acaaatcaaa atgttcactt ttcattccaa ccaaaacaag caataaatct cttcatccat 40380
actcacaaga agaacaatct ctcacactac ccacttgatt agtaaaaacc ccaatcaaaa 40440
acaaaatcca acccacataa acaaatcaaa tttagtaact acccataaac tcaaaaacct 40500
caaatcacaa taccaataaa agagatatac aatcaatcaa aaaaaataca acaacagcta 40560
aacaaataac atcataaact aaagttattc attttatttc ctaactagag atcaattaag 40620
cagcataaaa caacatcact aattcaagtt aataatcatc aaattctata ctataaaaca 40680
tacatacctt accaaaacta cccagctgaa aattagggta gagctccaga aatcccggcg 40740
aaaaatccgg tgagaaattc agctaaattt gaaaacttct ttaggttaag tagtgtacac 40800
gatgaattga agatttttac aagcatatga aaatggtggt tgaaattgaa atgggggttt 40860
ttgaaaattg ttgcgacgcg taaaagtgga aaaaaaaaag gagagaatca aagaaatgag 40920
caagtttttg taggtgggtt tactgttgtt gcttttgttt gtgcacatta ctgactattc 40980
ttaattcttc catgcgtgtg gggtgaagg aattgttttc ctaagttgtt tagccacttc 41040
atagagtcat tggatttgaa taatctaggg aataatgatc atgtgtttag tgtatctata 41100
aattataatt tatgtatgta tattgtatat gtggtgaggc atagaggaca aggtctaaga 41160
ggaatagagg attgtgaggg agtgtttcat gcttttaaga atgatgagtc attgagtgta 41220
ttaagttata agtagtattt gatcgagtag taaagtttgt atcacgtaaa tcagagtgat 41280
aattaggaat tgggatttgc tcaagtggtg agttttccca tctttccgag caaggtttct 41340
agggttcaat tcctacctca agcatttcct tgggatttaa ggggacggct cagaggaatt 41400
cttcttacca atattttaaa aaaaaaaaaa ttaagagtgg taatttagtt cagatcctac 41460
ctttatccgg ttcgaaacga cttcaagaaa aaaaaatccg acatcgttta aaattttta 41520 cttccgactc atttaatccg cctccaactt tgaaacaagt agtcttattt cttttatgtt 41580
aagaaaattt gccaaaaaaa cccttttttaa agtccagttt tgcgaaaaaa aaaaaacctta 41640 taaagcattc tttgtgaaaa caaaccaaaa agtaaattat ttttgcaaaa tgaaacctaa 41700
tctcattttt cggttttgac catggacttt tcgacattga ccacttctat ttatcttctt 41760
cctccataat cacagcctag ccaccactac caacacctgc cgctagcccc cacaacctgc 41820
acccccacaa cctccatcca ccccctcaag cggcaacccc ccttattccc atacgcggca 41880
accctacacc ttatcctcca cccccctccg cccttacctt ttctcctctc ccttcttccc 41940
tccatcaccc ctccccactc tcttctccct ttgcccccca tcgttgcacc acccataatc 42000
cctctctgta accccctctc ctcgcagctc cccctccctc ccagccaagg ttgaaaaatt 42060
acagaggcag tcgcatatgg ggatggggga ctatcgtcta aggggtggag agagggtttg 42120
ggggctgctg gtgggggtgg ggtaggctga atgtggtggg ggctgagggt ggggggtgaa 42180
ggtggggctg caggtcgggc tggcggtatg gagaaagaag ggaaatagaa gtggttaaca 42240
ccggaaagtc catgatcaac accgaaaaat gaaattaggt ttcatcttgc aaaaataatt 42300
tattactttt tgatttgttt tcgcaaagaa tgctttataa ggttttttcg cataacattt 42360
agacttttat catccctctt agatttgaca catattatac gaattatact aaaaagactc 42420
cttatagtaa ttcgactaat gttttattaa aatgaacctt tagaataact cgggtaatat 42480

<210> SEQ ID NO 54
<211> LENGTH: 201
<212> TYPE: DNA
<213> ORGANISM: Beta vulgaris

<400> SEQUENCE: 54

```
agagcagatt ggcatacttr tgaatattct cactggctat taaattctca gaagaaaaat     60

caacaccaag attatgacat gcttgtgcaa agacacaccc agtcatgaat gcatcatagc    120

cagcttcatg cttagcccca gagttccaat ttgaggayct gcaagaaaac atgggagtaa    180

gatggtttca cataaaacat g                                              201


<210> SEQ ID NO 55
<211> LENGTH: 201
<212> TYPE: DNA
<213> ORGANISM: Beta vulgaris

<400> SEQUENCE: 55

agagcagatt ggcatacttr tgaatattct cactggctat taaattctca gaagaaaaat     60

caacaccaag attatgacat gcttgtgcaa agacacaccc ggtcatgaat gcatcatagc    120

cagcttcatg cttagcccca gagttccaat ttgaggayct gcaagaaaac atgggagtaa    180

gatggtttca cataaaacat g                                              201


<210> SEQ ID NO 56
<211> LENGTH: 201
<212> TYPE: DNA
<213> ORGANISM: Beta vulgaris

<400> SEQUENCE: 56

gggtttcttc gaagtttgat tttgttacat ttttcaaaga gaaattagtt gttgatgttg     60

aataatgatg ataagtagtt agggttcgta gtaaggtgga cgaragagaa aatggcgtca    120

ctctgayrag cttcttcatt ttgttcttct tccttagctc tgttttcagt cactgcgcca    180

ttttttttt aaaaggaaga t                                              201


<210> SEQ ID NO 57
<211> LENGTH: 201
<212> TYPE: DNA
<213> ORGANISM: Beta vulgaris

<400> SEQUENCE: 57

gggtttcttc gaagtttgat tttgttacat ttttcaaaga gaaattagtt gttgatgttg     60

aataatgatg ataagtagtt agggttcgta gtaaggtgga ggaragagaa aatggcgtca    120

ctctgayrag cttcttcatt ttgttcttct tccttagctc tgttttcagt cactgcgcca    180

ttttttttt aaaaggaaga t                                              201


<210> SEQ ID NO 58
<211> LENGTH: 134
<212> TYPE: DNA
<213> ORGANISM: Beta vulgaris

<400> SEQUENCE: 58

caagcacaaa atcaaataat gagaatcaca ctatccaaag aaaatttcca tccacattta     60

tccaacacag ttatctctct tttacaccca aattatgtca accaaaaaca staaaacaag    120

tgagtgcagt agct                                                      134


<210> SEQ ID NO 59
<211> LENGTH: 134
<212> TYPE: DNA
<213> ORGANISM: Beta vulgaris

<400> SEQUENCE: 59
```

```
caagcacaaa atcaaataat gagaatcaca ctatccaaag aaaatttcca tccacattta     60

tccaacacaa ttatctctct tttacaccca aattatgtca accaaaaaca staaaacaag    120

tgagtgcagt agct                                                      134


<210> SEQ ID NO 60
<211> LENGTH: 134
<212> TYPE: DNA
<213> ORGANISM: Beta vulgaris

<400> SEQUENCE: 60

taagtaaaaa gtggtaaaag aattaccaaa arcgcacara ataaattaat tagytggatw     60

taactattta acctattcct tttttctgtc gctataacta cttttgctta acttattgat    120

ggtttgatcg ttga                                                      134


<210> SEQ ID NO 61
<211> LENGTH: 134
<212> TYPE: DNA
<213> ORGANISM: Beta vulgaris

<400> SEQUENCE: 61

taagtaaaaa gtggtaaaag aattaccaaa arcgcacara ataaattaat tagytggatw     60

taactaatta acctattcct tttttctgtc gctataacta cttttgctta acttattgat    120

ggtttgatcg ttga                                                      134


<210> SEQ ID NO 62
<211> LENGTH: 150
<212> TYPE: DNA
<213> ORGANISM: Beta vulgaris

<400> SEQUENCE: 62

ttataatgta gagtcaaaat taatatcctt aactagtttt taagtccggg ttatatccta     60

gatatttata atattcattt attagtaaca ttttatttta taaatataat actaagcatt    120

atttggtttg ctggttaaga ctttagtgta                                     150


<210> SEQ ID NO 63
<211> LENGTH: 150
<212> TYPE: DNA
<213> ORGANISM: Beta vulgaris

<400> SEQUENCE: 63

ttataatgta gagtcaaaat taatatcctt aactagtttt taagtccggg ttatatccta     60

gatattaata atattcattt attagtaaca ttttatttta taaatataat actaagcatt    120

atttggtttg ctggttaaga ctttagtgta                                     150


<210> SEQ ID NO 64
<211> LENGTH: 201
<212> TYPE: DNA
<213> ORGANISM: Beta vulgaris

<400> SEQUENCE: 64

acatctacac tgggagactg ataaggacgt ttgcagatgt caagtatggg aatcatcatc     60

taacatgggt ggagattgtg tacaatgtta tttcattcat cgtggcaata attaccattg    120

ttgcgtttac tgtatatgcc aagagagcct tcgaagaact taagagggca gaagctaagg    180

aggatcgaga agaagaaacc t                                              201
```

<210> SEQ ID NO 65
<211> LENGTH: 201
<212> TYPE: DNA
<213> ORGANISM: Beta vulgaris

<400> SEQUENCE: 65

```
acatctacac tgggagactg ataaggacgt ttgcagatgt caagtatggg aatcatcatc     60

taacatgggt ggagattgtg tacaatgtta tttcattcat agtggcaata attaccattg    120

ttgcgtttac tgtatatgcc aagagagcct tcgaagaact taagagggca gaagctaagg    180

aggatcgaga agaagaaacc t                                              201
```

<210> SEQ ID NO 66
<211> LENGTH: 21
<212> TYPE: DNA
<213> ORGANISM: Artificial Sequence
<220> FEATURE:
<223> OTHER INFORMATION: Primer pCRBM4_S2

<400> SEQUENCE: 66

```
gtagttgaat ggtgggaatc c                                               21
```

<210> SEQ ID NO 67
<211> LENGTH: 21
<212> TYPE: DNA
<213> ORGANISM: Artificial Sequence
<220> FEATURE:
<223> OTHER INFORMATION: Primer pCRBM4_S3

<400> SEQUENCE: 67

```
caatattgcc cttactttat c                                               21
```

<210> SEQ ID NO 68
<211> LENGTH: 20
<212> TYPE: DNA
<213> ORGANISM: Artificial Sequence
<220> FEATURE:
<223> OTHER INFORMATION: Primer pSeq_LbCpf1_F4

<400> SEQUENCE: 68

```
accactcact cctcgataag                                                 20
```

<210> SEQ ID NO 69
<211> LENGTH: 22
<212> TYPE: DNA
<213> ORGANISM: Artificial Sequence
<220> FEATURE:
<223> OTHER INFORMATION: SEQ 70: pSeq_LbCpf1_R3

<400> SEQUENCE: 69

```
tagacctgct tctcaacctt ca                                              22
```

<210> SEQ ID NO 70
<211> LENGTH: 21
<212> TYPE: DNA
<213> ORGANISM: Artificial Sequence
<220> FEATURE:
<223> OTHER INFORMATION: Primer pSeq_Ribozyme_F

<400> SEQUENCE: 70

```
tgcagcggat ccaaattact g                                               21
```

<210> SEQ ID NO 71
<211> LENGTH: 18
<212> TYPE: DNA

<213> ORGANISM: Artificial Sequence
<220> FEATURE:
<223> OTHER INFORMATION: Primer pSeq_Ribozyme_R

<400> SEQUENCE: 71
cctggtccca ttcgccat 18

<210> SEQ ID NO 72
<211> LENGTH: 20
<212> TYPE: DNA
<213> ORGANISM: Artificial Sequence
<220> FEATURE:
<223> OTHER INFORMATION: Primer pSeq_tDT_F

<400> SEQUENCE: 72
ttacaagaag ctgtccttcc 20

<210> SEQ ID NO 73
<211> LENGTH: 20
<212> TYPE: DNA
<213> ORGANISM: Artificial Sequence
<220> FEATURE:
<223> OTHER INFORMATION: Primer pSeq_tDT_R

<400> SEQUENCE: 73
gtactgttcc acgatggtgt 20

<210> SEQ ID NO 74
<211> LENGTH: 19956
<212> TYPE: DNA
<213> ORGANISM: Beta vulgaris

<400> SEQUENCE: 74
aaatgataca ggggtatatt tgactctatg aatttcagaa atctaatcaa atttgctaag 60
cttccaatga ttctactaag ccctacaaat tacaagaatt agttactttc atctctctgt 120
cggcttcaga accagaagtg tacaatatct tgtcaaacaa actctgctta gaggagctct 180
ttcgatcatc ttttttcgat ttggaagttc ccggtgatag gattgacatt gctgttttct 240
cggtcaattc ttctggatct tggttctgtc catctatctc tggctccatt aatctggtct 300
tccaattaat tccgatagcc tcagcttgct ctgcaaacaa gacctttgag atcggggagc 360
tgcagatatc cttataaact tcataaccag cagcacaggt tttcccacct tccaacaact 420
ttgataaagg atgtaggaga gagatagaat catcactcgt ttctaaccta tccttcaagg 480
caaggaagtt aacagccaag tctgccttac taaactgaac aaatactgca gtttcatcca 540
agttatagat gcaagcaact gagtatatac caaacacttt acagatgcat tgttttatgt 600
cacttgcctt gagttttggg gagaatcccc aaatcaaaac tatgttagga tgcaaaatgt 660
taagaaacct ccttttagct gaactgataa cgggaatttc attcatatca ccagtgctta 720
gattgatcac atctccactg ttccaactaa gatagagcag attggcatac ttgtgaatat 780
tctcactggc tattaaattc tcagaagaaa aatcaacacc aagattatga catgcttgtg 840
caaagacaca cccggtcatg aatgcatcat agccagcttc atgcttagcc ccagagttcc 900
aatttgagga cctgcaagaa aacatgggag taagatggtt tcacataaaa catgtgtaga 960
agtgcagtga acactggcga aaacaatcta attttacgaa ttcattcact cactcagctt 1020
caaattaagt ttccccttta tttagggtgc cccaaaaaga tacactcttc tgtttacctt 1080
ctctctccaa gcgaccaatc ttttctctct tctccaacat cgttttcttt ttctctctct 1140
acccactatc cattttgtcc tcctacattt gataactatt cttaatctcc aagaaaatcc 1200

```
aatgtgtgaa ataattacgg gacagggagt atacagaagc agccccccttg ccaatatagt   1260
ttacaaatta ccctcagaat taggcttacc tttcccaaag gagcaataaa ttcaaacaaa   1320
tctaaaaggt acaaggcatt aagtgccgaa cctcatgtca tcaacctgga cctccacctt   1380
cacacatgga tgtacaccac cattagagga ttgtccagag gctatctcag ggcacaacag   1440
agaaaatgct gaggccaatg acgtgctggc tttattcaag aatttttgaa ggctcgtgtc   1500
tgcattcaaa agtattttcg tgtcgacaac atgaggaaaa tacttgtgga tctcgagaac   1560
aaactcttca acagttgatg gaagaggacc aaagaattta tggtaaatat gtgccatatc   1620
tgcaaaaaat tataatggat aagatgacaa gaaaagatac taggaaggcc ttcaagtaca   1680
aatattatat catgatgctg gacgaccgat gctcccacaa ttatgtttgt taccaaatgc   1740
ttcgaaggat aattactaaa ttatgtgaat ggtggttacc aagtgtcccg gaccatgcaa   1800
taacttctcc tttcagtgac caacaagaag aagacgtacc taaaaagcaa ttgtgaccta   1860
caattagctt cttttcagca gcgagaaggt caaggacatg ccggaaacct gcagctgctt   1920
ttattttgcg agttgcttgc tggtgagacc catacttcac ctcctcctac aagaacaaac   1980
agaacaatca cacatgcaga aagttcccca cataccaagt tgctgtctgc taaacactga   2040
aactaactta tctctacaaa caatgaagga agttcctcac cagaaggttg atcttatcat   2100
tgtcagattc tacaaaaaca ataagcttct gcaagatggc actgccgtca tgagcacaca   2160
caaaaacaag atccttgaag tgcttccttg taacctgtaa ttgcagatca ttagtatata   2220
ttcaagatgt tataaattta ttgaaaagca gcgtctaaaa caataaaagt catgcttaag   2280
gcatagagcg atagagcata gacacttcag agtttaataa gagcaaatac tccaggagaa   2340
cataaatata tttcatatca caaatcctag taccaactgg caacggctaa ctgccaattt   2400
atgtactgct caaaaaggcc aagcatctaa aagatggctt aaaagtcgga ttttataaga   2460
aagtcgtcac atgattgcta ttacattgac atatcaaagg tcaaatgctg aaatttggtt   2520
cagcttgata tatattaagc atacaaacga tacgttgaca agaaagccta acaagacatg   2580
aagcatcagg cacataacat tcaaaagatt accaattcaa tcaacttcag ctgatgagaa   2640
gtaaatccat tcaatcgaag agcaggacgc atactaaaaa atatggtttc aaattgttgt   2700
ttagattcaa cagcacttgg aagctcggca tttctgttct gtagcaacat atcatgccaa   2760
tcactgagcc gaattttcat ccgttcggag aataaaaatat cagctacatt gcccaaaggt   2820
aaatctctaa cttcattaga atatgcccat ttcccgttat atactgaatt caagcgactc   2880
aaagcctcgt cttcctgtcg tctagataaa taagacacgc ctgagattat acaatgtgta   2940
aatttaccac aataatgaca tcatactgac aaaatctcaa acaaatagtt ctaataaagt   3000
catgttatct gaaatttcta tgaataggaa attgaacaaa accttcatgc ttttttccaa   3060
ctaaaattga catcttctac attaccttca tgtatgcatg cattgaagtc aaactggtat   3120
tttgccaaga agtcaatcga agttgtttgg cacaggaatt catatgatgg gccatcagtg   3180
ggaagctctt gacgtggaaa tatataaaaa ttatgcctga caatgaacca ttgtaaaatt   3240
attagatgga gtatctctat ttattgttta cagccaattg agcttttaac aattactata   3300
ggtagtgttt ggaaacttgt atttcatttc aaataatgga attgaaatct ggaatttaaa   3360
gtttgtattt caattcctaa tcactgtttt gtaaaggggg tttgatagaa gagagagaaa   3420
tagaggttta atggaggaga gagaaaaagt gtgggtttac taaaaaaaag agaaataaat   3480
attagaaagt gtgggtttac tcatagagtt gggatatgta tgaggagaga attttcaaat   3540
```

```
gccaaggtaa tagcttgaat gacaaattta ataatttcaa attccatgtc atccaaacaa   3600
tagatttcat ccaaatccaa gatttgaaat gaaatcttgc tatccaaaca tatcataaat   3660
taattagtaa tttagacttg ctttctgctg cacttactta tggaaataat tttacttcag   3720
tccttaaata acccgcaatt tacatcaaag gcactaatat aaacacctag ttacgaaatg   3780
gaaatatcag atatacctgt aaaagtaaag aaacaaaaat acaaccctga gcatgaaggt   3840
atccttcaaa agtgcaatat ctgcatactt agaaccggaa ttagaagtgc gaatgcagac   3900
aataaccatc ccaggatcag aaacgtccaa gaaagttgag attcatcatc cattctcttt   3960
agcaaattta tgaactctaa tatataaatc ataccccccc ccccatccaa aagcaattgt   4020
caagctgcct gaacccctca taatttagga tacaacaaag taatcctaaa agacccttta   4080
caatactagt actcgggtat ttccacaatc ttctcatcat tgaatccaaa gcattgcatt   4140
tgaagaaatc aaatcataat ccattactat attagagcaa aatctatgtc attatagtat   4200
tggagagcaa gtatgactat taccccttta cactaggcaa aacacattgt cacaatgcta   4260
acttagtcat taaccaatat caatatggga ctgtggatat tcataaaatc gaagtttttc   4320
gcttgctcat aaactatctt tcattccagc acagtacaag agagaaaaga cagcattttc   4380
atacacttct ttctttagtt caaattcaca cagcagcaaa aaattcactt cttcatagct   4440
ttagctcagc aaacaaagca caaagcatgc aattactctc acacatagca caccaaaaaa   4500
acaaaaacca ctaaaaattc acacaaaaaa aaccaacaaa aattccatcg caatttcaac   4560
aatcaaaaca atcttctaag ttaaaaagag agataaagat gagaagaaaa actaacggat   4620
gagcaacgaa ggaattcttc gaagaatccc atcgaaatgg acaaacacca aattgaacaa   4680
cggcgaattt ctcagcagaa tctttcattt taaggtatcg aacatcgtgc cgatcaaact   4740
cgaacgattc gcgccaaggt gagcttgtaa ttccagtcat ttcgagatca atggcgacaa   4800
aatcggcaga ttttacatgc gtagtgaggt caattagggt ttcttcgaag tttgattttg   4860
ttacattttt caaagagaaa ttagttgttg atgttgaata atgatgataa gtagttaggg   4920
ttcgtagtaa ggtggaggaa agagaaaatg gcgtcactct gacaagcttc ttcattttgt   4980
tcttcttcct tagctctgtt ttcagtcact gcgccatttt tttaaaaaaa aggaagatga   5040
acaaagcaaa tattgaaccc aaattttgta attttggccc actttatatg taccccctccg   5100
tttcaaaata tggagcacgc cgcacacacg acatttaggg tcgaattttg aacattcttc   5160
aagatgatct aatggtataa tctctataat ttatatgtgg catattataa taagagtttt   5220
atgaagtcaa aaagtggatg tcatatattt aatgcatggt aagtttttcc taaatctgta   5280
tactagggta acatacatat gttgacttga agtatatata attcttgtag tataaatatg   5340
gctttggcca taagtagtaa tacacaacaa ctagaaaaat tgaaatcagt ccactgttat   5400
cttgtactct ataattttct gtttcctttt gtttcgcaac aaagacatat ttgtggtgaa   5460
agataatttt cgtaaattga atgacttata ttttgaaata aagagagtat taggtaaggt   5520
tacgtgcttt tcgcttgaat ttgttagacc tcaaatgtat atgtgattag aacggattgg   5580
ctctagtttt tattttatag aagtatatat gcatttttct tagagcacac tcgaaattac   5640
tttcggatag atatattcgg gaaaaaaaga ggttgaaggg aagttcatca ataattatgg   5700
taaaggaaaa aggacatcgt tacaattcta aattctagat aggatgtgat gataatccaa   5760
aagtcatctg aaaaactaaa caagtccaag atgctaatga ttcgagtaga gattgaatga   5820
gtgaccctaa ggattgtcaa ccctcttatt ctaacgtgtg taaaagaatt gacaactcta   5880
agagttactc aaacattttt cgattcgagt ggttaatata ccaatttgaa actattgaca   5940
```

```
ggagttattt taatgagtat aatggtcaat ggagcactga attccatctc acatagtcac   6000
atatttcatc tcaagttctg atgatttcaa acattgaaaa aagatgatac aagcaattaa   6060
ttcctaggga aacatattgt ggttttcatg gatacaagag tgagaataaa tcaaaactta   6120
ggctctaaca tttcttttct ctactagtaa ttgctaatta tatcaattca attgtcagtg   6180
taatcagtta atcaccaaat ctcttgtata gtcagtaaac tatacactgt ttagtcctct   6240
ggattttgcc cggtcgaatt atgcagcata accaaacttt gaagtttagt acttcctttg   6300
cacccaagtt agcttcacgg cccctgcctt ctggtggatg gtcaccctat gctttgagca   6360
ttctctgcaa tgcgcacgat attcaatgag aacgtcgcct tgaaaatcta aattgcaact   6420
aaaaattaga ttgaaatgaa acccacaaga gttgtttttc tgagtagttg gtgtagaatt   6480
cacaagtctt gctccattgt ttgaagatat gaagacaata atgtgctatg taaagtgcag   6540
ccgctagcta acagtggaag tggaaacttg atcattttac actcgcacaa gcgaaagctc   6600
ggctgacgtt gcaaactgaa gaaaaacctc tcaaaccaat tcgacttttg ctcaaagttg   6660
caaactaaag aaaaaggctg aatgcaaagc aagttcacca atgaacaata gatcggtgtt   6720
ggcctgaggc cacatcaagt gaagttgcct aattgcggcc ctctcatctg ttcacaggaa   6780
tcattttcca tatagaatca ctccaaaata aaagagcaaa gctgcaccag atgcagaagc   6840
ataactttca agacaactga tgacagataa atagcaaaag aatgcttaag aaatgatcaa   6900
aattgaatgg ctctggaatt acctcatcag ctgattttcc tttctctcta tctctctatc   6960
tctttactcg tctatggagc taccacatca catggcgttt catatgcttt ctgccgtcga   7020
actagacgtg cagcaaaagc tccatccatt gaatgcttca ctgggcatga gcgataaaac   7080
ccatcttcag ttaaaaagtc agatggaaca tatctgctta cagaatctct ttggaagtcc   7140
tatcacccaa caaagaatat attaaaatag agaaggagaa aagaacgtat ctatctgtca   7200
gcatccatat gaggtggaaa ctaggagtac tatataaagc cagtgcagta gctcctaccg   7260
gatgtctaag aaggaaggca gaaaccctat cttcgttttc ttcaagatca atggagcagg   7320
tactgtacac aagcacgcca tctggtttga ccagcctgta gatgttaaac aatcccacag   7380
acaaaaggga ataatatgag tgaaacaagt caacaggggg aaataaccaa taattctagg   7440
actgtcaaac tcaagctctt caaaaacaaa gatagctctt aatctcactt gcaagcagca   7500
tcgaacagct cgtcctgcaa cttctttagc tcttccatat cctctgactt tctattccaa   7560
cgcaaatccg gcctcttcag caaaaatata aagttggaac aaggctctta gatacaagaa   7620
ctgaaaaacc ttcgacatat aatggactct atcaagggca caatgacaaa ttctaaacat   7680
gagcatgtat atcaataaaa tactaagaac cctttcaatg gtactgctag aaggtttatt   7740
gctacacttt ttagtacacc atctataggt tttatagtac catcaaaatg gttcatggtg   7800
ccataagaaa attttatgta tttatggtac tatctaccat atctaatttt ctctgtaaaa   7860
atgtatttgt agatagagac cacgagttcc tcttttagat actgactttt tttttctac    7920
atgatggcca acagacttct caaacaaaaa gaaaaagaaa atatttagat aatatgagca   7980
acaaaatagc aaccacctac ttttgatagt acacccaggc ccgaacaagg aacatctaaa   8040
agaactttat caaacttcga agtgttgctg tcctgaaaag aatagaaagt aactgcttca   8100
acaaagaaga agaggcagaa agcaaagcta gtacgcattt tgcaatgact tactgaaaag   8160
gagcgaagat cagcatggat gcaagtgatc acattatcaa cacgctgcag cttggctgtt   8220
tcttcaagta tccgtaaccg acctttattt atgtccattg ctgatatcat acctgaaaag   8280
```

```
ctacacattt agaatgcaga accagcatca ttggtagtta agttatcact ataccttggc   8340
cattcaagcg agatgccatg aagagtgtct tccctccagg agcagcacag caatcaatga   8400
tgtgatcacc aggctgtgga tccagaacag aaacagctag acctgcagcg aagtatagat   8460
gtaaacttgg gttgggctgt cacatttttt cacatcttat cttcctttct attctttcaa   8520
aactgaggag aaatggttgg gatttctata aacgtgagaa aaatggcatc agattagatg   8580
gttttactgc atgaaaaaaa ttgaatgtgt ttcggcatca cattactaca aggtcaaaag   8640
cactatcttt gaaaatgtag gacataatgg gacagagatg tgctgacctg cactctcatc   8700
ctggactgag cataaacctt cttttagaag tccagtttgt atcacaatct aggatatgag   8760
aaaacaactc aagatgtaat tgctcctaag atatcaatca tttcataata aacataaaag   8820
ttattattac aagacagcac ctgcatccca cttctgatgc agacaaagtc atccaaatgc   8880
aaggaaggct catgcgggac ctgcggacaa agtgttgtga tgcgcataga tatcgaaaga   8940
aggccctgta tagcactaat gagataagat tcagtaacct tcagcatgtt gagcttcaca   9000
acaaggtcat ctcgagttaa tccttttgca atattggccc tagtaccaag aaaaccatat   9060
gtattaacaa gagaaaagtg gcatagggat ctttatgact taggtaagca gttggcaatt   9120
agagagaata aaacccccaa acctcaagct gaaactcgga acactattgt tccacatcat   9180
caatttgata gctccttctt gcccaagata cttggtccac cgtcttacca tccactgaaa   9240
ggaaggtatt aaaagggaga aaagactcgt cagcatagaa aattgtacat cttaaatttt   9300
agaagtatag caccatcttc aggcatcagt caacgtaaat aaataccaca tctacaaata   9360
gaaccatact ttctggacag tcgggatcat gagcacagac aatactgcat gattattgcc   9420
tcgtattctc atgtatacaa gtatatgtaa cattaaatag cagtatttct tgagaaactc   9480
accacgggat gggaataagt tgtagcaagg gcacgtgctt gtgaacgatc atcaccctcc   9540
aatttgggta caggaaggga gtcattatcc tataaagaga aacagctttt gttttcaacc   9600
atatcaagac aaacagttta ttaaactata aacaacaaca atacacatgc acacacctac   9660
tgggaacaag atatatacta ctgataagta ttttctgatt gaagaaaaaa aatctcattt   9720
atttgcaaat atagatttaa tgacaagaaa gctttgaacc ttaaggaaaa ctagctttcg   9780
gaggatccca ttcaccatgt ttcctgcgcc tggtctaaga gcatacttgg caagattcac   9840
attctgcaat ataatccaac agtaagaaca cgacatggat ttagactcaa gtctctgaac   9900
ctatagaaca agtaaaatta gatcttatct catttgacaa tttaaaatta gatagtgcaa   9960
tattctgcag ttataagact tcatgtgtgc atactgcaca agtcatctta aaggtgttat  10020
taaagcttta attgccattt gacatcccct tgctcaactt tagcatgttt ttaggctaca  10080
acaatacgca ctgtctacat ggacatacaa attacaagcg tatggaaaag caataagcgc  10140
aaggaagtct tcagccagaa actctctatg agtccaacaa tatgcaacta aatatccaag  10200
taccgtgaat gagtaagaac taacctcgtc aacaacagca tatggtggca tttccagttt  10260
cacaatctca tagcatccaa tcctgaggat ctaaaattaa agataaatca atacacaaca  10320
tatgatatgg gtcggagcgt atataacaag tatagcaact acatttgaac agataacagc  10380
ctttgagaca ataaggaact ccgacattcc agtatatgcc agatttcata tctttagctc  10440
taaattgcca cgcaaaatgt tattgggcaa tatacctgta gcaggagagg ttccatgttc  10500
ctaaaggagc tttcatcatg gcatgaagaa acaataagat aatccagata ttttctccaa  10560
cgaattgaac caccaacaat gtcagtgacc tacaaagaca agttgtcaac ttaaaacttt  10620
tgaagcgtca tttcacttct gtagaccaat acaaaagcta ctactgcttt acatcataaa  10680
```

```
acctttagtc cttaggttca tctgattggc aaaaaaggtc cagatgcaag aaaagcaagt  10740
agctgtaatg ctgtattata tcagcattat tcagaacaga ataataaata tctacagatt  10800
ttgggtggaa gcttgatgat agagtatctc cacaaagaga actcgcttga gtcccaactc  10860
ccaaatctac tttttggag tcacattatc agtcattttt tctggactct tataggaata  10920
gtgtgctatg taatgattta tggagcaggg gcatttcatg aatagcttta taagttagta  10980
tgggtgtctt ggggaataag ttaaagggtt agttagaggg aagaagtaca acatatatat  11040
agagcttttg taagaagggt ggttatgttg aaaatagatg agaaattggg tgagctcata  11100
gtagttcaat ttggactttg ggagagaatt aagcctcttg aaagcttgaa tatcatttac  11160
atttgttgtt tttactctta ttaatcaacc aaagttcatt ttcttccttt aatttctcca  11220
ttttagcact atgatttgtc caagctaagt gatttcttag catagtgcac agtgtagtat  11280
atcggagaac tcatttgagt cctgaaaggt cccacaagtt acatttttcc tactactact  11340
tgcaccaaaa caataagcat cattaagaca ttgtcactgg tccttcttag gttcttttgg  11400
aggggattcc tcagatgggg gaggcaccca tgaaggaaca tgttaccaag caatgggaca  11460
atgcaaaatg caccaataca gtagcttcac ttcattgatt gcatctatgt cacggaaaac  11520
tgaagaaaga agcaacacct caactttatc caggacagat atccactaac ctaggatgca  11580
agcttgagac tatttagcaa ttgcctctgg gatattaaat cagattacga ctatatttct  11640
acagttattg cttaagaaaa aggtacgatt tgaagcttgg gaagaaagag aacaagagta  11700
aaagaccaat ctgagatctc tttcatccag gtctctggtg cgaaatccaa gagtcctctc  11760
aacatattcc atctcattgt tccctgaacc ctttcctctc tcatttagaa gatcagcgaa  11820
ggcaccacca aactctatcc gcatcaatct cacagcagcc actggattta cacatgaaag  11880
caaaccagga gaaccataaa aatcacaaca aacttcctga tagcctactc actagcatca  11940
accattgtgt tcagcctaaa atgagcggct gttttcaatt gaacagcaac ttacatggac  12000
cactgcataa aagtgatttc ttaatccaga caaacaaaaa tgtttacttc aaccaactga  12060
atttgcatca gctcattagt gatttgacaa gttctaattt atgtatcaac aaacaagacc  12120
atatagctag gaaacaagag gcttaggcta agcttaatgc gtgaacaatg ttagatttca  12180
acctatcagc actgtggata actgcaaact gcgacttaaa taaggaagat aaaggaactg  12240
aatatgcaat ttcaaggtgc tcagcatttg aatcaacagt tacttcagat aattcagaac  12300
ataaaagatt tgaacattct aaggctacct catgattgca agcaatgtta cctgattcgc  12360
taaccctcac aagccacaag ccaaagaagc aatttggtaa atggttcatg gtacaactgt  12420
tcgcttttgg actaatctaa caatactagg tggtaaatta tgttcccata tctattacca  12480
taatgtacag caaattaggc agcactaatt ccaaatgacc caacaaaaaa agaggaagaa  12540
aatccaaaaa ttcaagccaa catatgcact aaaattacaa gcacaaaatc aaataatgag  12600
aatcacacta tccaaagaaa atttccatcc acatttatcc aacacaatta tctctctttt  12660
acacccaaat tatgtcaacc aaaaacacta aaacaagtga gtgcagtagc ttcacatcaa  12720
agaatatcaa tcacaaacac cacataataa aatttcaact cctgcccaaa caaaaaaaat  12780
ataaagaaaa aaaaacagca aaatttcaaa gataaaatag aaaaaaaaaa atcaaaatac  12840
agggggaaaa aaagtaaatt taccagctct atgaggcgaa acctgcaaat tcagcttctg  12900
ggttttctct gaaatatcaa gcacaataac cagcaattaa aaaaaattat aaataaaatt  12960
aaaaagaaaa gattgataat taaaatcaaa agagagcaat ttaaagcaca atccttttt  13020
```

```
taccattttt tctgggagga agagcatcct tcgttttggg tttagacgaa aaaaatgaga  13080
gttgttgtat ttgtgcgcat gagtgatcat tgctggaaat gaaagtggga aagtggtaaa  13140
tgagtgcttt gtgaaattgg gttttgagga aaagtagaaa gaagaagaag ggtcgatgtc  13200
agagaagaga gagagtggat ggaaagtagt gatgattgcc tccattgttg ccggtgaagt  13260
gagctttctg caaatatttc actggactag tttttttag cagataacgc taaaacagag  13320
aaagatgttc ggttaatttt aatttttgga catttaaatg actattcaat atgtttcaac  13380
cttttttttt taaaacaaag gaacaatact agtattagat tacgttaatg tttagtacat  13440
ccaatactta tgtgtgtttg acctaactta aaatcgtaag ttgtttaaaa tgtcggtgtc  13500
ttgtttttaa gagatatcat acttactatc tttggttttt actcttccat tgttaacaga  13560
aactgtattt atttgggtaa ggggtttgag tgaattcctg taagtatgag aaagttttga  13620
gtgaagcaag agaaagagag aagaaaggaa cttcgagtga agattgagag aaacaacagt  13680
tagtgggaac tgttgttggg aacttgagtt taggagctca ggttgtaccc cgagagaatt  13740
aataggtttg taacagagtc ggtggcctat tatagtggaa agtttgagtc aaaatccatt  13800
gtggccgatg tcgtttcttc ttattgggcc taggaagttt ttcctcgcta aaatttcctg  13860
tgttcccatt gtgtgttcct tagctagctt tcaattccgc aaaaagttac gtttattctc  13920
tcactataat tcaccccccct cttatagtgc tcatattata caacaattga tatcaaagca  13980
ggaactctaa aaatacagaa atcatgttga gttcaagatc ttggaaaata tgaatactac  14040
agaaaaactg gaagaaaggt actctactca gagaccaccg atgttcaatg gcaaattcta  14100
cacaaactgg aagaactgaa tgaagatctt catcaaagcc gacaaatatc aggtttgtag  14160
aatcatagag gcaggcgatt ttgaagtcac taccactaat gacacatatg aggtaattcc  14220
taaattcata actcatttcg ataaagtata tttcgaaaag ttggaaatta acgttcttgc  14280
tattaaactg cttcattgtg gtcttagacc tcatgaacac aatcatgtca tgggatgcaa  14340
aatcgcaaaa caaatttggg atcttcttga agtcactcat gaaggtacgg gtaaagttaa  14400
gagatcaaaa atcgatcttt taatgaatca atatgaactt tttcaaatga aatataagga  14460
gtccactcaa gagatgttta cacgctttac taatactatt aatgagctaa cctctcttgg  14520
aaaagaaatt acatatgatg aacaggtaag aaaggtccca aggatcgttg gatggctaag  14580
gttacgcctt acaaaaaact aaggacttta cgaagttcaa tccggaacaa cttactggct  14640
cccttatgac tcacgagcta cacttggaca ctgagaatgg tgacttgtcc aaacagaagt  14700
cgattgcctt gaaagccatt tttgtcatac cgtcaattaa ttaagtaaaa agtggtaaaa  14760
gaattaccaa aaacgcacaa aataaattaa ttagttggat ataactaatt aacctattcc  14820
ttttttctgt cgctataact acttttgctt aacttattga tggtttgatc gttgaatcca  14880
agttttctcc acccacaaag atattataga ctttacttta aaaggtacga taaataatgt  14940
ttaatcaggt atgcatcaac cttgaaatta ttaatttatt aagatcaaat tatgcatatt  15000
tatattaaac gtacaggact tgtgcacaat ccatggatga tattgtagat tttgttgtaa  15060
aggagttagg gacaaatgat gttgaattaa gaatgatgag gaacaacatt gaggtaccta  15120
atggcataca agattatgtg gtaacaaagg tgaagaagtt ggttgtacca ggcaatacag  15180
cagcggcaag ccatatatag gatgagctac catacccta tgttgtgaac tattgtcacc  15240
accaacaaga cattggtcat tacgacatca ctttagttga ggaatgataa acctcttttt  15300
gctagatatt tgcaaacatc tagcagataa agaggaataa aacactattt atatttcatg  15360
aacactattt gttagttgca tgaacactat ttttagttac acgaacacta gttttagtag  15420
```

```
catcatgaac actatttttt agcatcggaa ttttcacgac tactttttgg tttgactgac  15480
actctgcaat tttcgagata actttttggt gatatgggtc ccatgaaata gaagatttat  15540
atttcatgaa cactatttgt tagttgcatg aacaatattt ttagttacac gaacactagt  15600
tttagtagca tgaacactat tttttagcat cggaatcttt gcgactactt tttggtttga  15660
ctgacacttt gcaattttcg agataacttt tttgtttgac tgacaactat ttcctatata  15720
tattgacagt tttacccctg ttagatgttt gcaaacatct agcaaaaaga ggtttatcat  15780
tcctccactt tagttagccc aacctccagt aacgccatcc agaccactgt cgtttgtcac  15840
tacgacactt acgcttggca accctatgtc ctagcccttc gatacctcga tatccgtccg  15900
ggcaatgtcc ccagtttgtc acttctctgc cattaatgac atattttgga gtatcaaacc  15960
caactccaag tatatatcgc aacatggctc agtaaagaga gtcatataat catgacgtag  16020
tttctatatg ccatcctacg tagtatcttg taacatgaat aacagcctgg tttgcaggtt  16080
gatggtacat ggtataaatt ggtattactc cctccggtct ttattagttt aatcctttct  16140
tttgtacaga gttataggag aaataatatt gtgggtcata gaaggaaaga gaaattatta  16200
ttttatgtta aagttgaatg tatgtgtgat gaaaagttag tagtcccatt tcaaaataga  16260
aaaaaaaaag gtaaactaat aagggacatc ccaaaaagga atacgggtaa actaataaat  16320
atccatgcag gttgttggta catggtacat gaagccgtcc aaaaccttca aaagcagtaa  16380
gtcctgctgc tatgccatat tcaaatattc aactccaaaa aaaaaaaaaa aaaaaatcaa  16440
aaatccgctt ttcagcgaaa atataggaaa taatccaaga atcgaaatcg aaataaagtc  16500
atgatgcaag tttggagagc tgaagttaca ctatatcgga gtacttactc aaatgttgat  16560
tagtactccg tgcgtttgaa gtaaagtcac atatggagta gttccaagct aggttgtaca  16620
gtgacggata aggatactgg gttgaaaagg tgaacgtcga gatttatacg tgtatttatt  16680
taaacaggat acgtatcata ttgggttctc atacgcgtac cagctgtgac ttagaaaaat  16740
taaccacgct atataggttc caagccctca tgattacctt ttcatagtgt aaatttcatg  16800
tagttgaatg gtgggaatcc aatcacaaaa acactgcagg taatggaaat gttccaactt  16860
tttccaagca ttttaaaata agacatgtga ttactaatta gggcgtgttc ggcaacagta  16920
attgtggtga tagtttttag ctgtgagagt agttgttagc tgtgctatta gcttttagtg  16980
gttggtgtgt agctgttagc tgttagatgt ccaagtagcg gtgtaaaata ttgatgttcg  17040
gtaaaagaag ctgtcaaagt agctgtctaa gaataactag ttaaaaattc aaataaaact  17100
ttaacatata atttatacac cactaaaagc tacccaaaag ctacaaattg tagcttttga  17160
caaacactac taaaacacta cttgtaccac taaaagctac ttacaccact atcttgccaa  17220
acactcttat tttttctaat tagtgttttg acctagtcaa gacactaaaa gctacttaaa  17280
aagcttgtgc cgaacatgcc aattctgaac caaggaacaa actataacaa aaaagtgcta  17340
tgtgaaactt ttgtaggcaa cagaagtaag gcatttttgg aatgtactaa caaatccgta  17400
ttaagacttg tacatgaaaa ttaccgtggt aacatttacc cacacttcct cattcacgta  17460
ctccgattca ttcttataag ggcataaccg cataaggcac atcaagatcc atgtatctaa  17520
tagtttaatt tgcctctgtg tttctgtatt aacaatgagc atagtgagtg caaaagccat  17580
ggaagctaga ttaaaaaggc catcattcta agttagacaa ttggaaacaa catcgagata  17640
cacgtacaca taagggctgc tcttctctat tactccctct gttcctaatc atttgctttt  17700
ttagcgggtt ccaaaggcct atgtttgacc actaatatat ttaaattaaa actggtgata  17760
```

```
tatattaaaa gaaaattatg atgaatttaa caaaaaccat atatgttatg tccttttttt  17820

tcctatatta atgaattttt acagtcaaag ttggtgaact ttgacccaaa aaaagaaatg  17880

gagcaaaaaa aaaaaaaaaa aaaaaaaact agggacaatg agtaacattt ttatctatgt  17940

ctttttaata tgaatatacg taacaaattc tgcaaaaata gagatagcaa ctaataacac  18000

gcatgaaaat gacaagttat attatacctt tttttctcaa tatatgaata tacgtaacaa  18060

attaactcca gtagttttta gtaaaactat tagattattg tgtaacatat actctggaaa  18120

tagtactaag atccattaca atctttattg agaaatttcc tcatgtaccc cctgaggttt  18180

ggcgtaattt ccaaataccc ctcatatttg aggaatttct caaataccct gatgtttttg  18240

tttagactca aaataccttt actatggaca gtaccctaat gtcattaagt tttccccttc  18300

tctctcccca attttctctc tcctcccatt cccccaccca ctacccactg cccactgcca  18360

agtaggggtg taagtggatt ggactggatt ggactttgcc aaattcaaat ccagtccaaa  18420

gtttttttgga ctcgagaaat tgagtccaag tccgatccaa atattttttg agtccagtcc  18480

aatctagtcc gataattttt tcttgagtcc gaatccagtc cagtccagtc cgattattat  18540

atcttttttc ccgatttagg ttcaatgatt cacaacattt tttgagatgc ttgagcattt  18600

gacatctgat tcaattatca atatccacaa ataagattga aagcttaaat taaagtaaaa  18660

tactatgaat aaaaagttga attagatgct taccttgatc taagttgaga ggaagcatag  18720

agactgagaa ttaatctgag ggacaaatag agaatgcgag agtcgagaca gtgaggtaga  18780

aagaaaatga agagtaagag gaagtgagta ttaaggactg aggagtaaag taagatagaa  18840

ttagttggct actagcctac taatgcagta ttgctagtat aatttactta tttaacaaat  18900

ggagctaagt gcaatagttt agcgccaatt gacatattta gagagagaag gctgaaaaat  18960

ccaatatttt taaaatagta tcattatttt taatatatac attatatata aaaatatttt  19020

tggactggac tggacatatt ggactccaaa gggatgagtc caaatccaga caaaaaaatat  19080

ttggacttga aaatttaagt ccgagtccag tccgaaaaat tttcagtcca atccagtccg  19140

acaaatttgg actggactgg attggactct gaacttttcg tagtccgctt acacccctac  19200

tgccaagtgc caaactgcca accccctttt ggttgagttg atatttgacg caaagacttg  19260

gcgtgttgga aggttcatta cacattttat ccaagtcaac tttgaagtct tcttagctag  19320

agactagagt gaacgtgttg gaaggttcat tacacatttt atccaatcaa actttgaagt  19380

cttcttagct agagactaga gtgaacgtgt tggaaggttc atgttcatga cattataaaa  19440

gtaataatag tgaaatttca caaagtattt ataaacccag gacagactca agagctctac  19500

ttattattag tgaaaaacaa acatacacac gacaataaca caacataaac aataatgaac  19560

atgaaaatcc tccttttgtt tgtcttcctt catcacctcc actacttcat ccatggcaga  19620

acacttacag aacgccaagc tttactaagt atcaaatctg ccattactta tgattattat  19680

aactctctct cctcatggaa aaacacaaca caccactgca gttggccata catcacttgc  19740

tcctcctctt cttcttcttc ttctgttatt tctctcaact tcaccatgtt atttctcgaa  19800

ggaattctct cccctgatat aggcttcctc accaacctgc aaaacctctc tattcgatct  19860

aacctttttt ctggcccact cccccattct ctctctctcc tcacccaact ccgctatctc  19920

gacgtttccc aaaacagttt cacaggtcca atccca                            19956
```

<210> SEQ ID NO 75
<211> LENGTH: 19206
<212> TYPE: DNA
<213> ORGANISM: Beta vulgaris

<400> SEQUENCE: 75

```
ccaacaattt gttagccgat gaagagcatc aaaaccaaaa aaaacaaaaa aaattgatta     60
atatgcatga gtgtgacctt gttttccaaa gtttagcatt actattagtg tctcaattca    120
taataataaa aaaattagct tgttcaagat ttgtattttt attcaaagat tttttttgtc    180
tcttgtgctt cttttatctt atatatattt tttgtatggt ttgtttttgt ttaatattag    240
tccctccgct caaaatgatc tttcacgctt gagattggca ttaaggtcaa gagatgttgc    300
taagctttag aataaaaaaa ttccaaatgc atagagggaa agaaagcgag acaaaatgtt    360
ggagaaggca gagtaaatga tgtgatggag gataaatagt agaagtgtga taccgaaagt    420
ttgaaaataa taaggaattt tatttcttgc tggcactttg ttctagtaca ggtttttagc    480
ccttcaaaat gtttataatg tagagtcaaa attaatatcc ttaactagtt tttaagtccg    540
ggttatatcc tagatattaa taatattcat ttattagtaa cattttattt tataaatata    600
atactaagca ttatttggtt tgctggttaa gactttagtg tatatctatt tctttttttt    660
tttattgtat gcgtgtttac ataaactaaa gactataagg gatagtacca cgtggcgcag    720
ttccttgctt aggaacgtct tttaatatat taactagtat ttgggcccgg gcgttgctcc    780
gggttggtat tgtgtttccg aacatgatgt gcagtttttc ccattcccac taaaatatat    840
aaaggaaaac tcaacattta aaagatacaa atataataat atggacactt aaaacatgat    900
taaaagttga ttgagatggt aattgtgtca tgttataata gtaagaggtt gcctaattga    960
ggttgaggtg gtggagtagt ggtatcgctt cccatctgtt atccctgagg tataaggatc   1020
aaacctcata ggactcattt gagtaatttc ccatatcctc ctctcaaatg agtccttttc   1080
atctgacaaa aaaaaagagt ctaattttaa attaaaatta gacgatcttt tataaaatcg   1140
gcactttctg cacataggtc acaatttttt tgtttctatc tctctgcttt ctttaatttc   1200
acagtctcca actctccatc aacatcttac ttattttaga atagatgatg tatggtagta   1260
ttaaatggta aagtactaaa gctcctataa tacacagaag cttacatagt atagattcgt   1320
acatgagaca aggttacaat atactttctc cgttcttttt atattacaat aattactatt   1380
ttaagtagtt tcacatctat tgtaacaatt ccaattttgt tatagaaagc aactttaata   1440
attgacaata ttgcccttac tttatcttat taaaaccatc attaattact cactttctct   1500
tataaaattg cttttatttt ctaaggatga tttctctcct attctagtta attaaagagt   1560
tacttttgtg ctaaactgct catttattcc aaatccttaa aaattgtgtc caaacgtatt   1620
gttgtaatat aaaaagaaca gaggtactat tagtttgaat aaattttgat cagattaggt   1680
cacctttagg gggcgtttgg ttaggggtat tctggaaagg gtaagggaat caacttactt   1740
aattccctta cttgttgttt gtttgctcaa tttaatgatt ccctttaccc acccccttact   1800
cccaaagtcc tttactctca ttctccccac cccccaaggt ttcacttacc ctttcttgat   1860
tcatcattga ccatatcttt gaccacccaa ctaccaccac cacttgacca cctaatcacc   1920
taaccaccta attacccaac cactattacc acccaacccc tccacctgcc caccaatcgg   1980
caccataact gcccaaccgt cgcccaatca agccacccaa ccggcaccat aaccgcccaa   2040
ccaagccacc caaccggcac cagaaattgt accaagctac ccacacacgt gaaaaccacc   2100
cacccacaag ccctagaaaa aatggaagaa tcgagagaaa gggaggggag agaaaagatg   2160
cagcgactag aaggggaggg ggaggatgtg acggcaaggg gagagggaac ttcgcagcgg   2220
caaagggagg ggaaacgtcg cgtcggcaaa gggctaaggt ggaattgacg gggttgcagc   2280
```

-continued

```
aacaagggga gggcatggag acgtcgtaac cgcaagggga ggggcagcgg cagtggaact   2340
ggggtggaga ggggtagtgg cggcactagg gtgtgggaga ggtggcgggg gatatcaaga   2400
gagggggat atggtggtgt tatggtggaa gcaagaagaa gaaagaggaa agacaatgta    2460
ctaaccaaac aacacattaa atctaagggt tttggtttcc tttccccatc taccccttc    2520
ttgattccat tccctttacc cctttacaac caaactcccc cttagttttt actacttata   2580
accttcaatt ttggctgttt tttgtgacat tttttacttc tccgagcctg gtcatatttt   2640
ctcccgaaac atttcgagga aagtcgaagt gacttgtgaa gttgtgcggg tgcttggcac   2700
catttgtgtt gcctcgaaaa gcatctgaat accccattta ttcctttctc ctgaaaccca   2760
aaattacctc gcaataaacg aaaagatatc catatatttg ttccaagcca catgactcct   2820
ttccaacgac ctcccatgtg accatgtcct tagaaggcat cccgtggcgt tcgaagctcg   2880
gacccccgga aagtccgaaa gtgtgtatta taactttcaa ttttggctgt ttttgggata   2940
tttttactt cttcgggcct tgtcatattt tctctcgaaa cattcatagg attgtcaatg    3000
tgacttgtaa gttgtaacgt tgcacgggtg cttggcacaa tttgcattgc ctcgaaaagc   3060
ctctgaacac cccatttgtt catttctcgt gaaatccaaa attgcctcga aaaaaacgta   3120
aaggcatcca catattcgtt ccaagccaca taactcattt ccaatgacct cccatagagt   3180
ccgtagctcg gaccccagga aagtccaaaa acgtgtacta taaccttcaa ttttggctgt   3240
ttttgggaca tgtttggact tcaccggcct ggtcatatta tcttccgaag cattcctaca   3300
aaatccgacg agactagtaa cgttgttacg cgggtgcttg acaccatatg tgttgcctta   3360
gaaagccttt aaacacccca tttgttcatt tttcgtgaaa cccaaaattg tcccgaaatg   3420
aacataaatg catccatgta ttcgttgcaa gccacatgat ttctttccaa tgacctccca   3480
tatccttagg aggcatgcat catgtggcgt tcggcgagcg ggtctcggga aagtccgaaa   3540
gcctgtgtta taaccttcaa ttttggctat ttttgggaca tttttggcct ttttcaagcg   3600
tgttcatatt ttctcccgaa gcattcctag gttaggcgat gtgacttgta aagcgtgggt   3660
acttggcacc attttctttg cctcgaaaag tctttgagca ccacatttgt tcatttctcg   3720
tgaaattcaa aattgcctcg aaatgaacgt aaagacattc acatattcat tccaagccac   3780
acatgactcc tttccaatga cctcccaagc ccctaggagt cgtcccgtgg cgttcggatc   3840
cggagctcgg gcccccgaga atgtccgaaa ccgtgtatta tgaccttcaa tttttgctgt   3900
ttttggaaca ttttttgact tctctgggct ggtcatattt tctcccgaaa catttgtagg   3960
actaccgacg tgacttgtaa tgttgcgtgg gtgcttggca caatttgcat tgcctcgaaa   4020
aacctttaaa caccgcattt gttcatttct cgtgacaccc aaaactgcct cgaaatgaac   4080
gtaaaggcat ccatatattc gtttcatgcc acatgactcc tttccactga cctcccatgt   4140
ccctagaaag caccccatat ccgaaagctt gtattataac cttcaatttt ggctgttttt   4200
gggacacttg gactttttcg gttcgttcat atttctctc gaaatgttcc tagaaaaggt    4260
gacgtgagtt gtaacgttgc gcgggtacat ggaaccattt gccttgcctc gaaaaacctc   4320
tgaacaccgc atttgttcat ttctcgtgaa actcataatt acctcaaaat gaacgtaaat   4380
gcatccatat attttttcca agccacttga ctcttatcca atgacattct atgtccttag   4440
aaggcactgc ttgtcgtcca taattcgggc cagggaaatg tatgaaagtg tgtattataa   4500
ccttcaattt tggctgtttt tgagacaatt ttttacttct ccgggactgg tcatattttc   4560
tcccgaaaaa atacttcgag tgccgacgtg acttgtaacg tcgcgcggat gcttgacacc   4620
atttgtgtta cctcgaaaag cctttgaaca ccacatttgt tcatttctcg tgaaacccaa   4680
```

```
aattgcctcg aaatgaacgt aaaggcatcc acatatttgt tccaagccac atgactcatt   4740
tccaattctc tcccatgtcc ctaggaggca tcccgtggcg ttcggagctc ggaccctggg   4800
aaagtccgaa agcgtgtatt ataaccttca attttggctg tttttgggtc attttttgac   4860
gtctcttggc ttggtcatat tttgtgccga aacattccca ggattgccga cttgacttgt   4920
aacattgctc gagtgcttgg cacaatttgc attgcctcaa aagactcta aacaccccat    4980
ttgttcattt ctcgggaaac ccaaaattac ctcgaaatga acgtaaaggc atccacatat   5040
tcgttccatg ccacatgact cttttccaat gacctcccat gtccctagga ggcatcccat   5100
ggcattcgga gctcgaacac tgggaaagtc cgaaagcgtg tattgtaacc ttcaattttg   5160
gttgtttgtg ggacattttt gggcttctcc gggcctggcc atattttctc ccgaaacgtt   5220
ccttggaaag ccgaagtgag ttgtaacatt gcacgggtgt ttggcaccat tagtgttgcc   5280
tcgaaaagcc tttaaccaac ccatttgttc atttctcgtg aaacctaaaa ctgcctcgaa   5340
atgaacgtaa atgcatccac atattcgttc caagccacat gactcctttc caatgacctt   5400
ccaggcccct aggagtcatc ttgtggcgtt tggagctcag tccccggtaa agtctgaaag   5460
cgtgtattat aaccttcaat tttggttgtt tttaagacat tatttgactt ctccgggact   5520
gggcatatta tctcccgaaa cattactagg agtgccgacg tgacttgtaa cgccgcgtgg   5580
gtgcttggcg caattgtgtt gcctcgaaaa gccattgaac acccccattt gttcatttct   5640
cgagaaaccc aaaattgcct cgaaatgaat gtaaaggcat cgacatattc attccaagcc   5700
acatggctca tttccaatga cctcccatat ccctaggtgt acaccccatt tgtctgatgt   5760
tataatagca agaggtcacg ggttcaaatc ttgttacaag ctaattttac ttttgttaat   5820
tgacatgact tatgtacaca ttggacaatt atagtggagt aacaaaggtg acatgtgacg   5880
cgtatacatt atcacacacg tcttttaata tatttgtata gatctagatt taagagtaat   5940
ttttttaatg cgcaatactt ggccaatttc ttctgtatca aatcataggt ctttggttgg   6000
ttcataagag taaagaccaa aataataatc tgaactgcaa aaattttctc caagagttaa   6060
aagtttgtat aagttagatt aaaaaaatta atgacatatg atgtagttgg acattaaata   6120
tgtaagttta gaagtaattg tgttaacata aaaaaagatt cgattataac ataaaaacta   6180
aagaaacaca aaggcgccgt acaacaatca atattaccca agtcccctca ttaatattaa   6240
gggatgacct agctcgtaca tatttaatta tctttgaaaa ttcgttgttc agacttgcta   6300
gttgctattc tatatttgta tattcattaa tcaatttttc aatatgtgag catttacatt   6360
ttaaactaga gcaaatattg tctcttttac tattttgttg ttgtcaaatt ttcaaaaata   6420
aattgctcaa atacttttcc tagtgacata aaaaatagag caaataatca aacagtagca   6480
gacccaggaa cttttacata atgtagacgg cataatgtgt taatttttgc ttcttttttc   6540
taatatcatc caataacaca attctgcttc tattagtttg tagtttcaga tgatgatacc   6600
caaacaataa gaccaagcaa caaattgata agattttgct tctctttctt ccacttggtg   6660
taactgtaac agctttgaag tttaacttca gtaatcagtt gcatatttgg catatgatca   6720
aaacaatcaa attattatgt atggaaaagc aaaaaacttc caggtttcca tctgaacaag   6780
gaggccaaga gggtggaagc aagcaaggat atatgatcat aaaatcctat gaatatgatg   6840
tacaaacctt ttctactgca attaggtaac ctaaatgata ccacctagga acagcaacaa   6900
cttatttaca gcactaaacc taaatcaggt taaagttaat cagaccacca tgtatctggg   6960
tggtctctcg agggaaagcg tctccatctg tatccgggta acagaggttt cttcttctcg   7020
```

-continued

```
atcctccttg gcttctgccc tcttaagttc ttcgaaggct ctcttggcat atacagtaaa   7080
cgcaacaatg gtaattattg ccactatgaa tgaaataaca ttgtacacaa tctccaccca   7140
tgttagatga tgattcccat acttgacatc tgcgaacgtc cttatcagtc tcccactgca   7200
aatgaatgct atcagcgtca atattcgaga taccaactca tttaactatt gaattgccaa   7260
aaacagatat ctttgaccat atatttgtta ctaaaaataa cgattgataa tgtgaaacta   7320
tcactgatag atttaaaaga acttttataa aagtatagtt tctctaatgt ataactgcag   7380
aaaatagaat ggggtagaca aatgaagtaa ttgttttgaa gaatgcaaaa ggtcaattca   7440
gtaatacttt tatacgtgat tgggggaagc attaaaaatc ccttctaaga taaagatgac   7500
ctcattggca atggaatcga catccacaga cccttgcatt agaacagagt ggaagtttct   7560
gtgaacttac gtgtagatgt aaagaaaagc ttctggcacc atccctgcaa ttgatcccca   7620
tagataaggc caaaacgtca tacttgtcac cacaactgcg tagttgaaga tagtataggg   7680
aaatggtgaa accctaaaga gtgccaccac gcggaactga tgaaaccagc taccttcggc   7740
agcaagccta agcatagcag ccttatccgg ccatctttgc aaccattgct aacaaggtac   7800
aaaaacataa acattgtgga cttaattaga caagaaagtt aaattaaaat caacattaga   7860
taatcaataa atcaaatgta agcagggaac atatttctta catggattct atcccggaag   7920
agcaatccaa gtaaataggg aagaatcatt ccaatagtag ttccaaccat gattatcaca   7980
aaaccaagac cataaccaaa gatcatgcct gcaagccaca tggatgggcc agaaggaatc   8040
agaaatacag ggaagattgc tagggaagta acaaggacca cagcaagaac cggacggcca   8100
aaggcagtgg cttcccattg catcattgga acaagaacct gcagagaaag taccaaaaac   8160
tttgaggcaa aaatttcctg cttgtatatt gcaaaaagta gtacagcgaa ggcattccgt   8220
gcagaatggc ttatagattg gaaatacgga gaacaatgca actataagca caggcccatc   8280
tcttgacttt tgggacaata acatggaccc ccagattgat ttataagttc tcacaccata   8340
gctagatttt gttggaactt tcataaatca tagtgacata agtatagcat aatattcatg   8400
ccttcgacag aagttttcgc atatggtaag gctactattg aaaaaattcc cttgtgtttg   8460
aagtacgcat aaaaatatct agtggcagtc aaccaaataa aacattctag gagtccctca   8520
aaaaattaaa gagtcatcag ttcagaagac tttaatatca atactttcta ttatccgggt   8580
ttggcatgca gtaaatttca tgagaaaagg aaaaatcagc tatttgatta tataaggaac   8640
taattcggat gtatcactaa gctttccatc gactggaaca tcgggagcta gtctccaata   8700
ctcgtcaagg atctaacata aacatcttct ccgcaatcaa aaagccaagg tcacatacat   8760
ctaggcctct gtctcattct gatggcatgg tatgatgcaa gttagacaac actattattt   8820
ggcagatgac acttaggggt ctaatattta agctcattca agataatcaa gtaatcaagt   8880
tcaatctcaa ggtttcagtt gcgctaaaaa atgtaatact tggctcattc agaattagtt   8940
tgttgaagct ggttggtatt tgcttcattt gttaatggaa ccaggctcat aaacaagctt   9000
tcattaggct aaacttattt aacaaaatca aaagcttaat actataattt ttgataggat   9060
ttcttttggg cagttataca tgagtaatga acaagctcta cacaatcttt tttaatgaac   9120
aagctttaat cgagctaggg tacgttctat tcaacttatt ggacctgaac ttattggaac   9180
ttatctgaac tgaacttatt gaacctgaac tgaacttatt ggaacttatt aaacctgatt   9240
ggacctgatt caacttattg gacctgattg aacctgattg gaacttattg gacctgattg   9300
aacctgattg accttattgg accttattgg aacttattga ccctgattga aacttattag   9360
accttattgg acctgattga aacttattag accttattga acctgattga aacttatttg   9420
```

```
accttattag acaaaaacat tattattatt attgttatta ttattattat tattattatt   9480
attattatta ttattattat tattattatt attattgtta acctgattga taacatttat   9540
atctttcata gttattagta acgaaaacat gttatctcta gttattcaaa gacgaattgc   9600
aaaatattgt aataataata ataataatat attattatta ttattattgt taaccttaat   9660
tatttgacca tgattataat attattcaat agcaatatga ataatcaaat aatagacaat   9720
aatacaagta taatactata cattgtggta ctttaataaa aaaattctaa taataacata   9780
atcagctaat agtaatatga ataataaaat aatagacata atacaaataa ataataaaat   9840
aatagacata atacagataa ataataaaat aatttacact aatacaagta taatactata   9900
taatcattgt ggtactttaa ttaaaattct aataataaca taatccgcta atagtgatat   9960
gaaattatga ataacaaaat agtggacaat aatacaaatg tttattaaac attgactatt  10020
tggaccttat tggaccttat tagacctgat tggaacttat tggaccttat tagacctgat  10080
tggaacttat tgcacctgat tggaacttat tacacctgat tggaacttat tgcacctgat  10140
tggaacttat tgcacctgat tggaacttat tgcacttatt agaccttatt gcaacttatc  10200
tgaacttatc tgaacttatt ggacctgaaa cttaattttt taagttgaac agaacgcacc  10260
cctagtatcc acgaacatag ttagttgttc atcgacaagg gtgttaattc cttgactata  10320
aaaaaaatat ctgctaatat gtcctccata ccatgtcttg atctgattcc caaaatcacg  10380
tgttttcgtg tctggtgacc acgttgctag acatggaaga caggtctaat tgttcagttt  10440
caagtcaggt tgattaaaca tatgttagca atatacaatc attattagtc aaactaattc  10500
aactcgggtt tggtttgatt caggttatgt cgaggatcag gtccaaatcg ggttaatcct  10560
tccaggtcaa atatatctaa gtctgttttg ccaaagtcta ctttttgtat ccgtgtccat  10620
gctaaatgac aaacaaaaag cagcttttac caagctcgaa tcagatttgt tcgcttaaag  10680
agtcacttcg ctcatttaca gcaacaatta aaggacaaaa cattgtccat tcaactactt  10740
acggatatta acttattggc aactgctagc gtaataaggc aatcaacagc actcggcctc  10800
aataatgaac ctacaaggag tccaatgacc aatacaaatt atcactggca tcatctagca  10860
cgacaatctc ttaactctaa gagtctaagt gccttgacat acaaaagtat tccttttaaa  10920
agtacccccg tgtggatatt ctgccaagca aatgcaatcg atacacccaa ttagggcttt  10980
tccattatga gtcctcagag cctcagattg taaaacaggt cagtaaaaga ggaaaatagt  11040
atttgattct tttgctaaac ccttggatat aagaatggtg acttgtattg tcacgccaag  11100
cttctttcat aaaagctgat catattatta tatgagagtt ctgagtttca aggtccgcat  11160
tcgatctaac tagacatcac ttccaattaa agttgagaaa cgaaactagg tgtcctcttt  11220
gtttcccaaa ggtgaacttt agatacttat tataagcata ttttgttatg aatcgggcta  11280
aggagagggc tactcttggt attgcataat tagttaatta cttagtagta gcttgaggaa  11340
taaggaagca agtaagttag aggaaagagt atgaaaatct gctataaagt gaggagagga  11400
gggatagaag gataatcaca aaattattga gttaactttg gttttagttg cttaggttgg  11460
gagtgtccag ccactcgaat gtcttgggac tgtaaacacc attgttcatg atctaattgc  11520
atcaatatta caattaactc atttctcttc ttatccatat tcatcttctt acaatcacaa  11580
ctatttccag atcatccatc caaatcttca tccacttgcc ttagtttcta ctccagattt  11640
cagtctatta caaattgatt tctacaatat gtcaattcat cacaaattat catgttttct  11700
gaacaaaagt tcactgtttc aggacaaata cagaaagaac tactttgatg cttagaacag  11760
```

-continued

```
atatattgta aaattgtatt cggaatttgg gatacaactg gagaagatat gaataaatag  11820
gcattcaggg agctcagaaa aacagaccgt gccatatggt gctctgctgc ataacaggaa  11880
ataatggata aagtatgaat aacgttataa cttcttaaaa acctagatga caagtatttt  11940
ggttgctttt tattattggt aggcaaggag aatactcaac aacagtttag ccttaaactg  12000
cttcttattt ctcctcttcc ccttttttcct gatgatttgg ggttgtcact cagttctttt  12060
acctctcatt tccaggtact ttagagttat attacacaaa ggattgcaag agaagaacag  12120
gtcgccctgg catgcactca gaaagtatac gacccttcac aggaaatgtg gtgctccaag  12180
acttatatct caggctctca tgagtcatgt caaggaccat ctttaatcat ttgtattcta  12240
ggtttctcag gcgatgcggt gtgctggtgt gtctctccct cccacttgag tgtgtgtatt  12300
gtttgtgccc ctaagttttt atcttaacaa tcactactag tcaattagtc attaccaacc  12360
ctacccacct ctcttgttac tgttgttctt ggagatattt catatatgtc agcttagaac  12420
ttatattacg tttcttatta catattctct taagctcgcg cacatactct gtgatcgaag  12480
ggatccatat tagttatctt ttagtggagt tgttgtgaaa aaagactgca tagaaaaatt  12540
aagatagctc atagttgtaa atgtaattga acttttagat tgatagcctt gaggctgctt  12600
gcattgaacc aaccaaattc agccaggcta gtctatgcct ctttggtgtc acctggtagg  12660
ttgaatttgt gtagctgtag ttctacaaga gactgattta aaaatgtttt cgcactgaaa  12720
cagcttaaac cacaaaacag gaaagtgcag aacaaactcc agaaaatggt gcagaacata  12780
ccttctcaaa aaggaaagga actccccatt ttaacagtac gaggacaact gctacagcac  12840
taatggagga gatcaagatt ttgatccacc agatgaagga ttctgatctt gtttcagcct  12900
gagaatgtaa ggttgaagct tcaggcctct ttgtaatagc agatgtcacc agactaacaa  12960
attcactgtc gtcttgcata gcaggcccaa catctatgtc atgcttagtt agctccattg  13020
aatttggcat ctccaagaga tctcaagagc tgcccaaaaa gacggtacaa tattatgagc  13080
atacatgaca tgatgacaac ccataaagaa tatcataacc tgtcacattt tttattcaaa  13140
gttcaacagc cctcttacaa catgattgag aatggagggg aagagagaga gagttggtct  13200
cagacattga tcacataatc atttcaatta gttttaaagg tgctcatgaa atagaactag  13260
tgtcttaagc tggagacttc tgtatttttc atggttttag attatcaatc atattcttag  13320
aatctttgat ctctagaact ctttcctttc ctcccaatat tttttccact ttgtcttttg  13380
ttaattacgg cttcgctgca ggcctgcaat aaatctttta aatttttaca gatactatgt  13440
agagttgtat acataagctc taatctgaag acgattggtt tcgatgctag ttaatacaaa  13500
taaatatatt atggatataa tatgcagtaa attgggccat gggcaccagg gacaacttag  13560
acaagtatag tgcaactacc aggaaattta agctgggtac ctctgattca tcatgctggt  13620
tgataatatt attgcttcca caagtgttcg ctacggctca accaaactaa gtcacaactc  13680
acaagctgca caacccaact gacaattatc gcctattgtc taagctatac attacattac  13740
cccaatgcca caacgtggct cacgcctagg catggtaagg aagttcagat gtacgcagcc  13800
ttaccctttt aataacaaag aggctgtttc caggtgaccc ttaaatctta attgcaaaca  13860
ccatctgctg cttcacataa ataagcgact tcaaaattgt aaattaaaga atttgaatgc  13920
aaattgtgtg aaaaacaact ccatcaagaa tccattaagc acgctttact attagtatca  13980
ataataggaa acccttatat cccttttgac gaaggcacac atgcaacact aatgtgtcct  14040
tataaacttc atgaaagtat atctctacga aaccctttta gtcttatgtg attctttaag  14100
tgtccaactg atgattggtt acaaggtatt tagcccaaag tagcatttca gagagatggt  14160
```

```
gtagaatgag tagcttataa accgaggttg aggtgtaatc ctaataaatt aggaactaat  14220
accacaagag agatggacat gtagagatac aatatagtac agaataagat tatttgaaat  14280
ctttttacca gggaaactcc agaggtgttc cataaaacac aataccatat aactgggaga  14340
tcaatatttt agattaaaaa atataaaaat ctatttgggt tgagtatata gttggttagt  14400
ccaataatat ataaatttat aaggtggagg tcttcggtat atgacattcc aaatttgagt  14460
atcaaatgat atatatggtt ttccatactt gaatcccttt tcatgtacta cctctgtttc  14520
aaattaatag ttacacttac acttttcacg catgccaatg cagaactttg aggacatata  14580
tctttagttt tgtatttgta aaaattataa aaagtacata ttaataaaat acatattaat  14640
acgaatctaa caagatccca catgactatg attttattca cgtataaatc acaaacgagg  14700
gtcaaaatgc aattgtgaat agtgtaaaat gtcaaagtgt aactattaat ttgaaacgga  14760
ggtagtatgt gtttatgcaa cacttttcct tttccctttt ttgctattta gtaatttatg  14820
taaaatactt ccattgaccc aaaagttggg tgattatagt ttacatctat cattattatt  14880
tatcattact atagattatt caccattgta atcaacttta taaaagtata cacaggtaac  14940
tcaggagtca ggggtgctgg gccaaacact tttatagttt aaggtgaaaa atctcgagaa  15000
tcttctcctg ccacgcaaaa tgagtgttct tccactttaa agatgttata acacttatct  15060
taacctacta ttcgtaaata acacttatct taacctacta ttcgtcaaga catacttgct  15120
tcatctcact aagaacgtct tagttttcat ttgaaattcg taccagaaag attcacttca  15180
aatctattta tttttagata aattgttatt aaaaacgacg aagaaacgtc agaggacaac  15240
aaatcctcta aactccaaat tataagtgag tccaactatg ttgacgtaag gtaattagag  15300
tatccataaa agccctggcc gctttggccc acaaagcagc ttagaatact acccaacccc  15360
aaatataatc aatcaggtga ggaagctcgc aacagatgcg agagttccac tccaatcaaa  15420
ggcaccagaa catagccatc gacatcttct cttctttacc cccctgaaa ccaacagatc  15480
ttaaggaagt ccactagtga acaaggacat aaccactact catgtggaat gccaatcagc  15540
ctctgtcaaa gggaagtcca ttagtgaaca aggacatacc cactgctcaa ggtagtcatg  15600
tggaaattgg aatcccaatc agcctttgtc aaaaggaata agccacatcg caatgaagaa  15660
aaaggtgcaa accagattta ttgcatctcc aacacgacat aaatatcgag aatgaggcct  15720
ttactgacaa aggaactctg gatttccaat ttccactgag cattggactc agttgagaag  15780
taattggtct tgctagattc tgtttacgca catactctta atgataaata aatgtaacag  15840
gccaattggt ctggaaaaaa acagttgata aaaggctagt ttgggccttg gggataaata  15900
taatctggta tgagttaata aatttctgtt taaggtaaag agaatgtgtt atgtgggata  15960
atttaatcaa gaaaatctta gtaagatgga ggtagtctaa cttccattcc tcaaaatgtg  16020
taattcctta taaaatcagt cagcctctag atacatagtt agcaaaaatg gaaggtatag  16080
aagtgggggt gagggaagag gaaggaaaga gaaccgcgat caatcatatt gttcgtgctc  16140
aagtttgagt tgtgcctata gctagttaga gtttgtctat ttcattgttt ttggtcagtg  16200
ttcatattct gagtgtcatc gtgtttgggt tctagaatgc tccttttcct aatgtcgaca  16260
tttctccact ttactctaga aaaatgatct cattgtagcc attccagctt caattttaat  16320
ggatactaag atccctttca ggaacaatgt taaggtagat gttagtgttt taacagccat  16380
gtggatgtta gtgtctagaa cgagtggtca aaacactact agcctcaaaa tattgtgatc  16440
agtctgaaaa ctctatgtta gatggttgct ttttttggta ggttcgcttg ttttgggggg  16500
```

-continued

```
ttagctttgt ttattttctt cacaatttgc ccttaaactt ttcacaaaat ctacaattga  16560
agattcttaa atagataaca gacgtgtcag ctacttcaac agctaattgt acgaaaaagt  16620
tcagctacct tgaaaccaaa ccactaacag ctagtacagt ttgtttctac tattacattt  16680
atctaatata acagctagta tttagtccaa cgatgtataa tatcaatgaa atggaactaa  16740
tctgtaaatt ggaccttagg cataagagtc gagttgagca ggtacactcc aatcaccaag  16800
ttatttaagc ttaaaatgtc taacttccaa tgctgtttga cgatactcat tgccaagtgt  16860
ttgttacaga tcaaccaagc aaataaagca acaagtgaac agctgcacta gtacccaact  16920
gcgaattttc gtcgattgcc aagtgcatgt ctgggacaca ataccatcat gtccataccc  16980
attaccttgc ttagccagct atcgtaatcc ataacacata aaaaccaaca aagtcttgat  17040
agtttcacaa atcaaaatgt tcacttttca ttccaaccaa aacaagcaat aaatctcttc  17100
atccatactc acaagaagaa caatctctca cactacccac ttgattagta aaaaccccaa  17160
tcaaaaacaa aatccaaccc acataaacaa atcaaattta gtaactaccc ataaactcaa  17220
aaacctcaaa tcacaatacc aataaaagag atatacaatc aatcaaaaaa aatacaacaa  17280
cagctaaaca aataacatca taaactaaag ttattcattt tatttcctaa ctagagatca  17340
attaagcagc ataaaacaac atcactaatt caagttaata atcatcaaat tctatactat  17400
aaaacataca taccttacca aaactaccca gctgaaaatt agggtagagc tccagaaatc  17460
ccggcgaaaa atccggtgag aaattcagct aaatttgaaa acttctttag gttaagtagt  17520
gtacacgatg aattgaagat ttttacaagc atatgaaaat ggtggttgaa attgaaatgg  17580
gggtttttga aaattgttgc gacgcgtaaa agtggaaaaa aaaaaggaga gaatcaaaga  17640
aatgagcaag tttttgtagg tgggtttact gttgttgctt ttgtttgtgc acattactga  17700
ctattcttaa ttcttccatg cgtgtggggg tgaaggaatt gttttcctaa gttgtttagc  17760
cacttcatag agtcattgga tttgaataat ctagggaata atgatcatgt gtttagtgta  17820
tctataaatt ataatttatg tatgtatatt gtatatgtgg tgaggcatag aggacaaggt  17880
ctaagaggaa tagaggattg tgagggagtg tttcatgctt ttaagaatga tgagtcattg  17940
agtgtattaa gttataagta gtatttgatc gagtagtaaa gtttgtatca cgtaaatcag  18000
agtgataatt aggaattggg atttgctcaa gtggtgagtt ttcccatctt tccgagcaag  18060
gtttctaggg ttcaattcct acctcaagca tttccttggg atttaagggg acggctcaga  18120
ggaattcttc ttaccaatat tttaaaaaaa aaaaaattaa gagtggtaat ttagttcaga  18180
tcctaccttt atccggttcg aaacgacttc aagaaaaaaa aatccgacat cgtttaaaat  18240
tttttacttc cgactcattt aatccgcctc caactttgaa acaagtagtc ttatttcttt  18300
tatgttaaga aaatttgcca aaaaaaccct ttttaaagtc cagttttgcg aaaaaaaaaa  18360
accttataaa gcattctttg tgaaaacaaa ccaaaaagta aattattttt gcaaaatgaa  18420
acctaatctc atttttcggt tttgaccatg gacttttcga cattgaccac ttctatttat  18480
cttcttcctc cataatcaca gcctagccac cactaccaac acctgccgct agcccccaca  18540
acctgcaccc ccacaacctc catccacccc ctcaagcggc aacccccctt attcccatac  18600
gcggcaaccc tacaccttat cctccacccc cctccgccct taccttttct cctctccctt  18660
cttccctcca tcacccctcc ccactctctt ctccctttgc cccccatcgt tgcaccaccc  18720
ataatccctc tctgtaaccc cctctcctcg cagctccccc tccctcccag ccaaggttga  18780
aaaattacag aggcagtcgc atatggggat gggggactat cgtctaaggg gtggagagag  18840
ggtttggggg ctgctggtgg gggtggggta ggctgaatgt ggtgggggct gagggtgggg  18900
```

```
ggtgaaggtg gggctgcagg tcgggctggc ggtatggaga aagaagggaa atagaagtgg  18960

ttaacaccgg aaagtccatg atcaacaccg aaaaatgaaa ttaggtttca tcttgcaaaa  19020

ataatttatt actttttgat ttgttttcgc aaagaatgct ttataaggtt ttttcgcata  19080

acatttagac ttttatcatc cctcttagat ttgacacata ttatacgaat tatactaaaa  19140

agactcctta tagtaattcg actaatgttt tattaaaatg aacctttaga ataactcggg  19200

taatat                                                             19206


<210> SEQ ID NO 76
<211> LENGTH: 2000
<212> TYPE: DNA
<213> ORGANISM: Beta vulgaris

<400> SEQUENCE: 76

tacgtaacaa attctgcaaa aatagagata gcaactaata acacgcatga aaatgacaag     60

ttatattata cctttttttc tcaatatatg aatatacgta acaaattaac tccagtagtt    120

tttagtaaaa ctattagatt attgtgtaac atatactctg gaaatagtac taagatccat    180

tacaatcttt attgagaaat ttcctcatgt accccctgag gtttggcgta atttccaaat    240

acccctcata tttgaggaat ttctcaaata ccctgatgtt tttgtttaga ctcaaaatac    300

ctttactatg gacagtaccc taatgtcatt aagttttccc cttctctctc cccaattttc    360

tctctcctcc cattccccca cccactaccc actgcccact gccaagtagg ggtgtaagtg    420

gattggactg gattggactt tgccaaattc aaatccagtc caaagttttt tggactcgag    480

aaattgagtc caagtccgat ccaaatattt tttgagtcca gtccaatcta gtccgataat    540

tttttcttga gtccgaatcc agtccagtcc agtccgatta ttatatcttt tttcccgatt    600

taggttcaat gattcacaac attttttgag atgcttgagc atttgacatc tgattcaatt    660

atcaatatcc acaaataaga ttgaaagctt aaattaaagt aaaatactat gaataaaaag    720

ttgaattaga tgcttacctt gatctaagtt gagaggaagc atagagactg agaattaatc    780

tgagggacaa atagagaatg cgagagtcga gacagtgagg tagaaagaaa atgaagagta    840

agaggaagtg agtattaagg actgaggagt aaagtaagat agaattagtt ggctactagc    900

ctactaatgc agtattgcta gtataattta cttatttaac aaatggagct aagtgcaata    960

gtttagcgcc aattgacata tttagagaga gaaggctgaa aaatccaata tttttaaaat   1020

agtatcatta tttttaatat atacattata tataaaaata tttttggact ggactggaca   1080

tattggactc caaagggatg agtccaaatc cagacaaaaa atatttggac ttgaaaattt   1140

aagtccgagt ccagtccgaa aaattttcag tccaatccag tccgacaaat ttggactgga   1200

ctggattgga ctctgaactt ttcgtagtcc gcttacaccc ctactgccaa gtgccaaact   1260

gccaaccccc ttttggttga gttgatattt gacgcaaaga cttggcgtgt tggaaggttc   1320

attacacatt ttatccaagt caactttgaa gtcttcttag ctagagacta gagtgaacgt   1380

gttggaaggt tcattacaca ttttatccaa tcaaactttg aagtcttctt agctagagac   1440

tagagtgaac gtgttggaag gttcatgttc atgacattat aaaagtaata atagtgaaat   1500

ttcacaaagt atttataaac ccaggacaga ctcaagagct ctacttatta ttagtgaaaa   1560

acaaacatac acacgacaat aacacaacat aaacaataat gaacatgaaa atcctccttt   1620

tgtttgtctt ccttcatcac ctccactact tcatccatgg cagaacactt acagaacgcc   1680

aagctttact aagtatcaaa tctgccatta cttatgatta ttataactct ctctcctcat   1740
```

```
ggaaaaacac aacacaccac tgcagttggc catacatcac ttgctcctcc tcttcttctt   1800

cttcttctgt tatttctctc aacttcacca tgttatttct cgaaggaatt ctctcccctg   1860

atataggctt cctcaccaac ctgcaaaacc tctctattcg atctaacctt ttttctggcc   1920

cactccccca ttctctctct ctcctcaccc aactccgcta tctcgacgtt tcccaaaaca   1980

gtttcacagg tccaatccca                                               2000
```

<210> SEQ ID NO 77
<211> LENGTH: 2000
<212> TYPE: DNA
<213> ORGANISM: Beta vulgaris

<400> SEQUENCE: 77

```
ccaacaattt gttagccgat gaagagcatc aaaaccaaaa aaaacaaaaa aaattgatta     60

atatgcatga gtgtgacctt gttttccaaa gtttagcatt actattagtg tctcaattca    120

taataataaa aaaattagct tgttcaagat ttgtattttt attcaaagat tttttttgtc    180

tcttgtgctt cttttatctt atatatattt tttgtatggt ttgtttttgt ttaatattag    240

tccctccgct caaaatgatc tttcacgctt gagattggca ttaaggtcaa gagatgttgc    300

taagctttag aataaaaaaa ttccaaatgc atagagggaa agaaagcgag acaaaatgtt    360

ggagaaggca gagtaaatga tgtgatggag gataaatagt agaagtgtga taccgaaagt    420

ttgaaaataa taaggaattt tatttcttgc tggcactttg ttctagtaca ggtttttagc    480

ccttcaaaat gtttataatg tagagtcaaa attaatatcc ttaactagtt tttaagtccg    540

ggttatatcc tagatattaa taatattcat ttattagtaa cattttattt tataaatata    600

atactaagca ttatttggtt tgctggttaa gactttagtg tatatctatt tctttttttt    660

tttattgtat gcgtgtttac ataaactaaa gactataagg gatagtacca cgtggcgcag    720

ttccttgctt aggaacgtct tttaatatat taactagtat ttgggcccgg gcgttgctcc    780

gggttggtat tgtgtttccg aacatgatgt gcagtttttc ccattcccac taaaatatat    840

aaaggaaaac tcaacattta aaagatacaa atataataat atggacactt aaaacatgat    900

taaaagttga ttgagatggt aattgtgtca tgttataata gtaagaggtt gcctaattga    960

ggttgaggtg gtggagtagt ggtatcgctt cccatctgtt atccctgagg tataaggatc   1020

aaacctcata ggactcattt gagtaatttc ccatatcctc ctctcaaatg agtccttttc   1080

atctgacaaa aaaaaagagt ctaattttaa attaaaatta gacgatcttt tataaaatcg   1140

gcactttctg cacataggtc acaatttttt tgtttctatc tctctgcttt ctttaatttc   1200

acagtctcca actctccatc aacatcttac ttattttaga atagatgatg tatggtagta   1260

ttaaatggta aagtactaaa gctcctataa tacacagaag cttacatagt atagattcgt   1320

acatgagaca aggttacaat atactttctc cgttcttttt atattacaat aattactatt   1380

ttaagtagtt tcacatctat tgtaacaatt ccaattttgt tatagaaagc aactttaata   1440

attgacaata ttgcccttac tttatcttat taaaaccatc attaattact cactttctct   1500

tataaaattg cttttatttt ctaaggatga tttctctcct attctagtta attaaagagt   1560

tacttttgtg ctaaactgct catttattcc aaatccttaa aaattgtgtc caaacgtatt   1620

gttgtaatat aaaaagaaca gaggtactat tagtttgaat aaattttgat cagattaggt   1680

cacctttagg gggcgtttgg ttaggggtat tctggaaagg gtaagggaat caacttactt   1740

aattccctta cttgttgttt gtttgctcaa tttaatgatt ccctttaccc accccttact   1800

cccaaagtcc tttactctca ttctccccac cccccaaggt ttcacttacc ctttcttgat   1860
```

tcatcattga ccatatcttt gaccacccaa ctaccaccac cacttgacca cctaatcacc 1920
taaccaccta attacccaac cactattacc acccaacccc tccacctgcc caccaatcgg 1980
caccataact gcccaaccgt 2000

<210> SEQ ID NO 78
<211> LENGTH: 5488
<212> TYPE: DNA
<213> ORGANISM: Artificial Sequence
<220> FEATURE:
<223> OTHER INFORMATION: Codon-optimized LBcpf1

<400> SEQUENCE: 78
aagcttatcg atgtcgacag gccttaaggg ccagatcccc cgggctgcag gaattcgatc 60
tggcacgaca ggtttcccga ctggaaagcg ggcagtgagc gcaacgcaat taatgtgagt 120
tagctcactc attaggcacc ccaggcttta cactttatgc ttccggctcg tatgttgtgt 180
ggaattgtga gcggataaca atttcacaca ggaaacagct atgacatgat tacgaattca 240
aaaattacgg atatgaatat aggcatatcc gtatccgaat tatccgtttg acagctagca 300
acgattgtac aattgcttct ttaaaaaagg aagaaagaaa gaaagaaaag aatcaacatc 360
agcgttaaca aacggccccg ttacggccca aacggtcata tagagtaacg gcgttaagcg 420
ttgaaagact cctatcgaaa tacgtaaccg caaacgtgtc atagtcagat cccctcttcc 480
ttcaccgcct caaacacaaa aataatcttc tacagcctat atatacaacc ccccttcta 540 tctctccttt ctcacaattc atcatctttc tttctctacc cccaatttta agaaatcctc 600
tcttctcctc ttcattttca aggtaaatct ctctctctct ctctctctct gttattcctt 660
gttttaatta ggtatgtatt attgctagtt tgttaatctg cttatcttat gtatgcctta 720
tgtgaatatc tttatcttgt tcatctcatc cgtttagaag ctataaattt gttgatttga 780
ctgtgtatct acacgtggtt atgtttatat ctaatcagat atgaatttct tcatattgtt 840
gcgtttgtgt gtaccaatcc gaaatcgttg attttttca tttaatcgtg tagctaattg 900
tacgtataca tatggatcta cgtatcaatt gttcatctgt ttgtgtttgt atgtatacag 960
atctgaaaac atcacttctc tcatctgatt gtgttgttac atacatagat atagatctgt 1020
tatatcattt tttttattaa ttgtgtatat atatatgtgc atagatctgg attacatgat 1080
tgtgattatt tacatgattt tgttatttac gtatgtatat atgtagatct ggactttttg 1140
gagttgttga cttgattgta tttgtgtgtg tatatgtgtg ttctgatctt gatatgttat 1200
gtatgtgcag cgaattcggc gcgccatggc tcctaagaag aagaggaagg ttagcaagct 1260
cgagaagttt accaactgct acagcctctc taagaccctc aggttcaagg ctatccctgt 1320
gggaaagacc caagagaata tcgacaacaa gaggctcctc gtcgaggatg agaagagagc 1380
tgaagattac aagggcgtga agaagctcct cgacaggtac tacctcagct tcatcaacga 1440
tgtgctccac agcatcaagc tcaagaacct caacaactac atcagcctct tccgtaagaa 1500
aaccaggacc gagaaagaga acaaagagct tgagaacctc gagatcaacc tccgtaaaga 1560
gatcgccaag gctttcaagg gaaacgaggg atacaagagc ctcttcaaga aggatattat 1620
cgagacaatc ctgcctgagt tcctggacga taaggatgag atcgctctcg tgaacagctt 1680
caacggattc actactgcct tcaccggatt cttcgacaac agggaaaaca tgttcagcga 1740
agaggccaag agcacctcta tcgctttcag atgcatcaac gagaacctca cgcgttacat 1800
cagcaacatg gacatcttcg agaaggtgga cgccatcttc gataagcacg aggtgcaaga 1860

-continued aatcaaagag aagatcctca acagcgacta cgacgtcgag gactttttg aaggggagtt 1920 cttcaacttc gttctcaccc aagagggcat cgacgtgtac aacgctatta tcggaggatt 1980
cgtgaccgag tctggggaga agattaaggg actcaacgag tacatcaacc tgtacaacca 2040
gaaaacgaag cagaagctcc cgaagttcaa gccgctctac aagcaggttc tctctgatcg 2100
tgagagcctc tcattttacg gtgagggtta cacctctgac gaggaagtgc ttgaggtttt 2160
ccgtaacacc ctcaacaaga acagcgagat cttctcgtcc atcaagaagt tggagaaact 2220
tttcaagaac ttcgacgagt acagcagcgc tgggatcttc gttaagaacg gacctgctat 2280
cagcaccatc agcaaggata ttttcggcga gtggaacgtg atcagggaca agtggaatgc 2340
tgagtacgat gacatccacc tcaagaagaa ggctgtcgtc actgagaagt acgaggatga 2400
caggcgtaag tcgttcaaga agatcggctc tttcagcctc gagcagcttc aagaatacgc 2460
tgatgctgat ctcagcgtgg tcgagaagct caaagagatc atcatccaga aggtcgacga 2520
gatctacaag gtgtacgggt cctctgagaa gttgttcgat gctgatttcg tcctcgagaa 2580
gagtctgaag aagaacgacg ctgtcgtcgc gatcatgaag gatttgctcg acagcgtgaa 2640
gtccttcgag aactatatca aggccttctt cggagagggc aaagagacta atagggacga 2700
gtctttctac ggggatttcg tgctcgctta cgatatcctc ctcaaggtgg accatatcta 2760
cgacgccatc agaaactacg tgacccagaa gccttacagc aaggacaagt tcaagttgta 2820
ctttcagaac ccgcagttca tgggcggatg ggacaaagac aaagagacag attacagggc 2880
caccatcctc aggtacgggt ctaagtacta cctggccatc atggacaaga aatacgccaa 2940
gtgcctccaa aagatcgaca aggatgacgt gaacgggaac tatgagaaga tcaactacaa 3000
gctccttccg ggaccgaaca agatgcttcc taaggtgttc ttcagcaaga aatggatggc 3060
ctactacaac ccgtctgagg acatccagaa aatctacaag aacgggacct tcaagaaagg 3120
cgacatgttc aacctcaacg actgccacaa gctcatcgat ttcttcaagg acagcatctc 3180
gcgttacccg aagtggtcta acgcttacga ctttaacttc agcgagacag aaaagtacaa 3240
ggatatcgcc gggttctacc gtgaggttga ggaacagggt tacaaggtta gcttcgagag 3300
cgcctccaag aaagaggttg acaagttggt cgaagagggc aagctctaca tgttccagat 3360
ctataacaag gacttctccg acaagagcca cggaactcct aacctccata cgatgtactt 3420
caagctgctt ttcgacgaga acaaccacgg gcagatcaga ctttctggtg gtgctgaact 3480
cttcatgcgt agggcctcac tcaagaaaga agagttggtt gttcacccgg ccaactctcc 3540
aatcgctaac aagaatcctg acaacccgaa aaagaccacc acgctgtctt acgacgtcta 3600
caaggacaaa aggttcagcg aggaccagta cgagcttcat atcccgatcg ctatcaacaa 3660
gtgcccgaag aacatcttca agatcaatac cgaggtgagg gtgctgctca agcacgatga 3720
taacccttac gtgatcggaa tcgatcgtgg tgagagaaac ctcctctaca tcgttgtggt 3780
ggacggaaag ggaaacatcg tcgagcagta cagcctgaac gagattatca acaatttcaa 3840
cggcatcagg atcaagaccg actaccactc actcctcgat aagaaagaaa aagagcgttt 3900
cgaggccagg cagaactgga cttctatcga aaacatcaaa gagttgaagg ccggctacat 3960
ctctcaggtg gtgcataaga tctgcgagct ggtggaaaag tacgatgctg tgatcgctct 4020
tgaggacctc aactctgggt tcaagaacag tagagtgaag gttgagaagc aggtctacca 4080
aaagttcgag aagatgctca tcgacaagct caactacatg gtggacaaaa agagcaaccc 4140
ttgcgctacc ggtggtgctc ttaagggata ccagatcacg aacaagttcg agtccttcaa 4200
gagcatgagc acccagaacg gcttcatctt ctatatccct gcttggctca ccagcaagat 4260

```
cgatccttct actggtttcg tgaacctgct caagaccaag tacacctcga tcgccgacag   4320

caagaagttc atctcgtctt tcgacaggat catgtacgtg ccggaagagg atcttttcga   4380

gttcgctctc gactataaga acttcagcag gaccgacgcc gactacatta agaagtggaa   4440

gctctactcc tacgggaacc gtatcaggat cttccgaaat ccgaagaaaa acaacgtgtt   4500

cgactgggaa gaagtgtgcc tcacctctgc ctacaaagaa ctgttcaaca agtacggcat   4560

caactaccag cagggtgata tcagggctct tttgtgcgag cagagcgaca aggcattcta   4620

cagctcattc atggccctca tgtctctcat gctccagatg aggaactcta tcaccggaag   4680

gaccgatgtg gacttcctta tctctccggt caagaactct gacgggatct tctacgacag   4740

ccgtaactat gaggctcaag agaacgctat cctgccgaag aatgctgatg caaacggggc   4800

ttacaacatt gcgagaaagg ttctctgggc tatcgggcag tttaagaaag cggaagatga   4860

gaagctcgac aaggtgaaga tcgccatctc caacaaagag tggcttgagt acgctcagac   4920

ctccgttaag cacaagaggc ctgctgctac taagaaagct ggccaggcca aaaagaagaa   4980

gtgaggcgcg ccgagctcca ggcctcccag ctttcgtccg tatcatcggt ttcgacaacg   5040

ttcgtcaagt tcaatgcatc agtttcattg cccacacacc agaatcctac taagtttgag   5100

tattatggca ttggaaaagc tgttttcttc tatcatttgt tctgcttgta atttactgtg   5160

ttctttcagt ttttgttttc ggacatcaaa atgcaaatgg atggataaga gttaataaat   5220

gatatggtcc ttttgttcat tctcaaatta ttattatctg ttgtttttac tttaatgggt   5280

tgaatttaag taagaaagga actaacagtg tgatattaag gtgcaatgtt agacatataa   5340

aacagtcttt cacctctctt tggttatgtc ttgaattggt ttgtttcttc acttatctgt   5400

gtaatcaagt ttactatgag tctatgatca agtaattatg caatcaagtt aagtacagta   5460

taggcttgag ctccctagga tcaagctt                                      5488
```

<210> SEQ ID NO 79
<211> LENGTH: 989
<212> TYPE: DNA
<213> ORGANISM: Petroselinum crispum

<400> SEQUENCE: 79

```
aattcgaatc caaaaattac ggatatgaat ataggcatat ccgtatccga attatccgtt     60

tgacagctag caacgattgt acaattgctt ctttaaaaaa ggaagaaaga aagaaagaaa    120

agaatcaaca tcagcgttaa caaacggccc cgttacggcc caaacggtca tatagagtaa    180

cggcgttaag cgttgaaaga ctcctatcga aatacgtaac cgcaaacgtg tcatagtcag    240

atcccctctt ccttcaccgc ctcaaacaca aaaataatct tctacagcct atatatacaa    300

ccccccctte tatctctcct ttctcacaat tcatcatctt tctttctcta cccccaattt    360

taagaaatcc tctcttctcc tcttcatttt caaggtaaat ctctctctct ctctctctct    420

ctgttattcc ttgttttaat taggtatgta ttattgctag tttgttaatc tgcttatctt    480

atgtatgcct tatgtgaata tctttatctt gttcatctca tccgtttaga agctataaat    540

ttgttgattt gactgtgtat ctacacgtgg ttatgtttat atctaatcag atatgaattt    600

cttcatattg ttgcgtttgt gtgtaccaat ccgaaatcgt tgattttttt catttaatcg    660

tgtagctaat tgtacgtata catatggatc tacgtatcaa ttgttcatct gtttgtgttt    720

gtatgtatac agatctgaaa acatcacttc tctcatctga ttgtgttgtt acatacatag    780

atatagatct gttatatcat tttttttatt aattgtgtat atatatatgt gcatagatct    840
```

```
ggattacatg attgtgatta tttacatgat tttgttattt acgtatgtat atatgtagat    900

ctggactttt tggagttgtt gacttgattg tatttgtgtg tgtatatgtg tgttctgatc    960

ttgatatgtt atgtatgtgc agctgaacc                                      989


<210> SEQ ID NO 80
<211> LENGTH: 8726
<212> TYPE: DNA
<213> ORGANISM: Artificial Sequence
<220> FEATURE:
<223> OTHER INFORMATION: Resistance gene expression cassette

<400> SEQUENCE: 80

tttatttaaa catgatacgt atcatattga gtactcatac gcgtaccagc tgtgacttag     60

aaaaattaac cacgctatat aggttccaag ccctcatgat taccttttca tagtgtaaat    120

ttcatgtagt tgaatggtgg gaatccaatc acaaaaacac tgcaggtaat ggaaatgttc    180

caactttttc caagcatttt aaaataagac atgtgattac taattagggc gtgttcggca    240

acagtaactg tggtgatagt ttttagctgt gagaatagtt gttagctgtg ctgttagctt    300

ttagtggttg gtgtgtaact gttagctgtt agatgtccaa gtagcggtgt aaaatattga    360

tgttcgataa aagaagctgt caaagtagct gtttaagaat aactagttat aaattcaaat    420

aaatctttaa tatataattt atacaccact aaaagctacc caaaagctac aatctaccca    480

aaagctacaa tctacccaaa agctacaaat tgtagctttt gacaaacact actaaaacac    540

tacttgtacc actaaaagct acttacacca ctatcttgcc aaacgctctt atttttttcta    600

attagtgttt tgacctaatc aagacactaa aagctactta aaaagcttgt gccgaacacg    660

ccaattctga accaaggaac aaactataac aaaaaaagtgc tatgtggaac ttttgtaggc    720

aacagaagta aggcattttt ggaatgtact aacaaatccg tattaagact tgtacatgaa    780

aattaccgtg gtaacatttg cccacacttc ctcattcacg tactccgatt cattctgata    840

aggcacatca agatccatgt atctaatagt ttaatttgcc tctgtgtttc tgtattaaca    900

atgagcatag tgagtgcaaa agccatggaa gctagattaa aaaggccatc attctaagtt    960

agacaattgg aaacaacatc gagatacacg tacacataag ggctgctctt ctctattact   1020

ccctctgttc ctaatcattt gctttttttag cgggttccaa aggcctatgt ttgaccacta   1080

atatatttaa attaaaactg gtgatatata ttaaaagaaa attatgatga atttaacaaa   1140

aaccatatat gttatgtcct tttttttcct atattaatga atttttacag tcaaagttgg   1200

tgaactttga cccaaaaaaa gaaatggagc aaaaaaaaaa aaaaaaaaaa aaaactaggg   1260

acaatgagta acatttttat ctatgtcttt ttaatatgaa tatacgtaac aaattctgca   1320

aaaatagaga tagcaactaa taacacgcat gaaaatgaca agttatatta taccttttttt   1380

tctcaatata tgaatatacg taacaaatta actccagtag tttttagtaa aactattaga   1440

ttattgtgta acatatactc tggaaatagt actaagatcc attacaatct ttattgagaa   1500

atttcctcat gtaccccctg aggtttggcg taatttccaa ataccccctca tatttgagga   1560

atttctcaaa taccctgatg tttttgttta gactcaaaat acctttacta tggacagtac   1620

cctaatgtca ttaagttttc cccttctctc tccccaattt tctctctcct cccattcccc   1680

cacccactac ccactgccca ctgccaagta ggggtgtaag tggattggac tggattggac   1740

tttgccaaat tcaaatccag tccaaagttt tttggactcg agaaattgag tccaagtccg   1800

atccaaatat tttttgagtc cagtccaatc tagtccgata attttttcttt gagtccgaat   1860

ccagtccagt ccagtccgat tattatatct tttttcccga tttaggttca atgattcaca   1920
```

-continued

```
acatttttttg agatgcttga gcatttgaca tctgattcaa ttatcaatat ccacaaataa   1980
gattgaaagc ttaaattaaa gtaaaatact atgaataaaa agttgaatta gatgcttacc   2040
ttgatctaag ttgagaggaa gcatagagac tgagaattaa tctgagggac aaatagagaa   2100
tgcgagagtc gagacagtga ggtagaaaga aaatgaagag taagaggaag tgagtattaa   2160
ggactgagga gtaaagtaag atagaattag ttggctacta gcctactaat gcagtattgc   2220
tagtataatt tacttattta acaaatggag ctaagtgcaa tagtttagcg ccaattgaca   2280
tatttagaga gagaaggctg aaaaatccaa tatttttaaa atagtatcat tatttttaat   2340
atatacatta tatataaaaa tatttttgga ctggactgga catattggac tccaaaggga   2400
tgagtccaaa tccagacaaa aaatatttgg acttgaaaat ttaagtccga gtccagtccg   2460
aaaaatttc agtccaatcc agtccgacaa atttggactg gactggattg gactctgaac   2520
ttttcgtagt ccgcttacac ccctactgcc aagtgccaaa ctgccaaccc ccttttggtt   2580
gagttgatat ttgacgcaaa gacttggcgt gttggaaggt tcattacaca ttttatccaa   2640
gtcaactttg aagtcttctt agctagagac tagagtgaac gtgttggaag gttcattaca   2700
cattttatcc aatcaaactt tgaagtcttc ttagctagag actagagtga acgtgttgga   2760
aggttcatgt tcatgacatt ataaaagtaa taatagtgaa atttcacaaa gtatttataa   2820
acccaggaca gactcaagag ctctacttat tattagtgaa aaacaaacat acacacgaca   2880
ataacacaac ataaacaata atgaacatga aaatcctcct tttgtttgtc ttccttcatc   2940
acctccacta cttcatccat ggcagaacac ttacagaacg ccaagcttta ctaagtatca   3000
aatctgccat tacttatgat tattataact ctctctcctc atggaaaaac acaacacacc   3060
actgcagttg gccatacatc acttgctcct cctcttcttc ttcttcttct gttatttctc   3120
tcaacttcac catgttattt ctcgaaggaa ttctctcccc tgatataggc ttcctcacca   3180
acctgcaaaa cctctctatt cgatctaacc ttttttctgg cccactcccc cattctctct   3240
ctctcctcac ccaactccgc tatctcgacg tttcccaaaa cagtttcaca ggtccaatcc   3300
catcttctct ctctctcctc acccaactcc gctatctcca cgtttccggc aacagtttca   3360
caggtccaat cccatctttt ctctctctcc tcacccaact ccgctatctc gacgtttccg   3420
acaacagttt cacaggtcca atcccatctt ctctctctct cctcacccaa ctccgctatc   3480
tcgacgtttc ctacaacaat ctaaatggca ctcttccctt atcggtcgtt gagaagatgt   3540
cggagctcag ctaccttaac cttaggtata actctttcta cggtgagatt ccaccggagt   3600
ttgggaaact taagaagctt gaaacattga atcttggtaa caacactctt tctgggagtc   3660
ttccatctga gttgggttca ttaaagagtt tgaaacatat ggacttttct agtaatatgc   3720
tatttggtga gatcccacaa tcttattctc ttcttcgaaa cttaatcgat attgatctta   3780
atagaaacaa gttatatggg agtatacctg attatattgg agattttccg gagttggaat   3840
cacttttatt agactcgaat aacttcacag ggagtatccc acaaaagtta ggtacaaacg   3900
ggaagttgca atatctagat ataagtaaca acaattttag tggtagtttg ccactaagtc   3960
tttgcaaagg agacaaactc caagatctgg acgcatccta taatttgttg gttgggtcaa   4020
ttcctgagag tttgggaagt tgcaagtcac ttgaaggagt gtacatggga aataatttct   4080
taaacgggtc gattcctaag ggcttgtttg ggagtgatgt ttcacttaat gacaaacttc   4140
ttagtggagg tctcgatgag aaattcggtg attgcgttaa tcttcgggac attgatctct   4200
ctaataataa gctatcaggg aagttacctg cgaccatcgg aaactgtatt catcttcggt   4260
```

```
ccttgacgct ttataataac acctgtaccg gacgtatccc tcaagagatt agcaagtgta   4320
agcagctaca gaccctcgat ctcagccaaa atcagttctc tggtgtgata cccaatgata   4380
ttacaggtaa gaaagtatat taaacttgtt acttttgaaa atattcgctc tagtttttgt   4440
ttcagttggt ccattctcac tttgtattat tgaaatatat cccaaaaaag taaatataat   4500
tatataaaag aatcttgcta aaaataatat gaattatttt tgtatgtgca aaataatgta   4560
caaatctaac taatttgttg tggataataa tattaattgt gtgaaatagt aaatgtgtgg   4620
agatatataa ctttatttat catattcact caggttttta ggtatttatt atgagttttg   4680
cattggagat atccaacttg acaatagtat ttttgtaata taccaatata taaagattac   4740
tgtacataac caaaatgtat acttttctta tttttataaa cttatatatt cctcttcttt   4800
gtatttatca caacattttt tataccettt tgcctcatat taatagcaac acttataatt   4860
tatttattta ctttttattt cttggtctat aacctcatct acccacatat gacacaccct   4920
ataaaggacc cacatgatta accaaaatat acaaatatct tcaatgaaat taactttaac   4980
actaatatga taaaaatcat gtcccgcttt ttatcctcta actaagactc tgcataaagg   5040
tatattgcaa ttaatatgag atggaagagg tataataatt atatgatcaa attcctggat   5100
tgaaaaataa atatgagatt aaaagtggta tgtttttggt taaaagaaac tatccataaa   5160
gtatgttttt ggttaaaaga aactatgcaa cataccaatc aaatgtttat acgcttacaa   5220
tttatgtacc actttttgt cattgttttt ctattgtttg ccatacgtac gttactaaat   5280
catgttgtct tttcacattt taactaacaa taaattacta ttgatacacc aaaaaaatct   5340
atgagcattg gagtacgttg tttgatagaa gcttcgtgct attatttctt gtcaaagaat   5400
ttcatatctc aatatcttct aatttaacaa tctaacgaaa tttttttgac ccaggaaaca   5460
aatccatttg caatctggaa aagatacaaa cacttaaatt atcaaacaat gctttgactg   5520
gtgaaatccc tcattgtgtt ggaaatatcg agctcatagc attatttctc caatcaaaca   5580
aactgaacgg taccataccc gcaaacttct caaagttatg tgattcattg atatatctag   5640
atcttagtga caatcaactc gaaggagttc tacctaagtc cttgtccaaa tgtcaaagtc   5700
tagaactcct aaatgtcggg aacaataggc taagagataa atttccttca tggttagaca   5760
acctcccacg tctccaagtt ttcagtgtgc gttttaacgc cttctacggt cctataacta   5820
gctcaccaaa agttagtcac ccatttccta tgctacaaat tatcgaccta tctaacaata   5880
agttttgtgg caagttgcca agaagatata tcaaaaactt tgcaaccatg cgcaatatga   5940
atgagtctgg tgttgggaat ccacagtacc tgggggactc atcaatatat agtattacgt   6000
actctatggt attgacattc aatgggttac aacaaaaata tgaaaagctt attgtgacga   6060
tgtcgacctt tgatatatcc agcaacaact ttactggaca gattccatat gttatagggg   6120
gattacgctc acttcgtaac cttaatctct ctcataatgt cttaaccggg aacattcctc   6180
catcaattgc aaaattgtct ttgcttcaag atttggacct ttcatcaaac agacttactg   6240
gtcgtatccc tcaagaatta gttagtttaa catttcttgg gagtttcaat gtttcgaaca   6300
atctattgga ggggtctata cctcatggtt tcaacttcga cacgtacaca gctaattcat   6360
accaggggaa tctcgaatta tgtggaaaac cattacctga gtgtggagaa agaagggcaa   6420
aaggcaccac taataatcaa gatgatccta aaaatgataa tgaacgaatg ttgtcgatgt   6480
ccgaaatcgt agttatgggg tttggcagtg gtgtactagt tgggttggct tggggatact   6540
atatgttttc agtgggaaag cccttttggt ttatcaagat ggctagcaaa atggaatcaa   6600
tattgattgg ttttttctga ccaacaattt gttagccgat gaagagcatc aaaaccaaaa   6660
```

```
aaaacaaaaa aaattgatta atatgcatga gtgtgacctt gttttccaaa gtttagcatt   6720

actattagtg tctcaattca taataataaa aaaattagct tgttcaagat ttgtattttt   6780

attcaaagat tttttttgtc tcttgtgctt cttttatctt atatatattt tttgtatggt   6840

ttgtttttgt ttaatattag tccctccgct caaaatgatc tttcacgctt gagattggca   6900

ttaaggtcaa gagatgttgc taagctttag aataaaaaaa ttccaaatgc atagagggaa   6960

agaaagcgag acaaaatgtt ggagaaggca gagtaaatga tgtgatggag gataaatagt   7020

agaagtgtga taccgaaagt ttgaaaataa taaggaattt tatttcttgc tggcactttg   7080

ttctagtaca ggtttttagc ccttcaaaat gtttataatg tagagtcaaa attaatatcc   7140

ttaactagtt tttaagtccg ggttatatcc tagatattaa taatattcat ttattagtaa   7200

cattttattt tataaatata atactaagca ttatttggtt tgctggttaa gactttagtg   7260

tatatctatt tctttttttt tttattgtat gcgtgtttac ataaactaaa gactataagg   7320

gatagtacca cgtggcgcag ttccttgctt aggaacgtct tttaatatat taactagtat   7380

ttgggcccgg gcgttgctcc gggttggtat tgtgtttccg aacatgatgt gcagtttttc   7440

ccattcccac taaaatatat aaaggaaaac tcaacattta aaagatacaa atataataat   7500

atggacactt aaaacatgat taaaagttga ttgagatggt aattgtgtca tgttataata   7560

gtaagaggtt gcctaattga ggttgaggtg gtggagtagt ggtatcgctt cccatctgtt   7620

atccctgaga tataaggatc aaacctcata ggactcattt gagtaatttc ccatatcctc   7680

ctctcaaatg agtccttttc atctgacaaa aaaaaatgtc taattttaaa ttaaaattag   7740

acgatctttt ataaaatcgg cactttctgc acataggtca caattttttt gtttctatct   7800

ctctgctttc tttaattcta cagtctccaa ctctccatca acatcttact tattttagaa   7860

tagatgatgt atggtagtat taaatggtaa agtactaaag ctcctataat acacagaagc   7920

ttacatagta tagattcgta catgagacaa ggttacaata tactttctcc gttcttttta   7980

tattacaata attactattt taagtagttt cacatctatt gtaacaattc caattttgtt   8040

atagaaagca actttaataa ttgacaatat tgcccttact ttatcttatt aaaaccatca   8100

ttaattactc actttctctt ataaaattgc ttttattttc taaggataat ttctctccta   8160

ttctagttaa ttaaagagtt acttttgtgc taaactgctc atttgttcca aatccttaaa   8220

aattgtgtcc aaacgcattg ttgtaatata aaaagaacag aggtactatt agtttgaata   8280

aattttgatc ggattaggtc acctttaggg ggcgtttggt taggggtatt ctggaaacgg   8340

taagggaatc aacttactta attcccttac ttgttgtttg tttgctcaat ttaatgattc   8400

cctttaccca ccccttactc ccaaagtcct ttactctcat tccccccacc ccccaaggtt   8460

tcacttaccc tttcttgatt catcattgac catatctttg accacccaac taccaccacc   8520

acttgaccac ctaatcacct aaccacctaa cccaaccact attaccaccc aacccctcca   8580

cctgcccacc aatcggcacc agaactgccc aaccgtcgcc caatcaagcc acccaaccgg   8640

caccataacc gcccaaccaa gccacccaac cggcaccaga aattgtacca agctacccac   8700

acacgtgaaa accacccacc cacaaa                                          8726
```

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
atgttatctt taccacagtt 20

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
gtccctaaat gaaatacgta aaac 24

<210> SEQ ID NO 83
<211> LENGTH: 3706
<212> TYPE: DNA
<213> ORGANISM: Artificial Sequence
<220> FEATURE:
<223> OTHER INFORMATION: PCR Product

<400> SEQUENCE: 83
atgttatctt taccacagtt tgttgctctg acacaaccgg taaatgcatt ggcctttgtt 60
tttgatggca tcaactttgg agcatctgat tttgcatatt cagccttttc catggtaatt 120
cttttacaag aattttcatt ctttcttaag tataaacact tagcttggga caaacttctg 180
atcctatttc ttaatttttg caggtgatgg tggctgttat gagcattttg tgtttgatgt 240
ttctttcttc tcattacggt tttattggga tctgggtggc tctaactatt tacatgagcc 300
tccgcgcgtt tgctgaaggc gggaaacgac aatctgatcc ccatcaagct tgagctcagg 360
atttagcagc attccagatt gggttcaatc aacaaggtac gagccatatc actttattca 420
aattggtatc gccaaaacca agaaggaact cccatcctca aaggtttgta aggaagaatt 480
ctcagtccaa agcctcaaca aggtcagggt acagagtctc caaaccatta gccaaaagct 540
acaggagatc aatgaagaat cttcaatcaa agtaaactac tgttccagca catgcatcat 600
ggtcagtaag tttcagaaaa agacatccac cgaagactta aagttagtgg gcatctttga 660
aagtaatctt gtcaacatcg agcagctggc ttgtggggac cagacaaaaa aggaatggtg 720
cagaattgtt aggcgcacct accaaaagca tctttgcctt tattgcaaag ataaagcaga 780
ttcctctagt acaagtgggg aacaaaataa cgtggaaaag agctgtcctg acagcccact 840
cactaatgcg tatgacgaac gcagtgacga ccacaaaaga attccctcta tataagaagg 900
cattcattcc catttgaagg atcatcagat actcaaccaa tccttctaga agatctaagc 960
ttatcgataa gcttgatgta attggaggaa gatcaaaatt ttcaatcccc attcttcgat 1020
tgcttcaatt gaagtttctc cgatggcgca agttagcaga atctgcaatg gtgtgcagaa 1080
cccatctctt atctccaatc tctcgaaatc cagtcaacgc aaatctccct tatcggtttc 1140
tctgaagacg cagcagcatc cacgagctta tccgatttcg tcgtcgtggg gattgaagaa 1200
gagtgggatg acgttaattg gctctgagct tcgtcctctt aaggtcatgt cttctgtttc 1260
cacggcgtgc atgcttcacg gtgcaagcag ccgtccagca actgctcgta agtcctctgg 1320
tctttctgga accgtccgta ttccaggtga caagtctatc tcccacaggt ccttcatgtt 1380
tggaggtctc gctagcggtg aaacccgtat caccggtctt ttggaaggtg aagatgttat 1440
caacactggt aaggctatgc aagctatggg tgccagaatc cgtaaggaag gtgatacttg 1500
gatcattgat ggtgttggta acggtggact ccttgctcct gaggctcctc tcgatttcgg 1560
taacgctgca actggttgcc gtttgactat gggtcttgtt ggtgtttacg atttcgatag 1620

```
cactttcatt ggtgacgctt ctctcactaa gcgtccaatg ggtcgtgtgt tgaacccact   1680

tcgcgaaatg ggtgtgcagg tgaagtctga agacggtgat cgtcttccag ttaccttgcg   1740

tggaccaaag actccaacgc caatcaccta cagggtacct atggcttccg ctcaagtgaa   1800

gtccgctgtt ctgcttgctg gtctcaacac cccaggtatc accactgtta tcgagccaat   1860

catgactcgt gaccacactg aaaagatgct tcaaggtttt ggtgctaacc ttaccgttga   1920

gactgatgct gacggtgtgc gtaccatccg tcttgaaggt cgtggtaagc tcaccggtca   1980

agtgattgat gttccaggtg atccatcctc tactgctttc ccattggttg ctgccttgct   2040

tgttccaggt tccgacgtca ccatccttaa cgttttgatg aacccaaccc gtactggtct   2100

catcttgact ctgcaggaaa tgggtgccga catcgaagtg atcaacccac gtcttgctgg   2160

tggagaagac gtggctgact tgcgtgttcg ttcttctact ttgaagggtg ttactgttcc   2220

agaagaccgt gctccttcta tgatcgacga gtatccaatt ctcgctgttg cagctgcatt   2280

cgctgaaggt gctaccgtta tgaacggttt ggaagaactc cgtgttaagg aaagcgaccg   2340

tctttctgct gtcgcaaacg gtctcaagct caacggtgtt gattgcgatg aaggtgagac   2400

ttctctcgtc gtgcgtggtc gtcctgacgg taagggtctc ggtaacgctt ctggagcagc   2460

tgtcgctacc cacctcgatc accgtatcgc tatgagcttc ctcgttatgg gtctcgtttc   2520

tgaaaaccct gttactgttg atgatgctac tatgatcgct actagcttcc cagagttcat   2580

ggatttgatg gctggtcttg gagctaagat cgaactctcc gacactaagg ctgcttgatg   2640

agctcaagaa ttcgagctcg gtaccggatc ctctagctag agctttcgtt cgtatcatcg   2700

gtttcgacaa cgttcgtcaa gttcaatgca tcagtttcat tgcgcacaca ccagaatcct   2760

actgagtttg agtattatgg cattgggaaa actgtttttc ttgtaccatt tgttgtgctt   2820

gtaatttact gtgtttttta ttcggttttc gctatcgaac tgtgaaatgg aaatggatgg   2880

agaagagtta atgaatgata tggtcctttt gttcattctc aaattaatat tatttgtttt   2940

ttctcttatt tgttgtgtgt tgaatttgaa attataagag atatgcaaac attttgtttt   3000

gagtaaaaat gtgtcaaatc gtggcctcta atgaccgaag ttaatatgag gagtaaaaca   3060

cttgtagttg taccattatg cttattcact aggcaacaaa tatattttca gacctagaaa   3120

agctgcaaat gttactgaat acaagtatgt cctcttgtgt tttagacatt tatgaacttt   3180

cctttatgta attttccaga atccttgtca gattctaatc attgctttat aattatagtt   3240

atactcatgg atttgtagtt gagtatgaaa atatttttta atgcatttta tgacttgcca   3300

attgattgac aacatgcatc aatcgacctg cagccactcg aagcggccgc cactcgagtg   3360

gtggccgcat cgatcgtgaa gtttctcatc taagccccca tttggacgtg aatgtagaca   3420

cgtcgaaata aagatttccg aattagaata atttgtttat tgctttcgcc tataaatacg   3480

acggatcgta atttgtcgtt ttatcaaaat gtactttcat tttataataa cgctgcggac   3540

atctacattt ttgaattgaa aaaaattggt aattactctt tctttttctc catattgacc   3600

atcatactca ttgctgatcc atgtagattt cccggacatg aagccattta caattgaata   3660

tatcctaagt aaaacctcat aggttttacg tatttcattt agggac                  3706
```

<210> SEQ ID NO 84
<211> LENGTH: 26
<212> TYPE: DNA
<213> ORGANISM: Artificial Sequence
<220> FEATURE:
<223> OTHER INFORMATION: Primer

<400> SEQUENCE: 84
cgctgcggac atctacattt ttgaat 26

<210> SEQ ID NO 85
<211> LENGTH: 28
<212> TYPE: DNA
<213> ORGANISM: Artificial Sequence
<220> FEATURE:
<223> OTHER INFORMATION: agttaacttt ccacttatcg gggcactg

<400> SEQUENCE: 85
agttaacttt ccacttatcg gggcactg 28

<210> SEQ ID NO 86
<211> LENGTH: 751
<212> TYPE: DNA
<213> ORGANISM: Artificial Sequence
<220> FEATURE:
<223> OTHER INFORMATION: PCR Product

<400> SEQUENCE: 86
cgctgcggac atctacattt ttgaattgaa aaaaaattgg taattactct ttctttttct 60
ccatattgac catcatactc attgctgatc catgtagatt tcccggacat gaagccattt 120
acaattgaat atatcctaag taaaacctca taggttttac gtatttcatt tagggactaa 180
aatggtttag gataattact ttagctaaca taagataata aataaataaa taaataaaaa 240
taaaatggtt gtagataaat aaggaaatca ataatgaata tgagtgtgag tgataggacg 300
ggaatgggaa acttttacac tactttaacg ctattgaacg agtatgagta tgttataaac 360
gtaaaatgtt ttatgtgtta gacaatggcc tcaagtgaaa gtgaccctat taatggagga 420
aatgcaaacc acgagtctga ggtcacgctc gaagaaatga gggcaaggat cgacgcattg 480
cgtagcgacc ctgtttttgg agatgccacg ggagatgcta gtgataaccg aatggattta 540
atgaggttga tgatgatgga gcttttacaa ggaaatcgac aaaggcctag aactgaacaa 600
gaagagtgct caaacatgtt caagaggttt tcggctcata agcccccaac ttatgatgga 660
aagccagacc ccactgagtt tgaagaatgg ctcaacggca tggaaaaatt gttcgatgcc 720
acccagtgcc ccgataagtg gaaagttaac t 751

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
gctctgacac aaccggtaaa tgcattggcc 30

<210> SEQ ID NO 88
<211> LENGTH: 29
<212> TYPE: DNA
<213> ORGANISM: Artificial Sequence
<220> FEATURE:
<223> OTHER INFORMATION: Primer

<400> SEQUENCE: 88
gcagattctg ctaacttgcg ccatcggag 29

<210> SEQ ID NO 89
<211> LENGTH: 1042

```
<212> TYPE: DNA
<213> ORGANISM: Artificial Sequence
<220> FEATURE:
<223> OTHER INFORMATION: PCR Product

<400> SEQUENCE: 89

gctctgacac aaccggtaaa tgcattggcc tttgtttttg atggcatcaa ctttggagca      60

tctgattttg catattcagc cttttccatg gtaattcttt tacaagaatt ttcattcttt     120

cttaagtata aacacttagc ttgggacaaa cttctgatcc tatttcttaa tttttgcagg     180

cgatggtggc tgttatgagc attttgtgtt tgatgtttct ctcttctcat tacggtttta     240

ttgggatctg ggtggctcta actatttaca tgagcctccg cgcgtttgct gaaggcggga     300

aacgacaatc tgatccccat caagcttgag ctcaggattt agcagcattc cagattgggt     360

tcaatcaaca aggtacgagc catatcactt tattcaaatt ggtatcgcca aaaccaagaa     420

ggaactccca tcctcaaagg tttgtaagga agaattctca gtccaaagcc tcaacaaggt     480

cagggtacag agtctccaaa ccattagcca aaagctacag gagatcaatg aagaatcttc     540

aatcaaagta aactactgtt ccagcacatg catcatggtc agtaagtttc agaaaaagac     600

atccaccgaa gacttaaagt tagtgggcat ctttgaaagt aatcttgtca acatcgagca     660

gctggcttgt ggggaccaga caaaaaagga atggtgcaga attgttaggc gcacctacca     720

aaagcatctt tgcctttatt gcaaagataa agcagattcc tctagtacaa gtggggaaca     780

aaataacgtg gaaaagagct gtcctgacag cccactcact aatgcgtatg acgaacgcag     840

tgacgaccac aaaagaattc cctctatata agaaggcatt cattcccatt tgaaggatca     900

tcagatactg aaccaatcct tctagaagat ctaagcttat cgataagctt gatgtaattg     960

gaggaagatc aaaattttca atccccattc ttcgattgct tcaattgaag tttctccgat    1020

ggcgcaagtt agcagaatct gc                                              1042


<210> SEQ ID NO 90
<211> LENGTH: 665
<212> TYPE: PRT
<213> ORGANISM: Beta vulgaris

<400> SEQUENCE: 90

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
```

-continued

```
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220

Ile Val Lys Glu Ala Phe Phe Leu Ala Asn Ser Gly Arg Pro Gly Pro
225                 230                 235                 240

Val Leu Ile Asp Leu Pro Lys Asp Ile Gln Gln Gln Leu Val Val Pro
                245                 250                 255

Asp Trp Asp Arg Pro Phe Lys Leu Gly Gly Tyr Met Ser Arg Leu Pro
            260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
    290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
            340                 345                 350

Asn Tyr Ala Val Asp Lys Ala Asp Leu Leu Leu Ala Phe Gly Val Arg
        355                 360                 365

Phe Asp Asp Arg Val Thr Gly Lys Leu Glu Ala Phe Ala Ser Arg Ala
    370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
        435                 440                 445

Ser Phe Lys Thr Phe Gly Asp Ala Ile Pro Pro Gln Tyr Ala Ile Gln
    450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
            500                 505                 510

Pro Ala Ala Ile Gly Ala Ala Val Ala Arg Pro Asp Ala Val Val Val
        515                 520                 525

Asp Ile Asp Gly Asp Gly Ser Phe Ile Met Asn Val Gln Glu Leu Ala
    530                 535                 540

Thr Ile Arg Val Glu Asn Leu Pro Val Lys Ile Met Leu Leu Asn Asn
545                 550                 555                 560

Gln His Leu Gly Met Val Val Gln Trp Glu Asp Arg Phe Tyr Lys Ala
                565                 570                 575
```

```
Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
        595                 600                 605

Arg Val Ser Asn Val Ala Asp Leu Arg Ala Ala Ile Gln Thr Met Leu
    610                 615                 620

Asp Thr Pro Gly Pro Tyr Leu Leu Asp Val Ile Val Pro His Gln Glu
625                 630                 635                 640

His Val Leu Pro Met Ile Pro Ser Gly Ala Gly Phe Lys Asp Thr Ile
                645                 650                 655

Thr Glu Gly Asp Gly Arg Thr Ser Tyr
            660                 665
```

<210> SEQ ID NO 91
<211> LENGTH: 1998
<212> TYPE: DNA
<213> ORGANISM: Artificial Sequence
<220> FEATURE:
<223> OTHER INFORMATION: Acetolactate synthase with mutation

<400> SEQUENCE: 91

```
atggcggcta ccttcacaaa cccaacattt tccccttcct caactccatt aaccaaaacc      60

ctaaaatccc aatcttccat ctcttcaacc ctcccctttt ccacccctcc caaaacccca     120

actccactct ttcaccgtcc cctccaaatc tcatcctccc aatcccacaa atcatccgcc     180

attaaaacac aaactcaagc accttcttct ccagctattg aagattcatc tttcgtttct     240

cgatttggcc ctgatgaacc cagaaaaggg tccgatgtcc tcgttgaagc tcttgagcgt     300

gaaggtgtta ccaatgtgtt tgcttaccct ggtggtgcat ctatggaaat ccaccaagct     360

ctcacacgct ctaaaaccat ccgcaatgtc ctccctcgcc atgaacaagg cggggttttc     420

gccgccgagg gatatgctag agctactgga aaggttggtg tctgcattgc gacttctggt     480

cctggtgcta ccaacctcgt atcaggtctt gctgacgctc tccttgattc tgtccctctt     540

gttgccatca ctggccaagt tccacgccgt atgattggca ctgatgcttt tcaggagact     600

ccaattgttg aggtgacaag gtctattact aagcataatt atttagtttt ggatgtagag     660

gatattccta gaattgttaa ggaagccttt tttttagcta attctggtag gcctggacct     720

gttttgattg atcttcctaa agatattcag cagcaattgg ttgttcctga ttgggatagg     780

ccttttaagt tgggtgggta tatgtctagg ctgccaaagt ccaagttttc gacgaatgag     840

gttggacttc ttgagcagat tgtgaggttg atgagtgagt cgaagaagcc tgtcttgtat     900

gtgggaggtg ggtgtttgaa ttctagtgag gagttgagga gatttgttga gttgacaggg     960

attccggtgg ctagtacttt gatggggttg ggtcttaccc cttgtaatga tgaactgtct    1020

cttcatatgt tggggatgca cgggactgtt tatgccaatt atgcggtgga taaggcggat    1080

ttgttgcttg ctttcggggt taggtttgat gatcgtgtga ccgggaagct cgaggcgttt    1140

gctagccgtg ctaagattgt gcatattgat attgactctg ctgagattgg gaagaacaag    1200

cagccccatg tgtccatttg tgctgatgtt aaattggcat tgcggggtat gaataagatt    1260

ctggagtcta gaatagggaa gctgaatttg gatttctcca agtggagaga agaattaggt    1320

gagcagaaga aggaattccc actgagtttt aagacatttg gggatgcaat tcctccacaa    1380

tatgccattc aggtgcttga tgagttgacc aatggtaatg ctattataag tactggtgtt    1440

gggcagcacc aaatgtgggc tgcgcagcat tacaagtaca gaaaccctcg ccaatggctg    1500
```

```
acctctggtg ggttgggggc tatggggttt gggctaccag ccgccattgg agctgcagtt   1560

gctcgaccag atgcagtggt tgtcgatatt gatggggatg gcagttttat tatgaatgtt   1620

caagagttgg ctacaattag ggtggaaaat ctcccagtta agataatgct gctaaacaat   1680

caacatttag gtatggttgt ccaattggaa gataggttct ataaagctaa ccgggcacat   1740

acataccttg gaaacccttc caaatctgct gatatcttcc ctgatatgct caaattcgct   1800

gaggcatgtg atattccttc tgcccgtgtt agcaacgtgg ctgatttgag ggccgccatt   1860

caaacaatgt tggatactcc agggccgtac ctgctcgatg tgattgtacc gcatcaagag   1920

catgtgttgc ctatgattcc aagtggtgcc ggtttcaagg ataccattac agagggtgat   1980

ggaagaacct cttattga                                                 1998
```

<210> SEQ ID NO 92
<211> LENGTH: 21
<212> TYPE: DNA
<213> ORGANISM: beta vulgaris

<400> SEQUENCE: 92

```
cctgagagtt tgggaagttg c                                               21
```

<210> SEQ ID NO 93
<211> LENGTH: 23
<212> TYPE: DNA
<213> ORGANISM: beta vulgaris

<400> SEQUENCE: 93

```
atgtcccgaa gattaacgca atc                                             23
```

<210> SEQ ID NO 94
<211> LENGTH: 3720
<212> TYPE: DNA
<213> ORGANISM: Artificial Sequence
<220> FEATURE:
<223> OTHER INFORMATION: modified genomic sequence of the gene mediating resistance towards cercospora
<220> FEATURE:
<221> NAME/KEY: variation
<222> LOCATION: (16)..(18)

<400> SEQUENCE: 94

```
atgaacatga aaatcttact tttgtttgtc ttccttcatc acctccacta cttcatccat     60

ggcagaacac ttacagaacg ccaagcttta ctaagtatca aatctgccat tacttatgat    120

tattataact ctctctcctc atggaaaaac acaacacacc actgcagttg gccatacatc    180

acttgctcct cctcttcttc ttcttcttct gttatttctc tcaacttcac catgttattt    240

ctcgaaggaa ttctctcccc tgatataggc ttcctcacca acctgcaaaa cctctctatt    300

cgatctaacc ttttttctgg cccactcccc cattctctct ctctcctcac ccaactccgc    360

tatctcgacg tttcccaaaa cagtttcaca ggtccaatcc catcttctct ctctctcctc    420

acccaactcc gctatctcca cgtttccggc aacagtttca caggtccaat cccatctttt    480

ctctctctcc tcacccaact ccgctatctc gacgtttccg acaacagttt cacaggtcca    540

atcccatctt ctctctctct cctcacccaa ctccgctatc tcgacgtttc ctacaacaat    600

ctaaatggca ctcttccctt atcggtcgtt gagaagatgt cggagctcag ctaccttaac    660

cttaggtata actctttcta cggtgagatt ccaccggagt ttgggaaact taagaagctt    720

gaaacattga atcttggtaa caacactctt tctgggagtc ttccatctga gttgggttca    780

ttaaagagtt tgaaacatat ggacttttct agtaatatgc tatttggtga gatcccacaa    840
```

```
tcttattctc ttcttcgaaa cttaatcgat attgatctta atagaaacaa gttatatggg    900
agtatacctg attatattgg agattttccg gagttggaat cacttttatt agactcgaat    960
aacttcacag ggagtatccc acaaaagtta ggtacaaacg ggaagttgca atatctagat   1020
ataagtaaca acaattttag tggtagtttg ccactaagtc tttgcaaagg agacaaactc   1080
caagatctgg acgcatccta taatttgttg gttgggtcaa ttcctgagag tttgggaagt   1140
tgcaagtcac ttgaaggagt gtacatggga aataatttct taaacgggtc gattcctaag   1200
ggcttgtttg ggagtgatgt ttcacttaat gacaaacttc ttagtggagg tctcgatgag   1260
aaattcggtg attgcgttaa tcttcgggac attgatctct ctaataataa gctatcaggg   1320
aagttacctg cgaccatcgg aaactgtatt catcttcggt ccttgacgct ttataataac   1380
acctgtaccg gacgtatccc tcaagagatt agcaagtgta agcagctaca gaccctcgat   1440
ctcagccaaa atcagttctc tggtgtgata cccaatgata ttacaggtaa gaaagtatat   1500
taaacttgtt actttgaaa atattcgctc tagtttttgt ttcagttggt ccattctcac   1560
tttgtattat tgaaatatat cccaaaaaag taaatataat tatataaaag aatcttgcta   1620
aaaataatat gaattatttt tgtatgtgca aaataatgta caaatctaac taatttgttg   1680
tggataataa tattaattgt gtgaaatagt aaatgtgtgg agatatataa ctttatttat   1740
catattcact caggttttta ggtatttatt atgagttttg cattggagat atccaacttg   1800
acaatagtat ttttgtaata taccaatata taaagattac tgtacataac caaaatgtat   1860
acttttctta tttttataaa cttatatatt cctcttcttt gtatttatca caacattttt   1920
tatacccttt tgcctcatat taatagcaac acttataatt tatttattta ctttttattt   1980
cttggtctat aacctcatct acccacatat gacacaccct ataaaggacc cacatgatta   2040
accaaaatat acaaatatct tcaatgaaat taactttaac actaatatga taaaaatcat   2100
gtcccgcttt ttatcctcta actaagactc tgcataaagg tatattgcaa ttaatatgag   2160
atggaagagg tataataatt atatgatcaa attcctggat tgaaaaataa atatgagatt   2220
aaaagtggta tgtttttggt taaaagaaac tatccataaa gtatgttttt ggttaaaaga   2280
aactatgcaa cataccaatc aaatgtttat acgcttacaa tttatgtacc actttttttgt   2340
cattgttttt ctattgtttg ccatacgtac gttactaaat catgttgtct tttcacattt   2400
taactaacaa taaattacta ttgatacacc aaaaaaatct atgagcattg gagtacgttg   2460
tttgatagaa gcttcgtgct attatttctt gtcaaagaat ttcatatctc aatatcttct   2520
aatttaacaa tctaacgaaa tttttttgac ccaggaaaca aatccatttg caatctggaa   2580
aagatacaaa cacttaaatt atcaaacaat gctttgactg gtgaaatccc tcattgtgtt   2640
ggaaatatcg agctcatagc attatttctc caatcaaaca aactgaacgg taccataccc   2700
gcaaacttct caaagttatg tgattcattg atatatctag atcttagtga caatcaactc   2760
gaaggagttc tacctaagtc cttgtccaaa tgtcaaagtc tagaactcct aaatgtcggg   2820
aacaataggc taagagataa atttccttca tggttagaca acctcccacg tctccaagtt   2880
ttcagtgtgc gttttaacgc cttctacggt cctataacta gctcaccaaa agttagtcac   2940
ccatttccta tgctacaaat tatcgaccta tctaacaata agttttgtgg caagttgcca   3000
agaagatata tcaaaaactt tgcaaccatg cgcaatatga atgagtctgg tgttgggaat   3060
ccacagtacc tgggggactc atcaatatat agtattacgt actctatggt attgacattc   3120
aatgggttac aacaaaaata tgaaaagctt attgtgacga tgtcgacctt tgatatatcc   3180
```

agcaacaact ttactggaca gattccatat gttatagggg gattacgctc acttcgtaac 3240
cttaatctct ctcataatgt cttaaccggg aacattcctc catcaattgc aaaattgtct 3300
ttgcttcaag atttggacct ttcatcaaac agacttactg gtcgtatccc tcaagaatta 3360
gttagtttaa catttcttgg gagtttcaat gtttcgaaca atctattgga ggggtctata 3420
cctcatggtt tcaacttcga cacgtacaca gctaattcat accaggggaa tctcgaatta 3480
tgtggaaaac cattacctga gtgtggagaa agaagggcaa aaggcaccac taataatcaa 3540
gatgatccta aaaatgataa tgaacgaatg ttgtcgatgt ccgaaatcgt agttatgggg 3600
tttggcagtg gtgtactagt tgggttggct tggggatact atatgttttc agtgggaaag 3660
cccttttggt ttatcaagat ggctagcaaa atggaatcaa tattgattgg ttttttctga 3720

<210> SEQ ID NO 95
<211> LENGTH: 2652
<212> TYPE: DNA
<213> ORGANISM: artificial sequence
<220> FEATURE:
<223> OTHER INFORMATION: modified cDNA sequence of the gene mediating resistance towards cercospora
<220> FEATURE:
<221> NAME/KEY: variation
<222> LOCATION: (55)..(57)

<400> SEQUENCE: 95
atgaacatga aaatcctcct tttgtttgtc ttccttcatc acctccacta cttcatacat 60
ggcagaacac ttacagaacg ccaagcttta ctaagtatca aatctgccat tacttatgat 120
tattataact ctctctcctc atggaaaaac acaacacacc actgcagttg gccatacatc 180
acttgctcct cctcttcttc ttcttcttct gttatttctc tcaacttcac catgttattt 240
ctcgaaggaa ttctctcccc tgatataggc ttcctcacca acctgcaaaa cctctctatt 300
cgatctaacc ttttttctgg cccactcccc cattctctct ctctcctcac ccaactccgc 360
tatctcgacg tttcccaaaa cagtttcaca ggtccaatcc catcttctct ctctctcctc 420
acccaactcc gctatctcca cgtttccggc aacagtttca caggtccaat cccatctttt 480
ctctctctcc tcacccaact ccgctatctc gacgtttccg acaacagttt cacaggtcca 540
atcccatctt ctctctctct cctcacccaa ctccgctatc tcgacgtttc ctacaacaat 600
ctaaatggca ctcttccctt atcggtcgtt gagaagatgt cggagctcag ctaccttaac 660
cttaggtata actctttcta cggtgagatt ccaccggagt ttgggaaact taagaagctt 720
gaaacattga atcttggtaa caacactctt tctgggagtc ttccatctga gttgggttca 780
ttaaagagtt tgaaacatat ggacttttct agtaatatgc tatttggtga gatcccacaa 840
tcttattctc ttcttcgaaa cttaatcgat attgatctta atagaaacaa gttatatggg 900
agtatacctg attatattgg agattttccg gagttggaat cacttttatt agactcgaat 960
aacttcacag ggagtatccc acaaaagtta ggtacaaacg ggaagttgca atatctagat 1020
ataagtaaca acaattttag tggtagtttg ccactaagtc tttgcaaagg agacaaactc 1080
caagatctgg acgcatccta taatttgttg gttgggtcaa ttcctgagag tttgggaagt 1140
tgcaagtcac ttgaaggagt gtacatggga aataatttct taaacgggtc gattcctaag 1200
ggcttgtttg ggagtgatgt ttcacttaat gacaaacttc ttagtggagg tctcgatgag 1260
aaattcggtg attgcgttaa tcttcgggac attgatctct ctaataataa gctatcaggg 1320
aagttacctg cgaccatcgg aaactgtatt catcttcggt ccttgacgct ttataataac 1380
acctgtaccg gacgtatccc tcaagagatt agcaagtgta agcagctaca gaccctcgat 1440

```
ctcagccaaa atcagttctc tggtgtgata cccaatgata ttacaggaaa caaatccatt   1500

tgcaatctgg aaaagataca aacacttaaa ttatcaaaca atgctttgac tggtgaaatc   1560

cctcattgtg ttggaaatat cgagctcata gcattatttc tccaatcaaa caaactgaac   1620

ggtaccatac ccgcaaactt ctcaaagtta tgtgattcat tgatatatct agatcttagt   1680

gacaatcaac tcgaaggagt tctacctaag tccttgtcca aatgtcaaag tctagaactc   1740

ctaaatgtcg ggaacaatag gctaagagat aaatttcctt catggttaga caacctccca   1800

cgtctccaag ttttcagtgt gcgttttaac gccttctacg gtcctataac tagctcacca   1860

aaagttagtc acccatttcc tatgctacaa attatcgacc tatctaacaa taagttttgt   1920

ggcaagttgc caagaagata tatcaaaaac tttgcaacca tgcgcaatat gaatgagtct   1980

ggtgttggga atccacagta cctgggggac tcatcaatat atagtattac gtactctatg   2040

gtattgacat tcaatgggtt acaacaaaaa tatgaaaagc ttattgtgac gatgtcgacc   2100

tttgatatat ccagcaacaa ctttactgga cagattccat atgttatagg gggattacgc   2160

tcacttcgta accttaatct ctctcataat gtcttaaccg ggaacattcc tccatcaatt   2220

gcaaaattgt ctttgcttca agatttggac ctttcatcaa acagacttac tggtcgtatc   2280

cctcaagaat tagttagttt aacatttctt gggagtttca atgtttcgaa caatctattg   2340

gaggggtcta tacctcatgg tttcaacttc gacacgtaca cagctaattc ataccagggg   2400

aatctcgaat tatgtggaaa accattacct gagtgtggag aaagaagggc aaaaggcacc   2460

actaataatc aagatgatcc taaaaatgat aatgaacgaa tgttgtcgat gtccgaaatc   2520

gtagttatgg ggtttggcag tggtgtacta gttgggttgg cttggggata ctatatgttt   2580

tcagtgggaa agccctttg gtttatcaag atggctagca aaatggaatc aatattgatt   2640

ggtttttttct ga                                                      2652
```

<210> SEQ ID NO 96
<211> LENGTH: 883
<212> TYPE: PRT
<213> ORGANISM: artificial sequence
<220> FEATURE:
<223> OTHER INFORMATION: modified protein sequence of the gene mediating resistance towards cercospora
<220> FEATURE:
<221> NAME/KEY: VARIANT
<222> LOCATION: (209)..(209)

<400> SEQUENCE: 96

```
Met Asn Met Lys Ile Leu Leu Leu Phe Val Phe Leu His His Leu His
1               5                   10                  15

Tyr Phe Ile His Gly Arg Thr Leu Thr Glu Arg Gln Ala Leu Leu Ser
            20                  25                  30

Ile Lys Ser Ala Ile Thr Tyr Asp Tyr Tyr Asn Ser Leu Ser Ser Trp
        35                  40                  45

Lys Asn Thr Thr His His Cys Ser Trp Pro Tyr Ile Thr Cys Ser Ser
    50                  55                  60

Ser Ser Ser Ser Ser Ser Val Ile Ser Leu Asn Phe Thr Met Leu Phe
65                  70                  75                  80

Leu Glu Gly Ile Leu Ser Pro Asp Ile Gly Phe Leu Thr Asn Leu Gln
                85                  90                  95

Asn Leu Ser Ile Arg Ser Asn Leu Phe Ser Gly Pro Leu Pro His Ser
            100                 105                 110

Leu Ser Leu Leu Thr Gln Leu Arg Tyr Leu Asp Val Ser Gln Asn Ser
```

```
        115                 120                 125

Phe Thr Gly Pro Ile Pro Ser Ser Leu Ser Leu Leu Thr Gln Leu Arg
    130                 135                 140

Tyr Leu His Val Ser Gly Asn Ser Phe Thr Gly Pro Ile Pro Ser Phe
145                 150                 155                 160

Leu Ser Leu Leu Thr Gln Leu Arg Tyr Leu Asp Val Ser Asp Asn Ser
                165                 170                 175

Phe Thr Gly Pro Ile Pro Ser Ser Leu Ser Leu Leu Thr Gln Leu Arg
            180                 185                 190

Tyr Leu Asp Val Ser Tyr Asn Asn Leu Asn Gly Thr Leu Pro Leu Ser
        195                 200                 205

Val Leu Glu Lys Met Ser Glu Leu Ser Tyr Leu Asn Leu Arg Tyr Asn
    210                 215                 220

Ser Phe Tyr Gly Glu Ile Pro Pro Glu Phe Gly Lys Leu Lys Lys Leu
225                 230                 235                 240

Glu Thr Leu Asn Leu Gly Asn Asn Thr Leu Ser Gly Ser Leu Pro Ser
                245                 250                 255

Glu Leu Gly Ser Leu Lys Ser Leu Lys His Met Asp Phe Ser Ser Asn
            260                 265                 270

Met Leu Phe Gly Glu Ile Pro Gln Ser Tyr Ser Leu Leu Arg Asn Leu
        275                 280                 285

Ile Asp Ile Asp Leu Asn Arg Asn Lys Leu Tyr Gly Ser Ile Pro Asp
    290                 295                 300

Tyr Ile Gly Asp Phe Pro Glu Leu Glu Ser Leu Leu Leu Asp Ser Asn
305                 310                 315                 320

Asn Phe Thr Gly Ser Ile Pro Gln Lys Leu Gly Thr Asn Gly Lys Leu
                325                 330                 335

Gln Tyr Leu Asp Ile Ser Asn Asn Asn Phe Ser Gly Ser Leu Pro Leu
            340                 345                 350

Ser Leu Cys Lys Gly Asp Lys Leu Gln Asp Leu Asp Ala Ser Tyr Asn
        355                 360                 365

Leu Leu Val Gly Ser Ile Pro Glu Ser Leu Gly Ser Cys Lys Ser Leu
    370                 375                 380

Glu Gly Val Tyr Met Gly Asn Asn Phe Leu Asn Gly Ser Ile Pro Lys
385                 390                 395                 400

Gly Leu Phe Gly Ser Asp Val Ser Leu Asn Asp Lys Leu Leu Ser Gly
                405                 410                 415

Gly Leu Asp Glu Lys Phe Gly Asp Cys Val Asn Leu Arg Asp Ile Asp
            420                 425                 430

Leu Ser Asn Asn Lys Leu Ser Gly Lys Leu Pro Ala Thr Ile Gly Asn
        435                 440                 445

Cys Ile His Leu Arg Ser Leu Thr Leu Tyr Asn Asn Thr Cys Thr Gly
    450                 455                 460

Arg Ile Pro Gln Glu Ile Ser Lys Cys Lys Gln Leu Gln Thr Leu Asp
465                 470                 475                 480

Leu Ser Gln Asn Gln Phe Ser Gly Val Ile Pro Asn Asp Ile Thr Gly
                485                 490                 495

Asn Lys Ser Ile Cys Asn Leu Glu Lys Ile Gln Thr Leu Lys Leu Ser
            500                 505                 510

Asn Asn Ala Leu Thr Gly Glu Ile Pro His Cys Val Gly Asn Ile Glu
        515                 520                 525

Leu Ile Ala Leu Phe Leu Gln Ser Asn Lys Leu Asn Gly Thr Ile Pro
    530                 535                 540
```

```
Ala Asn Phe Ser Lys Leu Cys Asp Ser Leu Ile Tyr Leu Asp Leu Ser
545                 550                 555                 560

Asp Asn Gln Leu Glu Gly Val Leu Pro Lys Ser Leu Ser Lys Cys Gln
                565                 570                 575

Ser Leu Glu Leu Leu Asn Val Gly Asn Asn Arg Leu Arg Asp Lys Phe
            580                 585                 590

Pro Ser Trp Leu Asp Asn Leu Pro Arg Leu Gln Val Phe Ser Val Arg
        595                 600                 605

Phe Asn Ala Phe Tyr Gly Pro Ile Thr Ser Ser Pro Lys Val Ser His
    610                 615                 620

Pro Phe Pro Met Leu Gln Ile Ile Asp Leu Ser Asn Asn Lys Phe Cys
625                 630                 635                 640

Gly Lys Leu Pro Arg Arg Tyr Ile Lys Asn Phe Ala Thr Met Arg Asn
                645                 650                 655

Met Asn Glu Ser Gly Val Gly Asn Pro Gln Tyr Leu Gly Asp Ser Ser
            660                 665                 670

Ile Tyr Ser Ile Thr Tyr Ser Met Val Leu Thr Phe Asn Gly Leu Gln
        675                 680                 685

Gln Lys Tyr Glu Lys Leu Ile Val Thr Met Ser Thr Phe Asp Ile Ser
    690                 695                 700

Ser Asn Asn Phe Thr Gly Gln Ile Pro Tyr Val Ile Gly Gly Leu Arg
705                 710                 715                 720

Ser Leu Arg Asn Leu Asn Leu Ser His Asn Val Leu Thr Gly Asn Ile
                725                 730                 735

Pro Pro Ser Ile Ala Lys Leu Ser Leu Leu Gln Asp Leu Asp Leu Ser
            740                 745                 750

Ser Asn Arg Leu Thr Gly Arg Ile Pro Gln Glu Leu Val Ser Leu Thr
        755                 760                 765

Phe Leu Gly Ser Phe Asn Val Ser Asn Asn Leu Leu Glu Gly Ser Ile
    770                 775                 780

Pro His Gly Phe Asn Phe Asp Thr Tyr Thr Ala Asn Ser Tyr Gln Gly
785                 790                 795                 800

Asn Leu Glu Leu Cys Gly Lys Pro Leu Pro Glu Cys Gly Glu Arg Arg
                805                 810                 815

Ala Lys Gly Thr Thr Asn Asn Gln Asp Asp Pro Lys Asn Asp Asn Glu
            820                 825                 830

Arg Met Leu Ser Met Ser Glu Ile Val Val Met Gly Phe Gly Ser Gly
        835                 840                 845

Val Leu Val Gly Leu Ala Trp Gly Tyr Tyr Met Phe Ser Val Gly Lys
    850                 855                 860

Pro Phe Trp Phe Ile Lys Met Ala Ser Lys Met Glu Ser Ile Leu Ile
865                 870                 875                 880

Gly Phe Phe
```

<210> SEQ ID NO 97
<211> LENGTH: 2652
<212> TYPE: DNA
<213> ORGANISM: artificial sequence
<220> FEATURE:
<223> OTHER INFORMATION: modified cDNA of the gene mediating resistance towards cercospora
<220> FEATURE:
<221> NAME/KEY: variation
<222> LOCATION: (625)..(627)

<400> SEQUENCE: 97

```
atgaacatga aaatcctcct tttgtttgtc ttccttcatc acctccacta cttcatccat     60
ggcagaacac ttacagaacg ccaagcttta ctaagtatca aatctgccat tacttatgat    120
tattataact ctctctcctc atggaaaaac acaacacacc actgcagttg gccatacatc    180
acttgctcct cctcttcttc ttcttcttct gttatttctc tcaacttcac catgttattt    240
ctcgaaggaa ttctctcccc tgatataggc ttcctcacca acctgcaaaa cctctctatt    300
cgatctaacc tttttctgg cccactcccc cattctctct ctctcctcac ccaactccgc    360
tatctcgacg tttcccaaaa cagtttcaca ggtccaatcc catcttctct ctctctcctc    420
acccaactcc gctatctcca cgtttccggc aacagtttca caggtccaat cccatctttt    480
ctctctctcc tcacccaact ccgctatctc gacgtttccg acaacagttt cacaggtcca    540
atcccatctt ctctctctct cctcacccaa ctccgctatc tcgacgtttc ctacaacaat    600
ctaaatggca ctcttccctt atcgctcgtt gagaagatgt cggagctcag ctaccttaac    660
cttaggtata actctttcta cggtgagatt ccaccggagt ttgggaaact taagaagctt    720
gaaacattga atcttggtaa caacactctt tctgggagtc ttccatctga gttgggttca    780
ttaaagagtt tgaaacatat ggacttttct agtaatatgc tatttggtga gatcccacaa    840
tcttattctc ttcttcgaaa cttaatcgat attgatctta atagaaacaa gttatatggg    900
agtatacctg attatattgg agattttccg gagttggaat cacttttatt agactcgaat    960
aacttcacag ggagtatccc acaaaagtta ggtacaaacg ggaagttgca atatctagat   1020
ataagtaaca acaattttag tggtagtttg ccactaagtc tttgcaaagg agacaaactc   1080
caagatctgg acgcatccta taatttgttg gttgggtcaa ttcctgagag tttgggaagt   1140
tgcaagtcac ttgaaggagt gtacatggga aataatttct taaacgggtc gattcctaag   1200
ggcttgtttg ggagtgatgt ttcacttaat gacaaacttc ttagtggagg tctcgatgag   1260
aaattcggtg attgcgttaa tcttcgggac attgatctct ctaataataa gctatcaggg   1320
aagttacctg cgaccatcgg aaactgtatt catcttcggt ccttgacgct ttataataac   1380
acctgtaccg gacgtatccc tcaagagatt agcaagtgta agcagctaca gaccctcgat   1440
ctcagccaaa atcagttctc tggtgtgata cccaatgata ttacaggaaa caaatccatt   1500
tgcaatctgg aaaagataca aacacttaaa ttatcaaaca atgctttgac tggtgaaatc   1560
cctcattgtg ttggaaatat cgagctcata gcattatttc tccaatcaaa caaactgaac   1620
ggtaccatac ccgcaaactt ctcaaagtta tgtgattcat tgatatatct agatcttagt   1680
gacaatcaac tcgaaggagt tctacctaag tccttgtcca aatgtcaaag tctagaactc   1740
ctaaatgtcg ggaacaatag gctaagagat aaatttcctt catggttaga caacctccca   1800
cgtctccaag ttttcagtgt gcgttttaac gccttctacg gtcctataac tagctcacca   1860
aaagttagtc acccatttcc tatgctacaa attatcgacc tatctaacaa taagttttgt   1920
ggcaagttgc caagaagata tatcaaaaac tttgcaacca tgcgcaatat gaatgagtct   1980
ggtgttggga atccacagta cctgggggac tcatcaatat atagtattac gtactctatg   2040
gtattgacat tcaatgggtt acaacaaaaa tatgaaaagc ttattgtgac gatgtcgacc   2100
tttgatatat ccagcaacaa ctttactgga cagattccat atgttatagg gggattacgc   2160
tcacttcgta accttaatct ctctcataat gtcttaaccg ggaacattcc tccatcaatt   2220
gcaaaattgt ctttgcttca agatttggac ctttcatcaa acagacttac tggtcgtatc   2280
cctcaagaat tagttagttt aacatttctt gggagtttca atgtttcgaa caatctattg   2340
```

-continued

```
gaggggtcta tacctcatgg tttcaacttc gacacgtaca cagctaattc ataccagggg   2400

aatctcgaat tatgtggaaa accattacct gagtgtggag aaagaagggc aaaaggcacc   2460

actaataatc aagatgatcc taaaaatgat aatgaacgaa tgttgtcgat gtccgaaatc   2520

gtagttatgg ggtttggcag tggtgtacta gttgggttgg cttggggata ctatatgttt   2580

tcagtgggaa agccctttg gtttatcaag atggctagca aaatggaatc aatattgatt    2640

ggttttttct ga                                                       2652


<210> SEQ ID NO 98
<211> LENGTH: 21
<212> TYPE: DNA
<213> ORGANISM: Beta vulgaris

<400> SEQUENCE: 98

cgtttccggc aacagtttca c                                               21


<210> SEQ ID NO 99
<211> LENGTH: 21
<212> TYPE: DNA
<213> ORGANISM: Beta vulgaris

<400> SEQUENCE: 99

agagagagag aggagtgggt t                                               21
```

GENE FOR RESISTANCE TO PLANT DISEASE

CROSS-REFERENCE TO RELATED APPLICATIONS

This application is a U.S. National Phase of International Patent Application No. PCT/EP2019/054008, filed on Feb. 18, 2019. The entire contents of this application is incorporated herein by reference in its entirety.

FIELD OF THE INVENTION

The present invention relates to a nucleic acid molecule which encodes a polypeptide, which nucleic acid molecule is able to confer a resistance to *Cercospora*—in particular, to the fungus *Cercospora beticola* in a plant, and, in particular, in a plant of the species *Beta vulgaris* in which the polypeptide is expressed—as well as to the polypeptide encoded by the nucleic acid molecule according to the invention. In particular, the nucleic acid molecule according to the invention is characterized in that the resistance effect to *Cercospora* that is conferred by the polypeptide is dominant. Furthermore, the invention relates to a *Cercospora*-resistant plant, plant cell, plant organ, plant tissue, plant part, or a seed or descendant of a plant, which comprises the nucleic acid molecule or portions thereof as an endogenous gene, as an edited gene, or as a transgene. Furthermore, the present invention also encompasses methods for increasing the resistance to *Cercospora* in a plant of the species *Beta vulgaris*, as well as methods for producing or identifying and possibly selecting a *Cercospora*-resistant plant. The present invention also encompasses methods for monitoring an infestation by the pathogen *Cercospora beticola*, as well as oligonucleotide probes and primers for hybridization with the nucleic acid molecule according to the invention.

BACKGROUND OF THE INVENTION

*Cercospora* leaf spot is one of the most important, globally prevalent leaf diseases of plants from the species *Beta vulgaris*. It is caused by the fungus *Cercospora beticola*. Plants infested by this disease typically form small, relatively round leaf spots (2-3 mm) that are light gray in the middle and are surrounded by a red-brown border. In a severe infestation, the leaf spots overlap, so that entire portions of the leaf blade dry out. Small black dots (pseudostromata) are visible within the fully formed spots, and a gray, felt-like covering (conidia bearers with conidia) forms under damp conditions—predominantly, on the leaf underside. Severely infested leaves first turn yellow, then turn brown and die. New leaf growth occurs in parallel, wherein the leaves become diseased again and die, however. At first, damage symptoms only on individual plants are visible; however, with spread of the disease, formation of persistent infestation nests often occurs. The further propagation over the entire field takes place via rain and wind.

The pathogen *Cercospora beticola* was first described in the second half of the 19th century, in Italy. Up to 40% crop losses may occur due to a severe infestation, which may be triggered by humid weather, early row closure, a high infection potential from previous years, or strong irrigation. These losses result from a reduced beet crop and reduced sugar content; see Holtschulte ((2000) "*Cercospora beticola*—worldwide distribution and incidence," pp. 5-16, in "*Cercospora beticola* Sacc. Biology, Agronomic Influence and Control Measures in Sugar Beet," vol. 2 (M. J. C. Asher, B. Holtschulte, M. R. Molard, F. Rosso, G. Steinrücken, R. Beckers, eds.). International Institute for Beet Research, Brussels, Belgium, 215 pp.). In order to fight back against the disease, intercropping or fungicides are often used. A chemical control of *Cercospora beticola* via fungicides incurs costs to the farmer and pollutes the environment. Repeated applications of fungicides additionally increase the selection pressure on fungicide-tolerant *Cercospora beticola* strains. This is contrary to a sustainable agricultural practice.

Indirect combat is done via the selection of cultivars with healthy leaves and cultivation of the beets with at least a 3-year crop rotation. Markedly better control of the infestation may be achieved with a combination of tolerant or resistant cultivars. Less susceptible *Cercospora*-tolerant beet cultivars have been offered on the market since 2000 (Steinrücken 1997, "Die Züchtung von *Cercospora*-resistenten Zuckerrüben." ["The breeding of *Cercospora*-resistant sugar beets."], Vorträge für Pflanzenzüchtung [Lectures on Plant Breeding], Volume 37, Lecture symposium, Mar. 4-5, 1997, Kiel). These cultivars are furnished with a quantitative resistance to *Cercospora beticola*. The resistance of these cultivars is based upon several genes and is quantitatively passed down, wherein the exact number of the genes that are responsible for the resistance is not known; see Weiland and Koch (2004), Sugarbeet leaf spot disease (*Cercospora beticola* Sacc.), *The Plant Journal,* 5(3), 157-166. The complex quantitative heredity was confirmed via several Quantitative Trait Loci (QTL) analyses. This method allows the mapping of polygenic inherited resistances and is a reliable technique for identifying the number and position of genetic resistance factors on the genetic linkage map of a host plant. In this way, multiple causative QTL's could be determined on each chromosome of the sugar beet.

The mappings were performed with different *Cercospora*-resistance donors, wherein the observed QTL effects were, for the most part, small. The maximum declared phenotypical values were at 5%.

In continuative studies, lists of differentially expressed genes have been described. In a study by Weltmeier et al., ((2011) Transcript profiles in sugar beet genotypes uncover timing and strength of defense reactions to *Cercospora beticola* infection, *Molecular plant-microbe interactions,* 24(7), 758-772), a genome-side expression profile for various genotypes of sugar beet (i.e., *Cercospora*-resistant, -tolerant, -susceptible, etc.) was created with the aid of a microarray-based technology during the pathogen infection in order to analyze transcriptional changes in the expression profile in connection with leaf spot. Via these analyses, the authors were in a position to create a pathogen-induced transcription profile in various tested genotypes of sugar beet and to determine potential candidate genes. However, these genes have not yet been characterized in detail. The genetic and functional background of *Cercospora* resistance and the identity of the resistance genes have until now been entirely unclear.

However, with the quantitative heredity of QTL, not only is the desired resistance to *Cercospora beticola* introduced into the plant, but, rather, often unwanted features as well, such as, for example, reduced yield, due to the inheritance of additional genes that are linked with the positive feature of *Cercospora* resistance. This phenomenon is also known by the term, "linkage drag." Furthermore, the enormous breeding cost that is required in order to select for multiple resistance loci without thereby reducing the yield may have negative effects on the vitality of the plants; see Weiland and Koch, 2004.

Breeding companies have offered *Cercospora*-tolerant cultivars on the market for more than a decade. The resistance of these cultivars is inherited via multiple resistance genes with small effect. However, a disadvantage of these cultivars consists in the cultivar development being very laborious and complicated due to the complicated heredity, and in such cultivars having a markedly poorer yield performance relative to normal cultivars, in the absence of an infestation. Among other things, this may be linked to the epigenetic interaction of some resistance genes with genes that are responsible for sugar production, which leads to reduced fitness of the plants, in the absence of the pathogen.

The use of new breeding techniques based upon gene editing, e.g., by means of TALE nucleases or CRISPR systems, and of transgenic approaches, is impossible in practice due to the complicated heredity and the multitude of the genes which are involved in the resistance development, the majority of which have not yet been identified and characterized.

For sustainable breeding against *Cercospora* leaf spot that is to counteract the danger of *Cercospora* variants that overcome resistance, it is necessary to continuously identify new resistance genes and integrate these into the gene pools of cultivated plants such as sugar beets. In particular, the aim consisted in the provision of suitable resistance genes that, after expression in the plant, on their own already produce a very large, dominant resistance effect against *Cercospora beticola*. According to the invention, this aim is achieved via the embodiments characterized in the claims and in the specification.

ABSTRACT OF THE INVENTION

The present invention relates to a nucleic acid molecule that is able to confer a resistance to *Cercospora*—in particular, to the fungus *Cercospora beticola*—in a plant, and, in particular, in *Beta vulgaris* subsp. *vulgaris*. The polypeptide which is encoded by the nucleic acid molecule is thereby produced in the plant. The nucleic acid molecule, after whose expression the polypeptide is produced, on its own, already produces in the plant a very large, dominant resistance effect against *Cercospora beticola.*

Furthermore, the invention relates to a *Cercospora*-resistant plant, plant cell, plant organ, plant tissue, plant part, a seed, seed stock, or descendant of a plant, which comprises the nucleic acid molecule or portions thereof. The nucleic acid may be comprised for example endogenously or transgenically. Furthermore, the nucleic acid may be comprised as an introgresson. Optionally, those plants and their components that have been obtained via an essentially biological process are excluded.

Methods for increasing the resistance to *Cercospora* in a plant of the species *Beta vulgaris*, as well as methods for producing or identifying and possibly selecting a *Cercospora*-resistant plant, are likewise encompassed by the present invention. The present invention also encompasses methods for monitoring an infestation of the pathogen *Cercospora beticola*, as well as oligonucleotides as probes and primers for hybridization with the nucleic acid molecule according to the invention.

The present invention therefore relates to the embodiments that are listed in the following points and illustrated in the examples and figures.

[1] Nucleic acid molecule encoding a polypeptide that is able to confer resistance to *Cercospora* in a plant in which the polypeptide is expressed, characterized in that the nucleic acid molecule comprises a nucleotide sequence which is selected from
- (a) a nucleotide sequence encoding a polypeptide having an amino acid sequence according to SEQ ID No. 3;
- (b) a nucleotide sequence that comprises the DNA sequence according to SEQ ID No. 2;
- (c) a nucleotide sequence that comprises a DNA sequence selected from the group consisting of SEQ ID No. 1 or SEQ ID No. 53;
- (d) a nucleotide sequence that hybridizes to a nucleotide sequence which is complementary to the nucleotide sequence according to (a), (b), or (c), under stringent conditions;
- (e) a nucleotide sequence encoding a polypeptide which, via substitution, deletion, and/or addition of one or more amino acids of the amino acid sequence, differs from a polypeptide encoded by the nucleotide sequence according to (a), (b), or (c);
- (f) a nucleotide sequence encoding a polypeptide which has an amino acid sequence that is at least 70% identical to an amino acid sequence according to SEQ ID No. 3;
- (g) a nucleotide sequence that is at least 70% identical to a DNA sequence according to SEQ ID No. 1 or SEQ ID No. 2;

wherein the resistance to *Cercospora* is preferably a resistance to *Cercospora beticola*, or wherein the plant is preferably a plant of the subspecies *Beta vulgaris* subsp. *vulgaris*, and is, particularly preferably, sugar beet.

[2] Nucleic acid molecule according to [1], characterized in that the resistance effect to *Cercospora* that is conferred by the polypeptide is dominant in the plant—preferably, wherein the polypeptide confers a resistance effect of at least one rating score, and, preferably, of more than one rating score, particularly preferably, of at least two rating scores, particularly preferably, of at least three rating scores, and, especially preferably, of at least four rating scores.

[3] Nucleic acid molecule according to [1] or [2], characterized in that the nucleic acid molecule originates from *Beta vulgaris* subsp. *maritima.*

[4] Polypeptide encoded by the nucleic acid molecule according to one of [1] through [3].

[5] Vector or expression cassette comprising the nucleic acid molecule according to one of [1] through [3], wherein the nucleic acid molecule is preferably heterologous to the vector or to the expression cassette.

[6] Cell which comprises the nucleic acid molecule according to one of [1] through [3], or the vector or the expression cassette according to [5], wherein the nucleic acid molecule or the expression cassette are preferably present as an endogene or transgene.

[7] *Cercospora*-resistant plant or a portion thereof, characterized in that the plant or its portion contains the nucleic acid molecule according to one of [1] through [3], endogenously or transgenically, or the vector or the expression cassette according to [5], wherein the plant which endogenously contains the nucleic acid molecule is a plant of the species *Beta vulgaris*—but not *Beta vulgaris* subsp. *maritima*—or of *Beta vulgaris* subsp. *vulgaris.*

[8] Plant according to [7], characterized in that the plant is a hybrid plant.

[9] Plant according to [7] or [8], characterized in that the nucleic acid molecule is present heterozygously or homozygously in the genome of the plant.

[10] Seeds or descendants of the plant according to one of [7] through [9], wherein the seed or the descendant transgenically or endogenously comprises the nucleic acid molecule according to one of [1] through [3], or the vector or the expression cassette according to [5].

[11] Method for increasing the resistance to *Cercospora* in a plant, including the following steps:

(i) integration of the nucleic acid molecule according to one of [1] through [3], or of the vector or of the expression cassette according to [5], by means of homology-directed repair or homologous recombination—preferably, supported by a site-directed nuclease—into the genome of at least one cell of a plant, and optional regeneration of a plant from the at least one plant cell; or (ii) increase in the expression of the nucleic acid molecule according to one of [1] through [3] in at least one cell of the plant—preferably, via modification of the native promoter, e.g., comprising a DNA sequence according to SEQ ID No. 7, or via linking of the nucleic acid molecule according to one of [1] through [3] with a heterologous promoter that has a higher level of activity in comparison to the native promoter, e.g., comprising a DNA sequence according to SEQ ID No. 7—in particular, after *Cercospora* infection—and optional regeneration of a plant from the at least one plant cell; or (iii) increase in the activity and/or stability of the polypeptide according to [4] via modification of the nucleotide sequence of the nucleic acid molecule according to one of [1] through [3] in at least one cell of the plant, and optional regeneration of a plant from the at least one plant cell; or (iv) transformation of a plant cell with the nucleic acid molecule according to one of [1] through [3], or the vector or the expression cassette according to [5], and optional regeneration of a (transgenic) plant from the transformed plant cell;

wherein the resistance to *Cercospora* is preferably a resistance to *Cercospora beticola*, or the plant is preferably a plant of the species *Beta vulgaris*—preferably, *Beta vulgaris* subsp. *vulgaris*—and, in particular, is sugar beet.

[12] Method for producing a *Cercospora*-resistant plant according to one of [7] through [9], including the following steps:

(a) transformation of a plant cell with the nucleic acid molecule according to one of [1] through [3], or the vector or the expression cassette according to [5]; and (b) regeneration of the transgenic plant from the transformed plant cell; or (i) introduction of a site-directed nuclease and a repair matrix into a cell of a plant of the species *Beta vulgaris*, wherein the site-directed nuclease is able to generate at least one double-strand break of the DNA in the genome of the cell—preferably, upstream and/or downstream of a target region—and the repair matrix comprises the nucleic acid molecule according to one of [1] through [3];

(ii) cultivation of the cell from (i) under conditions that allow a homology-directed repair or a homologous recombination, wherein the nucleic acid molecule is incorporated from the repair matrix into the genome of the plant; and (iii) regeneration of a plant from the cell modified in (ii).

[13] Method according to [12], characterized in that the target region comprises an allelic variant of the nucleic acid molecule according to one of [1] through [3], wherein the allelic variant encodes a polypeptide not conferring resistance or a slight resistance to *Cercospora*.

[14] Method according to [12] or [13], characterized in that the at least one double-strand break occurs at a position that is at most 10,000 base pairs upstream and/or downstream of the target region, or that is at most 10,000 base pairs distant from the allelic variant as defined in [13].

[15] Method according to [12] or [13], characterized in that the allelic variant of the nucleic acid molecule comprises a nucleotide sequence which is selected from (a) a nucleotide sequence that encodes a polypeptide having an amino acid sequence according to SEQ ID No. 6;

(b) a nucleotide sequence that comprises the DNA sequence according to SEQ ID No. 5;

(c) a nucleotide sequence that comprises a DNA sequence according to SEQ ID No. 4;

(d) a nucleotide sequence that hybridizes to a nucleotide sequence which is complementary to the nucleotide sequence according to (a), (b), or (c), under stringent conditions;

(e) a nucleotide sequence that encodes a polypeptide which, via substitution, deletion, and/or addition of one or more amino acids of the amino acid sequence, differs from a polypeptide that is encoded by the nucleotide sequence according to (a), (b), or (c); or (f) a nucleotide sequence that encodes a polypeptide which has an amino acid sequence that is at least 80% identical to an amino acid sequence according to SEQ ID No. 6.

[16] Plant, or a portion thereof, obtained or obtainable according to a method according to one of [12] through [15].

[17] Method for identifying, and optionally providing, a plant of the species *Beta vulgaris* that is resistant to *Cercospora*, characterized in that the method includes at least step (i) or (ii):

(i) detection of the presence and/or expression of the nucleic acid molecule according to one of [1] through [3], or the presence of the polypeptide according to [4], in the plant or a portion of the plant; and/or (ii) detection of at least one marker locus in the nucleotide sequence of the nucleic acid molecule according to one of [1] through [3] or in a cosegregating region; and (iii) possible selection of the *Cercospora beticola*-resistant plant.

[18] Method for identification of a nucleic acid molecule which encodes a polypeptide that is able to confer a resistance to *Cercospora* in a plant of the species *Beta vulgaris* in which the polypeptide is expressed, characterized in that the method includes the following steps:

(i) comparison of the amino acid sequence of the polypeptide according to [4] with amino acid sequences from a sequence database, or identification of allelic variants which encode the polypeptide according to [4] in genotypes of the species *Beta vulgaris;*

(ii) identification of the amino acid sequence, or an allelic variant, encoding an amino acid sequence, wherein the amino acid sequence is at least 80% identical to the amino acid sequence of the polypeptide according to [4];

(iii) introduction of a nucleic acid molecule, or the allelic variant, encoding the identified amino acid sequence into a plant of the species *Beta vulgaris*, and expression of the nucleic acid molecule in the plant; and (iv) detection of the resistance to *Cercospora*.

[19] Method for farming of plants of the species *Beta vulgaris*, including
(i) the provision of plants according to one of [7] through [9], the production of plants of the species *Beta vulgaris* with the aid of a method according to one of [12] through [15], or the identification and selection of plants of the genus *Beta* with the aid of a method according to [17], and
(ii) cultivation of the plants from (i) or descendants thereof,
wherein the method counteracts an infestation of the cultivated plants with *Cercospora*.

[20] Oligonucleotide of at least 15, 16, 17, 18, 19, or 20—preferably, at least 21, 22, 23, 24, or 25, particularly preferably, at least 30, 35, 40, 45, or 50, and, especially preferably, at least 100, 200, 300, or 500—nucleotides in length, which oligonucleotide hybridizes with a nucleotide sequence as defined in one of [1] through [3].

[21] A pair of oligonucleotides—preferably, oligonucleotides according to [20] or a kit containing these oligonucleotides—wherein the oligonucleotides are suitable for hybridization as forward primer and reverse primer to a region in the *Beta vulgaris* genome that, in *Beta vulgaris*, has a cosegregation with the *Cercospora* resistance conferred by the polypeptide according to [4], or with the nucleic acid molecule according to one of [1] through [3].

[22] Use of the nucleic acid molecule according to one of [1] through [3] in the production of *Cercospora*-resistant plants of the subspecies *Beta vulgaris* subsp. *vulgaris*.

[23] Method for the production of an organism which comprises a mutated version according to
[1] and/or a mutated version of a promoter comprising a nucleic acid sequence selected from
(a) SEQ ID NO: 7
(b) a nucleotide sequence, which hybridizes under stringent conditions with a sequence which is complementary to the sequence according to (a)
(c) a nucleotide sequence which is at least 70% identical to a sequence according to SEQ ID NO: 7
wherein the method includes the following steps:
(I) Provision of an organism or a cell comprising the nucleic acid molecule and/or the promoter
(II) Increase of the mutation rate of the organism or the cell or mutagenesis of the organism or the cell
(III) Phenotypic selection of an organism, which as a result of a mutation exhibits an altered resistance or altered resistance level towards *Cercospora beticola* or Genotypic selection of an organism or a cell which comprises a mutation in the nucleic acid molecule and/or the promoter wherein the mutation has been created via step (II) and optionally
(IV) Regeneration of the organism from the cell obtained via step (III).

[24] Method according to [23], wherein the organism is a plant.

[25] Method according to [24] wherein the plant is a *Beta vulgaris*, preferably a *Beta vulgaris* subsp. *vulgaris*, more preferably a sugar beet.

First, some of the terms used in this application are explained in detail in the following:

What is understood by "rating score" in the sense of the present invention is a qualitative assessment of the resistance to a *Cercospora* infestation that is represented using a scale from 1 to 9 (with 1=strong resistance and 9=no resistance).

TABLE 1A 9-level resistance rating for Cercospora

| Rating score | Leaf phenotype | Whole plant phenotype |
|---|---|---|
| 1 | Healthy leaf | Healthy leaf, whole |
| 3 | Diseased leaf, spots on the outer leaves | Whole plant, beginning of disease, spots on the outer leaves |
| 5 | Diseased leaf, merging of the spots into dying areas | Whole plant, advanced disease, merging of the spots into dying areas |
| 7 | Diseased leaf, large part of the leaf brown and dead, only lower lamina is still alive | Whole diseased plant, large portions of the outer leaves are dying off |
| 9 | Diseased leaves, lamina and petiole are dead and dried | Whole diseased plant, outer leaves have died, inner leaves with severe damage, strong new leaf growth |

The genus *Cercospora* encompasses various species, e.g., the species *Cercospora arachidicola, Cercospora ariminiensis, Cercospora asparagi, Cercospora bertoreae, Cercospora beticola, Cercospora bizzozeriana, Cercospora canescens, Cercospora carotae, Cercospora chenopodii, Cercospora cistinearum, Cercospora cladosporioides, Cercospora diazu, Cercospora dulcamarae, Cercospora erysimi, Cercospora hayii, Cercospora kikuchii, Cercospora malvacearum, Cercospora malvicola, Cercospora medicaginis, Cercospora oryzaem, Cercospora personata, Cercospora plantaginis, Cercospora ricinella, Cercospora setariae, Cercospora unamunoi, Cercospora violae*, or *Cercospora zeae-maydis*.

In conjunction with the specification of a length of a nucleotide sequence, the term, "approximately," means a deviation by +/−200 base pairs—preferably, by +/−100 base pairs, and, particularly preferably, by +/−50 base pairs.

A "plant of the genus *Beta*" belongs to the amaranth family (Amaranthaceae). Numbering among these plants are plants of the species *Beta macrocarpa, Beta vulgaris, Beta lomatogona, Beta macrorhiza, Beta corolliflora, Beta trigyna*, and *Beta nana*. A plant of the species *Beta vulgaris* is, in particular, a plant of the subspecies *Beta vulgaris* subsp. *vulgaris*. For example, numbering among these are *Beta vulgaris* subsp. *vulgaris* var. *altissima* (sugar beet in a narrower sense), *Beta vulgaris* ssp. *vulgaris* var. *vulgaris* (chard), *Beta vulgaris* ssp. *vulgaris* var. conditiva (beetroot/red beet), *Beta vulgaris* ssp. *vulgaris* var. *crassa*/alba (fodder beet). It is noted that the nucleic acid according to the invention does not naturally occur in sugar beet, chard, beetroot, or fodder beet, but may be introduced into these via human action.

A "functional fragment" of a nucleotide sequence means a segment of a nucleotide sequence which has a functionality identical or comparable to that of the complete nucleotide sequence from which the functional fragment originates. As such, the functional fragment may possess a nucleotide sequence which is identical or homologous to the total nucleotide sequence over a length of at least 50%, 55%, 60%, 65%, 70%, 75%, 80%, 85%, 90%, 92%, 94% 96%, 97%, 98%, or 99%. This also explicitly encompasses the range of 90-100%. Furthermore, a "functional fragment" of a nucleotide sequence may also mean a segment of a nucleotide sequence which modifies the functionality of the entire nucleotide sequence, e.g., in the course of post-transcriptional or transcriptional gene silencing. As such, the functional fragment of a nucleotide sequence may comprise at least 14, 15, 16, 17, 18, 19, 20, 21, 22, 23, 24, or 25—preferably, at least 30, 35, 40, 45, 50, 60, 70, 80, 90, 100, 120, or 140, and, particularly preferably, at least 160, 180, 200, 250, 300, 350, 400, 450, 500, 600, 700, 800, 900, or 1,000—successive nucleotides of the total nucleotide sequence. This also explicitly encompasses the range of 21 to 50 nucleotides.

A "functional part" of a protein means a segment of a protein, or a section of the amino acid sequence, that encodes the protein, wherein the segment may exert functionality identical or comparable to that of the entire protein in a plant cell. Over a length of at least 50%, 55%, 60%, 65%, 70%, 75%, 80%, 85%, 90%, 92%, 94% 96%, 97%, 98%, or 99%, a functional part of a protein has an amino acid sequence that is identical or, with consideration of conservative and semi-conservative amino acid exchanges, similar to the protein from which the functional part originates.

The term, "heterologous," means that the introduced polynucleotide originates from a cell or an organism with a different genetic background, of the same species or a different species, or is homologous to the prokaryotic or eukaryotic host cell, but is then located in a different genetic environment and thus differs from a corresponding polynucleotide that is possibly naturally present. A heterologous polynucleotide may be present in addition to a corresponding endogenous gene.

In the sense of the invention, what is understood by a "homolog" is a protein of the same phylogenetic origin; what is understood by an "analog" is a protein which exerts the same function, but has a different phylogenetic origin; what is understood by an "ortholog" is a protein from a different species that exerts the same function; and what is understood by a "paralog" is a protein that has appeared within a species due to duplication, wherein this copy either retains the same protein function, alters its expression template, but not the function, changes its protein function, or divides up the original gene function between both copies.

What is to be understood by "hybridizing" or "hybridization" is a process in which a single-stranded nucleic acid molecule binds to a nucleic acid strand that is complementary to the greatest possible extent, i.e., forms base pairs with this. Standard methods for hybridization are described in, for example, Sambrook et al., Molecular Cloning: A Laboratory Manual, 3rd ed., Cold Spring Harbor Laboratory Press, Cold Spring Harbor, NY, 2001. What is preferably understood by this is that at least 60%—more preferably, at least 65%, 70%, 75%, 80%, or 85%, and, particularly preferably, 90%, 91%, 92%, 93%, 94%, 95%, 96%, 97%, 98%, or 99%—of the bases of the nucleic acid molecule form a base pairing with the nucleic acid strand that is complementary to the greatest possible extent. The possibility of such an annealing depends upon the stringency of the hybridization conditions. The term, "stringency," relates to the hybridization conditions. High stringency is present when a base pairing is made more difficult; low stringency is present if a base pairing is made easier. For example, the stringency of the hybridization conditions depends upon the salt concentration or ionic strength and the temperature. In general, the stringency may be increased by increasing the temperature and/or decreasing the salt content. What are to be understood by "stringent hybridization conditions" are those conditions given which a hybridization predominantly occurs only between homologous nucleic acid molecules. The term, "hybridization conditions," thereby relates not only to the conditions prevailing in the actual addition of the nucleic acids, but also to the conditions prevailing in the following washing steps. For example, stringent hybridization conditions are conditions under which, predominantly, only those nucleic acid molecules hybridize that have at least 70%—preferably, at least 75%, at least 80%, at least 85%, at least 90%, or at least 95%—sequence identity. Stringent hybridization conditions are, for example: hybridization in 4×SSC at 65° C., and subsequent repeated washing in 0.1×SSC at 65° C. for approximately 1 hour in total. A hybridization preferably occurs under stringent conditions.

In relation to a nucleic acid in the form of a double-stranded DNA, "complementary" nucleotide sequence means that the second DNA strand complementary to the first DNA strand has the nucleotides that correspond to the bases of the first strand, in accordance with the base pairing rules. A complementary sequence is, preferably, entirely complementary to the counter-sequence, and thus preferably has the same length.

What is understood by an "isolated nucleic acid molecule" is a nucleic acid molecule extracted from its natural or original environment. The term also encompasses a synthetically-produced nucleic acid molecule. What is understood by an "isolated polypeptide" is a polypeptide extracted from its natural or original environment. The term also encompasses a synthetically-produced polypeptide.

A "molecular marker" is a nucleic acid that is polymorphic in a plant population and is used as a reference or orientation point. A marker for the detection of a recombination event should be suitable for monitoring differences or polymorphisms within a plant population. Such a marker is thus able to detect and differentiate between various allelic states (alleles). The term, "molecular marker," also relates to nucleotide sequences which are complementary or at least largely complementary or homologous to genomic sequences—for example, nucleic acids which are used as probes or primers. These differences at the DNA level are to be found as markers and are, for example, polynucleotide sequence differences, e.g., SSR's (simple sequence repeats), RFLP's (restriction fragment length polymorphisms), FLP's (fragment length polymorphisms) or SNP's (single nucleotide polymorphisms). The markers may be derived from genomic or expressed nucleic acids, e.g., spliced RNA, cDNA, or EST's, and may also relate to nucleic acids that are used as probes or primer pairs and as such are suitable for amplifying a sequence fragment using PCR-based methods. Markers that describe genetic polymorphisms (between parts of a population) may be detected using well-established methods from the prior art (An Introduction to Genetic Analysis, 7th edition, Griffiths, Miller, Suzuki, et al., 2000). For example, among these are DNA sequencing, PCR-based, sequence-specific amplification, verification of RFLP's, verification of polynucleotide polymorphisms by means of allele-specific hybridization (ASH), detection of amplified variable sequences of the plant genome, detection of a 3SR (self-sustained sequence replication), detection of SSR's, SNP's, RFLP's, or AFLP's (amplified fragment length polymorphisms). Furthermore, the methods for detection of EST's (expressed sequence tags) and SSR markers derived from EST sequences and RAPD (randomly amplified polymorphic DNA) are also known. Depending upon the context, the term, "marker," in the description may also mean a specific chromosome position in the genome of a species where a specific marker (SNP, for example) may be found.

Markers also include synthetic oligonucleotides that may be connected with one or more detection molecules, wherein the detection molecules may be used for a detection reaction or the generation of a signal within the scope of a verification method. Synthetic oligonucleotides also include labeled primers. Synthetic oligonucleotides and labeled primers are artificial compounds, do not occur in nature, and cannot be isolated from nature. The production of such compounds is explained further below.

A "promoter" is a non-translated, regulatory DNA sequence, typically upstream of a coding region, which contains the binding point for the RNA polymerase and initiates the transcription of the DNA. A promoter additionally contains other elements that act as a regulator gene for gene expression (for example, cis-regulatory elements). A "core or minimal promoter" is a promoter that has the basic elements which are needed for transcription initiation (for example, TATA box and/or initiator).

A "pathogen" means an organism that, in interactions with a plant, leads to disease symptoms in one or more organs in the plant. For example, animal, fungal, bacterial, or viral organisms or oomycetes number among these pathogens.

What is to be understood by a "pathogenic infection" is the earliest point in time at which a pathogen interacts with a plant host tissue. In this sense, "infestation" means the occurrence of contact between pathogen and host. With an anchorage of a pathogen at a host, e.g., of a fungal spore on a leaf surface of a plant, mechanisms of pathogen detection and signal relaying begin in the plant host cell. In the case of *Cercospora beticola*, conidia are formed in humid, warm weather and transferred to neighboring plants by rain and wind. New infections most often show individual leaf spots first at the physiologically older outer leaves. These are most often quite clearly delimited from the healthy leaf tissue by a brown ring. The brown conidia carriers of the fungus in the middle part of the spots may be observed with the aid of a magnifying glass (rating score 3). The number of these brown spots increases rapidly, wherein the sporocarps initially overlap even smaller dead areas (rating score 5). In the further course of the disease, which now also spans to the inner leaves, dying-off of the outer leaves finally occurs for the first time (rating score 7), and, then, of practically all leaves (rating score 9). Course of disease and symptom severity are strongly dependent upon the site and on the annually fluctuating weather conditions.

Plant "organs" means, for example, leaves, shoot, stem, roots, hypocotyl, vegetative buds, meristems, embryos, anthers, ovula, seeds, or fruits. "Plant parts" include, but are not limited to, the shoot or the stalk, leaves, blossoms, inflorescence, roots, fruits, and seeds, as well as the pollen. The term, "plant parts," also means an association of multiple organs, e.g., a blossom or a seed, or a part of an organ, e.g., a cross-section through the plant shoot. Plant "tissues" are, for example, callus tissue, storage tissue, meristematic tissue, leaf tissue, shoot tissue, root tissue, plant tumor tissue, or reproductive tissue, as well as the cambium, parenchyma, vascular tissue, sclerenchyma, and epidermis. However, the tissue is not limited to this listing. For example, what are to be understood by plant "cells" are, for example, isolated cells having a cell wall or aggregates thereof, or protoplasts.

In conjunction with the present invention, the term, "regulatory sequence," relates to a nucleotide sequence which influences the specificity and/or the expression strength, e.g., in that the regulatory sequence conferres a defined tissue specificity. Such a regulatory sequence may be located upstream of the transcription initiation point of a minimal promoter, but also downstream thereof, e.g., in a transcribed, but not translated, leader sequence or within an initron.

The term, "resistance," is to be understood broadly and covers the range of the protection from a retardation up to a complete blocking of the development of the disease. One example of an important pathogen is *Cercospora beticola*. A resistant plant cell of the invention or resistant plant of the invention preferably achieves a resistance to *Cercospora beticola*. A resistance to a pathogen is to be equated to a resistance to the disease which this pathogen causes; for example, a resistance to *Cercospora beticola* is also a resistance to leaf spot disease. For example, an increase in the resistance can be measured via a reduced fungal biomass on the host plant; for this, the fungal DNA may be determined with the aid of quantitative PCR in comparison to the plant DNA in the infested plant tissue. An additional approach to the measurement of resistance is optical rating, wherein rating scores of 1 (not susceptible) to 9 (very susceptible) are awarded.

"Transgenic plant" relates to a plant into whose genome is integrated at least one polynucleotide. It may thereby be a heterologous polynucleotide. The polynucleotide is, preferably, stably integrated, which means that the integrated polynucleotide is stably preserved in the plant, is expressed, and also may be stably passed on to the descendants. The stable introduction of a polynucleotide into the genome of a plant also includes the integration into the genome of a plant of the preceding parental generation, wherein the polynucleotide may be stably passed on further. The term, "heterologous," means that the introduced polynucleotide originates from a cell or an organism with a different genetic background, of the same species or a different species, or is homologous to the prokaryotic or eukaryotic host cell, for example, but then is located in a different genetic environment and thus differs from a corresponding polynucleotide that is possibly naturally present. A heterologous polynucleotide may be present in addition to a corresponding endogenous gene.

"Raw material for industrial sugar production" means plant material which can be fed into a sugar production facility which is specialized in the extraction of sugar from sugar beets. Such raw material is typically the beet body (taproot) of the harvested sugar beet. To ensure the conformity with the extraction process the beet body needs to have sufficient mass, volume and a conical shape so that the raw material can be mechanically cut into shreds (beet strips). These beet strips maximize the surface area for sugar extraction and should have a low content of Sodium, Potassium and Nitrogen to allow an efficient extraction. After the extraction remaining beet pulp is pressed, dried and used as animal feed.

"Sucrose concentration" is expressed as percentage of the fresh weight of the root.

"Monogerm" means that a seed growth into exactly one plant whereas a polygerm seed (also called "seed ball") growth into several plants.

"Bolting" is the production of a flowering stem (or stems) on a sugar beet in a natural attempt to produce seeds and reproduce. Bolting is triggered in sugar beet due to a chilling stress—e.g. overwintering. However, commercially grown sugar beets are harvested before bolting as this process reduces the sugar content in the beet.

"Introgression" means that a nucleotide sequence has been transferred into the genome of a plant wherein this nucleotide sequence originates from a plant that does not belong to the same species or subspecies. This can for example mean that a nucleotide sequence deriving from a plant of the subspecies *Beta vulgaris maritima* has been transferred into a plant of the subspecies *Beta vulgaris vulgaris*.

Designs and embodiments of the present invention are described by way of example with reference to the pending sequences and figures.

FIG. 1: Protein sequence alignment between the resistant protein (protein which conferres *Cercospora* resistance in a plant) and the sensitive protein (protein which does not confer *Cercospora* resistance in a plant). The polymorphisms are highlighted in gray.

FIG. 2: Protein sequence alignment between the resistant protein (protein which conferres *Cercospora* resistance in a plant) and the sensitive protein (protein which does not confer *Cercospora* resistance in a plant). The polymorphisms are highlighted in gray.

Figure 3:
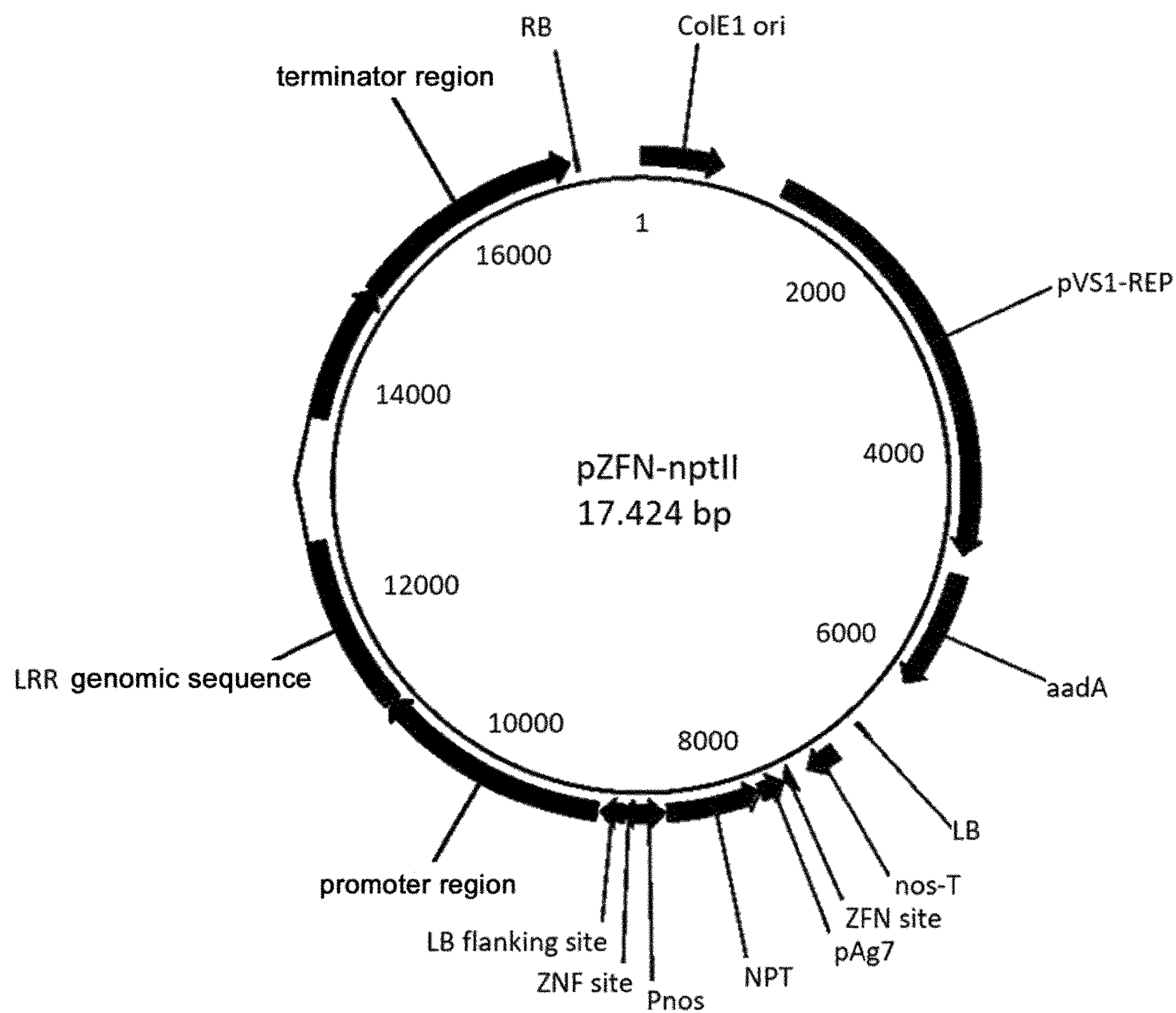

FIG. 3: Vector map of the vector pZFN-nptII including the LRR region.

Figure 4:
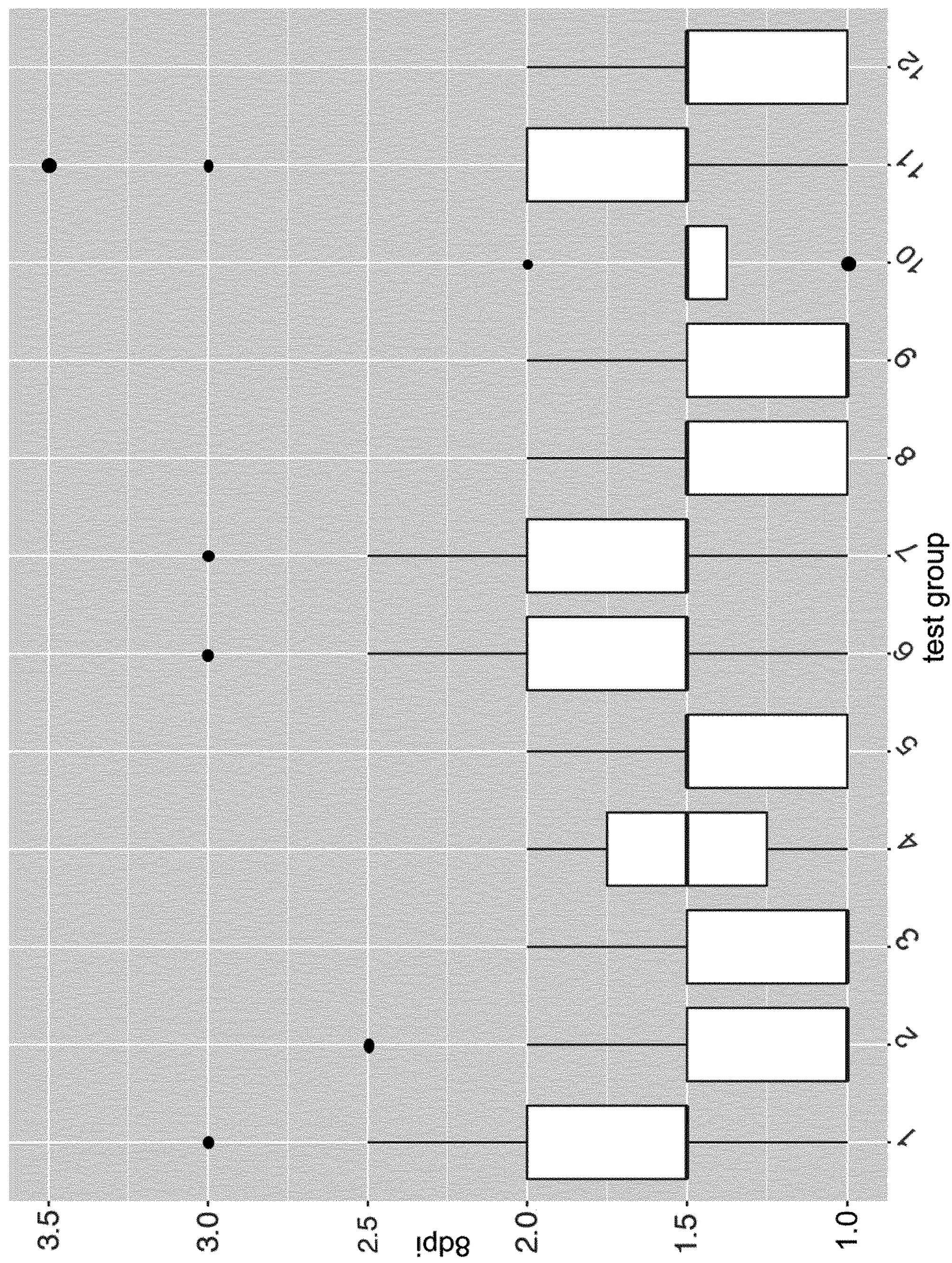

FIG. 4: Statistical box-plot evaluation of the data generated eight days post infection during the transgenic verification of the resistance gene.

Figure 5:
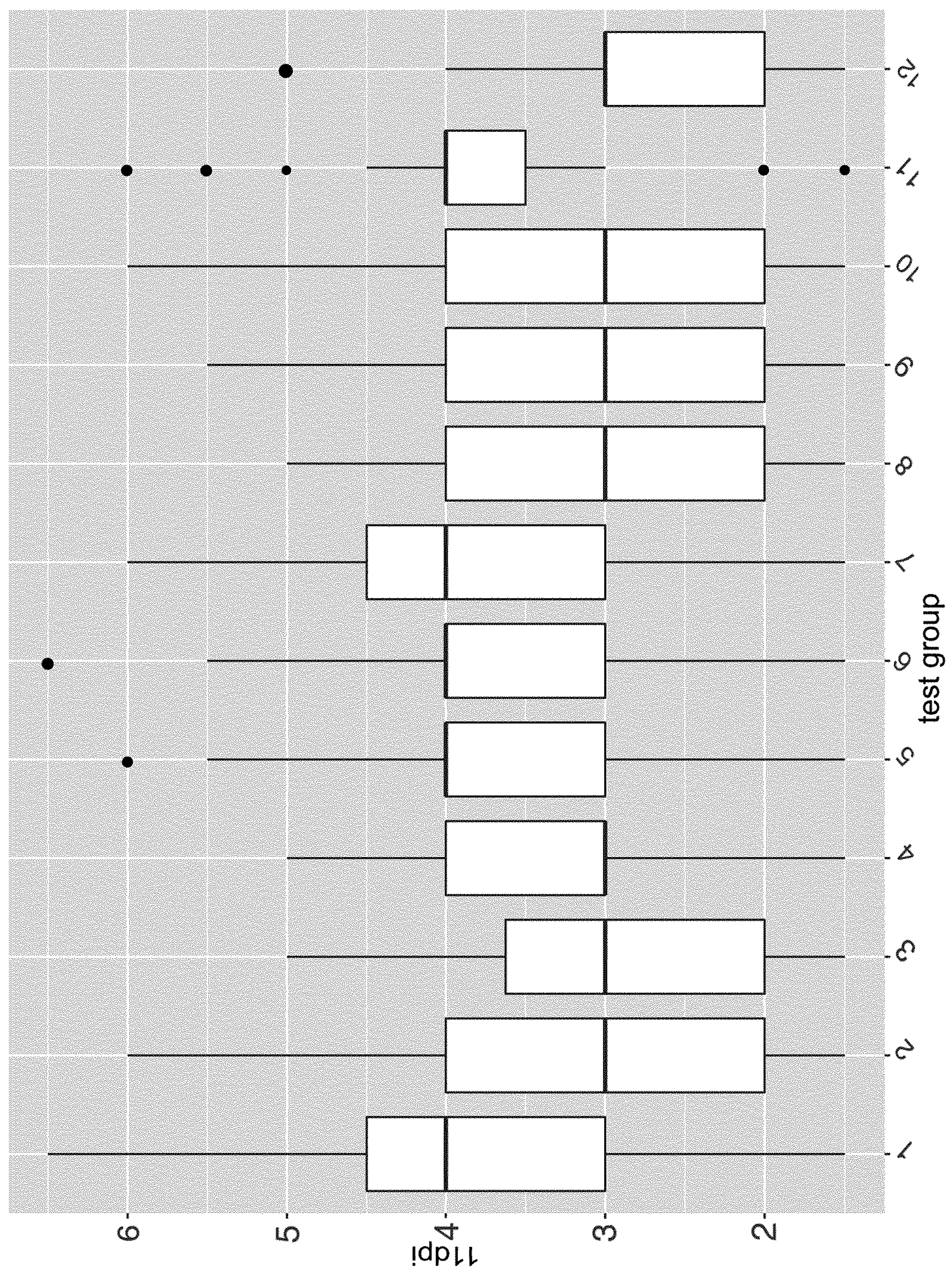

FIG. 5: Statistical box-plot evaluation of the data generated eleven days post infection during the transgenic verification of the resistance gene.

Figure 6:
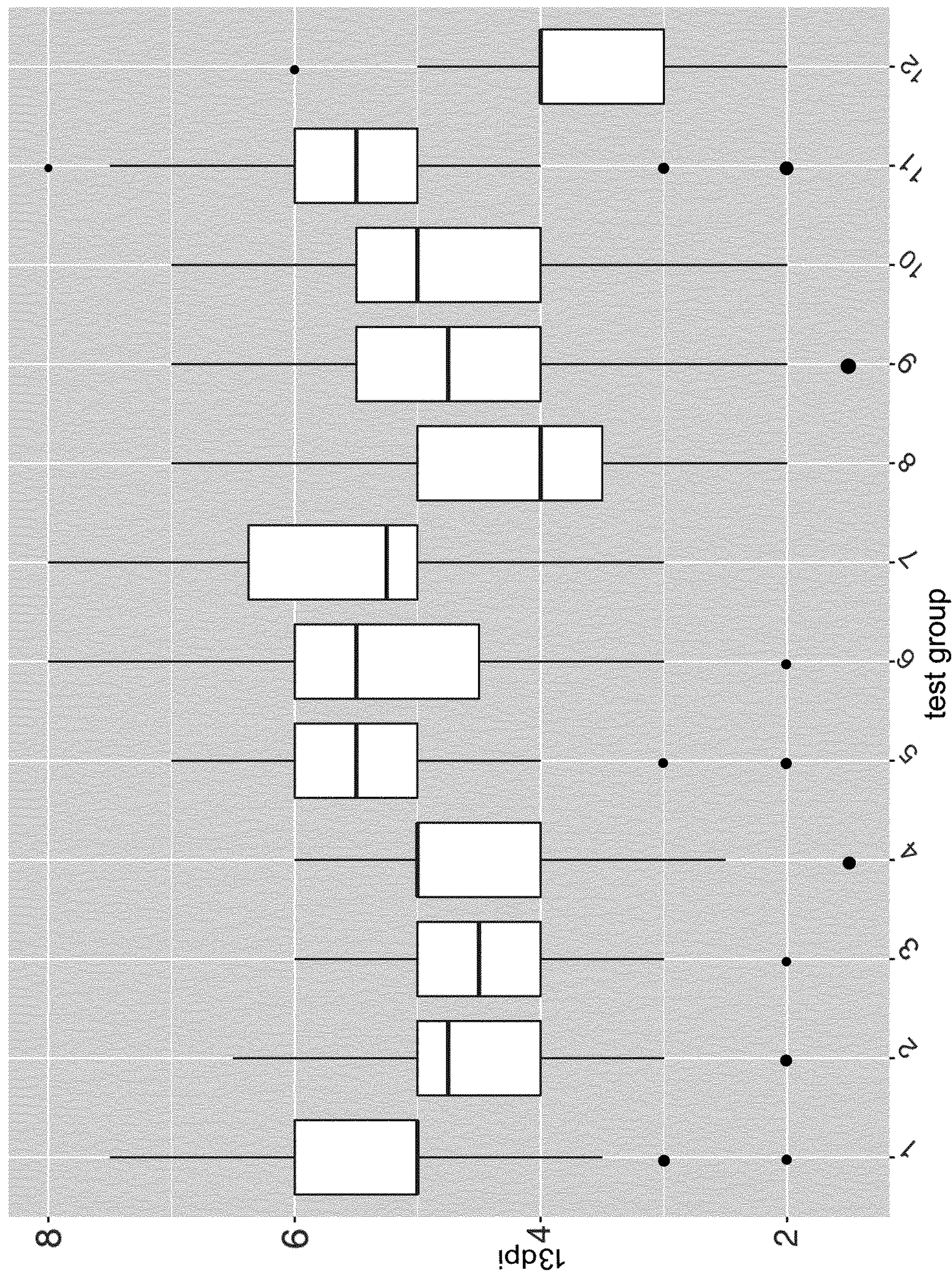

FIG. 6: Statistical box-plot evaluation of the data generated eight days post infection during the transgenic verification of the resistance gene.

Figure 7:
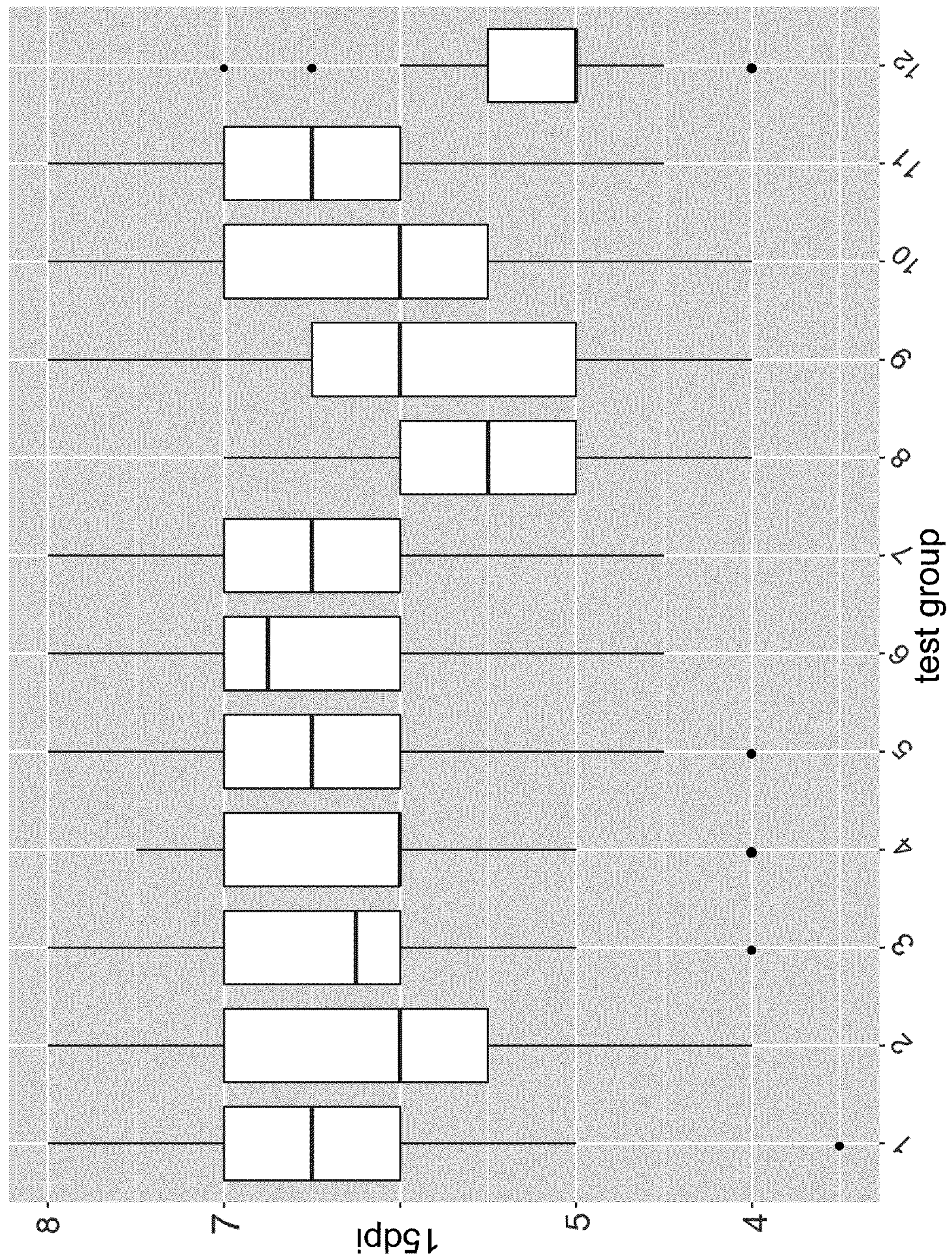

FIG. 7: Statistical box-plot evaluation of the data generated fifteen days post infection during the transgenic verification of the resistance gene.

DETAILED DESCRIPTION OF THE INVENTION

The present invention relates to a nucleic acid molecule that is able to confer a resistance to *Cercospora* in a plant—in particular, in *Beta vulgaris* subsp. *vulgaris*—in which the polypeptide which encoded by the nucleic acid molecule is expressed. According to a preferred embodiment of the invention, the pathogen is the fungus *Cercospora beticola*, which is among the most important and destructive leaf pathogens of sugar beets, beetroot, and chard, among others, and may cause crop losses of over 40%. The fungus produces the secondary metabolite cercosporin, which reacts with oxygen in the presence of light and leads to the formation of reactive oxygen species (ROS). The ROS cause massive cell damage in the leaf tissue of the infested plant that visible in the form of necroses.

The present invention is based upon the genetic fine mapping, identification, isolation, and characterization of a gene or of a gene locus that originates from the donor *Beta vulgaris* subsp. *maritima*, whose presence in a plant—in particular, in *Beta vulgaris* subsp. *vulgaris*—correlates with or is causative of the resistance of the plant concerned to *Cercospora* leaf spot disease. Initial material was a *Beta vulgaris* subsp. *maritima* population which was developed from 37 *Beta vulgaris* subsp. *maritima* accessions from different sources.

The nucleotide and amino acid encoding sequence of the nucleic acid molecule according to the invention is characterized by numerous polymorphisms, which differentiates the NPS-LRR gene identified according to the invention from the "sensitive" variant of the gene, i.e., the variant of the gene that does not confer resistance to *Cercospora*. Examples of polymorphisms are presented in FIG. 1.

The nucleic acid molecule according to the invention may be an isolated nucleic acid molecule. It is preferably DNA, and, particularly preferably, cDNA (coding DNA). The polypeptide which is encoded by the nucleic acid molecule according to the invention preferably confers a resistance to the pathogen *Cercospora beticola*, which causes the plant disease *Cercospora* leaf spot. Furthermore, the polypeptide which is encoded by the nucleic acid molecule according to the invention confers—in particular, in a plant of the genus *Beta*—a resistance to this pathogen. The plant is preferably a plant of the species *Beta vulgaris*—particularly preferably, a plant of the subspecies *Beta vulgaris* subsp. *vulgaris*; among these are, for example, the cultivars sugar beet, beetroot, fodder beet, chard, and Swiss chard.

In one embodiment of the present invention, the nucleic acid molecule according to the invention comprises a nucleotide sequence that encodes a polypeptide with an amino acid sequence according to SEQ ID No. 3 and/or the coding DNA sequence according to SEQ ID No. 2. Furthermore, the present invention provides a nucleotide sequence that comprises the DNA sequences according to SEQ ID No. 1 and SEQ ID No. 53.

The gene identified according to the invention is a resistance gene/protein of the type NBS-LRR, which is characterized by specific structural motifs. The general structure of such resistance proteins in plants has already been well-examined (Martin et al., Annual Review Plant Biology 54 (2003), 23-61). However, the principle of the structural embodiment—in particular, of what is known as the LRR domain, which applies as a potential detection domain for most unknown pathogenic effectors—is unpredictable, and the functional background of the resistance genes i.e., the genetic structure, is generally largely unknown. The identification of a *Cercospora* resistance-conferring gene or protein solely on the basis of the known structural motif is, consequently, impossible. Furthermore, the sequence region has turned out to be a highly repetitive region that contains, among other things, tandem repeats with very high sequence homology, which makes the development of diagnostic markers, as well as the assembly of sequence data, especially difficult.

With the aid of the setup of a population of over 4,000 dividing descendants and the development of special recombination screens, the target region was reduced, and thus ever further isolated, via analysis of informative recombinants (genotypical and phenotypical) in a series of resistance tests. This genetic mapping, as well as the creation of physical maps accompanied by WHG sequencing ("whole genome sequencing"), comparative BAC (Bac-by-Bac) sequencing, and bioinformatoric analyses, led to the identification of three recombinant genotypes that confirmed the resistance gene (1 recombinant in the neighboring gene, on the one hand, and 2 recombinants in the neighboring gene, on the other). In light of particular requirements, the inventors placed the highly repetitive structure in the target region, which, among other things, contains tandem repeats with very high sequence homology, which made the marker development, and thus the identification of informative recombinants, enormously more difficult. The following steps were particularly decisive for the location of the genetic structure of the resistance gene:

- development of the markers s4p0264s01, s4p2271s01, sxh0678s01, s4p4293s01, s4p4295s01, s4p4301s01 (see Table 1B).
- Fine mapping coupled with intensive phenotyping. The phenotypes were verified with 90-180 descendants per plant in a greenhouse test, and with intensive statistical methods (for example, t-test, power analysis, etc.).
- BAC clone identification and sequencing from BAC pools of the resistant genotype.
- Sequence evaluation, as well as sequence and protein comparison between RR (i.e., resistant) and ss (i.e., sensitive) genotypes; an unambiguous assembly of the RR and ss sequence data was thereby not always possible, due to the sequence complexity.

TABLE 1B

Marker in the target region; information in square brackets [X/Y] designates the diagnostic SNP, wherein X identifies the sensitive genotype and Y the resistant genotype.

| Marker | Sequence [sensitive/resistant/consensus] | Position on genetic map [cM] | Position on physical map [bp] |
|---|---|---|---|
| s4p0264s01 | SEQ ID No. 54/SEQ ID No. 55/ SEQ ID No. 10 | 62,79590373 | 57208510 |
| s4p2271s01 | SEQ ID No. 56/SEQ ID No. 57/ SEQ ID No. 11 | 62,81185523 | 57212240 |
| s4p4293s01 | SEQ ID No. 58/SEQ ID No. 59/ SEQ ID No. 12 | 62,84491806 | 57219956 |
| s4p4295s01 | SEQ ID No. 60/SEQ ID No. 61/ SEQ ID No. 13 | 62,85399055 | 57222060 |
| s4p4301s01 | SEQ ID No. 62/SEQ ID No. 63/ SEQ ID No. 14 | 62,94635089 | 57243521 |
| sxh0678s01 | SEQ ID No. 64/SEQ ID No. 65/ SEQ ID No. 15 | 62,97474964 | 57250119 |

The compounds provided in Table 1B can be used as molecular markers according to the invention.

Analyses yielded that the LRR gene has a moderate protein homology to the Cf-2 resistance protein from the tomato (UNIPROT|Q41397_SOLPIP. Cf-2.1) (sequence identity 322/830=38%). In fact, the identified *Cercospora* resistance-conferring protein is the best sugar beet protein homolog to the Cf-2 tomato resistance protein. The Cf-2 resistance protein from the tomato confers a resistance to *Cladosporium fulvum*—a type of black mold fungus (U.S. Pat. No. 6,287,865 B1)—via interaction with the avirulence protein Avr2 from *C. fulvum*. This leads to the activation of the plant immune defense against the pathogen; see Dixon et al., 1996 (Dixon, Mark S., et al., "The tomato Cf-2 disease resistance locus comprises two functional genes encoding leucine-rich repeat proteins." *Cell* 84.3 (1996): 451-459). Due to the sequence homology between the Cf-2 gene and the identified LRR gene, it is to be assumed—but without thereby being bound to one theory—that a similar defense mechanism forming the basis of *Cercospora* resistance also occurs in the case of the sugar beet. However, a different mechanism is not to be precluded, due to the moderate sequence homology.

Furthermore, substitutions, deletions, insertions, additions, and/or any other change may be introduced into the nucleotide sequence according to the invention that, alone or in combinations, do in fact change the nucleotide sequence, wherein the modified nucleotide sequence may, however, perform the same function as the initial sequence. The present case deals with the coding of an amino acid sequence which confers resistance to *Cercospora* leaf spot disease. In a further embodiment, the invention therefore includes a nucleotide sequence that encodes a polypeptide which represents a derivative of the polypeptide which is encoded by the nucleotide sequence according to the invention, or which includes the amino acid sequence according to the invention. A derived amino acid sequence which has at least one substitution, deletion, insertion, or addition of one or more amino acids, wherein the functionality of the encoded polypeptide/protein is preserved, represents a derivative of the polypeptide. Substitutions, deletions, insertions, additions, and/or any other change, either solely or in combinations, that do in fact change the nucleotide sequence, but perform the same function as the initial sequence, may thereby be introduced into the nucleotide sequence using conventional methods that are known in the prior art, e.g., via site-directed mutagenesis, PCR-mediated mutagenesis, transposon mutagenesis, genome editing, etc.

The substitution of one amino acid by a different amino acid having the same or equivalent or similar chemical/physical properties is referred to as a "conservative substitution" or "semi-conservative substitution." Examples of physical/chemical properties of an amino acid are, for example, hydrophobia or the charge. Which amino acid substitution represents a conservative or semi-conservative substitution is known to the person skilled in the art. Moreover, general expertise allows the person skilled in the art to recognize, identify, and detect which amino acid deletions and additions are harmless to the functionality of the resistance protein, and at which positions these are possible. The person skilled in the art is aware that, in the case of the present NBS-LRR protein for modifications of the amino acid sequence (substitutions, deletions, insertion, or additions of one or more amino acids), the functionality, in particular, of the conserved domains must be preserved, and that therefore only limited preceding modifications are possible in these domains.

The invention thus includes a functional fragment of the nucleotide sequence according to the invention. The term, "fragment," thereby includes genes with a nucleotide sequence sufficiently similar to the aforementioned nucleotide sequence. The term, "sufficiently similar," means that a first nucleotide sequence or amino acid sequence has a sufficient or minimum number of identical or equivalent nucleotides or amino acid groups relative to a second nucleotide sequence or a second amino acid sequence.

With regard to the amino acid sequence, after modification via an aforementioned method, this also has a common structural domain and/or possesses common functional activity. Nucleotide sequences or amino acid sequences that have an identity of at least approximately 70%, at least approximately 75%, at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99%, or at least approximately 100% with the nucleotide sequence or amino acid sequence according to the invention are defined here as being sufficiently similar. This also explicitly encompasses the range of 90% to 100%. For the functional fragments, a sufficient similarity is established if the nucleotide sequence or amino acid sequence generally has the same property as the previously-named nucleotide sequence or amino acid sequence of the present invention. Those nucleotide sequences which encode a derivative or for a derived amino acid sequence are generated either directly or indirectly (for example, via amplification or replication steps) from an initial nucleotide sequence which corresponds to the nucleotide sequence according to the invention over the entire length, or at least in part.

Accordingly, the present invention includes a nucleotide sequence that is able to hybridize, under stringent conditions, with a nucleotide sequence complementary to a nucleotide sequence according to the invention or to the nucleotide sequence that encodes the amino acid sequence according to the invention.

In a further embodiment, the nucleic acid molecule according to the invention is characterized in that, after expression in a plant, it already, on its own, confers a dominant resistance effect against a pathogen—preferably, against *Cercospora beticola*—or that it encodes for a polypeptide that is able to confer a dominant resistance effect against *Cercospora*. In a preferred embodiment, the nucleic acid molecule or the polypeptide confers a resistance effect of at least one rating score—preferably, of at least two rating scores, and, particularly preferably, of three to four rating scores. Such a gene that already, on its own, confers such a strongly pronounced resistance to *Cercospora* in a plant, or that encodes a polypeptide that is able to confer such a pronounced resistance, is not known from the prior art. As was already described above, in previously available varieties on the market, the *Cercospora* resistance is transmitted via many resistance genes having little effect, and a disadvantage of such varieties is that their development is very slow and expensive due to the complicated transmission, and that such varieties have a markedly poorer crop yield relative to normal varieties, in the absence of an infestation. Among other things, this may be linked to the epigenetic interaction of some resistance genes with genes that are responsible for sugar production, which leads to reduced fitness of the plants, in the absence of the pathogen.

The inventors could thus for the first time provide a *Cercospora* resistance gene that may be used for markedly simplified breeding. Via the incorporation of this gene in elite lines, it is now possible to very quickly develop very high-yield varieties with a high *Cercospora* resistance. Accordingly, in the framework of the present invention there are provided for the first time a sugar beet plant, a chard plant, a red beet or beetroot plant, a fodder beet plant having the resistance according to the invention against *Cercospora beticola* and thus being encompassed by the present invention. As the listed plants are all cultivated plants, crops or plants which are suitable for the agricultural cultivation and which have the resistance according to the invention, are part of the invention. Especially such crops are part of the invention which comprise a subterrestrial storage organ usable as food, raw material or industrial source of sugar and which comprise the resistance according to the invention are a further aspect of the present invention. The storage organ can be for example the sugar containing beet body of the sugar beet, the consumable beet body of the red beet or the feedable beet body of the fodder beet. The subterrestrial storage organ can sum up to more than 50% and for the sugar beet even to more than 70% of the total mass of the full-grown plant. Furthermore, also seeds or seeding material of these plants are part of the invention. The seeds or the seeding material can be technically treated as described further below.

In this context, the invention also includes a nucleic acid that encodes the protein according to SEQ ID No. 3, wherein, in a specific embodiment, the naturally occurring nucleic acid according to SEQ ID No. 1 is excluded.

Furthermore, the present invention relates to a recombinant and/or heterologous DNA molecule that comprises the sequences of the nucleic acid molecule according to the invention. This DNA molecule, furthermore, preferably has a regulatory sequence. It may thereby be operatively linked with this regulatory sequence or be under the influence of this regulatory sequence. This regulatory sequence is preferably a promoter sequence and/or other sequences of transcription or translation control elements—for example, cis-elements. The regulatory sequence, which controls the expression of a gene that includes the nucleic acid molecule according to the invention, is preferably a sequence that is able to confer or modulate the expression, as a result of a pathogenic infection. This promoter is preferably able to control the expression of the DNA sequence specifically in leaves of the plant. The regulatory sequence may be heterologous to the expressing sequence. Such an approach has the advantage that the person skilled in the art may better adjust the expression rate of the expressing sequence, the tissue in which the expression occurs, and the point in time at which the expression occurs, in that he selects that regulatory sequence which is best suited to the respective use case. The heterologous DNA sequence preferably includes a nucleotide sequence which encodes a component of the plant pathogen defense (example: resistance genes (R-genes) or genes which encode enzymes involved in signal transfer, such as kinases or phosphatases, and for G-protein, or which encode a pathogenic effector (what are known as avirulence genes (avr))). The heterologous DNA sequence may be one of the DNA sequences according to the invention. The heterologous DNA sequence may also additionally encode further components of the plant pathogen defense. The heterologous DNA sequence may therefore be designed such that a polycistronic mRNA is created after its transcription.

The present invention furthermore also relates to a polypeptide which can be encoded by the nucleic acid molecule according to the invention and a functionally and/or immunologically active fragment thereof, as well as an antibody that specifically binds to the polypeptide or to its fragment. The polypeptide particularly preferably has an amino acid sequence according to SEQ ID No. 3. The recombinant production of proteins, polypeptides, and fragments is familiar to the person skilled in the art (Sambrook et al., Molecular Cloning: A Laboratory Manual, 3rd ed., Cold Spring Harbor Laboratory Press, Cold Spring Harbor, NY, 2001, or Wingfield, P. T., 2008, Production of Recombinant Proteins, Current Protocols in Protein Science, 52:5.0:5.0.1-5.0.4). Polyclonal or monoclonal antibodies to the protein according to the invention may be produced by the person skilled in the art according to known methods (E. Harlow et al., editor, Antibodies: A Laboratory Manual (1988)). The production of monoclonal antibodies, as well as of Fab and F(ab')2 fragments that are also useful in protein detection methods, may be performed via various conventional methods (Goding, Monoclonal Antibodies: Principles and Practice, pp. 98-118, New York: Academic Press (1983)). The antibodies may then be used for the screening of expression cDNA libraries in order to identify identical, homologous, or heterologous genes by means of immunological screening (Sambrook et al., Molecular Cloning: A Laboratory Manual, Cold Spring Harbor Laboratory Press, Cold Spring Harbor, NY, 1989, or Ausubel et al., 1994, "Current Protocols in Molecular Biology." John Wiley & Sons), or may be used for western blot analyses. In particular, the present invention relates to antibodies that selectively detect a polypeptide encoded by the *Cercospora* resistance-conferring allele according to the invention, and essentially do not detect the polypeptide encoded by the correspondingly sensitive allele, i.e., that they detect less, by a factor of 2—preferably, a factor of 5, and, more preferably, a factor or 10 or more—of the polypeptide encoded by the correspondingly sensitive allele than the polypeptide encoded by the *Cercospora* resistance-conferring allele according to the invention.

In a preferred embodiment, the antibody according to the invention is characterized in that it is a synthetic polypeptide which does not occur in nature.

Furthermore, the antibodies according to the invention may be linked with a fluorescent dye in order to be usable in an immunohistochemical method, for example, and evoke an antibody coloration. The fluorescent dye may be fluorochrome. The antibodies according to the invention may also be present linked with other signaling molecules. Among these are, for example, biotin, radioisotopes, reporter enzymes such as alkaline phosphatase, or oligonucleotides.

An additional subject matter of the invention is vectors or expression cassettes that include the nucleic acid molecule or the recombinant DNA molecule according to the invention—possibly under control of regulatory elements and, in particular, under control of functional regulatory elements in plants, as well as negative and/or positive selection markers. The vector backbone is thereby heterologous to the nucleic acid molecule according to the invention, which means that such a vector does not occur in nature and cannot be isolated from nature. The vector is a plasmid, a cosmid, a phage or an expression vector, a transformation vector, shuttle vector or cloning vector; it may be double-stranded or single-stranded, linear or circular; or it may transform a prokaryotic or eukaryotic organism either via integration into its genome or extrachromosomally. The nucleic acid molecule or DNA molecule according to the invention in an expression vector or expression cassette is, preferably, operatively linked with one or more regulatory sequences which allow the transcription and, optionally, the expression in a prokaryotic or eukaryotic cell; (Sambrook et al., Molecular Cloning: A Laboratory Manual, 3rd ed., Cold Spring Harbor Laboratory Press, Cold Spring Harbor, NY, 2001). These regulatory sequences are preferably promoters or terminators—in particular, a transcription initiation starting point, a ribosome binding location, an RNA-processing signal, a transcription termination location, and/or a polyadenylation signal. For example, the nucleic acid molecule is here under the control of a suitable promoter and/or a terminator. Suitable promotors may be constitutive promotors (example: 35S promoter from the "Cauliflower mosaic virus" (Odell et al., Nature 313 (1985), 810-812); those promoters which are pathogenically inducible are especially suitable (example: PR1 promoter from parsley (Rushton et al., EMBO J. 15 (1996), 5,690-5,700)). Particularly suitable pathogenically-inducible promoters are synthetic or chimeric promoters which do not occur in nature, are composed of multiple elements, and contain a minimal promoter, and have at least one cis-regulatory element upstream of the minimal promoter, which at least one cis-regulatory element serves as a binding location for special transcription factors. Chimeric promoters are designed according to the desired requirements and are induced or repressed via different factors. Examples of such promoters are found in WO 00/29592, WO 2007/147395, and WO 2013/091612. For example, a suitable terminator is the nos-terminator (Depicker et al., J. Mol. Appl. Genet. 1 (1982), 561-573). Suitable promoters and terminators may also be the native promoter and the native terminator, whose DNA sequences are reproduced in SEQ ID Nos. 7 and 8. The vectors or expression cassettes additionally contain for conventional indicator/reporter genes or resistance genes for the detection of the transfer of the desired vector or DNA molecule/nucleic acid molecule, and for selection of the individuals that contain these, since a direct detection via the expression of the gene is for the most part rather difficult. Since the nucleic acid molecule according to the invention here itself encodes for a polypeptide which confers resistance to *Cercospora* leaf spot disease, it is not essential for the expression in plant cells to provide an additional resistance gene; however, it is recommended, in order to allow a rapid selection.

Examples of indicator/reporter genes are, for example, the luciferase gene and the gene encoding green fluorescent protein (GFP). These, furthermore, also allow tests for the activity and/or regulation of a promoter of the gene. Examples of resistance genes—especially, for plant transformations—are the neomycin phosphotransferase gene, the hygromycin phosphotransferase gene, or the gene encoding phosphinothricin acetyltransferase. Additional positive selection markers may be enzymes which provide the transformed plant a selection advantage over the non-transformed plant—in particular, a nutrient advantage, e.g., the mannose-6-phosphate isomerase or the xylose isomerase. However, this does not preclude additional indicator/reporter genes or resistance genes known to the person skilled in the art. In a preferred embodiment, the vector is a plant vector. Furthermore, the expression cassette may be present as integrated into a plant genome.

In a further aspect, the present invention relates to cells that include the vectors, recombinant DNA molecules, and/or nucleic acid molecules according to the invention. A cell in the sense of the invention may be a prokaryotic (for example, bacterial) or eukaryotic cell (for example, a plant cell or a yeast cell). The cell is preferably an *agrobacterium* such as *Agrobacterium tumefaciens* or *Agrobacterium rhizogenes*, an *Escherichia coli* cell, or a plant cell; the plant cell is particularly preferably a cell of a plant of the genus *Beta*, the species *Beta vulgaris*, or the subspecies *Beta vulgaris* subsp. *vulgaris*. The cell may also be present as a culture. The invention also consequently covers a cell culture which contains such cells. The cell culture is preferably a pure culture or an isolate that contains no cells of another type.

Known to the person skilled in the art are both numerous methods, such as conjugation or electroporation, with which he may introduce the nucleic acid molecule according to the invention, the recombinant DNA molecule, and/or the vector or the expression cassette of the present invention into an *agrobacterium*, and methods such as diverse transformation methods (biolistic transformation, *agrobacterium*-mediated transformation) with which he may introduce the nucleic acid molecule according to the invention, the DNA molecule, and/or the vector of the present invention into a plant cell (Sambrook et al., Molecular Cloning: A Laboratory Manual, 3rd ed., Cold Spring Harbor Laboratory Press, Cold Spring Harbor, NY, 2001.

Furthermore, the present invention preferably relates to a *Cercospora*-resistant plant—preferably, a plant of the species *Beta vulgaris* subsp. *vulgaris* or a portion thereof—that contains the nucleic acid molecule according to the invention which confers the *Cercospora* resistance. The *Cercospora*-resistant plant may contain the nucleic acid molecule according to the invention as a transgene or as an endogene. Within the scope of the invention, for the first time, plants of the subspecies *Beta vulgaris* subsp. *vulgaris* were produced which contain the nucleic acid molecule according to the invention. The invention here also includes plants of the subspecies *Beta vulgaris* subsp. *vulgaris* which contain the nucleic acid molecule according to the invention as an endogene.

A portion may thereby be a cell, a tissue, an organ, or a combination of multiple cells, tissues, or organs. A combination of multiple organs is, for example, a blossom or a seed. A *Cercospora*-resistant plant of the present invention preferably shows a higher resistance to *Cercospora*—in particular, *Cercospora beticola*—than a corresponding plant that does not contain the nucleic acid molecule according to the invention (control plant). The control plant ideally has the identical genotype as the transgenic plant, and has been cultured under identical conditions, but does not contain the resistance-conferring nucleic acid molecule. The level of the resistance, e.g., to *Cercospora beticola*, may be qualitatively established in plants of the genus *Beta* by determining rating scores. A higher resistance manifests in an improvement in the resistance by at least one rating score, by at least two rating scores, and, preferably, by at least three or more rating scores.

A plant cell or plant or portion thereof of the present invention that contains the nucleic acid molecule according to the invention—in particular, a plant of the genus *Beta*—preferably shows a higher resistance to a pathogen—in particular, to *Cercospora beticola*—than a corresponding plant cell or plant or portion thereof that does not contain the nucleic acid molecule according to the invention, or contains a sensitive allelic variant of the nucleic acid molecule. The level of the resistance, e.g., to *Cercospora beticola*, may be qualitatively established in plants of the genus *Beta* by determining rating scores. A higher resistance manifests in an improvement in the resistance by at least one rating score, by at least two rating scores, and, preferably, by at least three or more rating scores.

In the case of a transgenic plant cell, or plant or portion thereof, this comprises the nucleic acid molecule or DNA molecule according to the invention as a transgene or the vector or the expression cassette of the present invention. Such a transgenic plant cell or plant or portion thereof is, for example, one that is transformed—preferably, stably—with the nucleic acid molecule, DNA molecule according to the invention, or with the vector or the expression cassette of the present invention. In a preferred embodiment, the nucleic acid molecule is operatively linked with one or more regulatory sequences which allow the transcription and, optionally, the expression in the plant cell. The total structure made up of the nucleic acid molecule according to the invention and the regulatory sequence(s) then represents the transgene. Such regulatory sequences are, for example, a promoter or a terminator. Numerous functional promoters and terminators that are applicable in plants are known to the person skilled in the art.

The invention also includes a vacuole of the cell according to the invention, and the content substances stored therein.

Furthermore, the invention also relates to the cell extract from a cell—preferably, from a plant cell, particularly preferably, from a cell of *Beta vulgaris*, and, especially preferably, from a cell of one of the following crops: sugar beet, chard, or beetroot. No plant can be regenerated from the cell extract.

Likewise encompassed by the invention is a plant genome containing the nucleic acid according to the invention. No plant can be regenerated from the plant genome.

The sugar concentration from the cell extract may thereby be increased relative to a cell that is not a cell according to the invention, but that belongs to the same species or crop. This applies, in particular, under the conditions when infested by *Cercospora.*

Also encompassed by the invention is the use of the cell extract for the production of sugar (saccharose) or for the production of juice—preferably, beetroot juice.

Likewise encompassed by the invention is the sugar—in particular, saccharose—contained in the cells according to the invention and their vacuoles.

An additional aspect of the invention is seed stock comprising seeds that contain the nucleic acid according to the invention. The nucleic acid according to the invention may be present transgenically or endogenously. The seed stock and the seeds may be technically treated. The invention thus also comprises technically-treated seed stock and technically-treated seeds. The various embodiments of technically-treated seed stock are explained in detail in the following whereby the term seed stock also includes seeds: Technically-treated seed stock may be present in polished form. The outermost layer of the seed is thereby removed, so that the seed assumes a more rounded form. This is helpful in sowing, where an optimally uniform shape leads to a uniform distribution of the seed stock grains. Technically-treated seed stock furthermore encompasses pelleted seed stock. The seed stock is thereby embedded in a pelleting mass that protects the seed stock contained therein and leads to a larger mass, such that the pelleted seed stock shows a greater resistance capability with regard to wind drift and is thus less susceptible to being blown away by the wind, and, at the same time, a more precise positioning during sowing is enabled. In a preferred embodiment of the invention, all pelleted seed stock grains of a batch or unit designated for sale have essentially the same shape and the same mass. Deviations of 5% in diameter and mass are possible. However, the deviations preferably do not exceed 1%. As one of the main components, the pelleting mass may contain for example a mineral compound such as clay, bentonite, kaolin, humus and/or peat, for example. It is possible to add an adhesive material like polyacrylamide. Additional possible components are cited in U.S. Pat. No. 4,067,141. Moreover, the pelleting mass may contain additional chemical agents that positively influence the cultivation in practice. These may here be substances that are counted among fertilizing agents. These include compounds rich of one or more of the following elements: Nitrogen, Phosphorus and Potassium (macronutrients). Therefore, the fertilizing ingredients may contain for example Nitrate nitrogen, Ammonium nitrogen, Magnesium Nitrate, Calcium Ammonium Nitrate, Mono Ammonium Phosphate, Mono Potassium Phosphate and Potassium Nitrate. Furthermore, pelleting mass may contain fungicides, insecticides, and/or antifeedants. The fungicides may be thiram and/or hymexazol and/or other fungicides. The insecticide may be a substance from the neonicotinoid group. The substance from the neonicotinoid group is preferably imidacloprid (ATC Code: QP53AX17) and/or clothianidin (CAS number 210880-92-5). Furthermore, the insecticide may also be cyfluthrin (CAS number 68359-37-5), *beta*-cyfluthrin or tefluthrin. It is worth mentioned that the compound included in the dressing or pelleting mass are taken up by the plant and show systemic effect thereby providing suitable protection of the whole plant. Plants resulting from pelleted seed including one or more pesticides therefore differ from naturally occurring plants and show better performance under biotic stress conditions. In this context the invention also encompasses a mixture of a pelleting mass and a seed according to the invention. Furthermore, the invention also encompasses a method for producing a pelleted seed according to the invention comprising the following steps:

a) providing a sugar beet plant seed comprising the nucleic acid according to the invention
b) embedding the sugar beet plant seed in a pelleting mass
c) allow the pelleting mass to dry, wherein the seed may be optionally a primed or pregerminated seed or the seed may be allowed to be primed during step b).

The pelleted seed stock is a specific embodiment of dressed seed stock. In this context technically-treated seed stock encompasses also the dressed seed stock. However, the invention is not limited to pelleted seed stock, but, rather, may be applied with any form of dressed seed stock. The invention thus also relates to dressed seed stock, which includes pelleted seed stock, but is not limited to this. Dry dressing, wet dressing, and suspension dressing are thus also encompassed.

The dressing may thereby also contain at least one dye (coloring), such that the dressed seed stock may be quickly differentiated from undressed seed stock, and, furthermore, good visibility in the environment is ensured after sowing. The dressing may also contain those agrochemicals which are described in the context of the pilling mass. The invention includes thus such dressed seed stock whereby the dressing contains at least one anti-feedant such as an insecticide and/or at least one fungicide. Optionally, so called electronical dressing (dressing by application of electric energy) may be applied. However, electronic dressing is not a dressing in the strict sense of the word.

An additional form of technically-treated seed stock is encrusted seed stock. What is known as coating is also spoken of in this context as well as of seed stock treated with a coating. The difference to pelleted seed stock is that the seed grains retain their original shape, wherein this method is especially economical. The method is described in EP 0 334 258 A1, for example. An additional form of technically-treated seed stock is sprouted or primed seed stock. Sprouted seed stock is pretreated via a pre-germination, whereas primed seed stock has been pretreated via a priming ("germination"). Pre-germinated and primed seed stock have the advantage of a shorter emergence time. The point in time of the emergence after sowing is, at the same time, more strongly synchronized. This enables better agrotechnical processing during cultivation and especially during the harvest, and, additionally, increases the yield quantity. In pre-germination, the seed stock is germinated until the radicle exits the seed stock shell, and the process is subsequently stopped. In the priming, the process is stopped before the radicle exits the seed stock shell. Compared to pre-germinated seed stock, seed stock that has been subjected to a priming is insensitive to the stress of a re-drying and, after such a re-drying, has a longer storage life in comparison to pre-germinated seed stock, for which a re-drying is generally not advised. In this context, technically pre-treated seed stock also includes primed and re-dried seed stock. The process of pre-germination is explained in U.S. Pat. No. 4,905,411 A. Various embodiments of priming are explained in EP 0 686 340 A1. In addition to this, it is also possible to simultaneously pill and prime seed stock in one process. This method is described in EP 2 002 702 B1. Primed seed stock which is moreover pelleted, is encompassed by the present invention.

The technically-treated seed stock may additionally be furnished with one or more of the herbicide resistances explained above. This allows a further-improved agrotechnical cultivation, since the technically-treated seed stock may be deployed on a field that has previously been treated with weed killer, and that therefore is weed-free.

In addition to this, the invention also encompasses a mixture containing the seed stock according to the invention or the seeds according to the invention, and a dressing mass as defined above. The dressing mass is thereby preferably embodied as a pelleting mass, as defined above.

With storage of seed stock according to the invention, storage conditions are preferably to be chosen that do not negatively affect the stability or storage life of the seed stock. Fluctuations in humidity may, especially, have a disadvantageous effect here. Part of the invention is a method for the storage of the seed stock in a bag or container that is via simultaneously water-repellent and breathable. Such a bag or container may be designed as a carton or packing. Such a carton or packing may optionally possess an inner vapor barrier. If the carton or packing is designed as a duplex carton, its stability increases. A container, bag, carton or packing comprising the seed stock according to the invention, or technically-treated seed stock according to the invention, is likewise a part of the invention. It is likewise part of the invention to store seed stock according to the invention or technically-treated seed stock according to the invention in such a bag, container, packing or carton.

In one embodiment, the plant according to the invention is a hybrid plant or a double haploid plant. Hybrid plants and double haploid plants do not occur in nature and cannot be isolated from nature. In a further embodiment of the plant according to the invention, the nucleic acid molecule according to the invention is present in heterozygous or homozygous form. In the case of a hybrid plant, the nucleic acid molecule may also be present in hemizygous form. The invention also encompasses hybrid seeds and double haploid seeds which contain a nucleic acid according to the invention or a polypeptide according to the invention.

A further embodiment of the present invention comprises a plant—preferably, of the species *Beta vulgaris*—that is characterized in that the resistance to *Cercospora* in this plant is further increased. For example, this may be realized by means of "gene stacking," i.e., the resistance is increased using this dose effect. For this, the plants according to the invention that contain the *Cercospora* resistance-conferring allele are over-transformed with this resistance allele in order to increase the amount of the transcription of the gene in the plant. An alternative approach includes the gene editing/site-directed mutagenesis or TILLING-mediated modification of the native promoter of the resistance-conferring allele, in order to increase its expression rate, or the modification of the resistance-conferring LRR gene allele itself, in order to increase its activity or stability. Such a method for increasing the activity by means of modification of a resistance gene is described in WO 2006/128444 A2, for example, and may be performed by means of the techniques known to the person skilled in the art. An additional approach may include the fusion of the nucleic acid molecule according to the invention with a heterologous promoter that exhibits a higher activity in comparison to the native promoter—in particular, after *Cercospora* infection.

An additional embodiment of the present invention is directed to a sugar beet plant or a pelleted seed of such a plant which is harvestable before bolting because no bolting of the sugar beet plant occurs during the first 10, 11, 12, 13, 14 or 15 months after germination and the development of a beet body is finished during this period.

In one embodiment of the present invention the sugar beet plant or a pelleted seed of such a plant has a genome allowing the development of a beet body having a mass summing up to at least 50%, 60%, 70%, 80% or even 90% of the total mass of the full-grown plant.

In another embodiment of the present invention the sugar beet plant or a pelleted seed of such a plant has a genome allowing the development of a beet body having a minimum mass of 200 g, 250 g, 300 g, 350 g, 400 g, 450 g or 500 g and a maximum mass of 100 g, 1100 g, 1200 g, 1300 g, 1400 g, 1500 g, 1600 g, 1700 g, 1800 g, 1900 g or even 2000 g via photosynthesis.

An additional embodiment of the present invention is directed to a sugar beet plant or a pelleted seed of such a plant wherein the genome of the sugar beet plant allows development of a beet body having a saccharose concentration of at least 10%, 11%, 12%, 13%, 14%, 15%, 16%, 17%, 18%, 19% or even 20%.

In one embodiment of the present invention the sugar beet plant or a pelleted seed of such a plant includes at least one, at least two, at least three, at least four, at least five, at least ten, at least twenty or even at least thirty mutation(s) relative to SEQ ID No. 4.

The method for the production of an organism which comprises a mutated version of the nucleic acid molecule according to the above given embodiment [1] and/or a mutated version of a promoter comprising a nucleic acid sequence selected from the group consisting of (a) SEQ ID NO: 7, (b) a nucleotide sequence, which hybridizes under stringent conditions with a sequence which is complementary to the sequence according to (a), and (c) a nucleotide sequence which is at least 70% identical to a sequence according to SEQ ID NO: 7, wherein the method includes the following steps:

(I) Provision of an organism or a cell comprising the nucleic acid molecule and/or the promoter (II) Increase of the mutation rate of the organism or the cell or mutagenesis of the organism or the cell (III) Phenotypic selection of an organism, which as a result of a mutation exhibits an altered resistance or altered resistance level towards *Cercospora beticola* or Genotypic selection of an organism or a cell which comprises a mutation in the nucleic acid molecule and/or the promoter wherein the mutation has been created via step (II) and optionally (IV) Regeneration of the organism from the cell obtained via step (III).

The organism can be a plant. Preferably the plant is a *Beta vulgaris*. However, it is also possible to use unicellular organisms as bacteria. The bacterium can be *E. coli*. If the organism is a plant then the method can be applied in vivo as well as in vitro. If the organism is a plant and the method is applied in vitro, a cell culture of the plant may be established and the increase of the mutation rate or the mutagenization may occur in the cell culture. The increase of the mutation rate encompasses for example the application of mutagenic agents like for example 5-bromouracil or ethylmethane sulfonate (EMS) or the application of physical mutagens like ionizing radiation or UV light. The mutagenization encompasses also the targeted mutagenesis. The targeted mutagenesis can be achieved by precise methods as gene editing (as explained further below). The regeneration of organism out of cells is explained in various standard references of the cell biology. The regeneration of plants is for example explained in the standard reference "Plant biotechnology: comprehensive biotechnology, second supplement" (Michael W. Fowler, Graham Warren, Murray Moo-Young—Pergamon Press—1992). The regeneration of *Beta vulgaris* out of the cell culture is described in Lindsey & Gallois "Transformation of sugarbeet (*Beta vulgaris*) by *Agrobacterium tumefaciens.*" *Journal of experimental botany* 41.5 (1990): 529-536.

These references also describe how plant cell cultures are established. As explained further above the mutated version of the nucleic acid molecule respectively the promoter characterizes themselves preferably due to the expression rate of the resistance imparting nucleic acid molecule which is increased by the mutation. Such an effect can also rely on the presence of several mutations. For example, it is possible to introduce two, three, four, five or more mutations in the promoter or the nucleic acid molecule.

By the introduction of mutations thus more resistance imparting protein can be build in the cell or the protein has a better effect. Thereby, the resistance in comparison to a control plant comprising the unaltered nucleic acid according to the invention can be increased for example by at least 1, 2, 3, 4, 5 or more percent. The increase can be measured as explained further below. Moreover, the resistance due to the mutation or mutations can be increased by at least one rating score. The determination of rating scores is explained elsewhere herein. Furthermore, the resistance protein can impart—as a result of the mutations—an altered effect and in some circumstances can exhibit effect against such pathogens which have adapted themselves to the initial resistance mechanism. In this context the invention encompasses also such mutated variants of the nucleic acids according to the invention and mutated variants of the protein according to the invention. Preferably the invention encompasses such variants which do not occur in nature and cannot be isolated from nature to make sure that the pathogen had no opportunity to adapt itself to such variants. The above described method for the production of an organism which comprises a mutated version of the nucleic acid molecule may furthermore include a further step, in which those organisms or respectively plants are identified, which have a further increased resistance due to the mutation or mutations. If an increase of resistance has taken place may be determined by the herein explained rating scores or the measuring of the resistance level.

Besides the above described method for the production of organisms which comprise a mutated version of the nucleic acid molecule or of the promoter it is also possible to modify the according nucleic acids chemically in an isolated state to achieve the desired effects (as for example those which are described above). The advantage of this approach is that the compounds can be edited even more precisely. For this purpose, the following method is offered:

Production of a chemically modified nucleic acid molecule according to the above given embodiment [1] and/or a chemically modified promoter comprising a nucleotide sequence which is chosen from (a) SEQ ID NO: 7;

(b) a nucleotide sequence which hybridizes under stringent conditions to a nucleotide sequence according to (a);

(c) a nucleotide sequence which is at least 70% identical to a sequence according to SEQ ID NO: 7;

wherein the method comprises the following steps:

(I) Provision of the nucleic acid molecule as stated above in isolated form (II) chemical modification of the nucleic acid molecule or the promoter by one of the following steps:

(IIa) Mutagenization (IIb) Gene editing (IIc) Restriction and ligation respectively insertion or deletion.

Furthermore, chemical modifications can be generated by such approaches as stated elsewhere herein in context of allelic variants. The gene editing given under step (II) above is equal to the term "Genome-Editing". Optionally the chemically modified nucleic acid molecule or the chemically modified promoter can be subsequently introduced into a cell or can be stably integrated. With the help of such a cell, the chemically modified nucleic acid molecule and the modified promoter can be propagated in context of the cell proliferation. They can be subsequently isolated in vast number and expression analyses may be performed. Expression analyses are especially suitable when the chemical modification concerns the promoter. It is possible to harvest the cells and to isolate the chemically modified resistance protein for chemical analyses. If the cell which comprises the chemically modified nucleic acid molecule or the modified promoter is a plant cell, a complete plant may be regenerated out of this cell. The approaches described within this passage can be performed subsequently to the above given method for the production of a modified form of the nucleic acid molecule and/or a modified promoter and the obtained variants are also a part of this invention. Moreover, a plant comprising the chemically modified nucleic acid molecule or the modified promoter are also part of the invention. Thus, the invention is also related to a plant obtained by this method. Furthermore, the invention relates also to the chemically modified nucleic acid molecules obtained by this method and to the encoded polypeptides. These compounds may be optimized versions of the original (not modified) compounds, wherein the resulting resistance level—as explained further above—may be increased by at least by 1, 2, 3, 4, 5, or more percent or may be increased by at least one rating score. In this regard the method for the production of a chemically modified nucleic acid molecule is also a method for the optimization of the nucleic acid molecule. The method for optimization may furthermore contain an additional step, in which those modified variants of the nucleic acid molecule are identified which lead in comparison to the unamended variants to an increased resistance in a plant.

In a further embodiment, the plant of the present invention additionally, transgenically or endogenously, comprises a second nucleic acid molecule at a different position in the genome, which encodes a polypeptide that is able to confer a resistance to *Cercospora* in the plant in which the polypeptide is expressed. For example, one or more of the resistance genes or resistance loci that are described in the prior art may—insofar as they are not already present in the initial genotype—be introduced into the present plant by means of crossing, transformation, homology-directed repair, or homologous recombination in the plant. Among these are, for example, the rhizomania resistance RZ1 (Lewellen, R. T., I. O. Skoyen, and A. W. Erichsen, "Breeding sugar beet for resistance to rhizomania: Evaluation of host-plant reactions and selection for and inheritance of resistance." 50*th Winter Congress of the International Institute for Sugar Beet Research, Brussels* (*Belgium*), Feb. 11-12, 1987. IIRB. Secretariat General, 1987), or the rhizomania resistance RZ3 (WO 2014/202044).

The present invention additionally relates to a method for increasing the resistance to *Cercospora* in a plant of the species *Beta vulgaris*, wherein the increase in the resistance takes place without the resistance-conferring gene according to the invention, in comparison to an isogenic plant.

The increase in the resistance may take place via integration of the nucleic acid molecule according to the invention into the genome of at least one cell of a plant of the species *Beta vulgaris*, as well as possible regeneration of a plant from the plant cell. The integration may take place both by means of sexual crossing, e.g., with one of the aforementioned *Beta vulgaris* subsp. *maritima* and subsequent selection, and by means of homology-directed repair or homologous recombination. The two latter methods cited are preferably supported by site-directed nucleases which may be selected from, but are not limited to, the following: CRISPR nuclease, including Cas9, CasX, CasY, or Cpf1 nuclease, TALE nuclease, zinc finger nuclease, meganuclease, Argonaut nuclease, restriction endonuclease, including FokI or a variant thereof, recombinase, or two, site-specific, nicking endonucleases. The introduction of the resistance-conferring gene by means of CRISPR-mediated homologous recombination in *Beta vulgaris* subsp. *vulgaris* is shown in Example 1.

An alternative approach includes the increase in the expression of the nucleic acid molecule according to the invention in the plant. This may take place via modification of the native promoter, wherein the modification preferably takes place by means of gene editing or site-directed mutagenesis which is mediated via site-directed nucleases, and, optionally, repair models. Examples of such nucleases have already been cited above. The increase in the expression of the nucleic acid molecule according to the invention may likewise take place via fusion of the nucleic acid molecule with a heterologous promoter, which exhibits a higher activity in comparison to the native promoter—in particular, after *Cercospora* infection. The fusion may likewise take place via site-directed nuclease and repair models, but also by means of direct insertion after double-strand break.

As has already been mentioned above, a method for increasing the *Cercospora* resistance, may also result in the increase in the activity and/or stability of the polypeptide according to the invention, via modification of the nucleotide sequence of the nucleic acid molecule according to the invention. Such a method for increasing the activity by means of modification of a resistance gene is described in WO 2006/128444 A2, for example, and may be performed by means of the techniques known to the person skilled in the art. This approach is explained in detail further below.

Alternatively, a *Cercospora*-resistant genotype may be produced from a *Cercospora*-sensitive genotype by means of random or directed mutagenesis of the nucleic acid sequence of the sensitive gene, and thus the *Cercospora* resistance may be increased. Examples of polymorphisms which differentiate the sensitive allele from the resistant allele are presented in FIG. 1.

For example, the sensitive allele may be modified via gene mutation by means of TALE nucleases (TALEN's) or zinc finger nucleases (ZFN's), as well as CRISPR/Cas systems, which—among other things—are described by way of example in WO 2014/144155 A1 (Engineering plant genomes using CRISPR/Cas systems) and in Osakabe & Osakabe, Plant Cell Physiol., 56 (2015), 389-400. This may also be achieved via use of the method designated as TILLING (*Targeted Induced Local Lesions in Genomes*), wherein it is described, e.g., in the German patent application DE 10 2013 101 617, how point mutations are caused in the sensitive gene, and plants are subsequently selected that exhibit a suitable, i.e., resistance-conferring, mutation, e.g., a barley resistant to yellow mosaic virus; see DE 10 2013 101 617 on pp. 4, 8, and 12, in paragraphs [0014], [0026], and [0038]. The TILLING method is also described in detail in the publication by Henikoff et al. (Henikoff et al., Plant Physiol. 135, 2004, 630-636).

These methods preferably lead to an improvement in the resistance by at least one rating score—particularly preferably, to an improvement in the resistance by at least two, three, or more rating scores. After mutagenesis of the plant cells and subsequent regeneration of plants from the mutagenized plant cells, or mutagenesis of plants, the plants may then be identified that exhibit one or more mutations, as depicted in FIG. 1, in an endogenous nucleic acid molecule. In this context the already mentioned plant according to the invention may be characterized by that the resistance is increased by at least one rating score, preferably by at least two or more rating scores. Alternatively, the resistance of the plants according to the invention may be increased for example by at least 1, 2, 3, 4, 5 or more percent in comparison to a control plant, which does not comprise the nucleic acid according to the invention. The increase can be measured by inoculation of respectively one healthy leaf with an isolate of the pathogen and the determination of the infested surface after 15 days. A reduce of 5% of the infested surface corresponds to an increase of the resistance of 5%. Further parameters for the conduction of the measuring can be derived from the below given embodiment "resistance rest".

An additional embodiment of the present invention is a method for producing a *Cercospora*-resistant plant, which may take place via transformation of a plant cell with the nucleic acid molecule according to the invention, the recombinant DNA molecule, or with the vector or the expression cassette, and regeneration of the transgenic plant from the transformed plant cell (see Example 2), as well as, as described above, by means of random or targeted mutagenesis of the nucleic acid sequence of the sensitive gene to generate a *Cercospora*-resistant genotype, or via crossing and selection, e.g., with one of the aforementioned *Beta vulgaris* subsp. *maritima*. Vectors or expression cassettes, as well as methods for transforming plants, have already been described above.

The method for production of a *Cercospora*-resistant plant alternatively includes, as described above, the introduction of a site-directed nuclease and a repair matrix into a cell of a plant of the species *Beta vulgaris*, wherein the site-directed nuclease is able to generate at least one double-strand break of the DNA in the genome of the cell—preferably, upstream and/or downstream of a target region—and the repair matrix comprises the nucleic acid molecule according to the invention. The method furthermore includes the cultivation of this cell under conditions that allow a homology-directed repair or a homologous recombination, wherein the nucleic acid molecule is incorporated from the repair matrix into the genome of the plant. Furthermore, the regeneration of a plant from the modified plant cell is encompassed (see Example 1).

In a preferred embodiment, the target region is an allelic variant of the nucleic acid molecule according to the invention, wherein the allelic variant encodes a polypeptide which does not confer resistance to *Cercospora*. In a further preferred embodiment, this allelic variant comprises a nucleotide sequence that encodes a polypeptide with an amino acid sequence according to SEQ ID No. 6 and/or comprises the encoded DNA sequence according to SEQ ID NO: 5 or the genomic DNA sequence according to SEQ ID No. 4.

As described in connection with the nucleic acid molecule according to the invention, substitutions, deletions, insertions, additions, and/or any other change may be introduced that, either alone or in combinations, do in fact change the nucleotide sequence, but perform the same function as the initial sequence—here, the nucleotide sequence of the allelic variant of the nucleic acid molecule according to the invention. Therefore, in a further embodiment, the invention includes a nucleotide sequence that encodes a polypeptide which represents a derivative of the polypeptide which is encoded by the allelic variant of the nucleic acid molecule according to the invention, or which comprises the amino acid sequence of the allelic variant of the nucleic acid molecule according to the invention. A derived amino acid sequence which has at least one substitution, deletion, insertion, or addition of one or more amino acids, wherein the functionality of the encoded polypeptide/protein is preserved, represents a derivative of the polypeptide. The nucleotide sequence, using conventional methods that are known in the prior art, e.g., via site-directed mutagenesis, PCR-mediated mutagenesis, transposon mutagenesis, genome editing, etc., substitutions, deletions, insertions, additions, and/or any other change, either solely or in combinations with the gene, may thereby be introduced, which do in fact change the nucleotide sequence, but perform the same function as the initial sequence.

With regard to the amino acid sequence, after modification via an aforementioned method, this also has a common structural domain and/or possesses common functional activity. Nucleotide sequences or amino acid sequences that at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99%, or at least approximately 100% identical to the nucleotide sequence or amino acid sequence of the cited allelic variant of the nucleic acid molecule according to the invention are defined here as being sufficiently similar. Accordingly, the present invention includes a nucleotide sequence that is able to hybridize, under stringent conditions, with a nucleotide sequence that is complementary to a nucleotide sequence of the allelic variant of the nucleic acid molecule according to the invention or to the nucleotide sequence that encodes the corresponding amino acid sequence.

In a further preferred embodiment, the method according to the invention is characterized in that the double strand break occurs in an allelic variant of the nucleic acid molecule according to embodiment [1] or that the at least one double strand break occurs at a position which is at least 10,000 base pairs upstream or downstream of the allelic variant, wherein the allelic variant codes for a polypeptide which does not impart a resistance towards *Cercospora.*

For the person skilled in the art, it is obvious that numerous, different sensitive sequences may occur that derive from the nucleic acid molecule according to the invention, but do not confer resistance to *Cercospora*, such that the sequences listed above (SEQ ID Nos. 4, 5, and 6) should only be considered as an example of sequences, and the present invention is not limited to the aforementioned allelic variant of the nucleic acid molecule according to the invention. Such an allelic variant can comprise a nucleotide sequence, which is selected from:

(a) a nucleotide sequence encoding a polypeptide having an amino acid sequence according to SEQ ID No. 6;
(b) a nucleotide sequence that comprises the DNA sequence according to SEQ ID No. 5;
(c) a nucleotide sequence that comprises a DNA sequence according to SEQ ID No. 4;
(d) a nucleotide sequence that hybridizes with the complementary sequence according to (a), (b), or (c), under stringent conditions;
(e) a nucleotide sequence encoding a polypeptide which, via substitution, deletion, and/or addition of one or more amino acids of the amino acid sequence, differs from a polypeptide encoded by the nucleotide sequence according to (a), (b), or (c);
(f) a nucleotide sequence encoding a polypeptide which has an amino acid sequence that is at least 70%, 75%, 80%, 85%, 90%, 95%, 96%, 97%, 98% or 99% identical to an amino acid sequence according to SEQ ID No. 6;
(g) a nucleotide sequence that is at least 70%, 75%, 80%, 85%, 90%, 95%, 96%, 97%, 98% or 99% identical to a DNA sequence according to SEQ ID No. 4 or SEQ ID No. 5;

As described above, with quantitative heredity of QTL, not only is the desired resistance to often introduced into the plant, but, rather, also often unwanted features such as, for example, reduced yield, due to the inheritance of additional genes that are not linked with the positive feature of the resistance. This increasingly occurs if, as in the case of *Cercospora* resistance, the resistance is inherited in previously available cultivars via many resistance genes with small effect. Therefore, in a preferred embodiment, the introduction of the nucleic acid molecule according to the invention, which already shows, on its own, a dominant resistance effect, or of the vector or the expression cassette, is not linked with the introduction of unwanted features, wherein the yield is, preferably, not negatively affected. Furthermore, encompassed by the invention is the plant that is obtained via such a method.

Although the QTL analyses with that have previously been known from the prior art could detect actual QTL's, the underlying genomic regions that had shown a QTL effect also mediated the disadvantages described above, which is why "linkage drag" is also discussed in this context. At the same time, the QTL's and the effects connected therewith were not described uniformly in the respective prior art, and merely mediated a weak effect, such that the utilization of these results in the breeding of *Cercospora*-resistant plants was possible to only a limited extent and was largely uncertain. Targeted breeding and controlled integration of the resistance gene into the gene pool of the sugar beet are now enabled by means of the identification of the resistance gene described herein. This ensures the breeding and generation of entirely new *Cercospora*-resistant cultivars that exhibit a high resistance to the pathogen, without negatively affecting the sugar yield.

The present invention likewise relates to a method for the identification, and possibly the provision, of a plant of the species *Beta vulgaris* that is resistant to the pathogen *Cercospora*, characterized in that the method includes a step of the detection of the presence and/or of the expression of a nucleic acid molecule according to the invention or of the polypeptide according to the invention in the plant or a sample/portion thereof. The presence and/or the expression of a nucleic acid molecule according to the invention, or of the polypeptide according to the invention, may be tested by means of standard methods known to the person skilled in the art, e.g., by means of PCR, RT-PCR, or western blot.

Furthermore, the identification method according to the invention also includes the detection of the nucleic acid molecule according to the invention by means of detection of at least one polymorphism between resistant and sensitive sequences, i.e., between the sequences of the nucleic acid molecule according to the invention and the sequences of the allelic variant of the nucleic acid molecule according to the invention that is described above, using molecular markers that detect one or more polymorphisms. As has already been described above, it is obvious to the person skilled in the art that numerous sensitive sequences exist, i.e., numerous sequences that encode the allelic variant of the nucleic acid molecule according to the invention. One of these is presented by way of example in the sequence comparison with the nucleotide sequence of the nucleic acid molecule according to the invention in FIG. 1. A preferred embodiment of the method according to the invention consequently includes the detection of at least one polymorphism that is presented in FIG. 1 using molecular markers which detect the polymorphisms—in particular, diagnostic polymorphisms. This detection preferably occurs using at least one molecular marker per polymorphism—in particular, per diagnostic polymorphism. It is known to the person skilled in the art which marker techniques are to be applied to detect a corresponding polymorphism, and how molecular markers for this are constructed (see Advances in Seed Science and Technology Vol. I, Vanangamudi et al., 2008). Furthermore, the present invention encompasses molecular markers which describe or detect a polymorphism according to FIG. 1, such as the use of a molecular marker for detection of a polymorphism according to FIG. 1. It is thereby also possible to use markers that do not differentiate between various polymorphisms, as long as the markers are able to detect such a polymorphism as it occurs in the nucleic acid molecule according to the invention, but is not contained the sensitive allelic variant.

Alternatively or additionally, the identification method according to the invention includes a step of detecting at least one marker locus in the nucleotide sequence of the nucleic acid molecule according to the invention or in a cosegregating regions thereof. Preferably the cosegregating region is a genomic region in *Beta vulgaris* which cosegregates with the *Cercospora* resistance conferred by the polypeptide according to the present invention, or with the nucleic acid molecule according to the present invention, more preferably the cosegregating region comprises and is flanked by markers sxh0678s01 and s4p0264s01, by markers s4p4301s01 and s4p2271s01, by markers s4p4301s01 and s4p4293s01, or by markers s4p4301s01 and s4p4295s01. The detection may thereby take place via a method step in which at least one marker or at least one primer pair binds at the locus according to SEQ ID No. 74 or 75—preferably, at the locus according to SEQ ID No. 76 or 77—and, optionally as a result of this, a signal is generated, e.g., a fluorescence signal or a sequence amplificate. Thus, alternatively or additionally the cosegregating region may comprise a sequence according to SEQ ID NO 74 and/or 75, or SEQ ID NO: 76 and/or 77. Furthermore, the preceding identification methods also represent methods for selection of a plant which exhibits the resistance to *Cercospora* according to the invention. The method for selection includes a concluding step of selecting a resistant plant.

In this context, the present invention also includes the development or production of molecular markers that are suitable for detecting the aforementioned polymorphisms between the nucleic acid molecule according to the invention (resistant allele) and the sensitive allelic variant, wherein the markers are preferably suitable for detecting the polymorphisms presented in FIG. 1 or the construction of hybridization probes that specifically bind to the nucleotide sequence of the nucleic acid molecule according to the invention, or the production of a pair of nucleic acid molecules that is suitable for amplifying, in a PCR, a region that is specific to the nucleic acid molecule according to the invention, and thus for detecting these in a plant or plant cell.

The invention preferably includes a method for producing oligonucleotides of at least 15, 16, 17, 18, 19, or 20—preferably, at least 21, 22, 23, 24, or 25, particularly preferably, at least 30, 35, 40, 45, or 50, and, especially preferably, at least 100, 200, 300, 500 or 1,000—nucleotides in length that specifically hybridize with a nucleotide sequence of the nucleic acid molecule according to the invention or the nucleic acid molecule that is complementary thereto, or a pair of nucleic acid molecules—preferably, in the form of oligonucleotides—that is suitable for attachment as a forward and reverse primer to a region that is specific to the nucleic acid molecule according to the invention, and for amplifying this in a polymerase chain reaction (PCR), or that is suitable for hybrizidation as a forward and reverse primer to a region in the *Beta vulgaris* genome that, in *Beta vulgaris*, has a cosegregation with the *Cercospora* resistance conferred by the polypeptide according to the invention or with the nucleic acid molecule according to the invention.

An example for suitable primers for the detection of a resistance-mediating nucleotide sequence according to the invention are given by SEQ ID NO 98 and SEQ ID NO 99. These two sequences build a primer pair which can by used in the PCR.

The method for the production of oligonucleotides initially includes: the comparison of the nucleotide sequence of the nucleic acid molecule according to the invention with the nucleotide sequence of the corresponding nucleic acid molecule that does not confer resistance or of the sensitive allelic variant, which preferably has a nucleotide sequence according to SEQ ID No. 4 or 5; the identification of the sequence differences between the two nucleotide sequences; and the generation of nucleic acid molecules—here, meaning oligonucleotides—that specifically bind to the nucleic acid molecule according to the invention, but not to the nucleic acid molecule that does not mediate resistance.

Furthermore, the oligonucleotide according to the invention may be connected to a fluorescent dye in order to generate a fluorescence signal, e.g., under excitation via light of the corresponding wavelength. The fluorescent dye may be fluorochrome. The oligonucleotides according to the invention may be coupled with other compounds that are suitable for generating a signal. Such oligonucleotides do not occur in nature and also cannot be isolated from nature. The following is executed to produce such marked oligonucleotides: DNA may be marked bio-orthogonally. For this, DNA may be marked in vivo or in vitro with nucleoside analogs, which, for example, may subsequently be coupled with a fluorophore per Staudinger reaction. In addition to this, DNA may also be chemically provided with fluorophores. Oligonucleotides may be marked via a phosphoramidite synthesis with fluorophores that, for example, are used in QPCR, DNA sequencing, and in situ hybridization. Furthermore, DNA may be generated enzymatically in the course of a polymerase chain reaction with fluorescent nucleotides, or be marked with a ligase or a terminal deoxynucleotidyl transferase. DNA may also be detected indirectly via a biotinylation and fluorescent avidin. For couplings, fluorescein, fluorescent lanthanides, gold nanoparticles, carbon nanotubes, or quantum dots, among other things, are used as fluorophores. One of the most commonly used fluorescent substances is FAM (carboxyfluorescein). Consequently, oligonucleotides and, in particular, primers that possess a FAM marking are encompassed by the invention. FAM is preferably present as 6-FAM, wherein—depending upon the desired wavelength of the emission and excitation—other FAM variants, e.g., 5-FAM, may, however, also be used. Examples of additional fluorescence markers are AlexaFluor, ATTO, Dabcyl, HEX, Rox, TET, Texas Red, and Yakima Yellow. Depending upon the field of use, the oligonucleotides may be furnished with modifications of the bases or of the sugar phosphate spine. Among these are, among others, amino-dT, azide-dT, 2-aminopurine,5-Br-dC, 2'-deoxyinosine (INO), 3'-deoxy-A, C, G, 5-Met-dC, 5-OH-Met-dCN6-Met-dA, and others.

Furthermore, the present invention also relates to a marker chip ("DNA chip" or microarray) which contains at least one oligonucleotide according to the invention that is suitable for detection. The marker chip is suitable for application in one or more detection methods according to the invention.

The invention likewise includes a method for production of the protein according to the invention. The method includes the provision or cultivation of a cell culture which contains the SEQ ID No. 2, and the subsequent expression of the protein encoded by SEQ ID No. 2.

Furthermore, the present invention also relates to a *Cercospora*-resistant plant or a portion thereof which was identified, and, if applicable, selected, via a method as described in the preceding. In particular, the present invention relates to a population of plants comprising plants that are available according to one of the methods according to the invention as described in the preceding, and that preferably are resistant to *Cercospora* leaf spot disease or *Cercospora* infestation, and are characterized by the presence of a nucleic acid molecule according to the invention. The population preferably has at least 10—preferably, at least 50, more preferably, at least 100, particularly preferably, at least 500, and, particularly in agricultural farming, preferably at least 1,000—plants. The proportion of plants in the population that do not carry the nucleic acid molecule according to the invention and/or are susceptible to *Cercospora* leaf spot disease is preferably below 25%—preferably, below 20%, more preferably, below 15%, even more preferably, 10%, and, in particular, preferably below 5%, if present at all.

With the fine mapping described above, the position of the *Cercospora* resistance-conferring gene in the genome of *Beta vulgaris* subsp. *maritima* could be determined, and the gene itself and the surrounding sequence regions could be identified. This in turn represents the basis for the development of DNA hybridization probes or genetic markers in the target region, with the aid of which the *Cercospora* resistance-mediating gene could be detected, or could be differentiated from the gene that does not confer resistance.

DNA hybridization probes may be derived from the sequence of the *Cercospora* resistance-conferring gene and be used for the screening of genomic and/or cDNA banks of the desired organism. The probes may be used to amplify identified homologous genes via the known process of polymerase chain reaction (PCR), and to check whether the *Cercospora* resistance-conferring gene is present endogenously in an organism, or has been successfully introduced heterologously.

The person skilled in the art may here resort to customary hybridization, cloning, and sequencing methods, which, for example, are listed in Sambrook et al., Molecular Cloning: A Laboratory Manual, 3rd ed., Cold Spring Harbor Laboratory Press, Cold Spring Harbor, NY, 2001. The person skilled in the art may also synthesize and use oligonucleotide primers to amplify sequences of the *Cercospora* resistance-conferring gene. In order to achieve a specific hybridization, such probes should be specific and have at least a length of 15 nucleotides—preferably, at least 20 nucleotides. A detailed guide to hybridization of nucleic acids may be found in Tijssen, Laboratory Techniques in Biochemistry and Molecular Biology—Hybridization with Nucleic Acid Probes, Part 1, Chapter 2, "Overview of principles of hybridization and the strategy of nucleic acid probe assays." Elsevier, New York (1993); and in Current Protocols in Molecular Biology, Chapter 2, Ausubel et al., eds., Greene Publishing and Wiley lnterscience, New York (1995).

Therefore, a nucleic acid molecule of at least 15, 16, 17, 18, 19, or 20—preferably, at least 21, 22, 23, 24, or 25, particularly preferably, at least 30, 35, 40, 45, or 50, and, especially preferably, at least 100, 200, 300, 500, or 1,000—nucleotides in length is the subject matter of the present invention, wherein this nucleic acid molecule specifically hybridizes with a previously-described nucleotide sequence according to the invention that comprises the *Cercospora* resistance-conferring gene. This also explicitly encompasses the range of 15 to 35 nucleotides.

The present invention thus also relates to markers as oligonucleotides—in particular, primer oligonucleotides. These comprise a nucleic acid molecule of at least 15 nucleotides in length that specifically hybridizes with a nucleotide sequence defined as in the preceding.

In particular, the present invention encompasses a pair of nucleic acid molecules—preferably, in the form of oligonucleotides or a kit containing this pair of oligonucleotides—that is suitable for hybridization as a forward and reverse primer to a region that is specific to the nucleic acid molecule according to the invention, and for amplifying this in a polymerase chain reaction (PCR), or that is suitable as a forward and reverse primer for hybridization to a region in the *Beta vulgaris* genome that, in *Beta vulgaris*, exhibits a cosegregation with the *Cercospora* resistance conferred by the polypeptide according to the invention, or with the nucleic acid molecule according to the invention.

The following advantages for the breeding and development of new resistant plant lines of the genus *Beta* may also be achieved via the present invention. Sequence information, as well as the identified polymorphisms which allow a differentiation between resistant and susceptible alleles of the disclosed gene, i.e., between the alleles that confer a *Cercospora* resistance and the alleles that are not capable of conferring this resistance, make possible the marker development directly in the gene, as described above, as well as in the regions situated upstream and downstream, which represents an important facilitation for the plant breeder—in particular, with regard to the development of optimized elite lines without "linkage drag." Moreover, knowledge about the sequential structure may be used for the identification of additional resistance genes—in particular, against *Cercospora*—which are homologous or orthologous, for example.

Therefore, the present invention also encompasses a method for the identification of additional nucleic acid molecules encoding polypeptides or additional proteins that are able to confer a resistance to *Cercospora* in a plant in which the polypeptide is expressed. The person skilled in the art may thereby use databases, employing suitable search profiles and computer programs for the screening for homologous sequences or for sequence comparisons. Moreover, by means of conventional molecular biology techniques, the person skilled in the art may himself derive additional DNA sequences encoding *Cercospora* resistance proteins, and use these within the scope of the present invention. For example, suitable hybridization probes may be derived from the sequence of the nucleic acid molecule according to the invention and be used for the screening of genomic and/or cDNA banks of the desired organism. The person skilled in the art may here resort to customary hybridization, cloning, and sequencing methods, which, for example, are listed in Sambrook et al., Molecular Cloning: A Laboratory Manual, 3rd ed., Cold Spring Harbor Laboratory Press, Cold Spring Harbor, NY, 2001. Using known sequences, the person skilled in the art may also synthesize and use oligonucleotide primers to amplify sequences of *Cercospora* resistance-conferring nucleic acid molecules.

In one embodiment, the present invention therefore encompasses a method for the identification of a nucleic acid molecule which encodes a polypeptide that is able to confer a resistance to *Cercospora* in a plant of the species *Beta vulgaris* in which the polypeptide is expressed. The method thereby includes the comparison of the amino acid sequence of the polypeptide according to the invention which, in *Beta vulgaris* subsp. *vulgaris*, confers a *Cercospora* resistance with amino acid sequences from a sequence database, or with sequences of allelic variants of the polypeptide according to the invention in genotypes of the species *Beta vulgaris*. Furthermore, the method according to the invention includes the identification of an amino acid sequence or of an allelic variant that is at least 80% identical to the amino acid sequence of the polypeptide according to the invention, as well as the introduction of a nucleic acid molecule encoding the identified amino acid sequence or allelic variant in a plant of the species *Beta vulgaris*; expression of the nucleic acid molecule in the plant; and, optionally, subsequent verification of the resistance to *Cercospora*.

As described in the preceding, additional *Cercospora* resistance-conferrring proteins or their coding genes, i.e., homologs, analogs, and orthologs, that are at least 70%—preferably, at least 80%, particularly preferably, at least 90%, especially preferably, at least 95%, or even 98%—identical to the amino acid sequence of the polypeptide which is encoded by the nucleic acid molecule according to the invention may be identified via classical bioinformatic approaches (database searches and computer programs for screening for homologous sequences).

The term, homolog(s), thereby means that the genes concerned (from two different plant species) have essentially the same function and a common ancestor, and therefore typically show a significant identity in their nucleic acid or coded amino acid sequences. However, there are also many genes that are homologous to one another, without protein sequences resulting in a meaningful paired alignment. In contrast to this, the term, analog(s), describes genes or proteins that (likewise) have an identical or similar function, but are not created from the same structure, i.e., have no common ancestor. In this case, often, no significant identity can be established in their nucleic acid or encoded amino acid sequence, or, in the best case, in specific functional domains.

In the context of genome sequencing, homologs are, for annotation, more finely classified. The terms, orthology and paralogy, have been introduced for this. Orthologs are genes that are connected via a speciation event. Paralogs are genes that trace back to a duplication event.

A gene is, then, fundamentally a homolog or analog or ortholog in the sense of the present invention if it is able to confer *Cercospora* resistance in a plant. To check, methods, which have already been described in the preceding, known to the person skilled in the art are used, e.g., the amplification of the identified homolog or analog or ortholog by means of PCR, cloning in expression vectors, introduction into the target plant or plant cell, and checking the resistance.

As described above, the usage disclosed here of the resistant gene allele in cis- or transgenetic approaches opens up the possibility of new resistant species of the genus *Beta* which, using the dose effect, exhibit a higher resistance, or in which a resistance break may be avoided and the resistance development optimized via the stacking of the disclosed gene with other resistance genes. Modifications of the gene by means of tilling or targeted engineering to optimize the codon selection for an increased expression or for the development of new or modified resistance alleles are also possible. According to a preferred embodiment the codon-optimized sequences or the modified resistance alleles are not occurring in nature but are artificial. An example of a modified genomic sequence is provided by SEQ ID No. 94 in which the codon at position 16-18 is modified but the encoded amino acid sequence is unchanged and corresponds to SEQ ID No. 3. An example of a modified cDNA sequence is provided by SEQ ID No. 95 in which the codon at position 55-57 is modified but the encoded amino acid sequence is unchanged and corresponds to SEQ ID No. 3. An example of a modified resistance conferring allele is given by the amino acid sequence according to SEQ ID No. 96 in which the amino acid valine has been replaced with the amino acid leucine at position 209. The amino acid sequence according to SEQ ID No. 96 is encoded by the modified cDNA according to SEQ ID No. 97. These sequences do not occur in nature but are artificial. When replacing amino acids in for example the resistance-mediating Sequence according to SEQ ID No. 3 it is recommended to exchange amino acids within the following groups:

a) glycine, alanine, valine, leucine, isoleucine
b) serine, cysteine, selenocysteine, threonine, methionine
c) phenylalanine, tyrosine, tryptophan
d) histidine, lysine, arginine
e) aspartate, glutamate, asparagine, glutamine.

The present invention also relates to the use in a plant of the identified *Cercospora* resistance-conferring gene allele in a genetic or molecular stack with other genetic elements which may confer agronomically advantageous properties. The economic value of cultivated plants may thereby be markedly increased, in that, for example, the yield performance is increased in comparison to plants that possess the same genetics, but have not been furnished with the nucleic acid according to the invention. Furthermore, new crop areas for a plant may be opened up that were not previously accessible to the cultivation of this plant due to biotic factors such as strong pathogen pressure. In particular, the present invention relates to the use of the identified *Cercospora* resistance-conferring gene allele in methods for controlling an infestation with the pathogen *Cercospora beticola* in the agricultural or horticultural cultivation of plants of the genus *Beta*, e.g., encompassing the identification and selection of plants of the genus *Beta* with the aid of one of the methods described in the preceding and/or the cultivation of the plants so selected or descendants thereof. The present invention thus includes a method for the cultivation of plants of the species *Beta vulgaris*, including, in a first step, the provision of *Cercospora*-resistant plants of the species *Beta vulgaris* according to the invention, or the production of plants of the species *Beta vulgaris* with the aid of the production method according to the invention, or the identification and selection of plants of the species *Beta vulgaris* with the aid of the identification method according to the invention that has been described in the preceding; and including, in a second step, the cultivation of the plants from the first step, or the deployment of seed stock of the plants from the first step, or the raising of plants from the first step. The cultivation method thereby counteracts an infestation of the cultivated plants by *Cercospora*. The cultivation method may be part of a method for producing sugar. The method for the production of sugar includes the steps of the cultivation method, and additionally, as a penultimate step, the harvesting of the cultivated plants, and, as a last step, the extraction of sugar from the aforesaid plants.

The cultivation method may also be part of a method for producing seed stock. The method for the production of seed stock includes the steps of the cultivation method, and additionally, as a penultimate step, the vernalization of the cultivated plants, and, as a last step, the extraction of seeds from the aforesaid plants.

The extracted seeds may optionally be pelleted, in order to obtain pelleted seed stock of the species *Beta vulgaris*. In this instance, it is a method for the production of pelleted seed stock.

Moreover, the method for the production of seed stock may be designed as a method for the production of *Cercospora*-resistant seed stock. The method for the production of *Cercospora*-resistant seed stock includes the steps of the method described above for the production of seed stock, and additionally, as a last step, the verification of the nucleic acid according to the invention according to a method described herein in at least one of the extracted seeds—preferably, in at least 0.1% or in at least 1% of the extracted seeds. The verification is particularly preferably implemented so that the seed remains germinable. This means that the extraction of the DNA required for verification from the seed does not neutralize the germinability of the seed. In such an instance, the verification of the nucleic acid according to the invention may have taken place in an especially large proportion of all extracted seeds. For example, the verification may take place in at least 2%—preferably, at least 3%, particularly preferably, at least 4%—of all extracted seeds.

The plants according to the invention, their cells, or seeds or seed stock according to the invention may possess additional, agronomically advantageous properties, or be furnished with such. One example is the tolerance or resistance to an herbicide such as glyphosate, glufosinate, or ALS inhibitors. The tolerance to glyphosate or an ALS-inhibitor herbicide is preferred. A specific embodiment of the glyphosate resistance is disclosed in U.S. Pat. No. 7,335,816 B2. Such a glyphosate resistance is, for example, available from seed stock stored at the NCIMB, Aberdeen (Scotland, UK), under the access number, NCIMB 41158 or NCIMB 41159. Such seeds may be used in order to obtain a glyphosate-tolerant sugar beet plant. The glyphosate resistance may also be introduced into other species of the genus *Beta* via crossing.

The invention thus also encompasses plants, their cells, or seeds or seed stock, characterized in that these contain the nucleic acid according to the invention, and furthermore in that a) a DNA fragment of the genomic DNA of the plant, portions, or seeds thereof may be amplified via polymerase chain reaction with a first primer that has the nucleotide sequence of SEQ ID No. 81, and a second primer that has the nucleotide sequence of SEQ ID No. 82, wherein the DNA fragment is at least 95%—preferably, 100%—identical to the nucleotide sequence of SEQ ID No. 83, and/or
b) a DNA fragment of the genomic DNA of the plant, portions, or seeds thereof may be amplified via polymerase chain reaction with a first primer that has the nucleotide sequence of SEQ ID No. 84, and a second primer that has the nucleotide sequence of SEQ ID No. 85, wherein the DNA fragment is at least 95% identical—preferably, 100% identical—to the nucleotide sequence of SEQ ID No. 86, and/or
c) a DNA fragment of the genomic DNA of the plant, portions, or seeds thereof may be amplified via polymerase chain reaction with a first primer that has the nucleotide sequence of SEQ ID No. 87, and a second primer that has the nucleotide sequence of SEQ ID No. 88, wherein the DNA fragment is at least 95% identical—preferably, 100% identical—to the nucleotide sequence of SEQ ID No. 89.

A specific embodiment of the ALS-inhibitor herbicide resistance is disclosed in the document, WO2012/049268 A1. For example, such an ALS-inhibitor herbicide resistance is available from a deposit of NCIMB, Aberdeen, UK, under the number NCIMB 41705. Furthermore, such an ALS-inhibitor resistance may be produced via tilling or site-directed mutagenesis, e.g., via gene editing, such as through the use of CRISPR/Cas, CRISPR/Cpf1, TALENS or zinc finger nucleases. The invention thus also encompasses plants, their cells, or seeds or seed stock, characterized in that these contain the nucleic acid according to the invention, and furthermore in that these exhibit a mutation in an endogenous acetolactate synthase gene, wherein the acetolactate synthase gene encodes an acetolactate synthase protein which, as a result of the mutation at position 569, has a different amino acid than tryptophan. As a result of the mutation, the amino acid at position 569 is preferably alanine, glycine, isoleucine, leucine, methionine, phenylalanine, proline, valine, or arginine. Position 569 is preferably defined via the position 569 of SEQ ID No. 90. Furthermore, the specific sequence of the mutated acetolactate synthase gene SEQ ID No. 91 is preferred. The mutated sequence of the acetolactate synthase gene, or the sequence according to SEQ ID No. 91, does not occur in nature and cannot be isolated from nature. Furthermore, the mutation may be present both heterozygously and homozygously in the plants, their cells or seeds, or the seed stock. We recommend the homozygous presence of the mutation, since this promotes a more stable or more intensive phenotypical occurrence of the resistance.

Numerous additional herbicides and their applicability are known to the person skilled in the art from the prior art. He may resort to the prior art in order to achieve knowledge of which genetic elements are to be used in what manner in order to implement a corresponding tolerance in plants. Moreover, an herbicide tolerance has the synergistic effect that the occurrence of weeds is reduced via the use of herbicides. This is advantageous in combating *Cercospora*, because it is known that the conidia (asexual spores) or the pseudostroma (mycelium) of *Cercospora beticola* can survive for up to 2 years on plant material.

A further example of an agronomically advantageous property is an additional pathogen resistance, wherein pathogens may be insects, viruses, nematodes, bacteria, or fungi, for example. For example, a broad pathogen defense for a plant may be achieved via combination of different pathogen resistances/tolerances, since genetic elements may exhibit additive effects among one another. For example, numerous resistance genes for this are known to the person skilled in the art as genetic elements. For example, US20160152999A1 discloses an RZ resistance gene against the disease Rhizomania. This disease is caused by the agent, "Beet Necrotic Yellow Vein Virus." Several disease resistances contained in one plant have synergistic effects upon one another. If a plant is infested for the first time by a pathogen, its immune system is normally weakened, and the epidermis as an outer barrier is often damaged, such that the probability of further infections is increased. An additional example of an agronomically advantageous property is cold tolerance or frost tolerance. Plants which exhibit this property may already be sown earlier in the year, or may remain in the field longer, which may lead to increased yields, for example. Here, the person skilled in the art may also resort to the prior art to find suitable genetic elements. Additional examples of agronomically advantageous properties are water usage efficiency, nitrogen usage efficiency, and yield. Genetic elements which may be used to confer such properties might be found in the prior art.

Furthermore, numerous modifications for pathogen defense are known to the person skilled in the art. In addition to the families of the R-genes that are often described, the Avr/R approach, the Avr gene complementation (WO 2013/127379), the autoactivation of an R-gene (WO 2006/128444), or the HIGS (host-induced gene silencing) approach (e.g., WO2013/050024) may be advantageously used. In particular, the autoactivation of an R-gene might be important to the present invention. For this, a nucleic acid is to be created that encodes an autoactivated resistance protein for generation of a resistance to pathogens in plants. This nucleic acid then has only a limited portion of an NBS-LRR resistance gene, such as the wb-R-gene, which extends downstream from the 5' end of the coding region of the NBS-LRR resistance gene to the beginning of the coding for the NBS domain of the NBS-LRR resistance gene.

In this context, a method is also encompassed which contains the step of the removal of that region of the nucleic acid according to the invention which encodes the N-terminal region and which begins with the p-loop in the NBS domain, and extends up to the end of the N-terminal region.

The resistance proteins that are encoded for by such shortened nucleic acids are generally autoactivated, in that these resistance proteins trigger an immune reaction in the plant, even in the absence of the associated pathogen, and thus increase the base immunity of the plant. Furthermore, such a shortened nucleic acid according to the invention, and the polypeptide that is encoded by this, are encompassed.

Furthermore, the invention also includes the use of the *Cercospora* resistance-conferring gene allele, identified with a method described above, for combination with one of the preceding modifications, or with a genetic element described in the preceding which may convey in a plant one or more agronomically advantageous properties.

In addition to relating to the plant according to the invention, the present invention also relates to seeds or descendants, or to an organ, a plant part, a tissue, or a cell thereof in the production of products that are typically produced from sustainable raw materials, such as foodstuffs and animal feed—preferably, sugar or syrup (molasses), wherein the molasses is also used for industrial applications, e.g., in alcohol production or as a growing medium for the production of biotechnological products, in the production of materials or substances for the chemical industry, e.g., refined chemicals, pharmaceuticals or precursors thereof, diagnostics, cosmetics, bioethanol, or biogas. An example of the use of sugar beet as a biogenic raw material in biogas plants is described in the application DE 10 2012 022 178 A1; see, for example, paragraph 10.

The following examples explain the invention, but without limiting the subject matter of the invention. Unless indicated otherwise, standard molecular biology methods have been used; see, for example, Sambrook et al., Molecular Cloning: A Laboratory Manual, 3rd ed., Cold Spring Harbor Laboratory Press, Cold Spring Harbor, NY, 2001, Fritsch et al., Cold Spring Harbor Laboratory Press: 1989; Mayer et al., Immunochemical Methods in Cell and Molecular Biology, eds., Academic Press, London, 1987, and Weir et al., Handbook of Experimental Immunology, Volumes I-IV, Blackwell, eds., 1986.

Some of the most important sequences according to the invention are explained in detail in the following:

SEQ ID No. 1: genomic DNA sequence of the *Cercospora* resistance-conferring gene from *Beta vulgaris* subsp. *maritima*.

SEQ ID No. 2: cDNA sequence of the *Cercospora* resistance-conferring gene as it does not occur in nature.

SEQ ID No. 3: amino acid sequence of the *Cercospora* resistance-conferring protein as it is encoded by SEQ ID No. 1 or SEQ ID No. 2.

SEQ ID No. 4: genomic DNA sequence of the sensitive Variant of the *Cercospora* resistance-conferring gene SEQ ID No. 5: cDNA of the sensitive Variant of the *Cercospora* resistance-conferring gene—SEQ ID No. 6: Amino acid sequence of the sensitive Variant of the *Cercospora* resistance-conferring gene SEQ ID No. 7: native promoter of the *Cercospora* resistance-conferring gene from *Beta vulgaris* subsp. *maritima*.

SEQ ID No. 8: native terminator of the *Cercospora* resistance-conferring gene from *Beta vulgaris* subsp. *maritima*.

SEQ ID No. 53: sequence of the locus from *Beta vulgaris* subsp. *maritima* containing the *Cercospora* resistance-conferring gene according to SEQ ID No. 1.

EXAMPLES

Example 1: Introduction of the Resistance-Conferring Gene by Means of CRISPR-Mediated Homologous Recombination in *Beta vulgaris* Subsp. *Vulgaris*

Design and Selection of the crRNA:

Suitable crRNA's for Cpf1-mediated induction of double-strand breaks have been designed with the aid of CRISPR RGEN Tools (Park J., Bae S., and Kim J.-S. Cas-Designer: A web-based tool for choice of CRISPR-Cas9 target sites. *Bioinformatics* 31, 4014-4016 (2015); Bae S., Park J., and Kim J.-S. Cas-OFFinder: A fast and versatile algorithm that searches for potential off-target sites of Cas9 RNA-guided endonucleases. *Bioinformatics* 30, 1473-1475 (2014)). For this, suitable protospacers were sought within the genomic DNA sequences having a length of 500-1,300 bp which flank the 5'- and 3'-end of the *Cercospora* resistance gene from *Beta vulgaris* subsp. *maritima*. In order to ensure the functionality of the endonuclease Cpf1 from Lachnospiraceae bacterium ND2006 (Lb), protospacers having a length of 24 nt were selected whose genomic binding sequence at the 5'-end was flanked by an essential protospacer adjacent motif (PAM) having the sequence 5'-TTTV-3' (V=G or C or A). Suitable protospacers were selected according to the predetermined quality criteria of the tool and reconciled as to potential off-targets with a reference genome of *B. vulgaris* subsp. *vulgaris*. For the continuing tests, crRNA's, exclusively, were selected that, in addition to the actual target sequence, have at most 15 identical bases with a functional PAM. Since the first 18 nt of the protospacer are essential to the detection and cutting of the target sequence, an unwanted cutting within other genomic sequences could be precluded in this way (Tang, X., L. G. Lowder, T. Zhang, A. A. Malzahn, X. Zheng, D. F. Voytas, Z. Zhong, Y. Chen, Q. Ren, Q. Li, E. R. Kirkland, Y. Zhang, and Y. Qi (2017), "A CRISPR-Cpf1 system for efficient genome editing and transcriptional repression in plants." Nat Plants 3: 17018). In this way, four potential crRNA's at the 5'-flanking region (5'crRNA #1-4) and three crRNA's at the 3'-flanking region (3'crRNA #1-3) of the resistance gene could be identified (see Table A).

TABLE A

Selected target sequences within the 5' And 3' flanking DNA sequences of the resistance gene in *B. vulgaris*. The PAM is underlined.

| Name of the crRNA | Genomic target sequence with 5' flanking PAM (underlined) | Binding at the +/- strand |
|---|---|---|
| 5'crRNA#1 | TTTATTTCGATTTC GATTCTTGGATTAT (SEQ ID No. 16) | - |
| 5'crRNA#2 | TTTCAACCCAGTAT CCTTATCCGTCACT (SEQ ID No. 17) | - |
| 5'crRNA#3 | TTTATTTAAACATG ATACGTATCATATT (SEQ ID No. 18) | + |
| 5'crRNA#4 | TTTAAACATGATAC GTATCATATTGAGT (SEQ ID No. 19) | + |
| 3'crRNA#1 | TTTGTGGGTGGGTG GTTTTCACGTGTGT (SEQ ID No. 20) | - |
| 3'crRNA#2 | TTTCCCCTCCCTTT GCCGCTGCGAAGTT (SEQ ID No. 21) | - |
| 3'crRNA#3 | TTTCTTCTTCTTGC TTCCACCATAACAC (SEQ ID No. 22) | - |

Cloning of the genetic elements: For the cloning of the cpf1-expression cassette and the crRNA-expression cassette, first, a detection sequence of the restriction enzyme of BbsI that prevents cloning was removed from the target vector pZFNnptII via introduction of a point mutation (T to G). The mutagenesis was performed with a mutagenesis kit according to the specification of the manufacturer, using two mutagenesis primers (see Table B).

TABLE B

Mutagenesis primer used to introduce a point mutation (T to G, underlined) to remove the BbsI detection sequence.

| Name | Sequence 5'→3' |
|---|---|
| Mutagenesis primer 1 | TCAGTGCAGCCGTC GTCTGAAAACGACA (SEQ ID No. 23) |
| Mutagenesis primer 2 | TGTCGTTTTCAGAC GACGGCTGCACTGA (SEQ ID No. 24) |

For the expression of the Lbcpf1 gene in *B. vulgaris*, a DNA sequence codon-optimized for *A. thaliana*, with 5'-flanking PcUbi promoter sequence from *Petroselinum crispum* (SEQ ID No. 79) and a 3'-flanking 3A terminator sequence from Pea sp. as a DNA fragment, was synthetically produced. The restriction interface (HindIII) that is relevant to cloning within the Lbcpf1-coding sequence (CDS) [SEQ ID No. 78] were removed via the introduction of a silent mutation (base exchange, without modifying the amino acid sequence), in order to avoid an unintended cutting within the coding region. The codon optimization was performed with the aid of the GeneArt algorithm from Invitrogene/Thermo-Scientific. In order to enable the transport of the Cpf1 in the cell nucleus, the coding sequence of the nucleus location signal (NLS) of the SV40 was integrated into the cpf1 CDS at the 5'-end, and the NLS of the nucleoplasmin was integrated at the 3'-end. For the ligation in the binary target vector pZFNnptII (FIG. 2), the expression cassette was flanked by two HindIII restriction interfaces and subsequently ligated to pZFNnptII_LbCpf1. The successful insertion of the PcUbi::Cpf1::TPea expression cassette was verified by means of sequencing, wherein the binding regions of the primers used for the sequencing were situated both in the flanking vector regions and within the expression cassette (see Table C).

TABLE C

Primer used for the sequencing of the PcUbi::Cpf1::TPea expression cassette integrated into pZFNnptII

| Name | Sequence 5'→3' |
|---|---|
| pSeq_CRBM4_F1 | SEQ ID No. 25 |
| pSeq_CRBM4_R1 | SEQ ID No. 26 |
| pSeq_CRBM4_F2 | SEQ ID No. 27 |
| pSeq_CRBM4_R2 | SEQ ID No. 28 |
| pSeq_CRBM4_F3 | SEQ ID No. 29 |
| pSeq_CRBM4_R3 | SEQ ID No. 30 |
| pSeq_CRBM4_F4 | SEQ ID No. 31 |
| pSeq_CRBM4_R4 | (SEQ ID No. 32) |

After transcription into the plant cell, the crRNA's should be cut out via two flanking ribozymes. For this, the precursor crRNA was flanked by the coding sequences of a hammerhead ribozyme and an HDV ribozyme (Tang, X., L. G. Lowder, T. Zhang, A. A. Malzahn, X. Zheng, D. F. Voytas, Z. Zhong, Y. Chen, Q. Ren, Q. Li, E. R. Kirkland, Y. Zhang, and Y. Qi (2017), "A CRISPR-Cpf1 system for efficient genome editing and transcriptional repression in plants." Nat Plants 3: 17018).

For a perfect ligation of the individual protospacers at the coding sequence of the crRNA repeat, two BbsI detection sequences were integrated between crRNA repeat and HDV ribozyme, wherein the overhangs that were used for the cloning were adapted accordingly. In order to ensure an identical expression strength of the cpf1 and the crRNA's, the crRNA ribozyme cassette was bounded, at the 5 '-end, by the PcUbi promoter sequence and, at the 3'-end, by a 3A terminator sequence. For the later ligation in the target vector pZFNnptII_Cpf1, the crRNA expression cassette was flanked by two PstI interfaces and ordered as a synthetic DNA fragment. The protospacers were synthesized as complementary oligonucleotides and annealed according to a standard protocol. The 24-bp-long DNA fragment that was generated in this way was flanked by the 4-nt overhangs that are relevant to the ligation (see Table D).

TABLE D

Sequence of oligonucleotides that were used for the generation of short 24-bp protospacers. The 4-nt overhangs that are used for the ligation are the respective four first nucleotides of each listed sequence.

| Name of the crRNA | Sequence 5'→3' |
|---|---|
| 5'crRNA#1 | SEQ ID No. 33 |
| | SEQ ID No. 34 |
| 5'crRNA#2 | SEQ ID No. 35 |
| | SEQ ID No. 36 |
| 5'crRNA#3 | SEQ ID No. 37 |
| | SEQ ID No. 38 |
| 5'crRNA#4 | SEQ ID No. 39 |
| | SEQ ID No. 40 |
| 3'crRNA#1 | SEQ ID No. 41 |
| | SEQ ID No. 42 |
| 3'crRNA#2 | SEQ ID No. 43 |
| | SEQ ID No. 44 |
| 3'crRNA#3 | SEQ ID No. 45 |
| | SEQ ID No. 46 |

The efficiency of the four crRNA's was tested by means of agrobacteria-mediated gene transfer in leaves of *B. vulgaris*. The pZFNtDTnptII plasmid was co-transformed in order to check the transformation efficiency. The transformation of the leaf explant took place via vacuum infiltration according to a standard protocol. The fluorescence of the tDT was checked after six days by means of fluorescence microscopy, and leaf explants with heterogeneous fluorescence were discarded. Ten days after infiltration took place, the leaf explants were quick-frozen in liquid nitrogen, pestled, and the genomic DNA was isolated by means of the CTAB method (Clarke, Joseph D., "Cetyltrimethyl ammonium bromide (CTAB) DNA miniprep for plant DNA isolation." Cold Spring Harbor Protocols 2009.3 (2009): pdb-prot5177). The efficiency of the individual crRNA's was determined by an external service provider, using the frequency of the inserted editions (e.g., insertions, deletions, or base exchange) in comparison to unedited sequences in the genomic DNA, by means of NGS.

As a synthetic DNA construct, the most efficient crRNA's—5' crRNA #3 and 3' crRNA #1—with the previously described ribozymes, promoter, and terminator sequences, were ordered as reverse-oriented expression cassettes. The entire DNA construct was flanked by two PstI restriction interfaces for cloning in the target vector pZFNnptII_LbCpf1. After insertion of the crRNA's has taken place, the LbCpf1 and crRNA expression cassettes were ligated from the vector pZFNnptII_LbCpf1_crRNA into the pUbitDTnptII vector via HindIII.

As a repair template which should be integrated into the genome of *B. vulgaris* via homologous recombination, the resistance gene expression cassette was flanked, at the 5'-end, by the 5' crRNA #3 and, at the 3'-end, by the 3'crRNA #1 binding sequence. This enabled the excision of the resistance gene expression cassette from the plasmid via Cpf1. The entire DNA template was synthesized as an 87,326-bp-long synthetic DNA fragment (SEQ ID No. 80) and used directly in the vector backbone for the transformation. The resistance gene plasmid and the pUbitDTnptII_LbCpf1_crRNA plasmid were introduced into *B. vulgaris* callus cultures with the aid of a gene cannon.

The transformation efficiency was determined using the transient tDT fluorescence, one day after the transformation, by means of fluorescence microscopy. The callus cultures were cultivated on shoot induction medium without selection pressure (without Kanamycin), and the regenerated shoots were subsequently checked for the site-directed integration of the resistance-conferring resistance gene cassette. For this, the genomic DNA was isolated by means of CTAB. The integration of the resistance-conferring gene was amplified by means of PCR using the primers pCRBM4_F1 according to SEQ ID No. 47 and pCRBM4_R1 according to SEQ ID No. 48 (see Table E), and the PCR products were subsequently sequenced with both primers. Shoots, in which the successful insertion of the expression cassette could be verified in this manner, were identified in the following analyses of the integration site of the resistance gene. In order to verify the insertion within the desired target sequence in the genome, the flanking regions of the resistance gene expression cassette were amplified by means of PCR. The binding of a primer here took place within the resistance gene DNA sequence; the binding of the second primer took place outside of the 5'- or 3'-flanking homologous region of the inserted expression cassette (see Table E). The amplified DNA sequences were sequenced using the same primers, and the integration at the desired location was confirmed in this way. In order to preclude the binding of the primers pCRBM4_F1 (SEQ ID No. 47), pCRBM4_R1 (SEQ ID No. 48), pCRBM4_R2 (SEQ ID No. 50) and pCRBM4_F3 (SEQ ID No. 51) in sequence-similar regions of the genome, all primer sequences were compared beforehand with the *B. vulgaris* genome. For the primer pCRBM4_F3 (SEQ ID No. 51), it was not possible to select the nucleotide sequence such that a binding to the wild-type sequence could be precluded. Therefore, the 3'-flanking region was amplified in all shoots that tested positive for the resistance gene, and the site-specific insertion was verified exclusively via the subsequent sequencing. The generated PCR product thereby differs by 18 bp from the wild-type sequence. In order to enable the complete sequencing of the amplified sequences, the PCR products were additionally sequenced via a third primer with a binding location within the amplified sequence (pCRBM4_S2, pCRBM4_S3; see Table E). In order to preclude the nonspecific binding of the primers pCRBM4_F1 (SEQ ID No. 47), pCRBM4_R1 (SEQ ID No. 48) and pCRBM4_R2 (SEQ ID No. 50) within the wild-type genome, the nucleotide sequences were compared with an internal reference genome of *B. vulgaris*. The primers were additionally tested by means of PCR for the binding in genomic sequences of *B. vulgaris* wild-type plants.

In order to preclude the integration of the resistance gene in other regions of the genome, a targeted amplification of the target location was performed (Targeted Locus Amplification, TLA).

TABLE E

Primer used to verify the insertion of the resistance gene expression cassette at the desired integration site.

| Name | Sequence 5'→3' | Size of the PCR product | Binding |
|---|---|---|---|
| pCRBM4_F1 | SEQ ID No. 47 | 450 bp | within the resistance gene expression cassette |
| pCRBM4_R1 | SEQ ID No. 48 | | within the resistance gene expression cassette |
| pCRBM4_F2 | SEQ ID No. 49 | 1,140 bp | up-strand of the 5'-flanking homologous region |
| pCRBM4_R2 | SEQ ID No. 50 | | within the resistance gene promoter sequence |
| pCRBM4_S2 | SEQ ID No. 66 | | |
| pCRBM4_F3 | SEQ ID No. 51 | 1,280 | within the resistance gene terminator sequence |
| pCRBM4_R3 | SEQ ID No. 52 | | down-strand of the 3'-flanking homologous region |
| pCRBM4_S3 | SEQ ID No. 67 | | |

In addition to the verification and the successful insertion of the resistance gene expression cassette into the genome of *B. vulgaris*, the unwanted integration of plasmid DNA was also checked. For this, genomic DNA, in which the verification had already yielded a successful insertion of the resistance gene at the desired target site, was checked for the presence of plasmid DNA by means of PCR. Sequence regions within the cpf1, the crRNA ribozyme cassette, and the tDT were thereby amplified using the primers listed in Table F, and subsequently sequenced.

TABLE F

Primers used to verify stably-integrated, plasmid-specific sequences in the genome of the regenerated *B. vulgaris* shoots

| Name | Sequence 5'→3' | Size of the PCR product | Binding |
|---|---|---|---|
| pSeq_LbCpf1_F4 | SEQ ID No. 68 | 214 | Cpf1 |
| pSeq_LbCpf1_R3 | SEQ ID No. 69 | | |
| pSeq_Ribozyme_F | SEQ ID No. 70 | 172 | crRNA ribozyme cassette |
| pSeq_Ribozyme_R | SEQ ID No. 71 | | |
| pSeq_tDT_F | SEQ ID No. 72 | 400 | tDT |
| pSeq_tDT_R | SEQ ID No. 73 | | |

Example 2: Introduction of the Resistance-Conferring Gene as a Transgene by Means of Gene Transformation in *Beta vulgaris* Subsp. *Vulgaris*

The transgenic approach to the production of *Cercospora*-resistant plants served not only for the alternative validation of the LRR gene as the resistance-conferring gene, but also as a means of producing transgenic resistance events that confer a novel *Cercospora* resistance or improve already existing *Cercospora* resistances.

The binary vector pZFN-nptII-LRR was generated by means of the following standard cloning procedures: Within the T-DNA of this vector, the cDNA of the resistance gene according to SEQ ID NO 2 was cloned together with its native promoter sequence. The T-DNA furthermore included the neomycin phosphotransferase II (nptII) gene, which confers resistance to a bandwidth of aminoglycoside antibiotics such as kanamycin or paromomycin. These antibiotic resistances were used for the selection of the transgenic plant cells and tissues. The NOS promoter and the pAG7 terminator flanked the nptII gene. The backbone of the binary vector furthermore contained the colE1 and the pVS1 origin for the plasmid replication in *Escherichia coli* or *Agrobacterium tumefaciens*. The aadA gene confers streptomycin/spectinomycin resistance for bacteria selection. The pZFN-nptII-LRR plasmid was transformed in *agrobacterium* strain AGL-1 by means of standard procedure.

The transformation of the sugar beets took place according to Lindsey & Gallois (1990), "Transformation of sugarbeet (*Beta vulgaris*) by *Agrobacterium tumefaciens*." Journal of experimental botany 41.5, 529-536). For this, "micropropagated shoots" of genotype 04E05B1DH5, which did not carry the resistance gene according to the invention, were used as starting material. Shoots were multiplied in the corresponding medium according to Lindsey & Gallois (1990). In order to induce as many meristems as possible, the "shoots" were transferred into a different medium (see Lindsey & Gallois (1990)) and incubated in darkness for several weeks at approximately 30° C. *Agrobacterium* strain AGL-1 with vector pZFN-nptII-LRR (FIG. 3) was cultured in an additional medium (see Lindsey & Gallois (1990)), additionally provided with corresponding antibiotics for selection. Sections of meristemic tissue based upon the shoot to be treated were incubated with *agrobacterium* for several hours in an additional medium (see Lindsey & Gallois (1990)). Plant explants and agrobacteria were co-cultivated in darkness for at least 2 days in medium (see Lindsey & Gallois (1990)), and inoculated explants were subsequently incubated in darkness for approximately 2 weeks in an additional medium (see Lindsey & Gallois (1990)). The explants were thereupon further propagated in an additional medium (see Lindsey & Gallois (1990)) and sub-cultivated, in order to enable the selection of the transgenic tissue. In order to conclude the selection phase and to reduce the extent of chimera formation, green "shoots" were transferred to medium H, and all were propagated for 2 weeks. Leaf material was then extracted from the green, growing "shoots" and examined by means of PCT for the presence of the transgene. Suitable "shoots" were rooted in medium I and subsequently transferred to a greenhouse for production of T1 seed stock. Furthermore, leaf material derived from these "shoots" was used to analyse the expression of the transformed resistance gene.

Analysis of the Expression Level

RNA was isolated from the leafs of the in vitro "shoots" and used within an qRT-PCR. The qRT-PCR was performed according to Weltmeier et al. 2011 (s. background of invention). Measured values were normalized against the reference gene PLT3_075_F09 (s. Weltmeier et al. 2011). The expression was determined by the use of the following primer sequences:

| Sequence | Size [No. nucleotides] | $T_m$ [C.°] | Size of amplification product [No. nucleotides] |
|---|---|---|---|
| SEQ ID No. 92 | 21 | 59.8 | 170 |
| SEQ ID No. 93 | 21 | 58.9 | 170 |

Resistance Test in Sugar Beet after Inoculation with *Cercospora beticola* Under Greenhouse Conditions:

A pure *Cercospora beticola* culture with a known high virulence was propagated on vegetable juice agar in Petri dishes (9 cm diameter) at 20° C. under near-ultraviolet (NUV) light. After 14 days, the surface of the agar on which the mold was grown was flooded with 10 ml of sterile water per Petri dish, and the conidia and mycelium fragments were carefully scraped off with the aid of a subject carrier. An inoculum density of 20,000 conidia/mycelium fragments per ml, plus 0.1% TWEEN 20, was used to inoculate the plants. At the point in time of the inoculation, the plants had been cultivated for 8 to 9 weeks under greenhouse conditions. The top side and underside of the leaves were treated with the inoculum. The plants were subsequently incubated for 5 to 7 days at 25° C., 18 h/6 h light/dark, and approximately 100% humidity. The first *Cercospora* symptoms on the sugar beet leaves occurred after 12 to 14 hours. An assessment of the symptoms of the individual plants was performed regularly, with the assistance of the assessment of the rating score shown in Table 1A. The results are shown below.

TABLE G

Results of transgenic verification of the function of the resistance gene according to the invention in transformed plants;

| Test group | Number of Individuals | Average rating score 8 dpi | 11 dpi | 13 dpi | 15 dpi | Function | Expression level of the resistance gene according to the invention |
|---|---|---|---|---|---|---|---|
| 1 | 57 | 1.60 | 3.82 | 5.24 | 6.46 | negative control | 0.0 |
| 2 | 38 | 1.28 | 3.07 | 4.42 | 6.04 | transgenic validation | 4.6 |
| 3 | 60 | 1.26 | 2.83 | 4.38 | 6.20 | transgenic validation | 12.5 |
| 4 | 45 | 1.50 | 3.40 | 4.62 | 6.18 | no validated expression in vitro | 0.0 |
| 5 | 60 | 1.44 | 3.62 | 5.29 | 6.38 | transgenic validation | 2.6 |
| 6 | 57 | 1.68 | 3.69 | 5.30 | 6.52 | transgenic validation | 3.3 |
| 7 | 66 | 1.58 | 3.84 | 5.43 | 6.57 | transgenic validation | 2.9 |
| 8 | 60 | 1.31 | 2.81 | 4.19 | 5.48 | transgenic validation | 11.3 |
| 9 | 72 | 1.25 | 3.07 | 4.61 | 5.97 | transgenic validation | 26.8 |
| 10 | 60 | 1.44 | 3.26 | 4.77 | 6.00 | transgenic validation | 10.7 |
| 11 | 57 | 1.60 | 3.83 | 5.48 | 6.64 | transgenic validation | 4.4 |
| 12 | 72 | 1.34 | 2.62 | 3.75 | 5.19 | resistant source plant | not determined |
| mean value overall | 58.66 | 1.44 | 3.32 | 4.8 | 6.13 | | |
| LSD value | — | 0.17 | 0.47 | 0.48 | 0.4 | | |

LSD = least significant difference;
dpi = days post infection

Results of the Transgenic Validation of the Resistance Gene According to the Invention (s. Table G)

Test group 1 represents a negative control. The genotype is the same as for test groups 2 to 11 but no transformation has taken place. Therefore, no expression could be detected. Test group 4 has been transformed but no expression could be detected. Test groups 2, 3 and 5 to 11 represent transformants which carry the resistance gene according to the invention only due to the transformation. Test group 12 represents a breeding line comprising the resistance gene according to the invention in a non-transgenic version. The rating scores of all lines has been established after inoculating the plant material with *Cercospora beticola* as described above. Test group 12 shows the highest resistance which is indicated by a final value of 5.19.

The transgenic lines showed a rating score according to the following table:

TABLE H

Rating scores of the transgenic lines of table G

| | 8 dpi | 11 dpi | 13 dpi | 15 dpi |
|---|---|---|---|---|
| mean value transgenic validation | 1.42 | 3.33 | 4.87 | 6.2 |
| mean value transgenic validation for lines having an expression level >10 | 1.315 | 2.99 | 4.48 | 5.91 |

Table H shows that the rating scores for transgenic validation groups only. First the mean value for all transgenic test groups (excluding group 4) are shown. Below the rating scores only for those transgenic lines which showed an expression level of at least 10 (groups 3, 8, 9, 10; s. Table G) are given. Here, the final rating score is 5,91. That is a significantly higher resistance than the negative conrol of group 1 which has a rating score of only 6.46 (least significant difference=0.4; s. Table G). The best transgenic test group (group 8) shows an even better resistance due to a rating score is 5.48 (s. Table G).

It is worth mentioning that the expression level of transgenic insertions may be influenced by the integration locus. As the expression level was measured in vitro the actual expression level under infection conditions could be higher—especially under when the resistance gene is under control of a pathogen inducible promoter.

Statistical Evaluation of the Results of the Transgenic Validation

TABLE I statistic clustering

| test group | cluster 8 dpi | cluster 11 dpi | cluster 13 dpi | cluster 15 dpi |
|---|---|---|---|---|
| 1 | ab | a | a | ab |
| 2 | e | de | bc | cd |
| 3 | e | ef | c | bcd |
| 4 | bc | bcd | bc | bcd |
| 5 | cd | abc | a | abc |
| 6 | a | ab | a | ab |
| 7 | ab | a | a | a |
| 8 | de | ef | c | e |
| 9 | e | de | bc | d |
| 10 | cd | cd | b | d |
| 11 | ab | a | a | a |
| 12 | de | f | d | e |

Table I shows a statistical evaluation of the rating scores contained in Table G. Each letter symbolizes the allocation to a statistical group. For example, it is evident that after the final evaluation (15 dpi) test group 8 (transgenic verification) is in the same cluster as test group 12 (resistant source) but in a different cluster than test group 1 (negative control). According to this test group 8 is significantly different from test group 1 but not significantly different than test group 12.

In addition, a box-plot analysis has been performed. The illustration of the the box-plots is available from FIG. 4-7.

The invention claimed is:

1. A nucleic acid molecule which encodes a polypeptide that is able to confer resistance to *Cercospora beticola* in a *Beta vulgaris subsp. vulgaris* plant in which the polypeptide is expressed, wherein the nucleic acid molecule comprises the DNA sequence according to SEQ ID NO: 2.

2. A vector or expression cassette comprising the nucleic acid molecule according to claim 1.

3. A cell which comprises the nucleic acid molecule according to claim 1.

4. A *Cercospora beticola*-resistant *Beta vulgaris subsp. vulgaris* plant or a portion thereof, wherein the plant or its portion contains the nucleic acid molecule according to claim 1 transgenically.

5. A seed or descendant of the *Cercospora beticola*-resistant *Beta vulgaris subsp. vulgaris* plant according to claim 4, wherein the seed or the descendant comprises the nucleic acid molecule transgenically.

6. The seed according to claim 5, which has been technically treated, wherein the technical treatment is selected from the group consisting of:

(a) polishing;

(b) dressing;

(c) incrustation; and (d) coloring.

7. A method for increasing the resistance to *Cercospora beticola* in a plant of the species *Beta vulgaris subsp. vulgaris* comprising integrating the nucleic acid molecule according to claim 1 by means of homology-directed repair or homologous recombination into the genome of at least one cell of the *Beta vulgaris subsp. vulgaris*, and optional regeneration of a plant from the plant cell.

8. A method for producing a *Cercospora beticola*-resistant *Beta vulgaris subsp. vulgaris* plant according to claim 5, including the following steps:

(a) introducing a site-directed nuclease and a repair matrix into a cell of the *Beta vulgaris subsp. vulgaris* plant, wherein the site-directed nuclease is able to generate at least one double-strand break of the DNA in the genome of the cell and the repair matrix comprises the nucleic acid molecule;

(b) cultivating the cell from (a) under conditions that allow a homology-directed repair or a homologous recombination, wherein the nucleic acid molecule is integrated from the repair matrix into the genome of the plant; and (c) regenerating a plant from the cell modified in (b).

9. The method according to claim 8, wherein the at least one double strand break occurs in a sensitive allelic variant of the nucleic acid molecule or in that the at least one double strand break occurs at a position which is at most 10,000 base pairs upstream or downstream away from the sensitive allelic variant, wherein the allelic variant encodes a polypeptide which does not confer resistance to *Cercospora beticola*.

10. The method according to claim 9, wherein the sensitive allelic variant comprises a nucleotide sequence, which is selected from the group consisting of:

(a) a nucleotide sequence which encodes a polypeptide comprising the amino acid sequence according to SEQ ID NO: 6;

(b) a nucleotide sequence which comprises the sequence according to SEQ ID NO: 5;

(c) a nucleotide sequence which comprises the sequence according to SEQ ID NO: 4; and (d) a nucleotide sequence which encodes a polypeptide which differs from a polypeptide which is encoded by the nucleotide sequence according to (a), (b) or (c) by conservative substitution of one or more amino acids of the amino acid sequence.

11. A method for identifying, and optionally providing, a *Beta vulgaris subsp. vulgaris* plant that is resistant to *Cercospora beticola*, wherein the method comprises detecting the presence and/or expression of the nucleic acid molecule according to claim 1 in the plant or a portion of the plant and, optionally, selecting the *Cercospora beticola*-resistant plant.

12. A method for cultivating plants of the species *Beta vulgaris subsp. vulgaris*, the method comprising:

(i) providing plants according to claim 5, and (ii) cultivating the plants from (i) or descendants thereof, wherein the method counteracts an infestation of the cultivated plants with *Cercospora beticola.*

* * * * *